US012649725B2

(12) United States Patent
Ali et al.

(10) Patent No.: US 12,649,725 B2
(45) Date of Patent: Jun. 9, 2026

(54) SYNTHESIS OF SMALL MOLECULES INSPIRED BY PHOMOXANTHONE A

(71) Applicant: Worcester Polytechnic Institute, Worcester, MA (US)

(72) Inventors: Rameez Ali, Worcester, MA (US); Anita Mattson, Holden, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 1303 days.

(21) Appl. No.: 17/400,468

(22) Filed: Aug. 12, 2021

(65) Prior Publication Data

US 2022/0048879 A1 Feb. 17, 2022

Related U.S. Application Data

(60) Provisional application No. 63/065,066, filed on Aug. 13, 2020.

(51) Int. Cl.

| | |
|---|---|
| ***C07D 311/66*** | (2006.01) |
| ***A61K 47/54*** | (2017.01) |
| ***C07D 311/22*** | (2006.01) |
| ***C07D 409/06*** | (2006.01) |
| ***C07D 411/06*** | (2006.01) |
| ***C07D 413/14*** | (2006.01) |
| ***C12N 15/10*** | (2006.01) |

(52) U.S. Cl.

CPC .......... *C07D 311/66* (2013.01); *A61K 47/545* (2017.08); *C07D 311/22* (2013.01); *C07D 409/06* (2013.01); *C07D 411/06* (2013.01); *C07D 413/14* (2013.01); *C12N 15/1065* (2013.01)

(58) Field of Classification Search

CPC ... C07D 311/66; C07D 409/06; A61K 47/545
See application file for complete search history.

(56) References Cited

FOREIGN PATENT DOCUMENTS

| | | | |
|---|---|---|---|
| EP | 0618983 | A1 | 10/1994 |
| WO | 9409159 | A1 | 4/1994 |

OTHER PUBLICATIONS

Deratt et al. A Facile Enantioselective Alkynylation of Chromones, GDCh, Jun. 2019, pp. 8416-8420. (Year: 2019).*
Guan et al. Copper Bis(oxazoline)-Catalyzed Enantioselective Alkynylation of Benzopyrylium Ions, ChemPubSoc Europe, Dec. 2019, pp. 1742-1747 (Year: 2019).*
Baek, Doohyun, et al., "Catalytic enantioselective synthesis of tetrasubstituted chromanones via palladium-catalyzed asymmetric conjugate arylation using chiral pyridine-dihydroisoquinoline ligands", Chem. Sci., 2020, 11, pp. 4602-4607.
Becke, Axel D., "Density-functional thermochemistry. III. The role of exact exchange", J. Chern. Phys., vol. 98, No. 7, Apr. 1, 1993, pp. 5648-5652.
Biddle, Margaret, et al. "Catalytic Enantioselective Synthesis of Flavanone and Chromanones", J. Am. Chem. Soc. 2007, 129, pp. 3830-3831.
Brown, Kevin M., "Highly Enantioselective Cu-Catalyzed Conjugate Additions of Dialkylzinc Reagents to Unsaturated Furanones and Pyranones: Preparation of Air-Stable and Catalytically Active Cu-Peptides Complexes", Angew. Chem. Int. Ed. 2005, 44, pp. 5306-5310.
Contreras-Garcia, Julia, et al., "NCIPlot: A Program for Plotting Noncovalent Interaction Regions", J. Chem. Theory Comput. 2011, 7, 625-632.
Ditchfield, R, et al., "Self-Consistent Molecular-Orbital Methods. IX. An Extended Gaussian-Type Basis for Molecular-Orbital Studies of Organic Molecules", The Journal of Chemical Physics, vol. 54, No. 2, Jan. 15, 1971, pp. 724-728.
Gerten, Anthony L. , et al., "Palladium-catalyzed conjugate addition of arylboronic acids to 2-substittued chromones in aqueous media", Tetrahedron Letters 57 (2016) pp. 5460-5463.
Gordon, Mark S., "The Isomers of Silacyclopropane", Nov. 15, 1980, pp. 162-168, Chemical Physics Letters, Volum 79, No. 1.
Hariharan, P.C., et al., "Accuracy of AHn equilibrium geometries by singledeterminant molecular orbital theory", Molecular Physics, 1974, vol. 27, No. 1, pp. 209-214.
Hehre, W. J., et al., "Self-Consistent Molecular Orbital Methods. XII. Further Extensions of Gaussian-Type Basis Sets for Use in Molecular Orbital Studies of Organic Molecules", Mar. 1, 1972, pp. 2257-2261, the Journal of Chemical Physics, vol. 56, No. 5.
Kawasaki, Masashi, et al., "Asymmetric synthesis of 2-substituted 4-chromanones using enzyme-catalyzed reactions", Journal of Molecular Catalysis B: Enzymatic 54 (2008), pp. 9-102.
Kikuchi, Haruhisa, et al, "Structures of the Dimeric and Monomeric Chromanones, Gonytolides A-C, Isolated from the Fungus *Gonytrichum* sp. and Their Promoting Activities of Innate Immune Responses", Organic Letters, 2011, vol. 13, No. 17, pp. 4624-4627.
Kim, K. et al, "Comparison of Density Functional and MP2 Calculations on the Water Monomer and Dimer" J. Phys. Chem. 1994, 98, 10089-10094.
Liu, Yun-Lin, "Recent Advances in Catalytic Asymmetric Synthesis of Tertiary Alcohols via Nucleophilic Addition to Ketones", Sep. 4, 2018, pp. 1-39.
Masahiko Isaka, et al. "Phomoxanthones A and B, Novel Xanthone Dimers from the Endophytic Fungus *Phomopsis* Species", Published Jul. 13, 2001, J. Nat. Prod., 2001, 64, pp. 1051-1081, American Chemical Society and American Society of Pharmacognosy.
Masters, Kye-Simeon, et al., Xanthones from Fungi, Lichens and Bacteria: The Natural Products and Their Synthesis, Chem. Rev. 2012, 112, pp. 3717-3776.

(Continued)

*Primary Examiner* — Sarah Pihonak
*Assistant Examiner* — Mikhail O'Donnel Robinson
(74) *Attorney, Agent, or Firm* — Armis IP Law, LLC

(57) ABSTRACT

Methods, compositions, and kits are provided for synthesizing bioactive chromane, the method including: constructing a tertiary ether stereocenter enantioselectively by catalyzed alkynylation of a substituted chromenone to obtain a chromanone; reducing alkyne and ketone in the chromanone to obtain a chroman; and converting ester to methyl group thereby obtaining chromane.

2 Claims, 26 Drawing Sheets

(56) References Cited

OTHER PUBLICATIONS

Nibbs, Antoinette E. , et al. "Asymmetric Methods for the Synthesis of Flavanones, Chromanones, and Azaflavanones", Eur. J. Org. Chem 2012, pp. 449-462.

Nicklass, Andreas, et al., "Ab initio energy-adjusted pseudopotentials for the noble gases Ne through Xe: Calculation of atomic dipole and quadrupole polarizabilities"; J. Chem. Phys. 102 (22), Jun. 8, 1995, pp. 8942-8952.

Ronsberg, David, et al., "Pro-Apoptotic and Immunostimulatory Tetrahydroxanthone Dimers from the Endophytic Fungus *Phomopsis longicolla*", J. Org. Chem. 2013, 78, 12409-12425.

Stephens, P. J., et al. "Ab Initio Calculation of Vibrational Absorption and Circular Dichroism Spectra Using Density Functional Force Fields", The Journal of Physical Chemistry, vol. 98, No. 45, November 10m 1994, pp. 11623-11627.

Stewart, Michael et al., "Rugulotrosins A and B: Two New Antibacterial Metabolites from an Australian Isolate of a *Penicillium* sp." J. Nat. Prod. 2004, 67, pp. 728-730.

Trost, Barry M., "Direct Enantio- and Diastereoselective Vinylogous Addition of Butenolides to Chromones Catalyzed by Zn-ProPhenol", J. Am. Chem. Soc. 2019, 141, pp. 1489-1493.

Vila, Carolos, et al. "Catalytic asymmetric conjugate addition of Grignard reagents to chromones", Chem Commun, 2013, 49, pp. 5933-5935.

Wagenaar, Melissa M., et al., "Dicerandrols, New Antibiotic and Cytotoxic Dimers Produced by the Fungus *Phomopsis longicolla* Isolated from an Endangered Mint", J. Nat. Prod. 2001, 64, pp. 1006-1009.

Wezeman, Tim, et al., "Xanthone dimers: a compound family which is both common and privileged", Nat. Prod. Rep., 2015, 32, pp. 6-28.

Wu, Guangwei, et al., "Versixanthones A-F, Cytotoxic Xanthone-Chromanone Dimers from the Marine-Derived Fungus *Aspergillus versicolor* HN1009", J. Nat Prod. 2015, 78, pp. 2691-2698.

Zhang, Wen, et al., "New Mono- and Dimeric Members of the Secalonic Acid Family: Blennolides A-G Isolated from the Fungus *Blennoria* sp.", Chem. Eur. J. 2008, 14, pp. 4913-4923.

Zhongtao, Wu, et al, Total Synthesis of (R,R,R)-y-Tocopherol through Cu-Catalyzed Asymmetric 1, 2-Addition, Chem. Eur. J. 2014, 20, pp. 14250-14255.

Guan, et al., "Copper Bis(oxazoline)-Catalyzed Enantioselective Alkynylation of Benzopyrylium Ions. Chemistry". Author manuscript, Feb. 6, 2020, vol. 26, N.8, pp. 1742-1747, schemes 1, 2, tablee 1, abstract doi: 10.1002/chem.201904822.

Head, Sarah A., et al. "Identification of Small Molecule-binding Proteins in a Native Cellular Environment by Live-cell Photoaffinity Labeling" Journal of Visualized Experiments, Sep. 2016, vol. 115, pp. 1-9.

International Search Report, PCT/US2021/045667, Nov. 25, 2021, pp. 1-2.

* cited by examiner

Figure 1 A
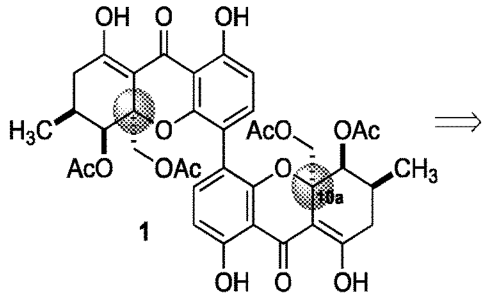
1
Phomoxanthone A
*immune response promoter*
*anticancer*
*antitubercular*
*antibacterial*
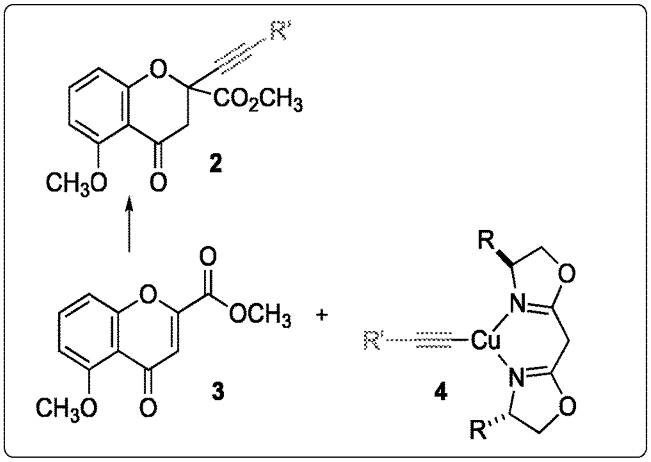
2
3
4
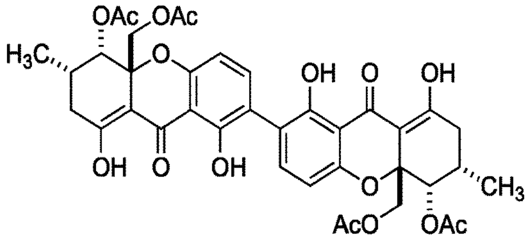
Dicerandrol C
*anticancer*
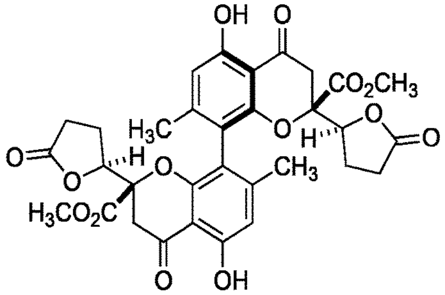
Gonytolide A
*immune response promoter*
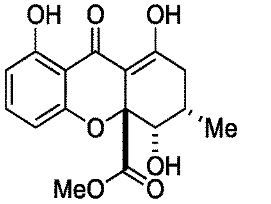
Blennolide A
*antibacterial*
*antifungal*
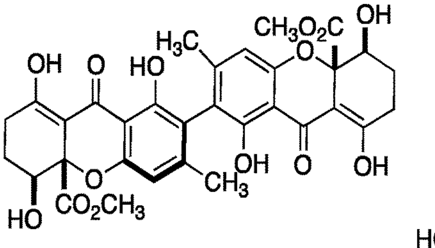
Rugulotrosin A
*antibacterial*
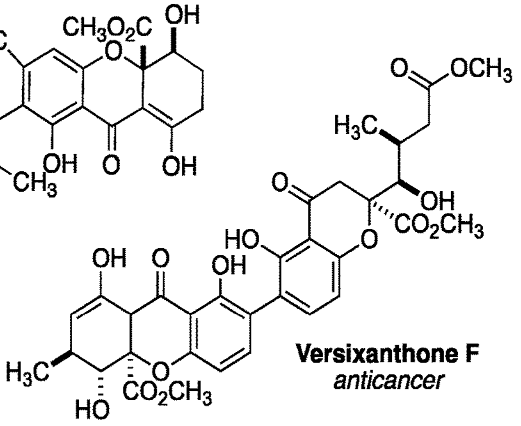
Versixanthone F
*anticancer*
Figure 1 B

5

12

7a 5 12 7

Chromone ester scope

7a: 68% yield
90% ee

7b: 53% yield
89% ee

7c: 59% yield
91% ee

7d: 57% yield
71% ee

7e: 60% yield
83% ee

7f: 46% yield
92% ee

Alkyne scope

7a: 68% yield
90% ee

7g: 60% yield
90% ee

7h: 60% yield
90% ee

7i: 66% yield
92% ee

7j: 50% yield
90% ee

7k: 57% yield
91% ee

7l: 70% yield
90% ee

7m: 53% yield
89% ee

7n: 67% yield
91% ee

7o: 60% yield
92% ee

7p: 80% yield
88% ee

7q: 51% yield
93% ee

7r: 65% yield
92% ee

7s: 42% yield
91% ee

7t: 61% yield
89% ee

7u: 42% yield
81% ee

7v: 89% yield
91% ee
(w/ 11)

7w: 66% yield
86% ee

7x: 64% yield
96% ee

7y: 75% yield
99% ee

7z: 67% yield
82% ee

7aa: 59% yield
85% ee

7ab: 73% yield
95% ee

7ac: 70% yield
93% ee

7ad: 73% yield
95% ee

7ae: 33% yield
97% ee

7af: 81% yield
99% ee

7ag: 68% yield
99% ee

7ah: 63% yield
99% ee

7ai: 40% yield
81% ee

7aj: 31% yield
98% ee

Ellipsoid plot of 7n:

7n

| Product | ΔΔG‡ | calc. ee | exp. ee |
|---|---|---|---|
| 7a | −1.5 kcal/mol | 92% | 90% |
| 7y | −1.2 kcal/mol | 85% | 99% |

5a

*S*-7a

9

| Ligand | ΔΔG‡ | exp. yield | calc. ee | exp. ee |
|---|---|---|---|---|
| **9** | 0.5 kcal/mol | 78% | –48% | –71% |
| **10** | –1.5 kcal/mol | 68% | 92% | 90% |

*S*-7a
*major enantiomer observed with ligand* *9*

*R*-7a

17: 65% yield
90% ee

NaN₃
H₂SO₄

0°C to 23 °C

18: 80% yield
90% ee

Pd/C, H₂
CH₃OH
40°C, 5 h

7a: 90% ee

Pd/C, H₂
CH₃OH
40 °C, 24 h i) DIBAL
ii) TsCl, Et₃N, DMAP

19: 81% yield
90% ee

20: 77% yield
90% ee tetrahydroxanthone
21

γ-lactone chromenone
22

23

24

25

26

27 6,6'-linked and

28 8,8'-linked 29 30 31 32 a-e $R_1$ =

32a 32b 32c 32d 32e 32d 33 32d 32 34 32 35a-e 27a-e 36 37a-e 38a-e 39a-e 28a-e a) i) NaH, $CH_3CH_2O_2R_1$, 23 °C, 24 h, ii) $CH_3OH$, aq. HCl 40-60%; b) $I_2$, $C_6H_5I(OCOF_3)_2$, $CH_2Cl_2$, 23 °C, 24 h, 58-76%; c) $Pd(OAc)_2$, S-Phos, $B_2Pin_2$, $K_3PO_4$, $CH_2Cl_2$, $H_2O$ (4:1) reflux, 18 h, 24-60%; d) $BBr_3$, $CH_2Cl_2$, 0°C, 6 h, 46-82%

36

40

41

42 R = $CH_3$)

43 R = H)

a) i) NaH, EtOAc, 23 °C, 24 h, 90%; b) NaOAc, $Ac_2O$, reflux, 24 h 78%; c) NIS, TFA, $CH_2Cl_2$, 45 °C, 2 h, 51%; c) $Pd(OAc)_2$, S-Phos, $B_2Pin_2$, $K_3PO_4$, $CH_2Cl_2$, $H_2O$ (4:1) reflux, 18 h, 59%; d) $BBr_3$, $CH_2Cl_2$, 0°C, 6 h, 62%

36

40

45

46a R = H (72 %)
46b R = $CH_3$ (81 %)
46c R = *i*-Pr (66 %)

47a R = H (62%)
47b R = $CH_3$ (54%)
47c R = *i*-Pr (51%)

48a R = H (48%)
48b R = $CH_3$ (53%)
48c R = *i*-Pr (40%)

a) i) NaH, EtOAc, 23 °C, 24 h, 90%; b) $CH_2Cl_2$, 23 °C, 5 d, 66-81%; c) $I_2$, $C_6H_5I(OCOF_3)_2$, $CH_2Cl_2$, 23 °C, 18 h, 51-62%; d) $Pd(OAc)_2$, S-Phos, $B_2Pin_2$, $K_3PO_4$, $CH_2Cl_2$, $H_2O$ (4:1) reflux, 18 h 40-53%

Figure 20A
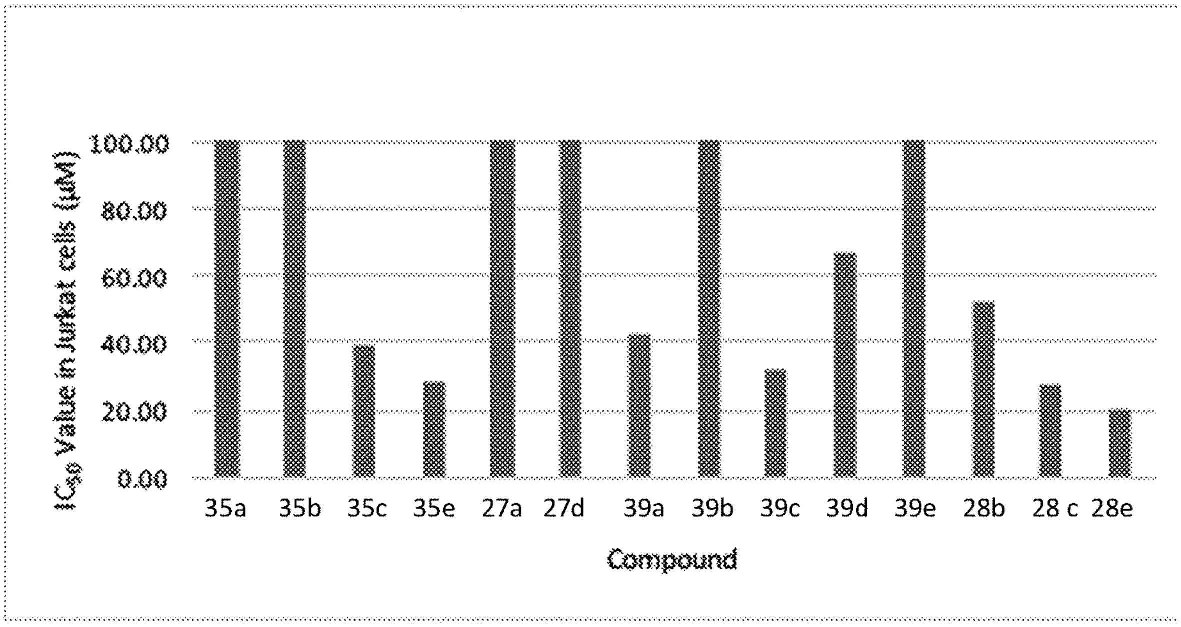
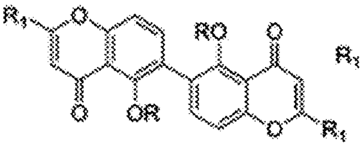
35 R = $CH_3$
27 R = H
$R_1$ =
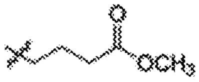
35a
27a
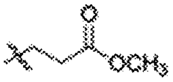
35b
27b
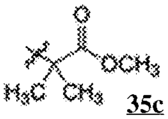
35c
27c
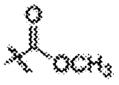
35d
27d
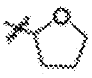
35e
27e
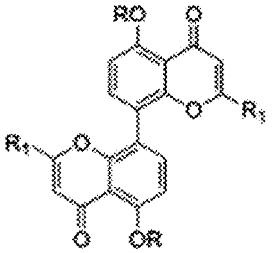
39 R = $CH_3$
28 R = H
$R_1$ =
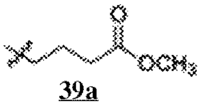
39a
28a
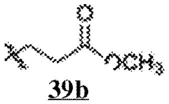
39b
28b
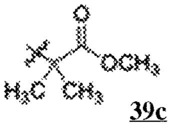
39c
28c
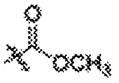
39d
28d
39e
28e
Figure 20B 5a 50a

51

5

50

51

50m 90% yield
95% ee 50n 90% yield
97% ee

X=F, 96% yield, 97% ee 50o
X=Cl, 69% yield, 94% ee 50p
X=Br, 71% yield, 96% ee 50q 50r 68% yield
98% ee 50s 23% yield
97% ee 50t 93% yield
84% ee 50u 75% yield
93% ee 50v 54% yield
d.r. 2:1, 63% ee 51a 69 % yield 95 % ee 51b 85 % yield 86 % ee 51c 64 % yield 93 % ee 51d 92 % yield 70 % ee 51e 77 % yield −26 % ee 51f 87 % yield 84 % ee 51g 52 % yield 34 % ee 51h 82 % yield 4 % ee 51i 11 % yield −41 % ee 51j 63 % yield −76 % ee

SYNTHESIS OF SMALL MOLECULES INSPIRED BY PHOMOXANTHONE A

RELATED APPLICATIONS

This application claims the benefit of priority to U.S. provisional application No. 63/065,066 filed Aug. 13, 2020, having the title, "Phomoxanthone A-Inspired Therapy for Cisplatin Resistant Cancer" by inventors, Rameez Ali and Anita Mattson, which is hereby incorporated by reference herein in its entirety.

GOVERNMENT SUPPORT

This invention was made with government support under contract No. 5 R35 GM124804 awarded by the National Institute of Health. The government has certain rights in the invention.

BACKGROUND

Bioactive natural products serve as important lead compounds in drug development. It is estimated that between 1940-2014 49% of small molecules approved for cancer treatment were natural products or compounds derived from natural products. Naturally occurring dimeric chromanones and tetrahydroxanthones often possess enticing biological activities. For example, the dimeric chromanone gonytolide A promotes an innate immune response while dimeric tetrahydroxanthones phomoxanthone A, dicerandrol C, and penexanthone A are cytotoxic toward various cancer cell lines. Rugulotrosin and phomalevone C retain antibacterial properties. Despite the promising bioactivity of these dimeric oxygen heterocycles, naturally occurring chromanone and/or xanthone dimers remain an understudied collection of compounds in terms of drug discovery and chemical probe development. The limited investigations dedicated toward advancing their biological performance in the context of drug discovery can be, at least in part, attributed to the synthetic challenges that naturally occurring dimeric chromanones and tetrahydroxanthones present. The chromanone and/or xanthone units of the dimers are bonded in several scenarios, including scaffolds that contain 8,8'-, 6,6'-, and 6,8'-linked chromenone/xanthone units. As a consequence of the sterically congested nature of the biaryl bonds connecting the monomers, the methodologies available for their construction are limited and often plagued by low yields and narrow substrate scopes. In addition to the biaryl bond, the multiple stereogenic centers present in these families of natural products intensify the synthetic challenge. The 2-stereogenic center is a particularly challenging aspect in the synthesis of dimeric chromanone and xanthone derivatives. There are few methodologies to establish the absolute stereochemistry at the 2-position and they are limited in substrate scope.

Given limitations associated with many natural occurring molecules (e.g., limited supply, challenging syntheses), including the dimeric chromanones and tetrahydroxanthones, there is a need for construction and study of structurally simplified bioactive derivatives for the purposes of drug development.

Therefore, there is a need for construction of structurally simplified bioactive derivatives of natural products for small molecule therapies of cancers.

SUMMARY

An aspect of the invention described herein provides a composition having the general formula:

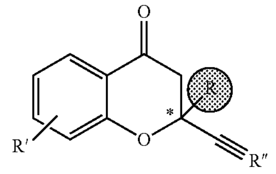

such that R is selected from: a bond, a hydrogen, a methyl, an ethyl, and an ester; R' is selected from: a bond, a hydrogen, a methyl, an ethyl, a benzyl, a phenyl, an isopropyl, a tertiary butyl, a methoxy, a halogen, a trifluoromethyl, and a cyclopropyl; and R" is selected from an alkyl, a vinyl, an aryl, a heteroaryl, and a phenyl acetylene.

In an embodiment of the composition, R is the ester having the formula $CO_2R_1$, and $R_1$ is selected from methyl, ethyl, isopropyl, tertiary butyl, benzyl, trichloroethyl, and trichloromethyl. In an embodiment of the composition, R" is the phenyl acetylene having the formula $PhR_2$, and $R_2$ is selected from methyl, ethyl, methoxy, chlorine, bromine, trifluoromethyl, naphthalene, thiophene, furan, and methoxy carbonyl. In an embodiment of the composition, the halogen is selected from chlorine, bromine, fluorine, and iodine. In an embodiment of the composition, R is $CO_2CH_3$, R' is hydrogen, and R" is phenyl.

In an embodiment of the composition, the composition is methyl 4-oxo-2-(phenylethynyl)chromane-2-carboxylate; ethyl 4-oxo-2-(phenylethynyl)chromane-2-carboxylate; isopropyl 4-oxo-2-(phenylethynyl)chromane-2-carboxylate; tert-butyl 4-oxo-2-(phenylethynyl)chromane-2-carboxylate; benzyl (R)-4-oxo-2-(phenylethynyl)chromane-2-carboxylate; 2,2,2-trichloroethyl (R)-4-oxo-2-(phenylethynyl)chromane-2-carboxylate; isobutyl (R)-4-oxo-2-(phenylethynyl)chromane-2-carboxylate; methyl (R)-4-oxo-2-(p-tolylethynyl)chromane-2-carboxylate; methyl (R)-4-oxo-2-(m-tolylethynyl)chromane-2-carboxylate; methyl (R)-4-oxo-2-(o-tolylethynyl)chromane-2-carboxylate; methyl (R)-2-((4-methoxyphenyl)ethynyl)-4-oxochromane-2-carboxylate; methyl (R)-2-((4-chlorophenyl)ethynyl)-4-oxochromane-2-carboxylate; methyl (R)-2-((4-bromophenyl)ethynyl)-4-oxochromane-2-carboxylate; Methyl(R)-4-oxo-2-((4-(trifluoromethyl)phenyl)ethynyl)chromane-2-carboxylate; methyl (R)-2-(naphthalen-1-ylethynyl)-4-oxochromane-2-carboxylate; methyl (R)-2-(naphthalen-2-ylethynyl)-4-oxochromane-2-carboxylate; methyl (R)-2-([1,1'-biphenyl]-4-ylethynyl)-4-oxochromane-2-carboxylate; methyl (R)-4-oxo-2-(thiophen-2-ylethynyl)chromane-2-carboxylate; methyl (R)-4-oxo-2-(thiophen-3-ylethynyl)chromane-2-carboxylate; methyl (R)-2-((5-methylfuran-2-yl)ethynyl)-4-oxochromane-2-carboxylate; methyl (R)-2-((5-(methoxycarbonyl)furan-2-yl)ethynyl)-4-oxochromane-2-carboxylate; methyl (R)-2-(cyclopropylethynyl)-4-oxochromane-2-carboxylate; methyl (R)-2-(cyclohexylethynyl)-4-oxochromane-2-carboxylate; methyl (R)-2-(3,3-dimethylbut-1-yn-1-yl)-4-oxochromane-2-carboxylate; methyl (R)-2-(cyclohex-1-en-1-ylethynyl)-4-oxochromane-2-carboxylate; methyl (R)-4-oxo-7-phenyl-2-(phenylethynyl)chromane-2-carboxylate; methyl (R)-7-(cyclopropylethynyl)-4-oxo-2-(phenylethynyl)chromane-2-carboxylate; methyl (R)-4-oxo-2-(phenylethynyl)-7-vinylchromane-2-carboxylate; methyl (R)-7-allyl-4-oxo-2-(phenylethynyl)chromane-2-carboxylate; methyl (R)-5-(cyclopropylethynyl)-4-oxo-2-(phenylethynyl)chromane-2-carboxylate; methyl (R)-6-(cyclopropylethynyl)-4-oxo-2-(phenylethynyl)chromane-2-carboxylate; methyl (R)-7- methyl-4-oxo-2-(phenylethynyl)chromane-2-carboxylate; methyl (R)-7-bromo-4-oxo-2-(phenylethynyl)chromane-2-carboxylate; methyl (R)-8-bromo-4-oxo-2-(phenylethynyl) chromane-2-carboxylate; methyl (R)-4-oxo-2-(phenylethynyl)-7-(trifluoromethyl)chromane-2-carboxylate; methyl (R)-7-fluoro-4-oxo-2-(phenylethynyl)chromane-2-carboxylate; methyl (R)-5-methoxy-4-oxo-2-(phenylethynyl)chromane-2-carboxylate; or methyl (R)-7-methoxy-4-oxo-2-(phenylethynyl)chromane-2-carboxylate.

An aspect of the invention described herein provides a method for synthesizing bioactive chromane, the method including: constructing a tertiary ether stereocenter enantioselectively by catalyzed alkynylation of a substituted chromenone to obtain a chromanone; reducing alkyne and ketone in the chromanone to obtain a chroman; and converting ester to methyl group thereby obtaining chromane.

In an embodiment of the method, constructing further includes adding a ligand, a copper source, a solvent, and at least one reagent to the substituted chromenone. In an embodiment of the method, the ligand is of a general formula,

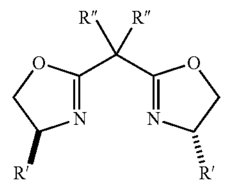

such that R' is selected from benzyl, tertiary butyl, phenyl, isopropyl, naphthyl, and indanyl and R" is selected from methyl, tertiary butyl, and phenyl. In an embodiment of the method, the ligand is selected from: benzyl bis(oxazoline), tertiary butyl bis(oxazoline), indanyl bis (oxazoline), and bis((4R,5S)-4,5-diphenyl-4,5-dihydrooxazol-2-yl)methane.

In an embodiment of the method, the substituted chromenone is benzopyrilium triflate. In an embodiment of the method, the copper source is selected from: $Cu(OTf)_2$, CuOTf, CuBr, and CuI. In an embodiment of the method, the reagent is selected from: tert-butyldimethylsilyl triflate (TBSOTf), trimethylsilyl triflate (TMSOTf), and triispropylsilyl triflate (TIPSOTf). In an embodiment of the method, the solvent is selected from: toluene, chlorobenzene, and o-Xylene.

An aspect of the invention described herein provides a method for identifying a receptor protein of phomoxanthone A, the method including: constructing a library having a plurality of compounds which are analogues of phomoxanthone A; labelling at least one of the plurality of compounds for photoaffinity assay; and thereby identifying the receptor protein of phomoxanthone A. In an embodiment of the method, the plurality of compounds having bioactivity and structure substantially similar to phomoxanthone A.

BRIEF DESCRIPTIONS OF DRAWINGS

FIG. 1 is a schematic showing Phomoxanthone A and enantioselective scheme for its synthesis. A selection of naturally occurring chromanones and tetrahydroxanthones are also schematically represented.

Figure 3:
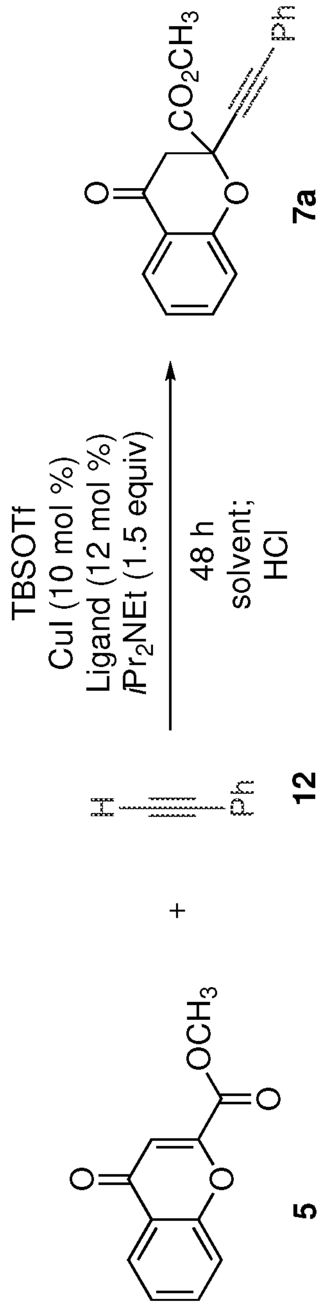

FIG. 3 is a schematic drawing showing alkynylation reaction of compound 5 and compound 12 to obtain compound 7a.

Figure 4:
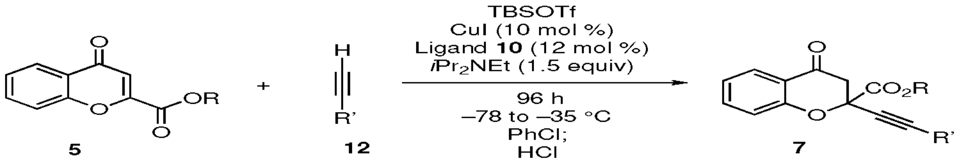
Figure 4:
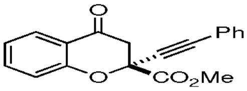
Figure 4:
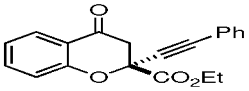
Figure 4:
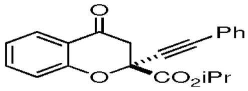
Figure 4:
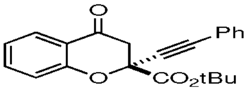
Figure 4:
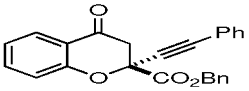
Figure 4:
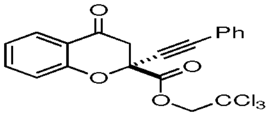
Figure 4:
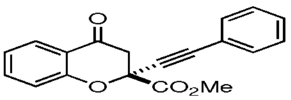
Figure 4:
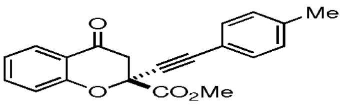
Figure 4:
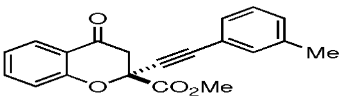
Figure 4:
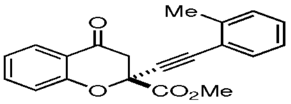
Figure 4:
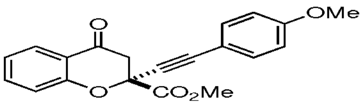
Figure 4:
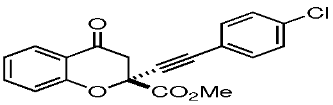
Figure 4:
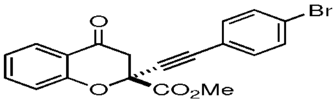
Figure 4:
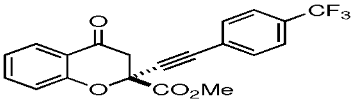
Figure 4:
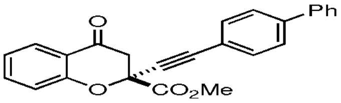
Figure 4:
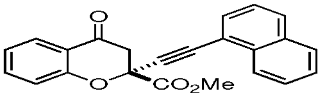
Figure 4:
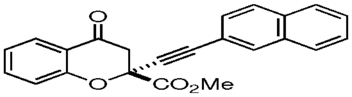
Figure 4:
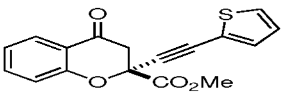
Figure 4:
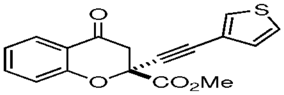
Figure 4:
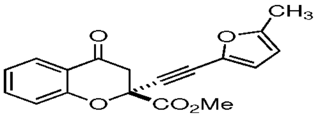
Figure 4:
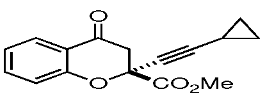
Figure 4:
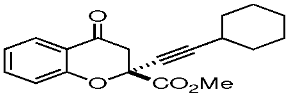
Figure 4:
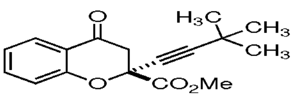
Figure 4:
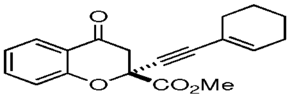

FIG. 4 is a schematic drawing showing ester and alkyne substrate reactions to obtain compounds 7a-7w.

Figure 5:
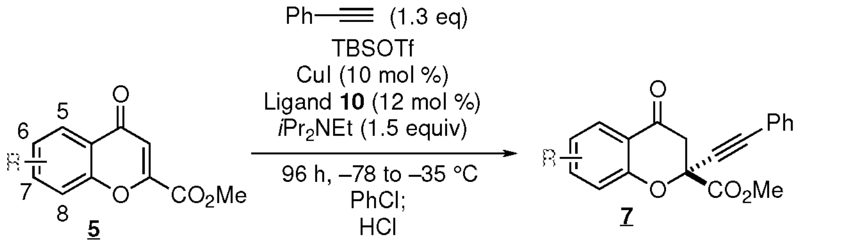
Figure 5:
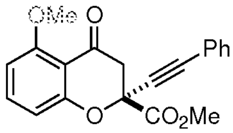
Figure 5:
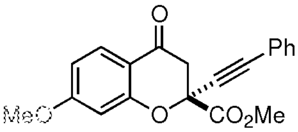
Figure 5:
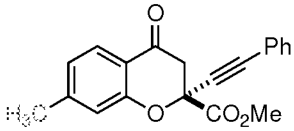
Figure 5:
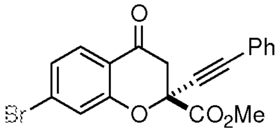
Figure 5:
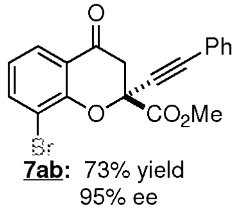
Figure 5:
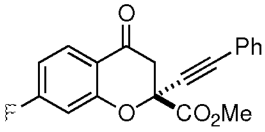
Figure 5:
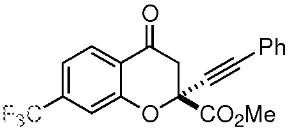
Figure 5:
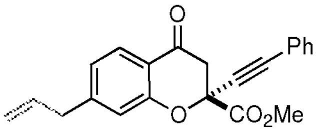
Figure 5:
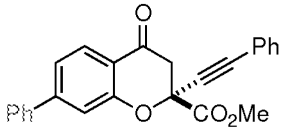
Figure 5:
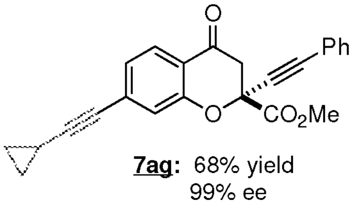
Figure 5:
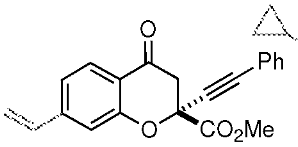
Figure 5:
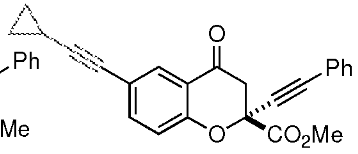
Figure 5:
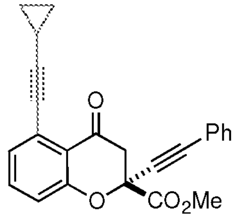

FIG. 5 is a schematic drawing of chromanone substrate reaction of compound 5 with ligand 10 to obtain compound 7 (7x-7aj).

Figure 6:
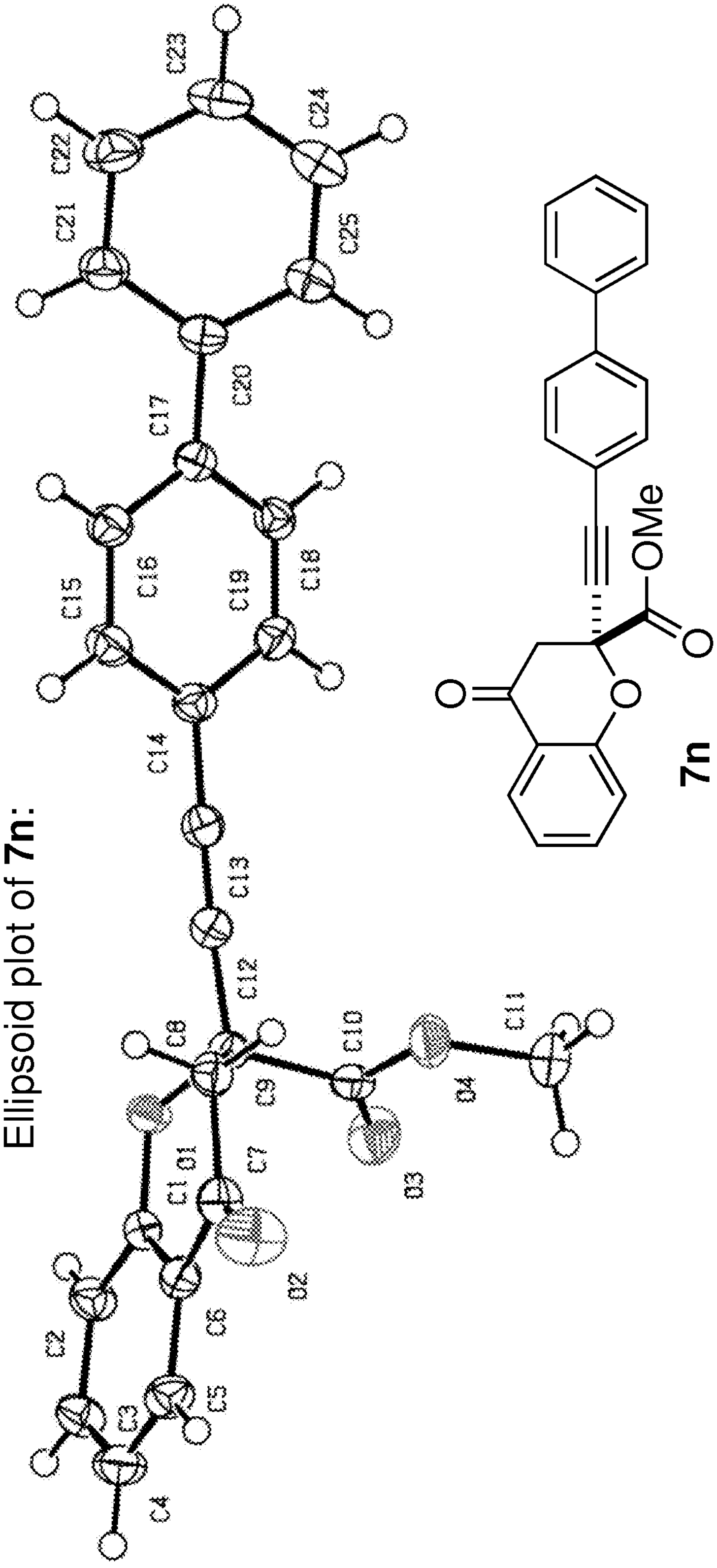

FIG. 6 is a schematic drawing of absolute stereochemistry of compound 7n. The anisotropic displacement parameters are drawn at 50% probability level.

Figure 7:
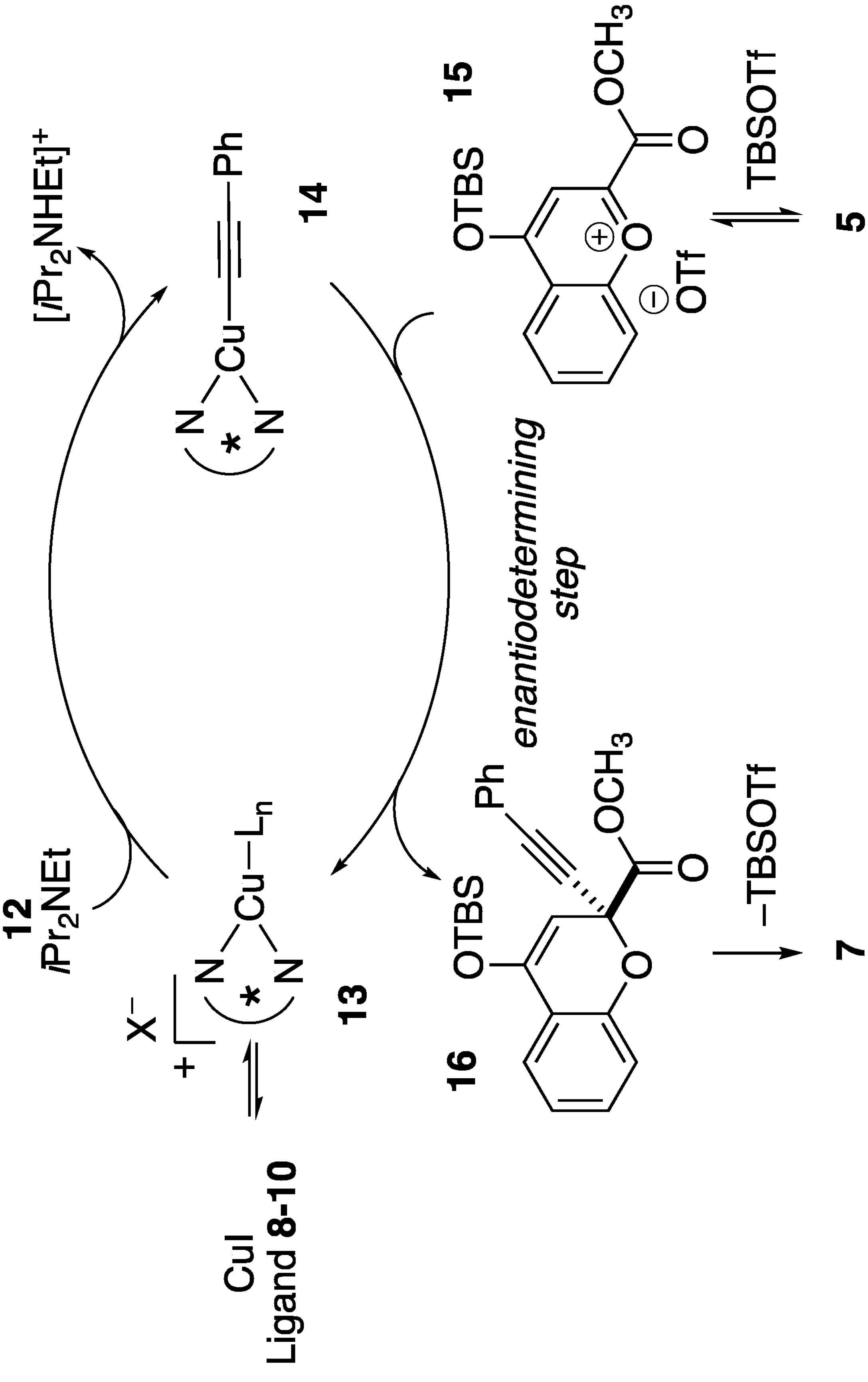

FIG. 7 is a schematic drawing of a reaction pathway to obtain compound 7 with a CuI ligand.

Figure 8:
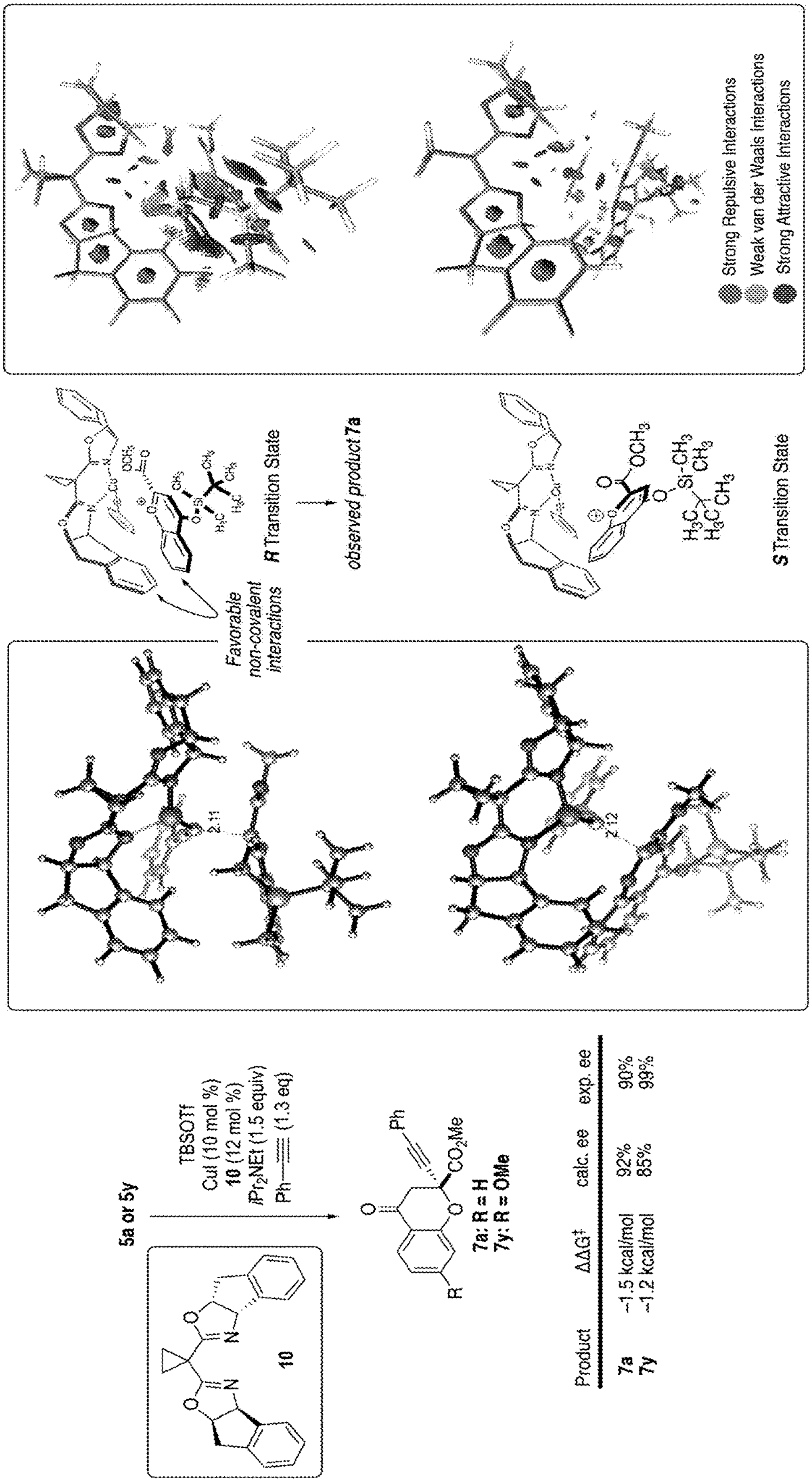

FIG. 8 is a schematic drawing showing DFT transition states calculated with B3LYP/6-31+G(d) (SDD for Cu) level of theory in the gas phase at −35° C. and non-covalent interaction plots for transition states.

Figure 9:
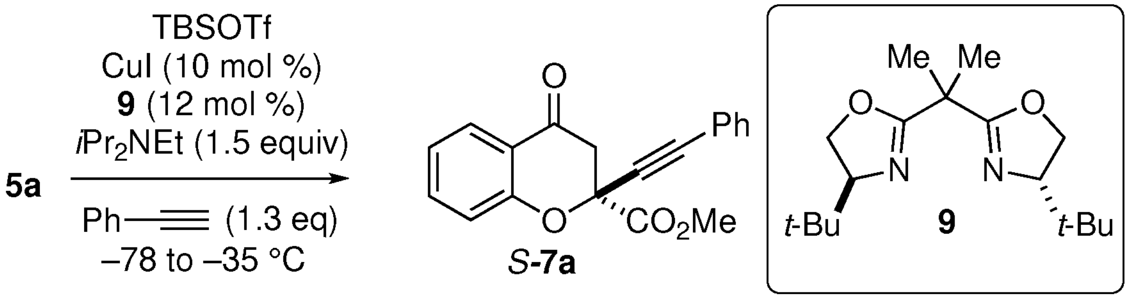
Figure 9:
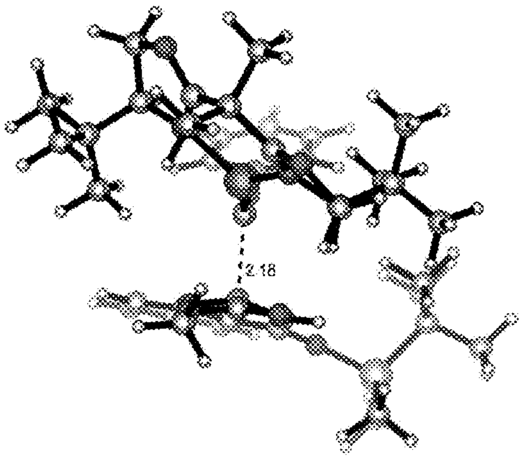
Figure 9:
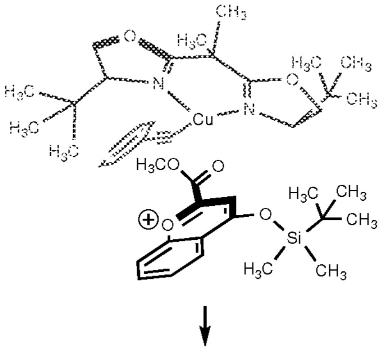
Figure 9:
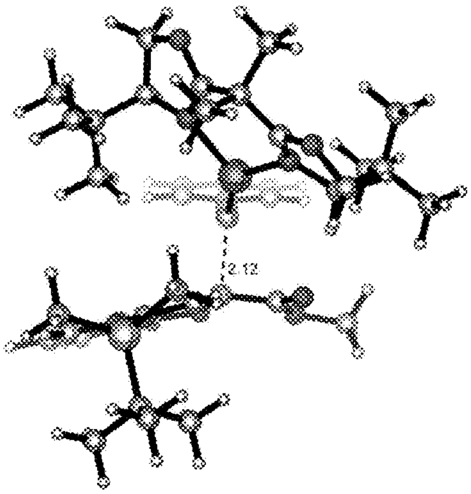
Figure 9:
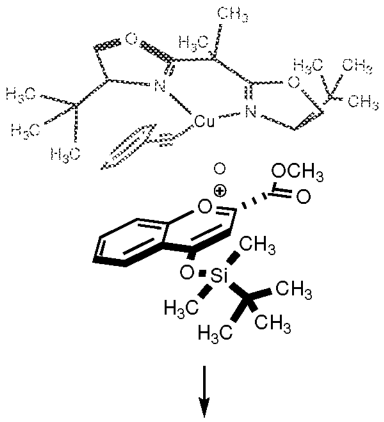

FIG. 9 is a schematic drawing showing DFT transition states calculated with B3LYP/6-31+G(d) (SDD for Cu) level of theory in the gas phase at −35° C. of alkynylation with Ligand 9.

Figure 10:
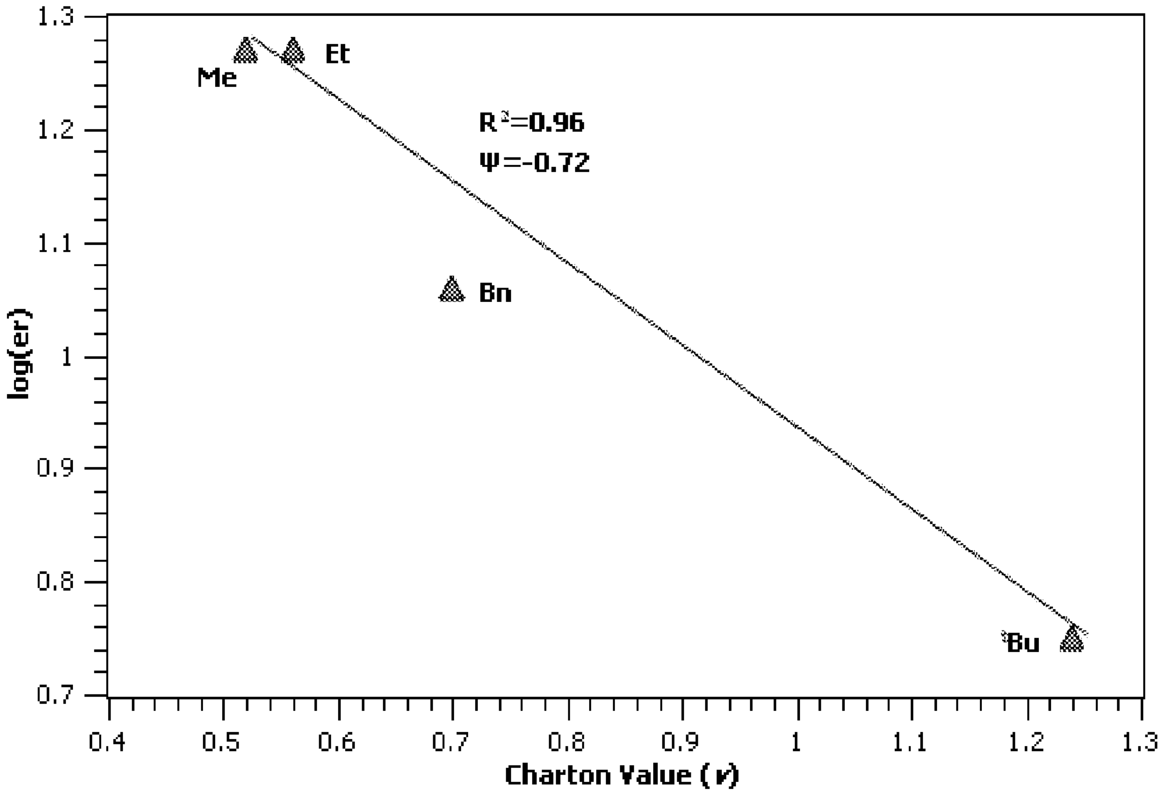

FIG. 10 is a line graph which plots enantiomeric ratio vs Charton values in the enantioselective alkynylation of benzopyrylium triflate esters.

Figure 11:
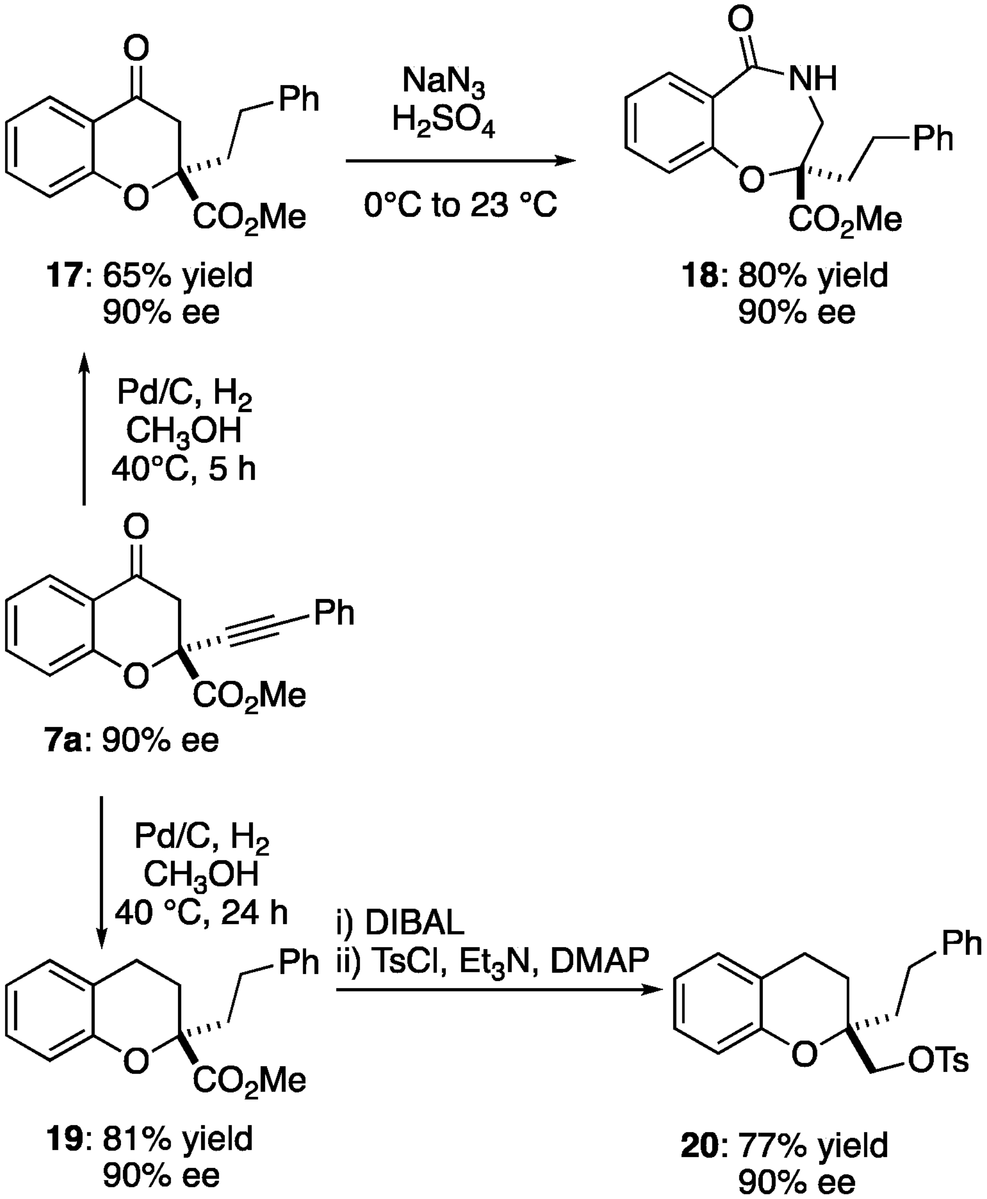

FIG. 11 is a schematic drawing of a scheme for select synthetic manipulations tolerated by enantioenriched chromanone 7a.

Figure 12:
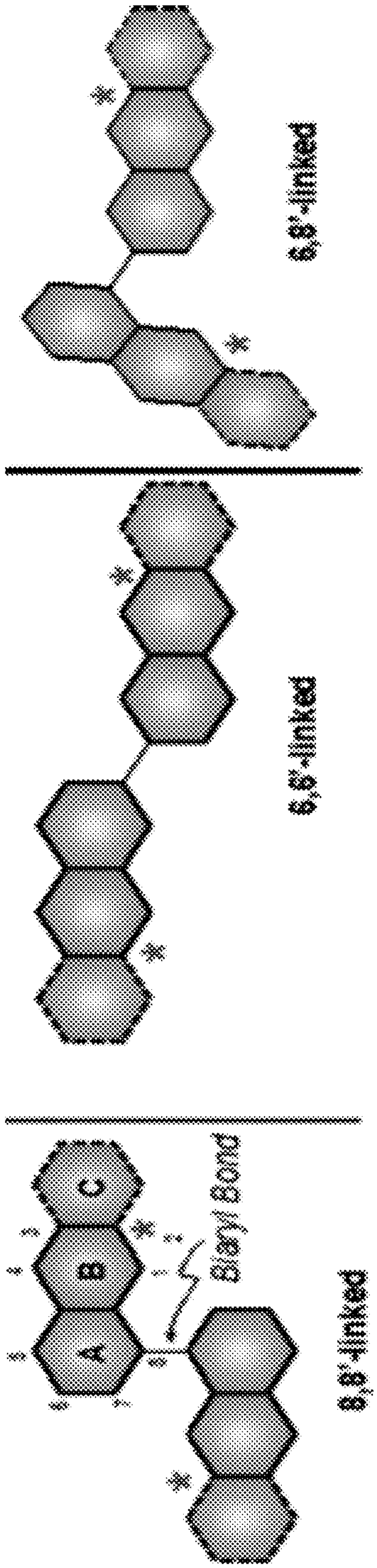

FIG. 12 is a schematic drawing showing connectivity patterns of dimeric chromenones and xanthones. The dimers have a biaryl bond and form 8,8'-dimers, 8,6'-dimers, and 6,6'-dimers.

Figure 13:
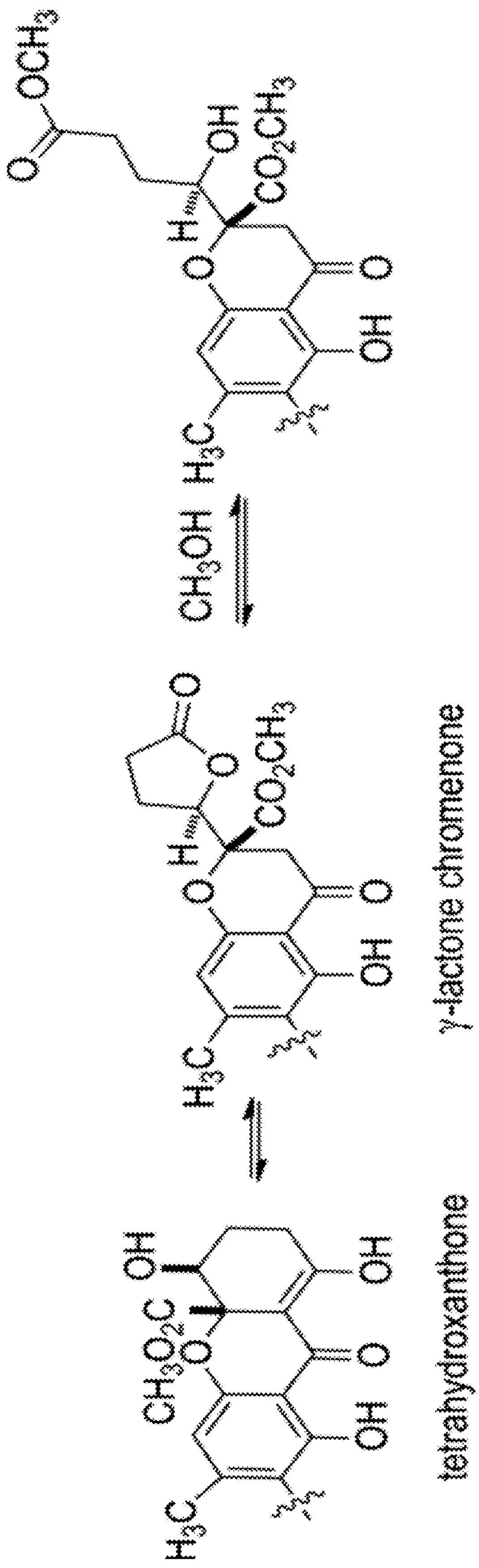

FIG. 13 is a schematic drawing showing the relationship of tetrahydroxanthone 21, γ-lactone chromanone 22, and ring-opened chromanone 23.

Figure 14:
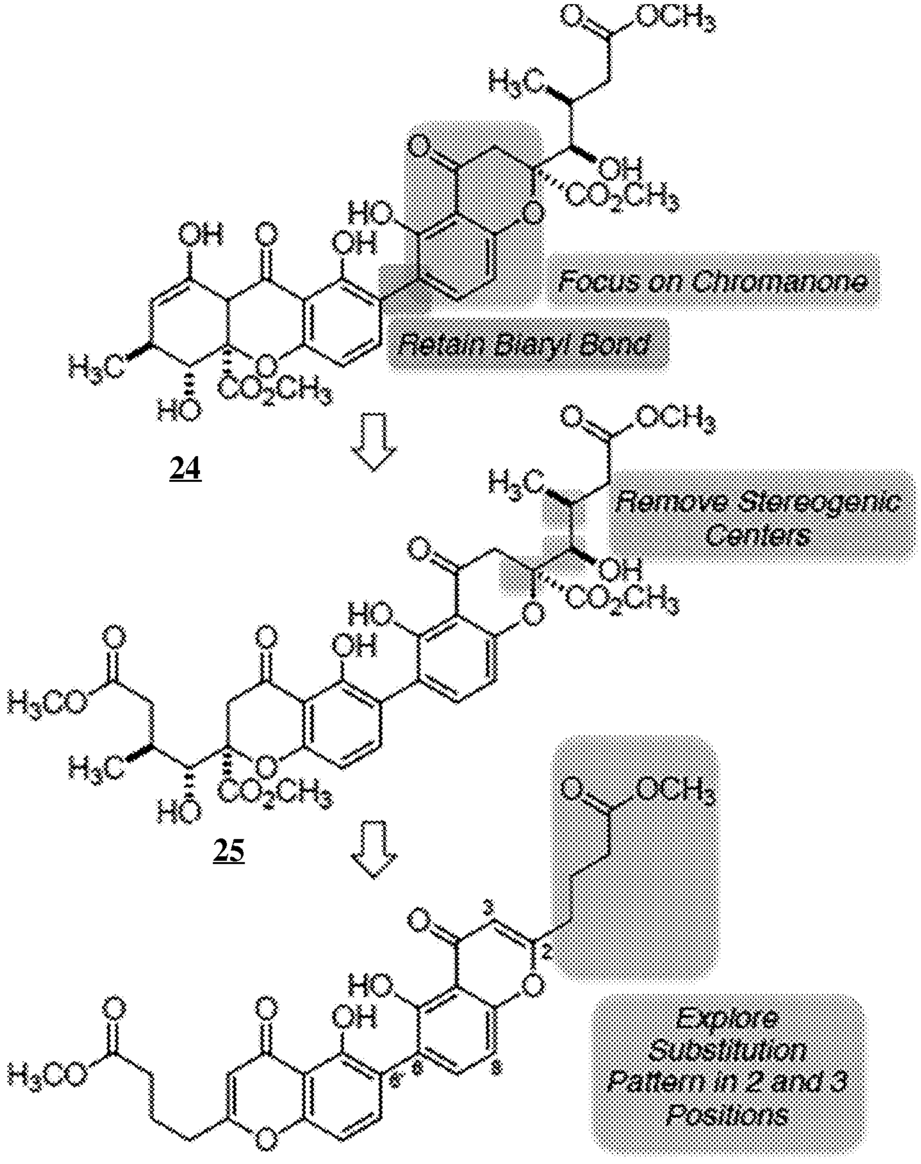
Figure 14:
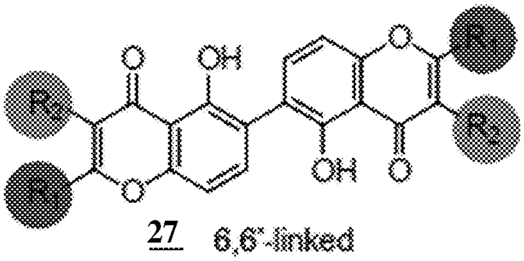
Figure 14:
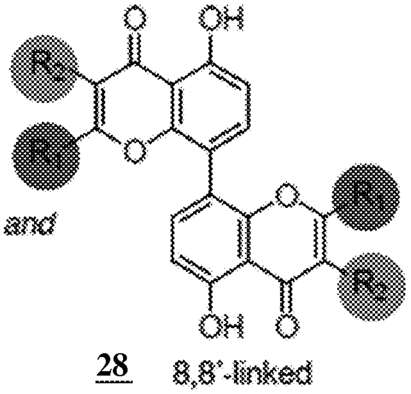

FIG. 14 is a schematic drawing showing a scheme for design of naturally inspired, structurally simplified dimeric chromanone derivatives.

Figure 15:
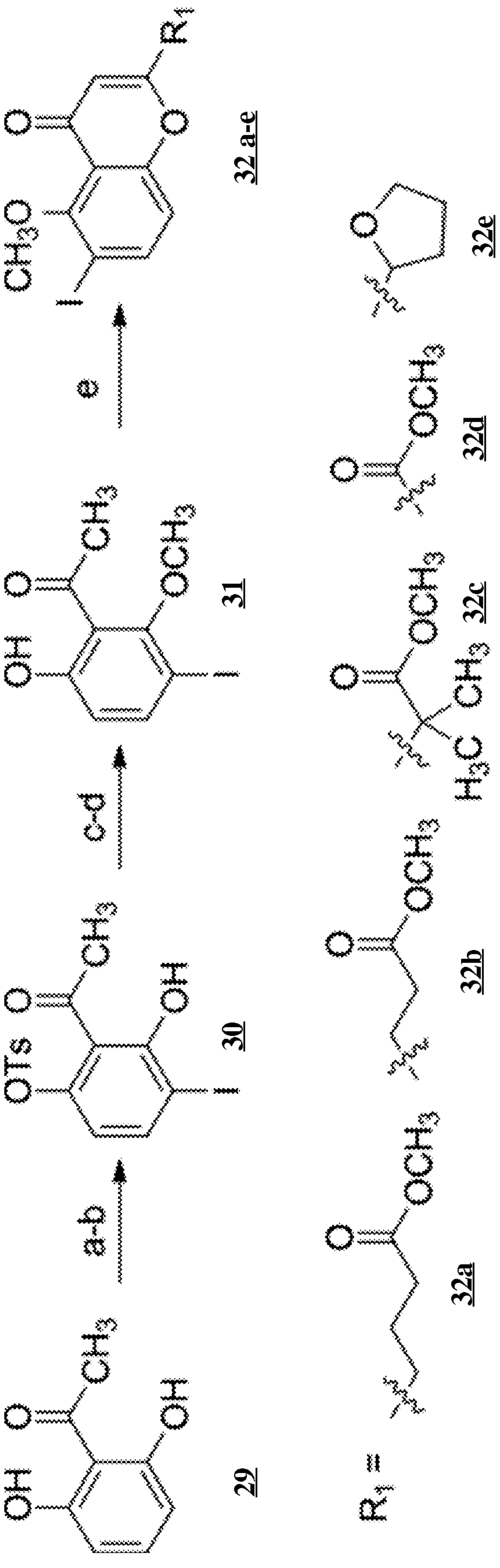

FIG. 15 is a schematic drawing showing a scheme for synthesis of monomers 32 a-e.

Figure 16:
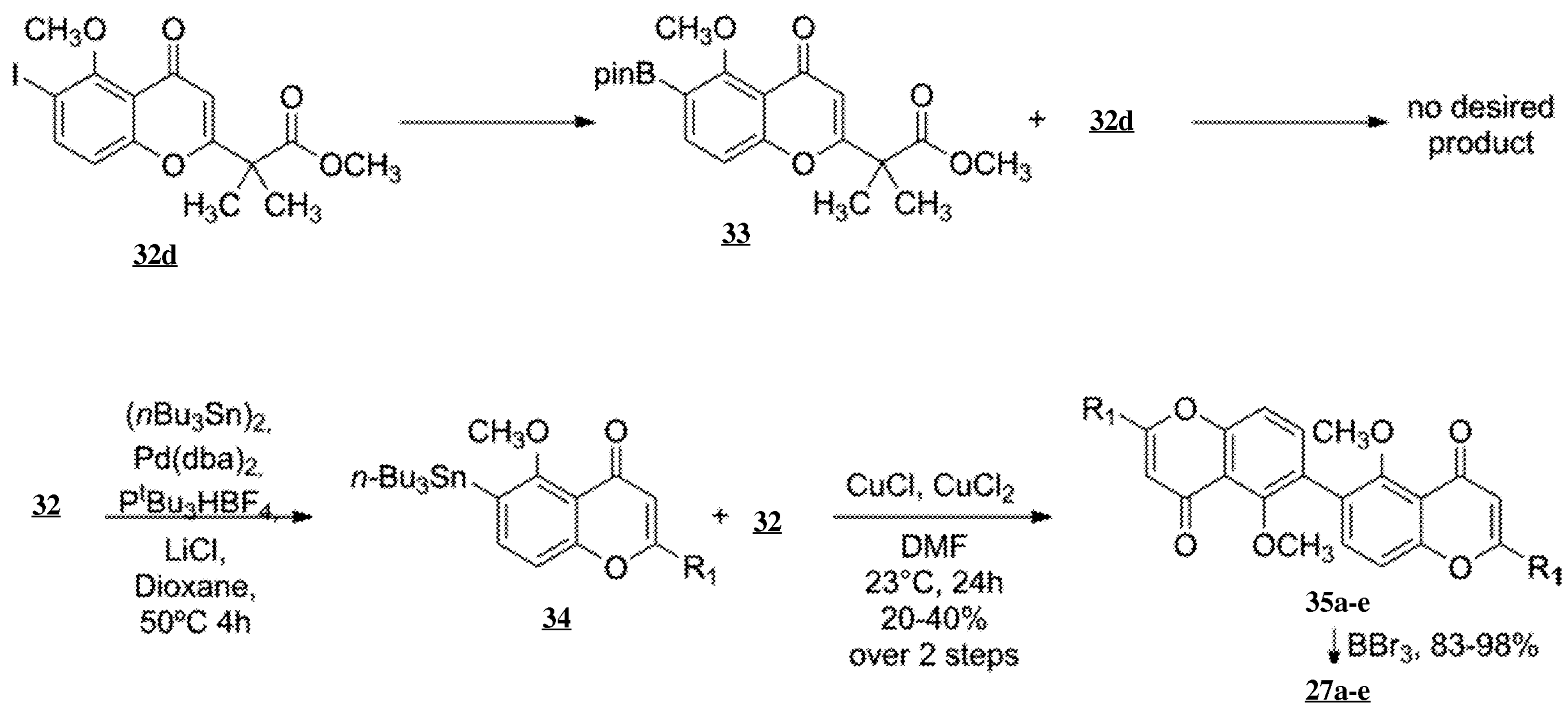

FIG. 16 is a schematic drawing showing dimerization of compound 32 to obtain 6,6'-linked chromenones using Suzuki-Miyaura cross coupling approach and Stille cross coupling approach.

Figure 17:
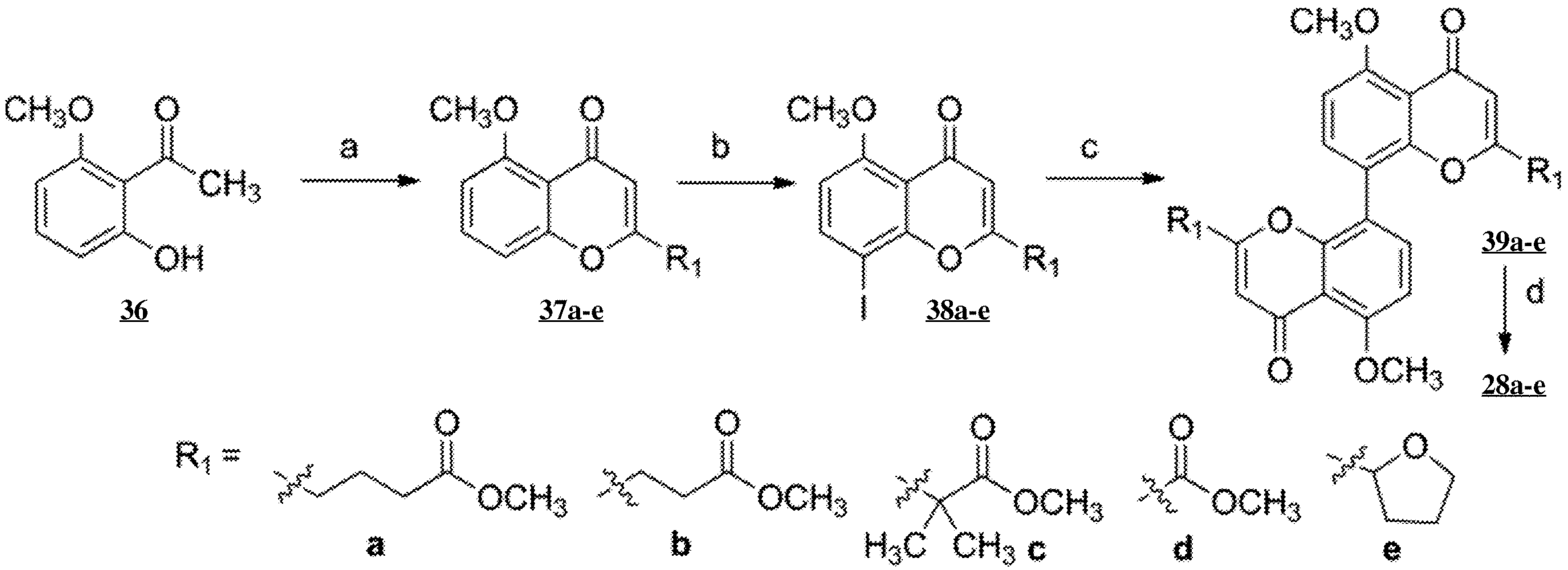

FIG. 17 is a schematic drawing showing dimerization of compound 28 to obtain 8,8'-linked chromenones.

Figure 18:
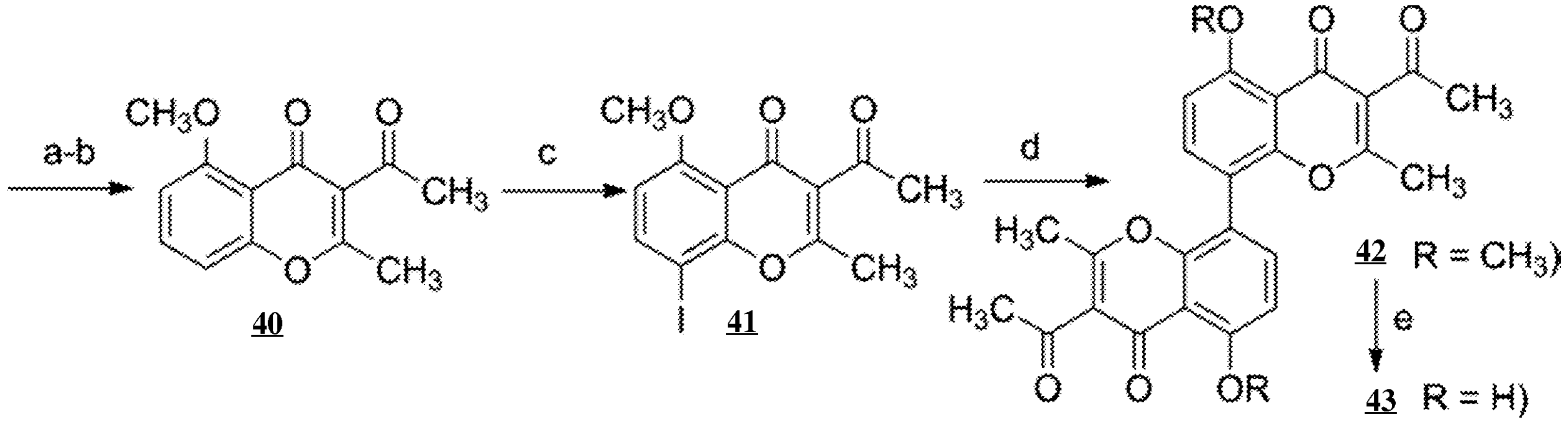

FIG. 18 is a schematic drawing showing synthesis reaction of 8,8'-linked dimers for compounds 42 and 43.

Figure 19:
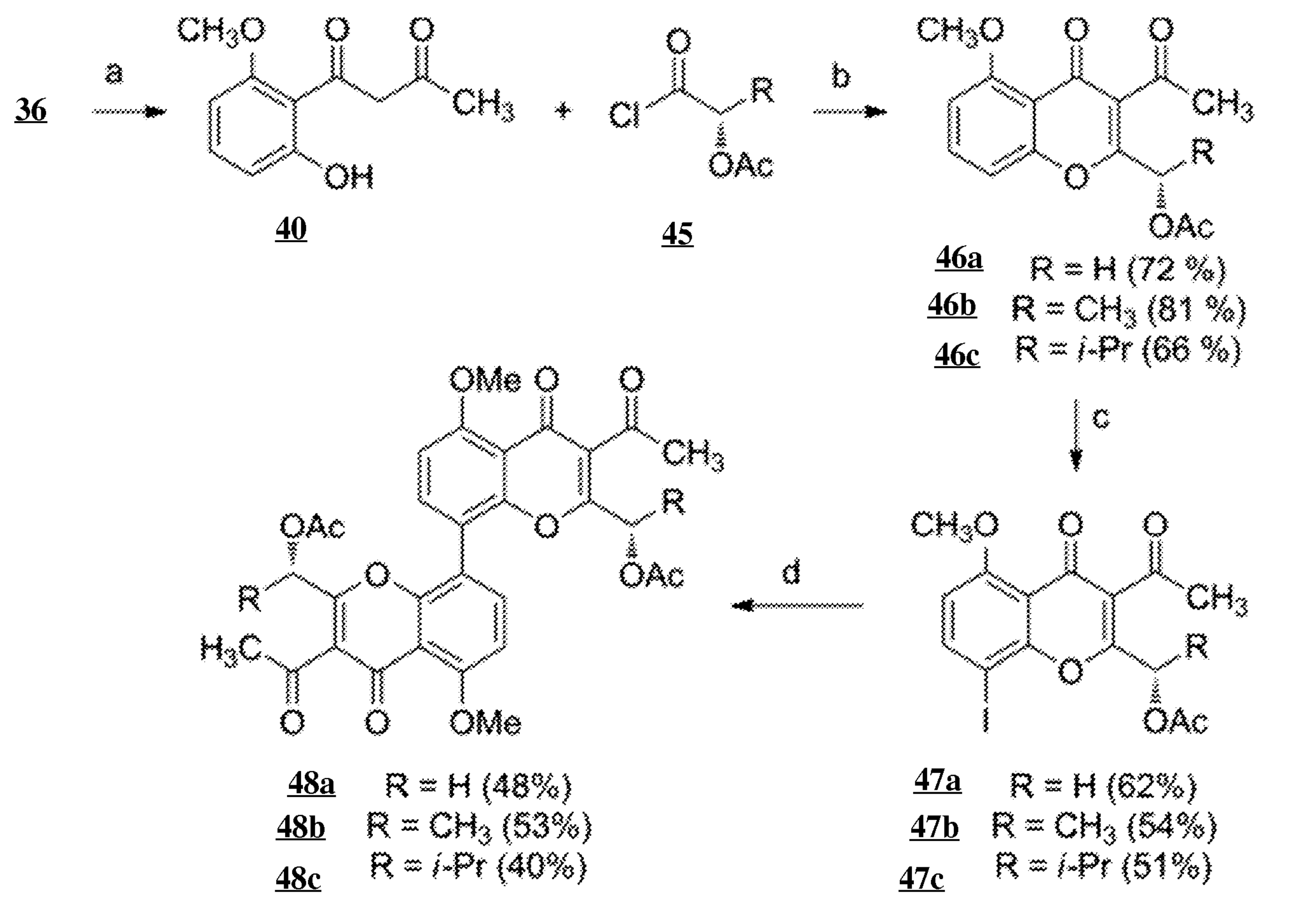

FIG. 19 is a schematic drawing showing synthesis reaction of 8,8'-linked dimers for compound 47a-47c.

FIG. 20A-FIG. 20B are a graph and schematic drawings showing $IC_{50}$ values of 6,6'-linked and 8,6'-linked dimeric chromenones in Jurkat cells for compounds 35, 27, 28 and 39.

Figure 21:
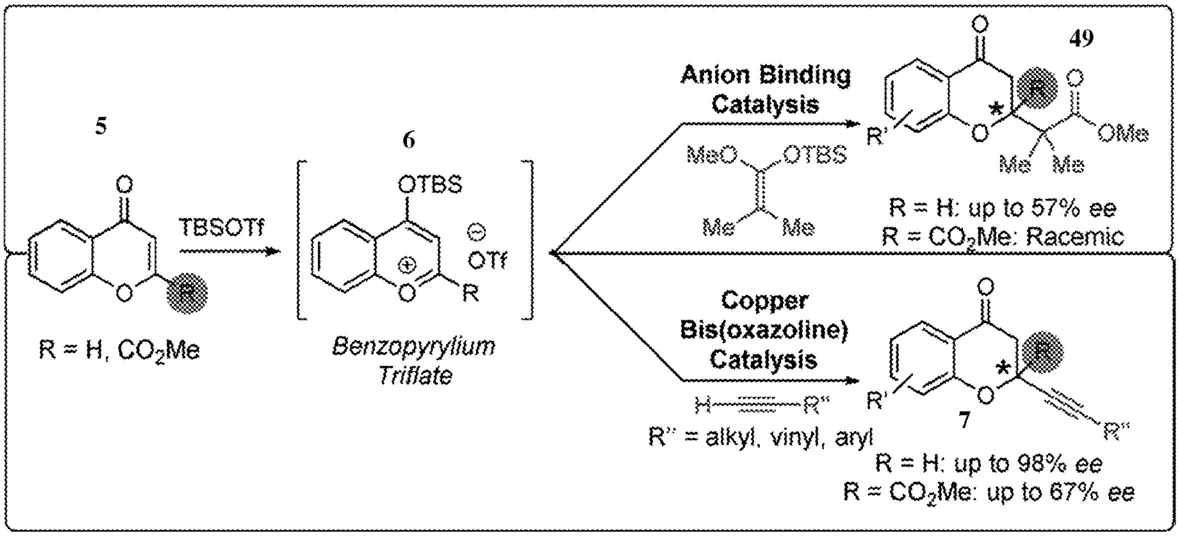

FIG. 21 is a schematic drawing showing scheme for synthesis of chromanones with a chiral tertiary ether stereocenter.

Figure 22:
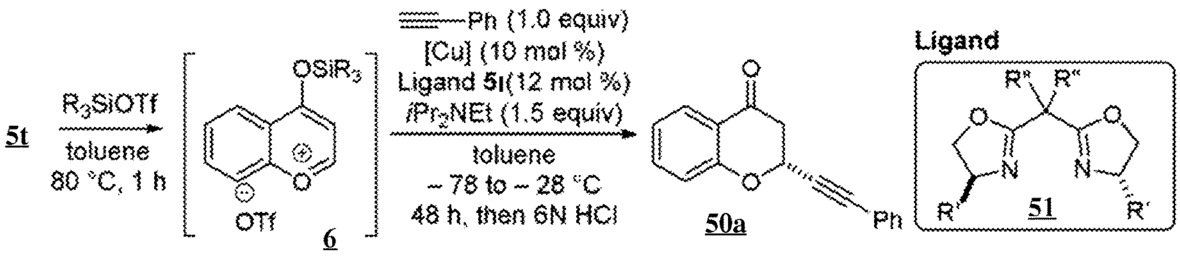

FIG. 22 is a schematic drawing showing a reaction of phenyl acetylene with benzopyrylium triflate in presence of copper source and ligand.

Figure 23:
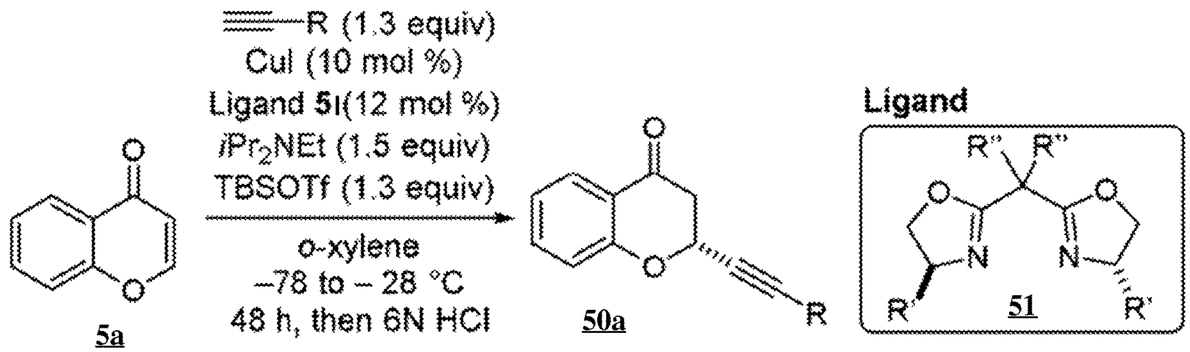

FIG. 23 is a schematic drawing showing alkyne substrate scope reaction in presence of copper source and ligand.

Figure 24:
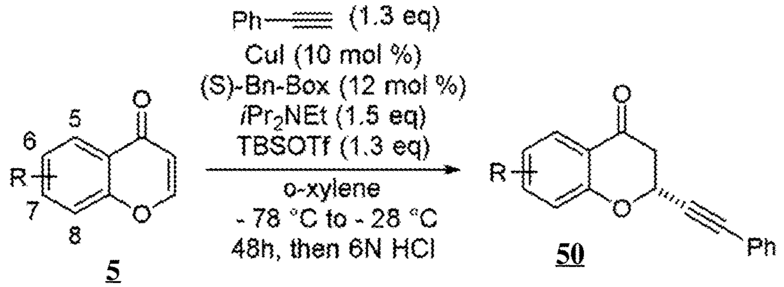
Figure 24:
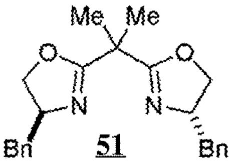
Figure 24:
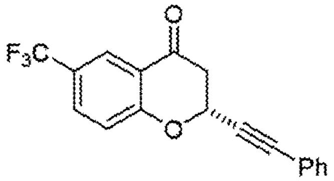
Figure 24:
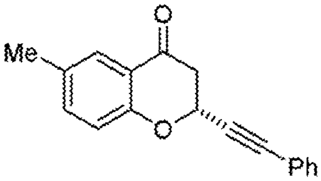
Figure 24:
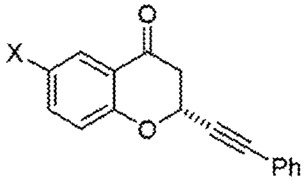
Figure 24:
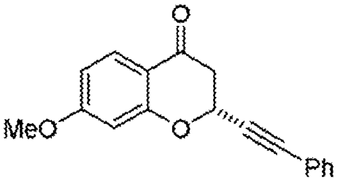
Figure 24:
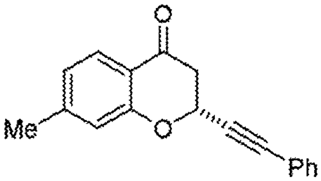
Figure 24:
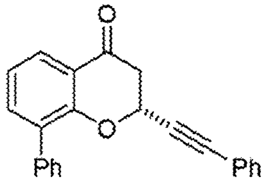
Figure 24:
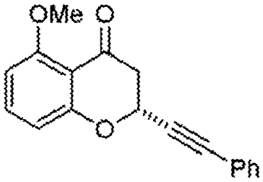
Figure 24:
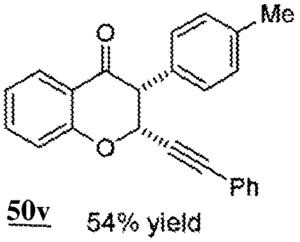

FIG. 24 is a schematic drawing showing chromonone substrate scope to obtain compound 51a and compound 50m-50v.

Figure 25:
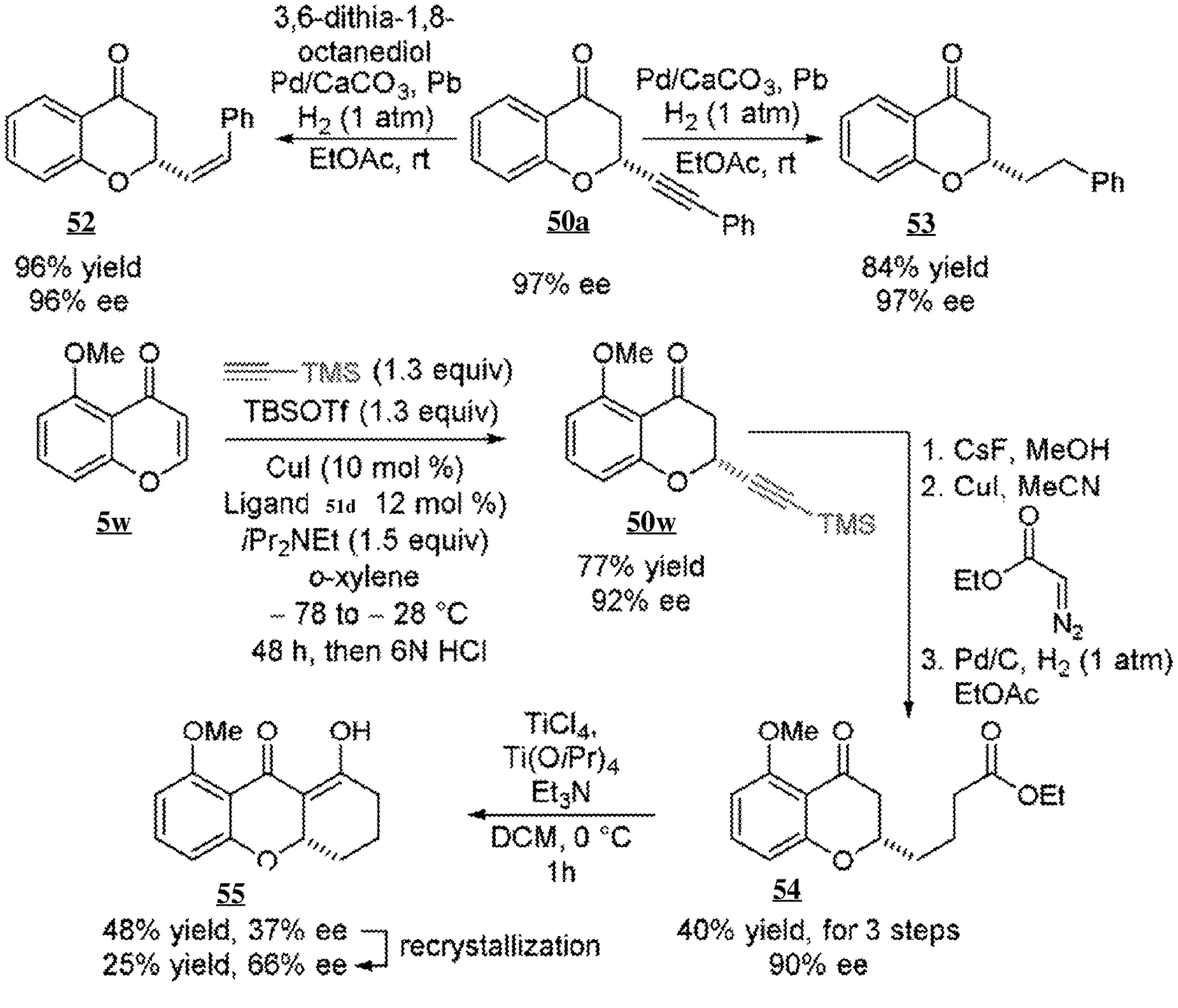

FIG. 25 is a schematic drawing showing a scheme for chromanone and tetrahydroxanthone synthesis.

Figure 26:
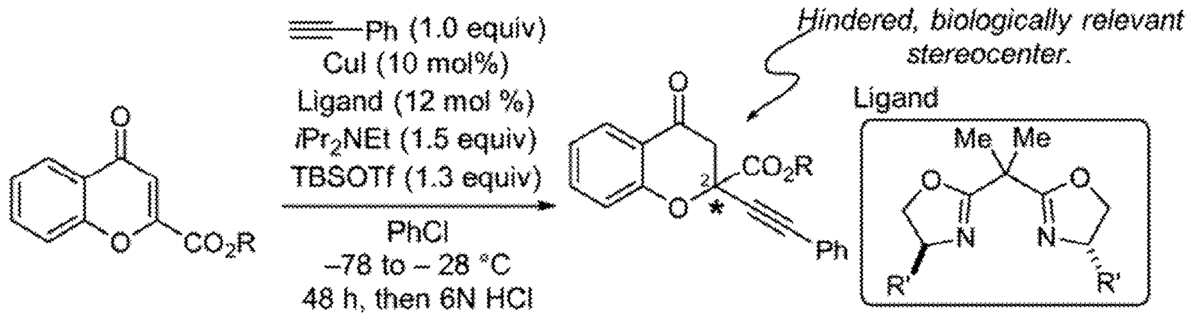

FIG. 26 is a schematic drawing showing tertiary ether stereocenter formation.

Figure 27:
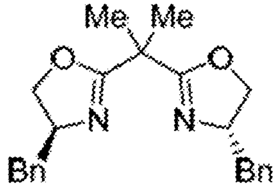
Figure 27:
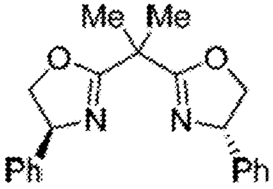
Figure 27:
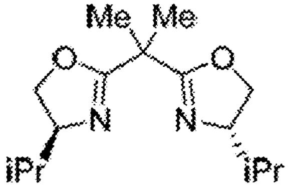
Figure 27:
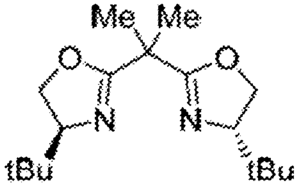
Figure 27:
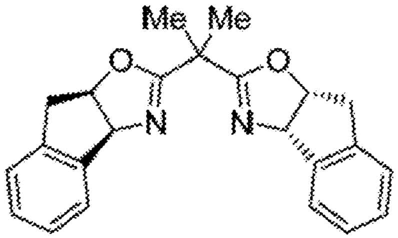
Figure 27:
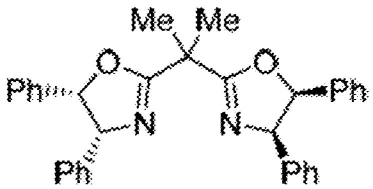
Figure 27:
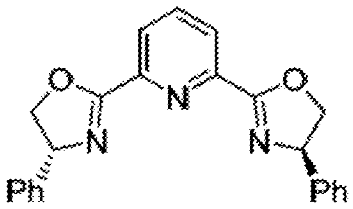
Figure 27:
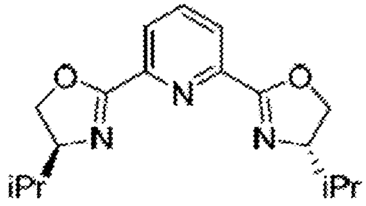
Figure 27:
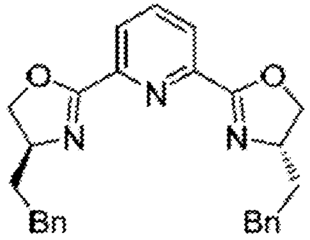
Figure 27:
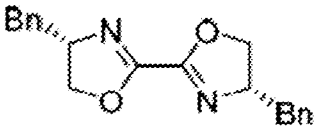

FIG. 27 is a schematic drawing showing structure formulas for ligands 51a-51j.

DETAILED DESCRIPTION

A series of methodologies to access the phomoxanthone A scaffold efficiently and reliably are identified. Phomoxanthone A was isolated in 2001 from the phomopsis fungus on a teak tree in northern Thailand. Phomoxanthone A is a secondary metabolite with a promising biological profile, including activity toward cisplatin resistant ovarian cancer. The methods described herein have resulted in the construction of a compound library of having more than 80 phomoxanthone A analogs. The library has resulted in understanding structure activity relationship and mechanism of phomoxanthone A analogs. The tetrahydroxanthone scaffold of phomoxanthone A is optimized to obtain an analog of phomoxanthone A and become targeted small molecule therapy for cisplatin resistant ovarian cancer. The examples herein show that a small molecule therapeutic phomoxanthone A operates as a mitochondrial toxin.

Phomoxanthone A targets the mitochondria and binds to 20-25 kD protein(s). Without being limited by any particular theory or mechanism of action it is here envisioned that phomoxanthone A sequesters within the cardiolipin head groups in the inner mitochondria membrane to destabilize the electrical and ionic gradients across the inner mitochondrial membrane and change the ability of this membrane to undergo fission and fusion. Further it is here envisioned that phomoxanthone A interacts with proteins housed in the inner mitochondrial membrane.

Select structure simplified analogs of phomoxanthone A have been identified to be cytotoxic toward cancer cells and operate by a similar mechanism of action to the naturally occurring molecule. The Applicants identify an active pharmacophore that exhibits less than single digit micromolar cytotoxicity in cancer cells and pharmacokinetic data that falls within the appropriate drug-like parameters.

Phomoxanthone A (Compound 1) is a naturally occurring dimeric tetrahydroxanthone with a desirable biological profile, including significant activity toward both cisplatin sensitive and -resistant cancer cells. The impressive biological properties of phomoxanthone A have spurred investigations into its possible mode of action. A 2018 study from Bohler and coworkers found that causes rapid disintegration of the inner mitochondrial membrane through a unique mode of action. Despite the recent studies, the full details of the biomolecular target(s) and mechanism of action of phomoxanthone A remain elusive. The limited understanding of the mechanisms of action of phomoxanthone A may be due, in part, to the synthetic challenge it poses. Phomoxanthone A has not yet been made by chemical synthesis. Originally isolated by Isaka and coworkers in 2001 from a strain of the phomopsis fungus that grew as an endophyte on teak trees in northern Thailand, phomoxanthone A possesses a synthetically demanding scaffold.

Figure 2:
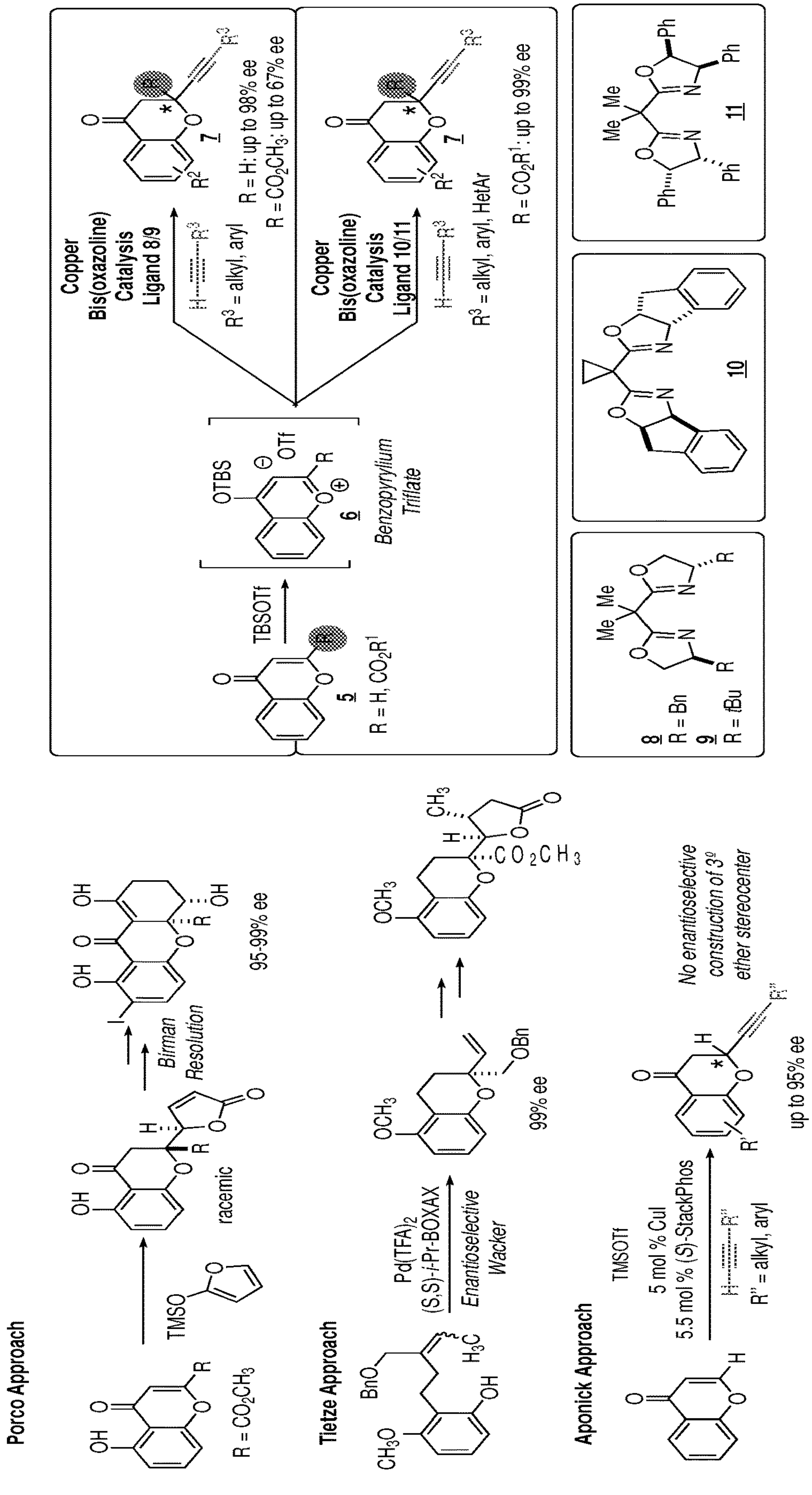
FIG. 2 is a schematic drawing of approach toward enantioselective construction of the 10a stereocenter of select chromanones and tetrahydroxanthones.

The 10a stereocenter is the most challenging aspect of Compound 1 (highlighted with circle in FIG. 1A). As a chiral tertiary ether, position 10a is a sterically encumbered center with limited options in the literature for enantiocontrolled construction. Further, 10a is a stereocenter that is sensitive to racemization under both overly acidic and basic reaction conditions. Although phomoxanthone A has not yet been synthesized, it belongs to a family of structurally related, secondary metabolites (FIG. 1B). Several of these species, such as rugulotrosin A and dicerandrol C, have attracted a synthetic following and routes have been established that enable their construction. The two most popular methods to construct the 10a stereocenter of the dimeric tetrahydroxanthones include (1) Porco's racemic siloxyfuran addition, followed by resolution, and (2) Tietze's intramolecular Wacker approach (FIG. 2). While both routes were brilliantly executed by the Porco and Tietze groups, they are limited to substrates only accommodated by the respective resolution and Wacker technologies required.

The examples described herein provide a method to establish the 10a stereocenter of naturally inspired, dimeric chromanones and tetrahydroxanthones that are efficient, easily executed, and robust to a broad substrate scope and applicable to library construction. Further, the methodology is used to synthesize a library of analogues of phomoxanthone A for structure-activity relationship studies and biomolecular target identification. The examples described herein provide methods for copper bis(oxazoline)-catalyzed alkynylation of substituted chromenones (compound 3), giving rise to chromanones (compound 2) in excellent (up to 99%) enantiomeric excess (FIG. 1A). The extensive substrate scope and transition-state models for this process are described herein.

As shown in FIG. 2, the enantioselective construction of the 10a tertiary ether stereocenter in 7 was based on alkyl and aryl copper acetylides under the influence of bis(oxazoline) ligation add to benzopyrylium triflates (R═H) with excellent levels of enantiocontrol (>90% ee, FIG. 2). The addition of copper acetylides to benzopyrylium triflates in the presence of StackPhos ligands is the Aponick approach shown in FIG. 2. The copper acetylide route was applied to the construction of the tertiary ether stereocenter in compound 7 (R═CO2CH3). The benzyl bis(oxazoline) ligand (compound 8) was applied toward the enantioselective construction of compound 7a. (FIG. 2, FIG. 3) However, given the steric demands of this center, a promising, albeit mediocre, enantiomeric excess of 34% was obtained (entry 1, Table 1). The reaction system required significant optimization mainly focused on the investigation of 30+bis(oxazoline) ligands to obtain excellent levels of enantiocontrol. The optimization of the alkynylation reaction conditions are listed in Table I.

TABLE I

Optimization of alkynylation reaction

| Entry | Ligand | Solvent | Temp (° C.) | Yield (%) | ee (%) |
|---|---|---|---|---|---|
| 1 | 8 | Toluene | 0 | 29 | 34 |
| 2 | 9 | Toluene | 0 | 87 | −38 |
| 3 | 9 | PhCl | 0 | 69 | −42 |
| 4 | 9 | PhCl | −78 to −28 | 87 | −66 |
| 5 | 9 | PhCl | −78 to −35 | 78 | −71 |
| 6 | 10 | PhCl | −78 to −28 | 71 | 88 |
| 7 | 10 | PhCl | −78 to −35 | 68 | 90 |

Some traction was gained in the improvement in yield and enantiomeric excess by switching from ligand 8 (FIG. 2) to t-butyl bis(oxazoline) ligand 9 (FIG. 2), giving rise to compound 7a in 87% yield and 38% ee (entry 2, Table I). Further optimization found that chlorobenzene improved the enantiomeric excess, especially when the reaction was conducted at low temperatures (entries 3-5, Table I). Specifically, a −71% ee of compound 7a was achieved when the reaction was conducted with ligand 9 at −78 to −35° C. (entry 5, Table I). Finally, excellent levels of enantiocontrol, with opposite stereochemistry relative to ligand 9, were achieved when the reaction was conducted with indanyl bis(oxazoline) ligand 10 (68% yield, 90% ee, entry 7, Table I).

The influence of the chromenone ester on enantiomeric excess was examined (FIG. 4). A wide range of esters were tolerated in the reaction. The methyl ester of compound 5 gave rise to compound 7a in 68% yield and 90% ee, and the ethyl ester afforded compound 7b in 53% yield and 89% ee (FIG. 4). The isopropyl and tert-butyl esters gave rise to compounds 7c and 7d in 91% ee and 71% ee, respectively, while the benzyl ester afforded compound 7e in 83% ee (FIG. 4). The trichloroethyl ester gave rise to compound 7f in 92% ee (FIG. 4). Although the trichloroethyl ester was slightly higher in terms of enantiomeric excess, methyl ester was used for screening as it is both higher yielding and easier to prepare than the trichloroethyl ester.

The influence of the alkyne on the yield and stereoselectivity of the reaction was observed (FIG. 4). A variety of substituted phenyl acetylenes were readily accepted as reaction partners in the process, giving rise to excellent levels of enantiocontrol in all cases. For example, methyl groups at the 4-, 3-, or 2-position on the phenyl ring gave rise to their respective products compounds 7g, 7h, and 7i in 90-92% ee. 4-Methoxyphenyl acetylene gave rise to compound 7j in 90% ee (FIG. 4). Halogen substituents performed equally well; for instance, 4-Cl and 4-Br phenyl acetylene afforded compounds 7k and 7l in 91% ee and 90% ee, respectively (FIG. 4). 4-Trifluoromethylphenyl acetylene generated compound 7m in nearly 90% ee (FIG. 4). Acetylenes containing 1-naphthyl and 2-naphthyl substituents were also well tolerated in the process.

Moving beyond phenyl acetylenes, the influence of terminal alkynes possessing heterocyclic and aliphatic substituents were studied in the reaction of chromenone 5 and alkyne 12 to yield compound 7 (FIG. 4). While the yields were reduced, thiophene and furan substituents on the alkyne were well tolerated and the corresponding product compounds 7q-7s were isolated in excellent enantiocontrol (91-93% ee). Cyclopropyl acetylene was well tolerated, giving rise to compound 7t in 61% yield and 89% ee. Cyclohexyl acetylene offered a decent performance, yielding compound 7u with 81% ee. tert-Butyl acetylene gave rise to compound 7v in 89% yield and 91% ee with ligand 11, while cyclohexenyl acetylene gave rise to compound 7w in 66% yield and 86% ee. The scope of the reaction was then investigated with respect to the chromenone 5 (FIG. 5). The reaction of the most biologically relevant 5-methoxy chromenone 5× with phenyl acetylene was observed to find that compound 7× was produced in 64% yield and 93% ee (FIG. 5). A methoxy group was also well tolerated in the 7-position to generate compound 7y in 75% yield and 99% ee (FIG. 5). Alkyl substituents were also accommodated; for instance, 7-methyl chromenone 5z afforded compound 7z in 67% yield and 82% ee (FIG. 5). Halogens were well tolerated as substituents at the 7- and 8-positions; specifically, compounds 7aa, 7ab, and 7ac were produced in 85, 95, and 93% ee, respectively (FIG. 5). A 7-trifluoromethyl substituent gave rise to compound 7ad in 95% ee. In fact, a wide array of substituents in the 7-position afforded the products with excellent levels of enantiocontrol. For example, allyl, phenyl, alkynyl, and alkenyl substituents gave rise to product compounds 7ae-7ah in 97-99% ee (FIG. 5). The cyclopropyl alkynyl group was also well tolerated in the 5- and 6-positions, affording 7ai and 7aj in 81 and 98% ee, respectively (FIG. 5).

Recrystallization is used to improve the enantiomeric excess of compound 7 if required. For example, after recrystallization, compound 7n was isolated in 99% ee and used for X-ray crystallographic analysis (vide infra). Using X-ray crystallographic analysis, evidence of the absolute configuration of the new stereocenter in compound 7n was observed to be R when the reaction was conducted with the indanyl ligand 10 (FIG. 6).

From this one example, the rest of the substrates were reasoned to also favor the R enantiomer as the major product by analogy. Without being by any particular theory or mechanism of action it is here envisioned that the possible reaction pathway is as shown in FIG. 7. The ligand coordinates to CuI, giving rise to complex 13 (FIG. 7). The reaction of complex 13 with the alkyne and Hunig's base generates the copper acetylide 14 (FIG. 7). The benzopyrylium ion 15, formed in situ upon exposure of compound 5 to TBSOTf, reacts with the copper acetylide in the enantiodetermining step to afford compound 16 (FIG. 7). The loss of the silyl group upon treatment with HCl then yields the final product compound 7 (FIG. 7). The enantiodetermining step was studied computationally with the B3LYP/6-31+G(d) (SDD for Cu)17 level of theory for the reaction phenyl acetylene with compound 5a under the influence of ligand 10. The transition states leading to the R enantiomer (the major enantiomer observed experimentally) and S enantiomer (the minor enantiomer observed experimentally) are shown in FIG. 8. The transition state leading to the observed major R enantiomer plausibly benefits from additional noncovalent interactions, such as π-stacking between the benzopyrylium ion and the indanyl side chain of the ligand (a length of 3.45 Å was found between the ligand H and the aromatic ring). The existence of additional noncovalent interactions in the R transition versus the S transition state was confirmed in a noncovalent interaction plot analysis of the two transition states (FIG. 8). The computationally predicted enantiomeric excess of 92% ee is similar to the experimentally observed 90% ee for compound 7a. The transition states for the formation of compound 7y were also determined using the same level and theory, and the calculated enantiomeric excess (85% ee) matched reasonably well with the experimentally determined value of 99% ee, although there appear to be some electronic effects caused by the —OCH3 substituent which are not fully accounted in the computational model, thus causing a mild difference in experimental vs computational enantiomeric excess.

It was observed that tert-butyl bis(oxazoline) ligand 9 affords the product compound 7a with opposite enantioselectivity when compared to the outcome of the alkynylation reaction with ligand 10 (see Table I). To better understand the reason behind the switch in facial selectivity between the two ligands, the DFT transition states were calculated for the alkynylation reaction of compound 5a to generate compound 7a under the influence of compound 9 (FIG. 9). A study of the transition state structures shows that the benzopyrylium ion is farther away from the ligand backbone (the closest distance found was 3.91 Å in the transition state, leading to the S enantiomer) with fewer noncovalent interactions present than what is observed with ligand 10. A steric component is supposedly driving the observed outcome of the alkynylation of compound 5a in the presence of ligand 9. Specifically, in the calculated transition state of the major enantiomer, the tert-butyldimethylsilyl group is oriented away from the tert-butyl side chain on the ligand, ultimately generating a transition state leading to S-7a (FIG. 9). Therefore, while ligand 9 may rely at least partially on steric hindrance for enantiocontrol, ligand 10 appears to involve a network of supportive noncovalent interactions between the ligand and benzopyrylium ion to control the facial selectivity of the alkyne addition reaction.

Due to the variability in enantiomeric excess observed in the alkynylation of different chromenone esters (compounds 7a-f, FIG. 4), it was assumed that the size of the ester substituent influences the stereochemical outcome of the reactions. The correlation of the steric parameters to the log of the enantiomeric ratio is possible and lends insights into the plausible role of steric bulk on reaction stereoselectivity. The Charton values of several esters explored in the reaction were plotted against their respective log(er) (FIG. 10) and demonstrated a linear correlation between the Charton value of the ester and the enantioselectivity of the alkynylation reaction. Specifically, smaller ester substituents (e.g., methyl and ethyl) led to higher enantiomeric ratios.

This synthetic tactic was applied toward the construction of biologically relevant compounds to probe manipulations that would be tolerated by the newly prepared, enantioenriched chromanone core (FIG. 11). The reduction of the alkyne was achieved upon treatment of compound 7a with Pd/C and H2 to give rise to compound 17 in an unoptimized 65% yield and 90% ee (FIG. 11). The Schmidt rearrangement of compound 17 was accomplished under the influence of NaN3 and H2SO4, producing compound 18, a desirable 1,2-amino alcohol precursor, in 80% yield and 90% ee (FIG. 11). The reduction of both the ketone and alkyne functional groups of compound 7a is achieved upon long exposure to Pd/C and H2. Under these conditions, chroman compound 19 was isolated in 81% yield and 90% ee from compound 7a. The ester is then converted to the methyl group, giving rise to motifs found in naturally occurring molecules such as vitamin E. Chromane compound 20 was isolated in 77% yield and 90% ee over two steps from compound 19 (FIG. 11). A highly enantioselective route to sterically hindered and biologically relevant tertiary ether stereocenters has been developed. The methodology benefits from a broad substrate scope and employs readily available indanyl bis (oxazoline) ligands to control the stereoselective addition of copper acetylides to benzopyrylium triflates. The transition state leading to the major enantiomer benefits from additional noncovalent interactions, such as π-stacking interactions between the ligand and the benzopyrylium ion.

The examples herein describe synthesis of a focused family of naturally inspired dimeric chromenones for study in cancer therapy. Further, the examples describe generalizable methods to prepare structure simplified compounds that resemble various bioactive chromenone and xanthone natural products, including both 8,8'-dimers, and 6,6'-dimers, (FIG. 12) and the results of their in vitro phenotypic screen in six cancer cell lines. The dimeric chromenones and xanthones can carry more potent bioactive activity than their monomeric counterparts. Therefore, 7-lactone chromenones and the tetrahydroxanthones are biosynthetically related (FIG. 13). Specifically, the carbonyl carbon of the enolized C ring of the tetrahydroxanthone serves as an electrophilic site for an intramolecular cyclization of the alcohol, resulting in the release from the B ring to form 7-lactone chromanone 22. The formation of ring opened variants, such as versixanthone F and bipolarinone, result from methanolysis during isolation. Notably, the ring-opened lactone form possesses more potent cytotoxicity than the corresponding ring closed forms.

The design of structurally simplified naturally inspired chromanone library focused on the following features: (1) retention of the biaryl bond, (2) inclusion of both 6,6'-linked and 8,8'-linked dimeric chromenone cores, (3) removal of the C-ring, (4) removal of the stereogenic centers, and (5) introduction of a focused selection of aryl and aliphatic groups at carbons 2 and 3 (FIG. 13).

While a significant amount of information is available in the literature about chromenone synthesis, in both 6,6'-linked, and 8,8'-linked dimers, most of these methods are very substrate specific and not generalizable to include a variety of functional groups. Therefore, the synthetic efforts toward both the 6,6'- and 8,8'-linked dimers focused on the development of a general approach to quickly prepare a library of the desired category of compounds that possess the structural features identified to be probed.

The synthesis of a family of 6,6'-linked dimeric chromenones begins with the construction of monomeric chromenones 32a-e (FIG. 15). After several failed attempts to directly introduce the iodo substituent ortho to the methoxy group on the chromenone, the introduction of the iodo substituent prior to chromenone formation was pursued and the following series of steps proved to be reliable in accessing compound 32. The mono-tosylation of commercially available 2'6'-dihydroxyacetophenone (compound 29) was achieved with careful stoichiometric control of the addition of tosyl chloride (TsCl) and diisopropylethylamine. The regioselective iodination of the resultant tosylate was carried out with N-iodosuccinimide (NIS) and trifluoroacetic acid (TFA) to give rise to compound 30 in good yield. Under the influence of iodomethane and K2CO3 methylation of the hydroxy group occurred. A subsequent detosylation was effected by addition of 20% aq. NaOH in tert-butanol, resulting in the formation of common intermediate compound 31. The 2-substituted chromenones 32a-e were prepared by first treating compound 31 with the desired diesters with NaH and then following with an acid mediated cyclization.

With the family of iodochromenones 32a-e prepared, efforts were directed toward dimer formation via transition metal catalyzed cross coupling. Initial studies focused on effecting the desired biaryl bonding forming event under the influence of Suzuki-Miyaura reaction conditions (FIG. 16). Unfortunately, all attempted Suzuki-type couplings were unsuccessful. Neither borylation to prepare compound 33 nor dimerization to prepare compound 35 led to the formation of desired product. Frequently, dehalogenation of compound 32 was observed under the Suzuki reaction conditions. A Stille cross coupling approach, depicted in FIG. 16, proved general and enabled the synthesis of dimeric chromenones compounds 35a-e. The deprotection of 35 was easily affected in high yield in the presence of BBr3. The members of the 8,8'-linked library of dimeric chromenones were accessible in four steps from commercially available acetophenone derivative compound 36 (FIG. 17). The sequence begins with the cyclization of compound 36 and appropriate diester reaction partners for the generalized syntheses of 2-substituted chromenones 37a-e. Chromenones 37 were often acid sensitive and susceptible to bisiodinations under many standard literature iodination conditions (e.g., NIS, TFA). As a result, a novel method was developed for the efficient and regioselective iodination of compound 37 using [bis(trifluoroacetoxy)iodo]benzene and 12. The resultant iodochromenones compound 38 were dimerized, typically giving rise to compound 39 in good yield, when subjected to Suzuki-Miyaura coupling conditions. The subsequent demethylation of compound 39 was achieved under the influence of BBr3, generating the desired dimers compound 28a-e.

To better mimic naturally occurring dimeric chromenones and tetrahydroxanthones, for example phomoxanthone A, the synthesis of 8,8'-linked dimeric chromenone analogs with hydrogen bond acceptor groups in the 2- and 3-positions was pursued (FIG. 18 and FIG. 19). The chromenone dimer compound 43, containing an acetate in the 3-position, was prepared beginning with a Claisen condensation of acetophenone derivative compound 36 with ethyl acetate followed by the treatment of the resulting diketone with acetic anhydride. The monomeric chromenone 40 was then subjected to p-iodination using NIS in dichloromethane to give rise to iodochromenone 41. The coupling of compound 41 under Suzuki-Miyaura reaction conditions afforded compound 42 in 59% yield. The demethylation of compound 42 went smoothly under standard reaction conditions, BBr3. The synthesis of compounds 48a-c, analogs containing substitution in the 2-position of the chromenone core that has a matching stereochemistry and oxidation state of many naturally occurring tetrahydroxanthones, such as phomoxanthone A, was carried out (FIG. 19). Attempts to directly oxidize the allylic methyl group in compound 40 were unsuccessful. Taken inspiration from the synthesis of compound 43, the diketone compound 44 was then reacted with appropriately substituted acid halides compound 45 to generate the desired chiral substituted chromenones 46a-c. This is a novel method developed to introduce chirality to these chromenones at this center.

Chromenones 46 were then regioselectively iodinated under the influence of [bis(trifluoroacetoxy)-iodo]benzene and 12 giving rise to compounds 47a-c. Upon treatment with palladium acetate, bis(pinacolato)diboron, and an appropriate phosphine ligand, the dimerization of compound 47a-c was achieved to afford desired chromenones 48a-c. The dimethoxy dimers 48, unfortunately, could not be demethylated under common literature conditions due to the decomposition of the materials.

With a small series of 6,6'-linked and 8,8'-linked dimeric chromenones in hand, cytotoxicity screening was conducted in Jurkat cell lines. The goal of this screening was to establish: (1) whether such simple dimeric chromenones would possess any cytotoxicity, (2) if there was a difference in biological activity of the 6,6'-linked compared to the 8,8'-linked, (3) if the substituent in the 2-position influenced biological activity, and (4) if the phenol group affected cytotoxicity. The results of the screening are depicted in FIG. 20 and include the following observations. Select simple dimeric chromenones exhibit moderate cytotoxicity in Jurkat cell lines (15e=20 μM). When all the data is considered together, the 8,8'-linked dimers tend to be more cytotoxic than the 6,6'-linked dimers. The substituent in the 2-position had a rather dramatic effect on cytotoxicity.

Specifically, compounds containing the methyl isobutyrate (35c, 39c, 28c) and tetrahydrofuran (35e and 28e) substituents gave rise to the highest levels of cytotoxicity in this screen. The most cytotoxic of the simple dimeric chromenones (27c, 28c, 28e, 35e, 39c) and the more functionalized chromenones (42, 43, 48a-c) were subject to further anticancer screening in six cell lines (Jurkat, L5178Y, HL60, KB, MCF7, and SKOV3 cells, Table II). Select simplified chromenone dimers possessed moderate cytotoxicities. The most active compounds in our series were methyl isobutyrate-derived dimeric chromenones 28c and 39c. Both 28c and 39c showed activity toward L5178Y and HL60 cells in the low micromolar range. 39c had an $IC_{50}$=14 μM against L5178Y cell lines and $IC_{50}$=24 μM against HL60 cells.

Compound 28c was active against HL60 and L5178Y cells with $IC_{50}$=15 μM and 23 μM, respectively. The dimeric chromenones described in this work were not significantly active ($IC_{50}$>50 μM) toward MCF7 and SKOV3 cell lines. A focused library of structure simplified dimeric chromenones, inspired by naturally occurring dimeric chromanones and tetrahydroxanthones, has been synthesized and studied in several cancer cell lines. The sequences used to synthesize the library are robust and generalizable to accommodate a wide range of substrates so as to permit the generation of a library of dimeric chromenone derivatives for study. The synthetic effort in the library development required invention of two new methodologies: (i) the regioselective p-iodination of sensitive substrates under neutral conditions and (ii) a novel approach for the introduction of a chiral center to generate naturally inspired dimeric chromenones.

TABLE II

Chromenone cytotoxicity studies ($IC_{50}$ in μM)

| Compound | Jurkat | L5178Y | HL60 | KB |
|---|---|---|---|---|
| Phomoxanthone A | 0.5 | 0.3 | — | 0.99 |
| Phomoxanthone B | Not available | Not available | Not available | 4.1 |
| Dicerandrol C | Not available | 10 | Not available | Na |
| Versixanthone F | Not available | Not available | 1.00 | Na |
| 35c | 39 ± 1.1 | 39 ± 1.1 | 39 ± 1.1 | 41 ± 1.1 |
| 28c | 39 ± 1.1 | 39 ± 1.1 | 39 ± 1.1 | >50 |
| 28e | 39 ± 1.1 | >50 | >50 | >50 |
| 39c | 39 ± 1.1 | 39 ± 1.1 | 39 ± 1.1 | Not determined |
| 35e | 39 ± 1.1 | 39 ± 1.1 | >50 | >50 |
| 42 | >50 | >50 | 39 ± 1.1 | >50 |
| 43 | 39 ± 1.1 | >50 | >50 | >50 |
| 48c | >50 | 39 ± 1.1 | >50 | >50 |

The results of the anticancer testing demonstrate that select members of the library give rise to favorable levels of biological activity. Specifically, the 8,8'-linked dimeric chromenones 28c and 39c containing methyl butyrate substituents are cytotoxic toward both L5178Y and HL60 cells, with $IC_{50}$ values in the low micromolar range.

The examples also describe an alternative method to creating the chiral tertiary ether stereocenter by copper bis(oxazoline) catalysis for the reaction of terminal alkynes and unhindered benzopyrylium triflates (R═H) to generate desirable products with excellent levels of enantiocontrol. This method represents a more practical approach because it requires readily accessible bis(oxazoline) ligands. Furthermore, copper bis(oxazoline) catalysis provides promising levels of enantiocontrol in the addition of terminal acetylides to substituted benzopyrylium triflates (R=esters) to create chromanones with highly substituted 2-stereocenters (FIG. 21).

TABLE III

Optimization

| Entry | Copper source | Ligand R'', R' | Silyl triflate | Yield % | ee % |
|---|---|---|---|---|---|
| 1 | $Cu(OTf)_2$ | Me, Bn (51a) | TBSOTf | 44 | 14 |
| 2 | CuOTf | Me, Bn (51a) | TBSOTf | 40 | 16 |
| 3 | CuBr | Me, Bn (51a) | TBSOTf | 41 | 14 |
| 4 | CuI | Me, Bn (51a) | TBSOTf | 69 | 95 |
| 5 | CuI | Me, Ph (51b) | TBSOTf | 85 | 86 |
| 6 | CuI | Me, iPr (51c) | TBSOTf | 64 | 93 |
| 7 | CuI | Me, tBu(51d) | TBSOTf | 92 | 70 |
| 8 | CuI | Me, Bn (51a) | TBSOTf | 68 | 94 |
| 9 | CuI | Me, Bn (51a) | TBSOTf | 87 | 91 |
| 10 | CuI | Me, Bn (51a) | TBSOTf | 72 | 97 |

TABLE III-continued

| Optimization | | | | | |
|---|---|---|---|---|---|
| Entry | Copper source | Ligand R'', R' | Silyl triflate | Yield % | ee % |
| 11 | CuI | Me, Bn (51a) | TBSOTf | 73 | 94 |
| 12 | CuI | Me, Bn (51a) | TBSOTf | 76 | 84 |

Phenyl acetylene was added to benzopyrylium triflate compound 6, generated in situ from 5, in the presence of a suitable copper source and ligand (FIG. 22, Table III). During a systematic investigation of the reaction parameters it was observed that the nature of the copper source, bis (oxazoline) ligand, and silyl triflate significantly affected the outcome of the reaction with respect to both yield and enantioselectivity. Cu(OTf)2, CuOTf, and CuBr gave rise to compound 50 with yields between 40-44% and low enantiomeric excess (Table III, entries 1-3). CuI was identified as the best reagent for this process, producing 50a with 69% yield and 95% enantiomeric excess (entry 4). The screening of several bis(oxazoline) ligands demonstrated the enantiomeric excess and yield were readily influenced by the structure of the ligand. The highest enantiomeric excess was realized with ligand 5a (R'=Bn, 95% ee, entry 4). Lower enantiomeric excesses were observed with ligands 51b, 51c, and 51d (R'=Ph, iPr, tBu, respectively) but the yields were higher in some cases (entries 4-7). Finally, the silyl triflate employed in the reaction had a small influence on the yield and stereocontrol. Specifically, tert-butyldimethylsilyl triflate (TBSOTf) gave rise to the best enantiomeric excess when compared to trimethylsilyl triflate (TMSOTf) and triispropylsilyl triflate (TIPSOTf) (entries 4, 8-9).

The yield of the reaction was improved from 69 to 72% by conducting the reaction in a single flask, the enantiomeric excess remained excellent at 97% (Table III, entry 10). The reduction of the catalyst loading from 10 to 5 mol % and 1 mol % resulted in small losses in enantiomeric excess (entries 11-12). After having identified a promising set of reaction conditions for the enantioselective alkynylation of chromenone 5, the scope of the reaction with respect to chromenone and alkyne was tested. First, the substituents on the alkyne were probed (FIG. 24, Table IV). A variety of aryl acetylides were found to operate well in the reaction regardless of their substitution pattern. For instance, nearly identical enantiomeric excesses were observed for phenyl acetylene, p-methoxy phenyl acetylene, p-trifluoromethyl phenyl acetylene, p-methyl phenyl acetylene, p-chloro phenyl aceytene, and m-methyl phenyl acetylene (Table IV, entries 1-6). The sterically encumbered o-methyl phenyl acetylene gave rise to product 4g in 67% yield and 82% enantiomeric excess (entry 7).

Alkynes containing non-aryl substituents (R=TMS, alkyl, vinyl) were also accommodated in the reaction (entries 8-12), although optimal yields and stereocontrol was achieved with different bis(oxazoline) ligands (entries 8-10). For example, trimethylsilyl acetylene, a reaction partner of interest in the context of tetrahydroxanthone synthesis, afforded product 50h in 86% yield and 95% enantiomeric excess under the influence of bis(oxazoline) 51d (entry 8). Synthetically relevant chromanone products 50i and 50j were also produced in high yield and high enantiomeric excess in the presence of ligands 51e and 51f, respectively (entries 9 and 10). Chromones with substituents on the 5-, 6-, 7-, and 8-positions were generally well tolerated, yielding corresponding 2-(phenylethynyl)chromanones in high enantiomeric excess. (FIG. 24). Chromenones with a variety of substituents in the 6-position (e.g., R=CF3, CH3, F, Cl, Br) performed well in the reaction giving rise to products 50m-q in excellent yield and enantiomeric excess. Donating substituents in the 7-position enabled formation of the desired products 50r-s with excellent enantiomeric excess but with reduced yield. 8-Phenyl chromenone (5t), was also a competent reaction partner affording 50t with 93% yield and 84% enantiomeric excess. The naturally-inspired substitution pattern on chromenone 5u was also easily incorporated into the reaction platform generating product 50u in 75% yield and with 93% ee. Moderate enantiomeric excess was obtained in the case of 3-(p-tolyl) chromone 5v, which yielded 50v as a 2:1 mixture of diastereomers in 63% ee.

TABLE IV

| Alkyne substrate scope | | | | |
|---|---|---|---|---|
| Entry | Alkyne R= | 50 | Yield % | ee % |
| 1 | Ph | 50a | 98 | 97 |
| 2 | p-MeOPh | 50b | 63 | 96 |
| 3 | p-$F_3$Ph | 50c | 82 | 97 |
| 4 | p-tolyl | 50d | 83 | 96 |
| 5 | p-ClPh | 50e | 86 | 97 |
| 6 | m-tolyl | 50f | 82 | 97 |
| 7 | o-tolyl | 50g | 67 | 82 |
| 8 | TMS | 50h | 86 | 95 |
| 9 | $CH_2OBn$ | 50i | 85 | 85 |
| 10 | $CH_2CH_2OBn$ | 50j | 96 | 85 |
| 11 | cyclopropyl | 50k | 45 | 82 |
| 12 | 1-cyclohexenyl | 50l | 50 | 71 |

The relevance of the methodology to natural product construction was tested in the synthesis of chromanones 52-53 and tetrahydroxanthone 55 (FIG. 25). The partial hydrogenation of the alkyne in chromanone 50a was easily achieved with a Pd/CaCO3, Pb catalyst system, 3,6-dithia-1,8-octanediol, and H2 to afford chromanone 52 in excellent yield with no loss in enantiomeric excess (FIG. 25). Under the influence of Pd/CaCO3, Pb, and H2, the synthesis of 53 was affected in 84% yield with no loss in enantiomeric excess. The application of the methodology to the synthesis of tetrahydroxanthones is depicted in FIG. 25. Chromanone 50w is prepared in 77% yield and excellent enantiomeric excess (92% ee) under the influence of CuI and ligand S1d. Silyl group deprotection in the presence of cesium fluoride (CsF), insertion of ethyldiazoacetate into the terminal alkyne C@H bond, and hydrogenation of the intermediate allene gives rise to 54 in 40% yield and 90% ee over three steps. Tetrahydroxanthone formation is achieved by a Lewis acid promoted intramolecular Dieckmann cyclization to yield 55. The final cyclization step does erode the enantiomeric excess slightly and investigations are ongoing to overcome this issue.

TABLE V

| Tertiary ether stereocenter formation | | | | | |
|---|---|---|---|---|---|
| Entry | Ligand R' | R= | T° C. | Yield % | ee % |
| 1 | Bn (51a) | Me | 0 | 29 | 34 |
| 2 | Ph (51b) | Me | 0 | 86 | 15 |
| 3 | tBu (51d) | Me | 0 | 87 | −38 |
| 4 | tBu (51d) | Me | −78 to −28 | 87 | −67 |
| 5 | tBu (51d) | Et | −78 to −28 | 91 | −35 |
| 6 | tBu (51d) | iPr | −78 to −28 | 88 | −54 |
| 7 | tBu (51d) | tBu | −78 to −28 | 15 | −60 |

The high levels of enantiocontrol and extensive substrate scope observed in the synthesis of 2-H chromanones 50a-w resulting in stressing the limits of the reaction system in the synthesis of more highly substituted stereogenic centers. Specifically, it is here envisioned that chromenones containing esters in the 2-position would render the methodology even more valuable in the context of naturally occurring tetrahydroxanthone synthesis by enabling the enantioselective construction of tertiary ether stereocenters. The reaction was put to the test with the addition of phenyl acetylene to chromone-2-carboxylate esters (Table V). An initial enantiomeric excess of 34% was observed with the bis(oxazoline) ligand 51a containing a benzyl group (R=Bn, Table V, entry 1). A quick screen of other readily available bis (oxazoline) ligands resulted in the identification of tBu as the best substituent identified to date with respect to both the yield and enantiomeric excess (entry 3). Upon cooling the reaction from 0 to −28° C. a very encouraging 67% enantiomeric excess was observed (entry 4). Ethyl, iso-propyl, and tert-butyl chromone-2-carboxylate esters were also tolerated but with reduced enantiomeric excess (entries 5-7).

Therefore, copper bis(oxazoline) complexes have proven to be easy to use, general catalyst systems for the synthesis of 2-stereogenic centers found in biologically relevant chromanones. Excellent levels of enantiocontrol can be achieved in the reaction of a diverse array of chromenone and alkyne reaction partners, generating desirable 2-ethynyl chromanone products in high yield. The reaction system can also be extended to the synthesis of more highly substituted 2-stereogenic centers that may have direct applications in naturally occurring bioactive chromanone and tetrahydroxanthone synthesis.

The following examples and claims are illustrative only and not intended to be further limiting. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference.

A portion of the embodiments herein were published in *ACS Catal.* 2021, 11, 10, 6325-6333 as “Robust, Enantioselective Construction of Challenging, Biologically Relevant Tertiary Ether Stereocenters” by co-authors Yong Guan, Tadas A. Buivydas, Remy F. Lalisse, Jonathan W. Attard, Rameez Ali, Charlotte Stem, Christopher M. Hadad, and Anita E. Mattson, which is hereby incorporated herein in its entirety. Another portion of the embodiments described herein were published in *Eur. J. Org. Chem.* 2019, 6917-6929 as “Synthesis and Anticancer Activity of Structure Simplified Naturally Inspired Dimeric Chromenone Derivatives” by co-authors Rameez Ali, Yong Guan, Alexandria N. Leveille, Elizabeth Vaughn, Sangram Parelkar, Paul R. Thompson, and Anita E. Mattson, which is hereby incorporated herein in its entirety. Another portion of the embodiments described herein were published in *Chem. Eur. J.* 2020, 26, 1742-1747 as “Copper Bis(oxazoline)-Catalyzed Enantioselective Alkynylation of Benzopyrylium Ions” by co-authors Yong Guan, Jonathan W. Attard, and Dr. Anita E. Mattson, which is hereby incorporated by reference herein in its entirety.

The invention now having been fully described, it is further exemplified by the following examples and claims.

Example 1: Reagents

Anhydrous toluene, dichloromethane, diethyl ether and THF were dried using a pure process technologies solvent system. Anhydrous DCE, chlorobenzene, m-xylene, and o-xylene were used as received. Substituted chromone-2-carboxylate esters were prepared according to literature. Guan, Y., et al., *Chem. Eur. J.* 2020, 26, 1742-1747. CuI was used as received and stored in a desiccator under ambient lab conditions. TBSOTf was vacuum distilled and stored under dry nitrogen. DIPEA was used as received. Alkynes were used as received or prepared according to literature. Guan Y., et al. The bis(oxazoline) ligands were used as received from Sigma Aldrich or TCl or prepared according to literature. Guan Y. et al., Denmark, S. E. et al., *J. Org. Chem.* 2000, 65, 5875-5878; Burguete, M. I. et al., *Org. Lett.* 2000, 2, 24, 3905-3908; Hao, E.-J. et al., *Org. Chem. Front.* 2019, 6, 863-867; Denmark, S. E. et al., *J. Org. Chem.* 1995, 60, 4884-4892; Fu, N. et al., *J. Am. Chem. Soc.* 2019, 141, 14480-14485; Nolin, K. A. et al., *Chem. Eur. J.* 2010, 16, 9555-9562; Xiong, H. et al., *J. Am. Chem. Soc.* 2013, 135, 7851-7854. All other reagents were used directly as received from the manufacturer unless otherwise noted. Preparative silica gel chromatography was performed using SiliaFlash F60 silica gel (40-63 μm). Analytical thin layer chromatography was performed using Analtech 250 μm silica gel HLF plates and visualized under UV 254 nm or 365 nm. All 1H NMR spectra were acquired using a Bruker BioSpin 500 MHz Avance III Digital NMR spectrometer and calibrated using the solvent signal (CDCl3 7.26 ppm). J Coupling constants are reported in Hz. Multiplicities are reported as follows: s, singlet; d, doublet; t, triplet; q, quartet; p, pentet; hept, heptet; μm, multiplet; b, broad; dd, doublet of doublets; ddd, doublet of doublet of doublets; td, triplet of doublets; ddt, doublet of doublet of triplets; dtd, doublet of triplet of doublets. All 13C NMR spectra were acquired using a Bruker BioSpin 126 MHz Avance III Digital NMR spectrometer and calibrated using the solvent signal (CDCl3 77.16 ppm). Infrared spectra were acquired using a Bruker Vertex 70 with an ATR accessory. High resolution mass spectra were acquired using an Agilent 6520 Q-TOF mass spectrometer. Chiral HPLC analysis was performed using an Agilent 1260 equipped with a diode array detector using Chiralcel OD-H or AD-H columns. Optical Rotations were acquired on a JASCO P-2000 Digital Polarimeter with a sodium lamp (λ=589 nm).

Example 2: General Procedure for Enantioselective Alkynylation with Cu-BOX Catalyst Procedure 1 (Pre-Generation of Siloxybenzopyrylium)

To an 8 mL screw top vail was added chromone methyl chromone-2-carboxylate (40.8 mg, 0.2 mmol, 1.0 eq) and toluene (0.8 mL). TBSOTf (60 μL, 0.26 mmol, 1.3 eq) was then added and the mixture was stirred for 1 h at 60° C. to generate siloxybenzopyrylium. To a separate 8 mL vial was added CuI (3.8 mg, 0.02 mmol, 10 mol %), (S)-tBu-Box (8.8 mg, 0.024 mmol, 12 mol %) and toluene (0.2 mL). The atmosphere in the flask was purged with dry N2. This flask was then cooled to −78° C. on a dry ice and acetone bath, then iPr2NEt (52.3 μL, 0.3 mmol, 1.5 eq), phenyl acetylene (28.6 μL, 0.26 mmol, 1.3 eq) and the pre-generated solution of siloxybenzopyrylium were added. The reaction mixture cooled to 0° C. and stirred for 48 h. The reaction was quenched by the addition of 6N HCl (2 mL) and stirred for 2 hours. The reaction mixture was extracted with EtOAc (3×2 mL), washed with saturated $NaHCO_3$ solution, dried over anhydrous NaSO4, and the solvent removed under vacuum to obtain the crude product. The crude product was purified by column chromatography on silica gel with Hexane:EtOAc (4:1) to afford yellow oil (87% yield, 38% ee).

Example 3: In-Situ Generation of Siloxybenzopyrylium (General Procedure 2)

To an 8 mL screw top vial was added methyl chromone-2-carboxylate (40.8 mg, 0.2 mmol, 1.0 eq), CuI (3.8 mg, 0.02 mmol, 10 mol %), (S)-Indanyl-BOX (8.8 mg, 0.024 mmol, 12 mol %), chlorobenzene (2 mL), i-Pr2NEt (52.3 μL, 0.3 mmol, 1.5 eq), and phenyl acetylene (28.6 μL, 0.26 mmol, 1.3 eq) in that order at room temperature. This mixture was allowed to stir for 30 minutes. The vial was purged with dry N2 and then cooled to −78° C. TBSOTf (60 μL, 0.26 mmol, 1.3 eq) was added at −78° C., then the reaction was transferred to the lab chiller at −35° C. and S3 allowed to react for 96 h. The reaction was quenched by the addition of 6N HCl (2 mL) and stirred for 2 hours. The reaction mixture was extracted with EtOAc (3×2 mL), washed with saturated $NaHCO_3$ solution, dried over anhydrous NaSO4, and the solvent removed under vacuum to obtain the crude product. The crude product was purified by column chromatography on silica gel with Hexane:EtOAc (4:1) to afford an orange oil (41.2 mg, 68% yield, 90% ee).

Example 4: Synthesis of methyl 4-oxo-2-(phenylethynyl)chromane-2-carboxylate (Compound 7a)

Prepared according to procedure of Example 3, using PhCl, (S)-Indanyl-BOX, chromone (40.8 mg, 0.20 mmol) and phenyl acetylene (29 μL, 0.26 mmol). Compound 7a was isolated as a yellow oil (41.2 mg, 0.135 mmol, 68% yield). Rf=0.43 (4:1, Hexanes:EtOAc), [α]23D=+90.7 (c=0.9, CHCl3), 1H NMR (500 MHz, CDCl3) δ 7.91 (ddd, J=7.8, 1.7, 0.5 Hz, 1H), 7.55 (ddd, J=8.4, 7.2, 1.8 Hz, 1H), 7.40-7.26 (m, 5H), 7.19-7.06 (m, 2H), 3.90 (s, 3H), 3.43-3.24 (m, 2H). 13C NMR (126 MHz, CDCl3) δ 188.88, 167.41, 158.79, 136.64, 132.28, 129.62, 128.44, 126.93, 122.70, 120.90, 118.67, 88.20, 83.18, 77.10, 54.09, 46.12 (1 aromatic signal overlapped). IR (neat, ATR) ν: 3066, 2955, 2234, 1751, 1695, 1607, 1460, 1299, 1259, 1221, 1116, 756, 645. Chiral HPLC: 94.8:5.2 e.r., 90% ee, Chiralcel OD-H column (5% iPrOH/Hexanes, 1 mL/min, 254 nm); tR (minor)=9.6 min, tR (major)=11.3 min. HRMS (ESI+) m/z calculated for C19H15O4 [M+H]+ 307.0965, found 307.0958.

Example 5: Synthesis of ethyl 4-oxo-2-(phenylethynyl)chromane-2-carboxylate (Compound 7b)

Prepared according to procedure of Example 3, using PhCl, (S)-Indanyl-BOX, chromone (43.6 mg, 0.20 mmol) and phenyl acetylene (29 μL, 0.26 mmol). Compound 7b was isolated as a yellow oil (33.8 mg, 0.106 mmol, 53% yield). Rf=0.45 (4:1, Hexanes:EtOAc), [α]22D=+75.1 (c=1.1, CHCl3), 1H NMR (500 MHz, CDCl3) δ 7.91 (dd, J=7.8, 1.7 Hz, 1H), 7.55 (ddd, J=8.4, 7.2, 1.8 Hz, 1H), 7.40-7.27 (m, 5H), 7.17 (dd, J=8.4, 1.1 Hz, 1H), 7.09 (ddd, J=8.0, 7.2, 1.1 Hz, 1H), 4.34 (qd, J=7.1, 1.2 Hz, 2H), 3.44-3.25 (m, 2H), 1.30 (t, J=7.1 Hz, 3H). 13C NMR (126 MHz, CDCl3) δ 189.02, 166.93, 158.95, 136.60, 132.28, 129.58, 128.45, 126.91, 122.65, 121.01, 120.95, 118.72, 88.07, 83.34, 63.33, 46.11, 14.09 (tertiary carbon signal overlapped). IR (neat, ATR) ν: 2984, 2233, 1745, 1696. Chiral HPLC: 94.7:5.3 e.r., 90% ee, Chiralcel OD-H column (2% iPrOH/Hexanes, 1 mL/min, 254 nm); tR (minor)=11.8 min, tR (major)=14.0 min. HRMS (ESI+) m/z calculated for C20H17O4 [M+H]+ 321.1121, found 321.1122.

Example 6: Synthesis of isopropyl 4-oxo-2-(phenylethynyl)chromane-2-carboxylate (Compound 7c)

Prepared according to general procedure 2, using PhCl, (S)-Indanyl-BOX, chromone (46.4 mg, 0.20 mmol) and phenyl acetylene (29 μL, 0.26 mmol). Compound 7c was isolated as a yellow oil (39.4 mg, 0.118 mmol, 59% yield). Rf=0.54 (4:1, Hexanes:EtOAc), [α]22D=+48.4 (c=1.1, CHCl3), 1H NMR (500 MHz, CDCl3) δ 7.96-7.85 (m, 1H), 7.61-7.49 (m, 1H), 7.43-7.26 (m, 5H), 7.20-7.14 (m, 1H), 7.12-7.06 (m, 1H), 5.13 (hept, J=6.3 Hz, 1H), 3.45-3.23 (m, 2H), 1.30 (d, J=6.3 Hz, 3H), 1.23 (d, J=6.3 Hz, 3H). 13C NMR (126 MHz, CDCl3) δ 189.11, 166.48, 159.10, 136.56, 132.25, 129.55, 128.45, 126.89, 122.60, 121.10, 120.98, 118.74, 87.94, 83.44, 77.25, 71.34, 46.08, 21.60, 21.50. IR (neat, ATR) ν: 2983, 2237, 1738, 1696, 1607, 1461. Chiral HPLC: 95.6:4.4 e.r., 91% ee, Chiralcel AD-H column (5% iPrOH/Hexanes, 1 mL/min, 254 nm); tR (minor)=7.5 min, tR (major)=9.5 min. HRMS (ESI+) m/z calculated for C21H19O4 [M+H]+ 335.1278, found 335.1280.

Example 7: Synthesis of tert-butyl 4-oxo-2-(phenylethynyl)chromane-2-carboxylate (Compound 7d)

Prepared according to general procedure 2, using PhCl, (S)-Indanyl-BOX, chromone (49.2 mg, 0.20 mmol) and phenyl acetylene (29 μL, 0.26 mmol). 7d was isolated as a yellow oil (39.7 mg, 0.114 mmol, 57% yield). Rf=0.58 (4:1, Hexanes:EtOAc), [α]22D=+41.3 (c=0.5, CHCl3), 1H NMR (500 MHz, CDCl3) δ 7.95-7.85 (m, 1H), 7.58-7.49 (m, 1H), 7.43-7.27 (m, 5H), 7.19-7.13 (m, 1H), 7.12-7.05 (m, 1H), 3.45-3.14 (m, 2H), 1.46 (s, 9H). 13C NMR (126 MHz, CDCl3) δ 189.35, 165.86, 159.28, 136.53, 132.24, 129.48, 128.45, 126.84, 122.49, 121.24, 121.01, 118.71, 87.64, 84.48, 83.77, 77.56, 46.20, 27.82. IR (neat, ATR) ν: 2980, 2236, 1736, 1697, 1608, 1491. Chiral HPLC: 85.4:14.6 e.r., 71% ee, Chiralcel AD-H column (5% iPrOH/Hexanes, 1 mL/min, 254 nm); tR (minor)=6.4 min, tR (major)=9.6 min. HRMS (ESI+) m/z calculated for C22H21O4 [M+H]+ 349.1434, found 349.1436.

Example 8: Synthesis of benzyl (R)-4-oxo-2-(phenylethynyl)chromane-2-carboxylate (Compound 7e)

Prepared according to general procedure 2, using PhCl, (S)-Indanyl-BOX, chromone (56 mg, 0.20 mmol) and phenyl acetylene (29 μL, 0.26 mmol). Compound 7e was isolated as a yellow oil (45.6 mg, 0.119 mmol, 60% yield). Rf=0.45 (4:1, Hexanes:EtOAc), [α]22D=+27.7 (c=1.0, CHCl3), 1H NMR (500 MHz, CDCl3) δ 7.89 (dd, J=7.8, 1.3 Hz, 1H), 7.53 (ddd, J=8.4, 7.2, 1.8 Hz, 1H), 7.37-7.26 (m, 10H), 7.17-7.05 (m, 2H), 5.33 (d, J=12.3 Hz, 1H), 5.27 (d, J=12.3 Hz, 1H), 3.40 (d, J=16.7 Hz, 1H), 3.30 (d, J=16.7 Hz, 1H). 13C NMR (126 MHz, CDCl3) δ 189.10, 167.03, 159.17, 136.86, 135.13, 132.74, 132.52, 129.86, 128.95, 128.85, 128.68, 128.44, 127.19, 122.94, 121.19, 121.17, 118.97, 88.54, 83.48, 77.46, 68.82, 46.27. IR (neat, ATR) ν: 3051, 2942, 2241, 1749, 1691, 1466, 1210, 1117, 725, 641. Chiral HPLC: 91.7:8.3 e.r., 83% ee, Chiralcel AD-H column (5% iPrOH/Hexanes, 1 mL/min, 254 nm); tR (minor)=11.7 min, tR (major)=14.5 min. HRMS (ESI+) m/z calculated for C25H18O4 [M+H]+ 382.1315, found 382.1311.

Example 9: Synthesis of 2,2,2-trichloroethyl (R)-4-oxo-2-(phenylethynyl)chromane-2-carboxylate (Compound 7f)

Prepared according to general procedure 2, using PhCl, (S)-Indanyl-BOX, chromone (64.3 mg, 0.20 mmol) and phenyl acetylene (29 μL, 0.26 mmol). Compound 7f was isolated as a yellow oil (39.2 mg, 0.93 mmol, 46% yield). Rf=0.53 (4:1, Hexanes:EtOAc), [α]22D=+23.4 (c=1.0, CHCl3), 1H NMR (500 MHz, CDCl3) δ 7.95-7.89 (m, 1H), 7.56 (ddd, J=8.4, 7.2, 1.8 Hz, 1H), 7.43-7.28 (m, 5H), 7.19 (dd, J=8.4, 0.8 Hz, 1H), 7.11 (ddd, J=8.1, 7.3, 1.0 Hz, 1H), 4.92 (d, J=11.8 Hz, 1H), 4.88 (d, J=11.9 Hz, 1H), 3.47 (d, J=16.7 Hz, 1H), 3.38 (d, J=16.7 Hz, 1H). 13C NMR (126 MHz, CDCl3) δ 188.31, 165.73, 158.78, 136.78, 132.30, 129.79, 128.51, 127.00, 122.94, 120.92, 120.74, 118.83, 94.17, 88.84, 82.50, 77.02, 75.18, 45.98. IR (neat, ATR) ν: 3009, 2945, 2153, 1735, 1681, 1469, 1209, 1097, 745, 568. Chiral HPLC: 95.9:4.1 e.r., 92% ee, Chiralcel OD-H column (2% iPrOH/Hexanes, 1 mL/min, 254 nm); tR (minor)=11.8 min, tR (major)=13.4 min. HRMS (ESI+) m/z calculated for C20H13Cl3O4 [M+H]+ 422.9979, found 422.999.

Example 10: Synthesis of isobutyl (R)-4-oxo-2-(phenylethynyl)chromane-2-carboxylate (Compound 7ff)

Prepared according to general procedure 2, using PhCl, (S)-Indanyl-BOX, chromone (49.2 mg, 0.20 mmol) and phenyl acetylene (29 μL, 0.26 mmol). 7ff was isolated as a yellow oil (44.5 mg, 0.128 mmol, 64% yield). Rf=0.56 (4:1, Hexanes:EtOAc), [α]22D=+38.4 (c=1.0, CHCl3), 1H NMR (500 MHz, CDCl3) δ 7.91 (dd, J=7.8, 1.7 Hz, 1H), 7.54 (ddd, J=8.4, 7.2, 1.8 Hz, 1H), 7.41-7.32 (m, 3H), 7.31-7.25 (m, 2H), 7.17 (dd, J=8.4, 1.0 Hz, 1H), 7.09 (ddd, J=8.1, 7.2, 1.1 Hz, 1H), 4.14-3.97 (m, 2H), 3.41 (d, J=16.6 Hz, 1H), 3.30 (d, J=16.6 Hz, 1H), 2.00 (dt, J=13.4, 6.7 Hz, 1H), 0.93 (d, J=6.8 Hz, 6H). 13C NMR (126 MHz, CDCl3) δ 188.98, 167.00, 159.03, 136.62, 132.24, 129.57, 128.46, 126.93, 122.63, 121.03, 120.92, 118.72, 88.00, 83.48, 77.23, 73.03, 46.13, 27.93, 18.95, 18.93. IR (neat, ATR) ν: 3060, 2911, 2276, 1740, 1681, 1461, 1251, 1181, 749, S18 635. Chiral HPLC: 96.2:3.8 e.r., 92% ee, Chiralcel OD-H column (2% iPrOH/Hexanes, 1 mL/min, 254 nm); tR (minor)=8.7 min, tR (major)=10.2 min. HRMS (ESI+) m/z calculated for C22H20O4 [M+H]+ 349.1440, found 349.1444.

Example 11: Synthesis of methyl (R)-4-oxo-2-(p-tolylethynyl)chromane-2-carboxylate (Compound 7g)

Prepared according to general procedure 2, using PhCl, (S)-Indanyl-BOX, chromone (40.8 mg, 0.20 mmol) and 4-S19 ethynyltoluene (32.9 μL, 0.26 mmol). 7g was isolated as a yellow oil (38.6 mg, 0.120 mmol, 60% yield). Rf=0.38 (4:1, Hexanes:EtOAc), [α]22D=+47.1 (c=1.0, CHCl3), 1H NMR (500 MHz, CDCl3) δ 7.91 (dd, J=7.8, 1.7 Hz, 1H), 7.54 (ddd, J=8.4, 7.2, 1.8 Hz, 1H), 7.28-7.25 (m, 2H), 7.16 (dd, J=8.3, 1.0 Hz, 1H), 7.13-7.06 (m, 3H), 3.89 (s, 3H), 3.38 (d, J=16.6 Hz, 1H), 3.28 (d, J=16.6 Hz, 1H), 2.33 (s, 3H). 13C NMR (126 MHz, CDCl3) δ 188.96, 167.50, 158.84, 139.96, 136.60, 132.19, 129.18, 126.91, 122.64, 120.92, 118.68, 117.82, 88.49, 82.57, 54.04, 46.17, 21.68. IR (neat, ATR) ν: 3021, 2915, 2198, 1761, 1684, 1461, 1310, 1219, 756 Chiral HPLC: 95.1:4.9 e.r., 90% ee, Chiralcel AD-H column (5% iPrOH/Hexanes, 1 mL/min, 254 nm); tR (minor)=12.1 min, tR (major)=13.0 min. HRMS (ESI+) m/z calculated for C20H16O4 [M+H]+ 321.1127, found 321.1121.

Example 12: Synthesis of methyl (R)-4-oxo-2-(m-tolylethynyl)chromane-2-carboxylate (Compound 7h)

Prepared according to general procedure 2, using PhCl, (S)-Indanyl-BOX, chromone (40.8 mg, 0.20 mmol) and mtolylacetylene (33.5 μL, 0.26 mmol). 7h was isolated as a yellow oil (38.3 mg, 0.120 mmol, 60% yield). Rf=0.38 (4:1, Hexanes:EtOAc), [α]22D=+57.2 (c=1.0, CHCl3), 1H NMR (500 MHz, CDCl3) δ 7.94-7.88 (m, 1H), 7.55 (ddd, J=8.3, 7.2, 1.8 Hz, 1H), 7.22-7.06 (m, 6H), 3.89 (s, 3H), 3.38 (d, J=16.6 Hz, 1H), 3.28 (d, J=16.6 Hz, 1H), 2.29 (s, 3H). 13C NMR (126 MHz, CDCl3) δ 188.91, 167.44, 158.82, 138.21, 136.61, 132.81, 130.50, 129.36, 128.33, 126.92, 122.66, 120.91, 120.69, 118.67, 88.41, 82.82, 77.11, 54.06, 46.14, 21.24. IR (neat, ATR) ν: 3029, 2910, 2214, 1738, 1687, 1460, 1221, 1110, 754, 696. Chiral HPLC: 94.9:5.1 e.r., 90% ee, Chiralcel AD-H column (5% iPrOH/Hexanes, 1 mL/min, 254 nm); tR (minor)=8.9 min, tR (major)=9.8 min. HRMS (ESI+) m/z calculated for C20H16O4 HRMS (ESI+) m/z calculated for C20H16O4 [M+H]+ 321.1127, found 321.1121.

Example 13: Synthesis of methyl (R)-4-oxo-2-(o-tolylethynyl)chromane-2-carboxylate (Compound 7i)

Prepared according to general procedure 2, using PhCl, (S)-Indanyl-BOX, chromone (40.8 mg, 0.20 mmol) and 2-ethynyltoluene (32.7 μL, 0.26 mmol). 7i was isolated as a yellow oil (42.4 mg, 0.132 mmol, 66% yield). Rf=0.37 (4:1, Hexanes:EtOAc), [α]22D=+65.1 (c=1.0, CHCl3), 1H NMR (500 MHz, CDCl3) δ 7.92 (dd, J=7.8, 1.7 Hz, 1H), 7.55 (ddd, J=8.4, 7.2, 1.8 Hz, 1H), 7.32 (dd, J=7.6, 1.4 Hz, 1H), 7.22 (td, J=7.5, 1.5 Hz, 1H), 7.19-7.05 (m, 4H), 3.92 (s, 3H), 3.39 (d, J=16.5 Hz, 1H), 3.28 (d, J=16.6 Hz, 1H), 2.19 (s, 3H). 13C NMR (126 MHz, CDCl3) δ 189.00, 167.39, 158.79, 141.24, 136.58, 132.35, 129.63, 129.60, 126.90, 125.65, 122.71, 121.11, 120.70, 118.76, 87.26, 87.08, 77.31, 54.05, 46.35, 20.39. IR (neat, ATR) ν: 3051, 2942, 2241, 1749, 1691, 1466, 1210, 1117, 745, 641. Chiral HPLC: 95.8:4.2 e.r., 92% ee, Chiralcel AD-H column (5% iPrOH/Hexanes, 1 mL/min, 254 nm); tR (minor)=9.3 min, tR (major)=9.9 min HRMS (ESI+) m/z calculated for C20H16O4 [M+H]+ 321.1127, found 321.1121.

Example 14: Synthesis of methyl (R)-2-((4-methoxyphenyl)ethynyl)-4-oxochromane-2-carboxylate (Compound 7j)

Prepared according to general procedure 2, using PhCl, (S)-Indanyl-BOX, chromone (40.8 mg, 0.20 mmol) and 4-ethynylanisole (33.7 μL, 0.26 mmol). 7j was isolated as a yellow oil (33.4 mg, 0.100 mmol, 50% yield). Rf=0.51 (2:1, Hexanes:EtOAc), [α]22D=+65.0 (c=1.0, CHCl3), 1H NMR (500 MHz, CDCl3) δ 7.91 (ddd, J=7.8, 1.7, 0.5 Hz, 1H), 7.54 (ddd, J=8.3, 7.2, 1.8 Hz, 1H), 7.34-7.29 (m, 2H), 7.15 (ddd, J=8.3, 1.1, 0.5 Hz, 1H), 7.09 (ddd, J=8.2, 7.2, 1.0 Hz, 1H), 6.83-6.77 (m, 2H), 3.89 (s, 3H), 3.79 (s, 3H), 3.38 (d, J=16.6 Hz, 1H), 3.28 (d, J=16.6 Hz, 1H). 13C NMR (126 MHz, CDCl3) δ 189.03, 167.55, 160.63, 158.86, 136.58, 133.90, 126.91, 122.62, 120.92, 118.68, 114.08, 112.88, 88.44, 81.99, 77.20, 55.45, 54.03, 46.20. IR (neat, ATR) ν: 2987, 2219, 1745, 1689, 1610, 1453, 1251, 1097, 743. Chiral HPLC: 95.2:4.8 e.r., 90% ee, Chiralcel AD-H column (5% iPrOH/Hexanes, 1 mL/min, 254 nm); tR (minor)=19.5 min, tR (major)=21.0 min. HRMS (ESI+) m/z calculated for C20H16O5 [M+H]+ 337.1076, found 337.1071.

Example 15: Synthesis of methyl (R)-2-((4-chlorophenyl)ethynyl)-4-oxochromane-2-carboxylate (Compound 7k)

Prepared according to general procedure 2, using PhCl, (S)-Indanyl-BOX, chromone (40.8 mg, 0.20 mmol) and 4-chlorophenylacetylene (35.5 mg, 0.26 mmol). 7k was isolated as a yellow oil (38.8 mg, 0.114 mmol, 57% yield). Rf=0.42 (4:1, Hexanes:EtOAc), [α]22D=+32.7 (c=1.0, CHCl3), 1H NMR (500 MHz, CDCl3) δ 7.94-7.88 (m, 1H), 7.55 (ddd, J=8.4, 7.2, 1.8 Hz, 1H), 7.33-7.23 (m, 4H), 7.17-7.14 (m, 1H), 7.10 (ddd, J=8.1, 7.2, 1.0 Hz, 1H), 3.90 (s, 3H), 3.38 (d, J=16.6 Hz, 1H), 3.27 (d, J=16.6 Hz, 1H). 13C NMR (126 MHz, CDCl3) δ 188.71, 167.23, 158.71, 136.69, 135.86, 133.50, 128.84, 126.94, 122.77, 120.86, 119.34, 118.64, 87.01, 84.16, 77.05, 54.13, 46.01. IR (neat, ATR) ν: 3015, 2925, 2278, 1737, 1618, 1439, 1211, 1120, 769. Chiral HPLC: 95.7:4.3 e.r., 91% ee, Chiralcel AD-H column (5% iPrOH/Hexanes, 1 mL/min, 254 nm); tR (minor)=13.9 min, tR (major)=15.2 min. HRMS (ESI+) m/z calculated for C19H13ClO4 [M+H]+ 341.0581, found 341.0575.

Example 16: Synthesis of methyl (R)-2-((4-bromophenyl)ethynyl)-4-oxochromane-2-carboxylate (Compound 7l)

Prepared according to general procedure 2, using PhCl, (S)-Indanyl-BOX, chromone (40.8 mg, 0.20 mmol) and 4-bromophenylacetylene (39.5 mg, 0.26 mmol). 7l was isolated as a yellow oil (53.9 mg, 0.140 mmol, 70% yield). Rf=0.40 (4:1, Hexanes:EtOAc), [α]22D=+31.2 (c=1.3, CHCl3), 1H NMR (500 MHz, CDCl3) δ 7.91 (dd, J=7.8, 1.7 Hz, 1H), 7.55 (ddd, J=8.3, 7.2, 1.8 Hz, 1H), 7.45-7.40 (m, 2H), 7.25-7.21 (m, 2H), 7.15 (dd, J=8.4, 1.0 Hz, 1H), 7.10 (ddd, J=8.0, 7.2, 1.1 Hz, 1H), 3.90 (s, 3H), 3.38 (d, J=16.6 Hz, 1H), 3.27 (d, J=16.6 Hz, 1H). 13C NMR (126 MHz, CDCl3) δ 188.69, 167.20, 158.70, 136.69, 133.66, 131.78, 126.94, 124.15, 122.78, 120.85, 119.80, 118.63, 87.07, 84.32, 77.06, 54.14, 45.99. IR (neat, ATR) ν: 3065, 2978, 2223, 1736, 1681, 1220, 1194, 756, 536. Chiral HPLC: 95.1:4.9 e.r., 90% ee, Chiralcel AD-H column S25 (5% iPrOH/Hexanes, 1 mL/min, 254 nm); tR (minor)=14.9 min, tR (major)=16.4 min HRMS (ESI+) m/z calculated for C19H13BrO4 [M+H]+ 385.0075, found 385.0070.

Example 17: Synthesis of Methyl(R)-4-oxo-2-((4-(trifluoromethyl)phenyl)ethynyl)chromane-2-carboxylate (Compound 7m)

Prepared according to general procedure 2, using PhCl, (S)-Indanyl-BOX, chromone (40.8 mg, 0.20 mmol) and 1-ethynyl-4-(trifluoromethyl) benzene (42.4 μL, 0.26 mmol). 7m was isolated as a yellow oil (39.8 mg, 0.106 mmol, 53% yield). Rf=0.42 (4:1, Hexanes:EtOAc), [α]22D=42.9 (c=1.0, CHCl3), 1H NMR (500 MHz, CDCl3) δ 7.92 (ddd, J=7.8, 1.7, 0.5 Hz, 1H), 7.60-7.52 (m, 3H), 7.51-7.45 (m, 2H), 7.16 (dd, J=8.4, 0.6 Hz, 1H), 7.14-7.09 (m, 1H), 3.91 (s, 3H), 3.40 (d, J=16.6 Hz, 1H), 3.28 (d, J=16.6 Hz, 1H). 13C NMR (126 MHz, CDCl3) δ 188.55, 167.09, 158.66, 136.76, 132.57, 131.37 (q, J=32.8 Hz), 126.98, 125.41 (q, J=3.8 Hz), 124.67, 123.77 (q, J=272 Hz), 122.87, 120.85, 118.64, 86.54, 85.49, 77.01, 54.21, 45.95. IR (neat, S26 ATR) ν: 3060, 2920, 2240, 1745, 1612, 1453, 1311, 1101, 810, 721. Chiral HPLC: 94.3:5.7 e.r., 89% ee, Chiralcel AD-H column (5% iPrOH/Hexanes, 1 mL/min, 254 nm); tR (minor)=12.0 min, tR (major)=13.8 min. HRMS (ESI+) m/z calculated for C19H13BrO4 [M+H]+ 375.0844, found 375.0847.

Example 18: Synthesis of methyl (R)-2-(naphthalen-1-ylethynyl)-4-oxochromane-2-carboxylate (Compound 7o)

Prepared according to general procedure 2, using PhCl, (S)-Indanyl-BOX, chromone (40.8 mg, 0.20 mmol) and 1-ethynylnaphthalene (36.9 μL, 0.26 mmol). 7o was isolated as a yellow oil (42.9 mg, 0.120 mmol, 60% yield). Rf=0.38 (4:1, Hexanes:EtOAc), [α]22D=+46.5 (c=1.0, CHCl3), 1H NMR (500 MHz, CDCl3) δ 7.96 (dd, J=7.9, 1.3 Hz, 1H), 7.90-7.78 (m, 3H), 7.65-7.55 (m, 2H), 7.53-7.43 (m, 2H), 7.38 (dd, J=8.3, 7.2 Hz, 1H), 7.22 (dd, J=8.4, 0.7 Hz, 1H), 7.14 S27 (ddd, J=8.2, 7.4, 1.0 Hz, 1H), 3.96 (s, 3H), 3.48 (d, J=16.6 Hz, 1H), 3.39 (d, J=16.6 Hz, 1H). 13C NMR (126 MHz, CDCl3) δ 188.95, 167.39, 158.87, 136.66, 133.41, 133.10, 131.47, 130.17, 128.45, 127.31, 127.01, 126.70, 125.72, 125.09, 122.81, 121.17, 118.84, 118.44, 87.99, 86.57, 77.47, 54.15, 46.38. IR (neat, ATR) ν: 3033, 2941, 2265, 1742, 1697, 1412, 1216, 1200, 744, 646. Chiral HPLC: 96.1:3.9 e.r., 92% ee, Chiralcel AD-H column (5% iPrOH/Hexanes, 1 mL/min, 254 nm); tR (minor)=11.5 min, tR (major)=12.4 min. HRMS (ESI+) m/z calculated for C23H16O4 [M+H]+ 357.1127, found 357.1121.

Example 19: Synthesis methyl (R)-2-(naphthalen-2-ylethynyl)-4-oxochromane-2-carboxylate (Compound 7p)

Prepared according to general procedure 2, using PhCl, (S)-Indanyl-BOX, chromone (40.8 mg, 0.20 mmol) and 2-ethynylnaphthalene (39.5 mg, 0.26 mmol). 7p was isolated as a yellow oil (57.2 S28 mg, 0.160 mmol, 80% yield). Rf=0.37 (4:1, Hexanes:EtOAc), [α]22D=+57.4 (c=1.0, CHCl3), 1H NMR (500 MHz, CDCl3) δ 7.96-7.90 (m, 2H), 7.82-7.71 (m, 3H), 7.56 (ddd, J=8.4, 7.2, 1.8 Hz, 1H), 7.53-7.45 (m, 2H), 7.39 (dd, J=8.4, 1.7 Hz, 1H), 7.22-7.15 (m, 1H), 7.11 (ddd, J=8.1, 7.2, 1.0 Hz, 1H), 3.92 (s, 3H), 3.43 (d, J=16.6 Hz, 1H), 3.34 (d, J=16.6 Hz, 1H). 13C NMR (126 MHz, CDCl3) δ 188.91, 167.43, 158.84, 136.67, 133.41, 132.83, 132.76, 128.29, 128.18, 128.01, 127.90, 127.43, 126.96, 126.89, 122.72, 120.93, 118.70, 118.10, 88.57, 83.40, 77.19, 54.12, 46.16. IR (neat, ATR) ν: 3030, 2951, 2196, 1745, 1683, 1401, 1220, 1119, 754, 681. Chiral HPLC: 96.1:3.9 e.r., 92% ee, Chiralcel AD-H column (5% iPrOH/Hexanes, 1 mL/min, 254 nm); tR (minor)=11.5 min, tR (major)=12.4 min. HRMS (ESI+) m/z calculated for C23H16O4 [M+H]+ 357.1127, found 357.1121.

Example 20: Synthesis of methyl (R)-2-([1,1'-biphenyl]-4-ylethynyl)-4-oxochromane-2-carboxylate (Compound 7n)

Prepared according to general procedure 2, using PhCl, (S)-Indanyl-BOX, chromone (40.8 mg, 0.20 mmol) and 4-ethynylbiphenyl (46.3 mg, 0.26 mmol). 7n was isolated as a yellow foamy solid (51.2 mg, 0.134 mmol, 67% yield).

Rf=0.40 (4:1, Hexanes:EtOAc), [α]22D=+52.1 (c=1.0, CHCl3), 1H NMR (500 MHz, CDCl3) δ 7.92 (ddd, J=7.8, 1.8, 0.5 Hz, 1H), 7.59-7.49 (m, 5H), 7.48-7.40 (m, 4H), 7.40-7.32 (m, 1H), 7.20-7.15 (m, 1H), 7.11 (ddd, J=8.1, 7.2, 1.1 Hz, 1H), 3.91 (s, 3H), 3.41 (d, J=16.6 Hz, 1H), 3.31 (d, J=16.6 Hz, 1H). 13C NMR (126 MHz, CDCl3) δ 188.89, 167.42, 158.81, 142.41, 140.13, 136.65, 132.72, 129.02, 128.02, 127.18, 127.10, 126.95, 122.71, 120.92, 119.70, 118.69, 88.14, 83.78, 54.10, 46.14. (1 sp2 carbon signal overlapped). IR (neat, ATR) ν: 3024, 2931 2251, 1751, 1665, 1414, 1210, 1197, 732, 645. Chiral HPLC: 95.4:4.6 e.r., 91% ee, Chiralcel AD-H column (5% iPrOH/Hexanes, 1 mL/min, 254 nm); tR (minor)=19.4 min, tR (major)=20.9 min. HRMS (ESI+) m/z calculated for C25H18O4 [M+H]+ 383.1283, found 383.1278.

Example 21: Synthesis of methyl (R)-4-oxo-2-(thiophen-2-ylethynyl)chromane-2-carboxylate (Compound 7q)

Prepared according to general procedure 2, using PhCl, (S)-Indanyl-BOX, chromone (40.8 mg, 0.20 mmol) and 2-ethynylthiophene (24.7 μL, 0.26 mmol). 7q was isolated as a yellow oil (31.6 mg, 0.101 mmol, 51% yield). Rf=0.37 (4:1, Hexanes:EtOAc), [α]22D=+45.0 (c=1.0, CHCl3), 1H NMR (500 MHz, CDCl3) δ 7.91 (dd, J=7.8, 1.7 Hz, 1H), 7.55 (ddd, J=8.3, 7.2, 1.8 Hz, 1H), 7.30 (dd, J=5.1, 1.2 Hz, 1H), 7.23 (dd, J=3.7, 1.2 Hz, 1H), 7.15 (dd, J=8.3, 1.1 Hz, 1H), 7.10 (ddd, J=8.1, 7.2, 1.1 Hz, 1H), 6.95 (dd, J=5.1, 3.7 Hz, 1H), 3.89 (s, 3H), 3.39 (d, J=16.7 Hz, 1H), 3.28 (d, J=16.7 Hz, 1H). 13C NMR (126 MHz, CDCl3) δ 188.67, 167.20, 158.76, 136.68, 134.28, 128.99, 127.18, 126.96, 122.74, 120.83, 120.60, 118.66, 86.96, 81.68, 77.20, 54.14, 45.89. IR (neat, ATR) ν: 3012, 2945, 2297, 1755, 1698, 1431, 1211, 1098, 741, 646. Chiral HPLC: 96.6:3.4 e.r., 93% ee, Chiralcel OD-H column (5% iPrOH/Hexanes, 1 mL/min, 254 nm); tR (minor)=12.1 min, tR (major)=14.8 min. HRMS (ESI+) m/z calculated for C17H12O4S [M+H]+ 312.0456, found 312.0459.

Example 22: Synthesis of methyl (R)-4-oxo-2-(thiophen-3-ylethynyl)chromane-2-carboxylate (Compound 7r)

Prepared according to general procedure 2, using PhCl, (S)-Indanyl-BOX, chromone (40.8 mg, 0.20 mmol) and 3-ethynylthiophene (25.6 μL, 0.26 mmol). 7r was isolated as a yellow oil (40.6 mg, 0.130 mmol, 65% yield). Rf=0.37 (4:1, Hexanes:EtOAc), [α]22D=+52.5 (c=1.0, CHCl3), 1H NMR (500 MHz, CDCl3) δ 7.91 (dd, J=7.8, 1.8 Hz, 1H), 7.55 (ddd, J=8.3, 7.2, 1.8 Hz, 1H), 7.48 (dd, J=3.0, 1.2 Hz, 1H), 7.23 (dd, J=5.0, 3.0 Hz, 1H), 7.15 (dd, J=8.4, 1.1 Hz, 1H), 7.10 (ddd, J=8.1, 7.2, 1.0 Hz, 1H), 7.05 (dd, J=5.0, 1.2 Hz, 1H), 3.89 (s, 3H), 3.38 (d, J=16.6 Hz, 1H), 3.27 (d, J=16.7 Hz, 1H). 13C NMR (126 MHz, CDCl3) δ 188.84, 167.37, 158.79, 136.64, 131.23, 130.04, 126.94, 125.71, 122.69, 120.87, 119.98, 118.67, 83.45, 82.93, 77.12, 54.09, 46.04. IR (neat, ATR) ν: 3020, 2921, 2256, 1741, 1430, 1209, 1019, 740, 645. Chiral HPLC: 96.1:3.9 e.r., 92% ee, Chiralcel OD-H column (5% iPrOH/Hexanes, 1 mL/min, 254 nm); tR (minor)=12.8 min, tR (major)=16.5 min. HRMS (ESI+) m/z calculated for C17H12O4S [M+H]+ 312.0456, found 312.0459.

Example 23: Synthesis of methyl (R)-2-((5-methylfuran-2-yl)ethynyl)-4-oxochromane-2-carboxylate (Compound 7s)

Prepared according to general procedure 2, using PhCl, (S)-Indanyl-BOX, chromone (40.8 mg, 0.20 mmol) and 2-ethynyl-5-methylfuran (28 mg, 0.26 mmol). 7s was isolated as a red oil (25.8 mg, 0.083 mmol, 42% yield). Rf=0.38 (4:1, Hexanes:EtOAc), [α]22D=+40.1 (c=0.6, CHCl3), 1H NMR (500 MHz, CDCl3) δ 7.91 (dd, J=7.8, 1.7 Hz, 1H), 7.54 (ddd, J=8.4, 7.2, 1.8 Hz, 1H), 7.14 (dd, J=8.4, 1.0 Hz, 1H), 7.09 (ddd, J=8.1, 7.2, 1.0 Hz, 1H), 6.59-6.51 (m, 1H), 5.99-5.91 (m, 1H), 3.88 (s, 3H), 3.37 (d, J=16.7 Hz, 1H), 3.27 (d, J=16.7 Hz, 1H), 2.27 (s, 3H). 13C NMR (126 MHz, CDCl3) δ 188.59, 167.10, 158.75, 155.16, 136.68, 133.40, 126.97, 122.73, 120.81, 119.30, 118.68, 107.37, 87.44, 78.97, 77.13, 54.14, 45.75, 13.96. IR (neat, ATR) ν: 3021, 2957, 2251, 1740, 1656, 1430, 1311, 1251, 1014, 732, 613. Chiral HPLC: 95.6:4.4 e.r., 91% ee, Chiralcel OD-H column (5% iPrOH/Hexanes, 1 mL/min, 254 nm); tR (minor)=9.9 min, tR (major)=11.7 min. HRMS (ESI+) m/z calculated for C18H14O5 [M+H]+ 311.0919, found 311.0914.

Example 24: Synthesis of methyl (R)-2-((5-(methoxycarbonyl)furan-2-yl)ethynyl)-4-oxochromane-2-carboxylate (Compound 7ss)

Prepared according to general procedure 2, using PhCl, (S)-Indanyl-BOX, chromone (40.8 mg, 0.20 mmol) and methyl 5-ethynylfuran-2-carboxylate (39 mg, 0.26 mmol). 7ss was isolated as a yellow oil (39.2 mg, 0.110 mmol, 55% yield). Rf=0.19 (4:1, Hexanes:EtOAc), [α]22D=+51.9 (c=1.0, CHCl3), 1H NMR (500 MHz, CDCl3) δ 7.91 (ddd, J=7.9, 1.8, 0.5 Hz, 1H), 7.56 (ddd, J=8.4, 7.2, 1.8 Hz, 1H), 7.17-7.08 (m, 3H), 6.69 (d, J=3.6 Hz, 1H), 3.90 (s, 3H), 3.89 (s, 3H), 3.38 (d, J=16.7 Hz, 1H), 3.27 (d, J=16.7 Hz, 1H). 13C NMR (126 MHz, CDCl3) δ 188.09, 166.59, 158.57, 158.29, 145.44, 138.10, 136.85, 127.05, 122.98, 120.72, 119.03, 118.65, 118.50, 89.24, 77.05, 54.32, 52.41, 45.46. IR (neat, ATR) ν: 3012, 2993, 2265, 1755, 1598, 1432, 1325, 1299, 1025, 754, 613. Chiral HPLC: 94.8:5.2 e.r., 90% ee, Chiralcel OD-H column (5% iPrOH/Hexanes, 1 mL/min, 254 nm); tR (minor)=30.8 min, tR (major)=35.7 min. HRMS (ESI+) m/z calculated for C19H14O7 [M+H]+ 355.0818, found 355.0812.

Example 25: Synthesis of methyl (R)-2-(cyclopropylethynyl)-4-oxochromane-2-carboxylate (Compound 7t)

Prepared according to general procedure 2, using PhCl, (S)-Indanyl-BOX, chromone (40.8 mg, 0.20 mmol) and cyclopropylacetylene (22.0 μL, 0.26 mmol). 7t was isolated as a colorless oil (33.0 mg, 0.122 mmol, 61% yield). Rf=0.43 (4:1, Hexanes:EtOAc), [α]22D=+25.5 (c=1.0, CHCl3), 1H NMR (500 MHz, CDCl3) δ 7.91-7.85 (m, 1H), 7.53 (ddd, J=8.4, 7.2, 1.8 Hz, 1H), 7.14-7.04 (m, 2H), 3.84 (s, 3H), 3.26 (d, J=16.6 Hz, 1H), 3.13 (d, J=16.6 Hz, 1H), 1.21 (tt, J=8.3, 5.0 Hz, 1H), 0.80-0.73 (m, 2H), 0.68-0.61 (m, 2H). 13C NMR (126 MHz, CDCl3) δ 189.17, 167.67, 158.83, 136.48, 126.81, 122.48, 120.85, 118.64, 93.17, 76.85, 69.81, 53.90, 46.30, 8.75, −0.47. IR (neat, ATR) ν: 3001, 2893, 2198, 1748, 1614, 1429, 1311, 1289, 1028, 746, 611. Chiral HPLC: S35 94.4:5.6 e.r., 89% ee, Chiralcel OD-H column (5% iPrOH/Hexanes, 1 mL/min, 254 nm); tR (minor)=9.2 min, tR (major)=11.8 min. HRMS (ESI+) m/z calculated for C19H14O7 [M+H]+ 271.0970, found 271.0965.

Example 26: Synthesis of methyl (R)-2-(cyclohexylethynyl)-4-oxochromane-2-carboxylate (Compound 7u)

Prepared according to general procedure 2, using PhCl, (S)-Indanyl-BOX, chromone (40.8 mg, 0.20 mmol) and cyclohexylacetylene (34.0 μL, 0.26 mmol). 7u was isolated as a colorless oil (26.4 mg, 0.084 mmol, 42% yield). Rf=0.50 (4:1, Hexanes:EtOAc), [α]22D=+60.9 (c=1.0, CHCl3), 1H NMR (500 MHz, CDCl3) δ 7.89 (ddd, J=7.8, 1.8, 0.4 Hz, 1H), 7.52 (ddd, J=8.4, 7.2, 1.8 Hz, 1H), 7.12 (dd, J=8.5, 0.8 Hz, 1H), 7.08 (ddd, J=8.1, 7.2, 1.1 Hz, 1H), 3.86 (s, 3H), 3.28 (d, J=16.6 Hz, 1H), 3.15 (d, J=16.6 Hz, 1H), 2.42-2.34 (m, 1H), 1.71-1.57 (m, 2H), 1.57-1.43 (m, 2H), 1.43-1.17 (m, 6H). 13C NMR (126 MHz, CDCl3) δ 189.31, 167.77, 158.84, 136.41, 126.77, S36 122.47, 121.06, 118.69, 93.99, 76.93, 75.14, 53.86, 46.55, 31.82, 28.75, 25.81, 24.32. IR (neat, ATR) ν: 3010, 2926, 2855, 2221, 1748, 1685, 1451, 1289, 1029, 743. Chiral HPLC: 90.5:9.5 e.r., 81% ee, Chiralcel AD-H column (5% iPrOH/Hexanes, 1 mL/min 254 nm); tR (minor)=7.0 min, tR (major)=7.3 min. HRMS (ESI+) m/z calculated for C19H20O4 [M+H]+ 313.1440, found 313.1444.

Example 27: Synthesis of methyl (R)-2-(3,3-dimethylbut-1-yn-1-yl)-4-oxochromane-2-carboxylate (Compound 7v)

Prepared according to general procedure 2, using PhCl, (S)-Indanyl-BOX, chromone (40.8 mg, 0.20 mmol) and 3,3-dimethyl-1-butyne (32.0 μL, 0.26 mmol). 7v was isolated as a colorless oil (50.8 mg, 0.178 mmol, 89% yield). Rf=0.52 (4:1, Hexanes:EtOAc), [α]22D=+182.8 (c=1.0, CHCl3), 1H NMR (500 MHz, CDCl3) δ 7.88 (dd, J=7.8, 1.7 Hz, 1H), 7.52 (ddd, J=8.4, 7.2, 1.8 Hz, 1H), 7.12 (dd, J=8.3, 1.1 Hz, 1H), 7.07 (ddd, J=8.1, 7.2, 1.1 Hz, 1H), 3.84 (s, 3H), 3.27 (d, J=S37 16.6 Hz, 1H), 3.14 (d, J=16.6 Hz, 1H), 1.11 (s, 9H). 13C NMR (126 MHz, CDCl3) δ 189.30, 167.84, 158.88, 136.38, 126.73, 122.46, 121.03, 118.68, 98.18, 73.56, 53.86, 46.57, 30.41, 27.58 (1 sp carbon signal overlapped). IR (neat, ATR) ν: 3015, 2976, 2246, 1754, 1665, 1469, 1301, 1289, 743, 605. Chiral HPLC: 95.7:4.3 e.r., 91% ee, Chiralcel AD-H column (2% iPrOH/Hexanes, 1 mL/min, 254 nm); tR (minor)=7.5 min, tR (major)=7.9 min. HRMS (ESI+) m/z calculated for C17H18O4 [M+H]+ 287.1283, found 287.1288.

Example 28: Synthesis of methyl (R)-2-(cyclohex-1-en-1-ylethynyl)-4-oxochromane-2-carboxylate (Compound 7w)

Prepared according to general procedure 2, using PhCl, (S)-Indanyl-BOX, chromone (40.8 mg, 0.20 S38 mmol) and 1-ethynylcyclohexene (30.5 μL, 0.26 mmol). 7w was isolated as a colorless oil (40.8 mg, 0.132 mmol, 66% yield). Rf=0.48 (4:1, Hexanes:EtOAc), [α]22D=+42.6 (c=1.0, CHCl3), 1H NMR (500 MHz, CDCl3) δ 7.89 (dd, J=7.8, 1.7 Hz, 1H), 7.53 (ddd, J=8.4, 7.2, 1.8 Hz, 1H), 7.12 (dd, J=8.3, 1.0 Hz, 1H), 7.08 (ddd, J=8.1, 7.1, 1.0 Hz, 1H), 6.14 (tt, J=3.9, 1.8 Hz, 1H), 3.85 (s, 3H), 3.31 (d, J=16.6 Hz, 1H), 3.19 (d, J=16.6 Hz, 1H), 2.09-1.97 (m, 4H), 1.61-1.49 (m, 4H). 13C NMR (126 MHz, CDCl3) δ 189.09, 167.62, 158.85, 138.44, 136.49, 126.83, 122.50, 120.89, 119.05, 118.65, 90.19, 80.56, 77.12, 53.94, 46.25, 28.60, 25.76, 22.10, 21.33. IR (neat, ATR) ν: 3043, 2989, 2221, 1746, 1608, 1443, 1342, 1235, 1012, 757, 610. Chiral HPLC: 93.2:6.8 e.r., 86% ee, Chiralcel AD-H column (5% iPrOH/Hexanes, 1 mL/min, 254 nm); tR (minor)=7.6 min, tR (major)=9.0 min. HRMS (ESI+) m/z calculated for C19H18O4 [M+H]+ 311.1283, found 311.1288.

Example 29: Synthesis of methyl (R)-4-oxo-7-phenyl-2-(phenylethynyl)chromane-2-carboxylate (Compound 7af)

Prepared according to general procedure 2, using PhCl, (S)-Indanyl-BOX, chromone (56.0 mg, 0.20 mmol) and phenyl acetylene (29 μL, 0.26 mmol). 7af was isolated as a yellow oil (62.2 mg, 0.162 mmol, 81% yield). Rf=0.39 (4:1, Hexanes:EtOAc), [α]22D=+75.2 (c=1.0, CHCl3), 1H NMR (500 MHz, CDCl3) δ 7.97 (dd, J=8.2, 0.4 Hz, 1H), 7.66-7.59 (m, 2H), 7.50-7.44 (m, 2H), 7.43-7.37 (m, 3H), 7.37-7.32 (m, 2H), 7.31-7.25 (m, 3H), 3.92 (s, 3H), 3.41 (d, J=16.6 Hz, 1H), 3.31 (d, J=16.6 Hz, 1H). 13C NMR (126 MHz, CDCl3) δ 188.55, 167.44, 159.06, 149.53, 139.34, 132.33, 129.63, 129.12, 128.88, 128.45, 127.45, 127.37, 121.65, 120.92, 119.63, 116.77, 88.25, 83.24, 77.21, 54.13, 46.11. IR (neat, ATR) ν: 3055, 2925, 2198, 1759, 1682, 1301, 1028, 758, 667. Chiral HPLC: 99.7:0.3 e.r., 99% ee, Chiralcel AD-H column (5% iPrOH/Hexanes, 1 mL/min, 254 nm); tR (minor)=14.4 min, tR (major)=17.0 min. HRMS (ESI+) m/z calculated for C25H18O4 [M+H]+ 383.1283, found 383.1285.

Example 30: Synthesis of methyl (R)-7-(cyclopropylethynyl)-4-oxo-2-(phenylethynyl)chromane-2-carboxylate (Compound 7ag)

Prepared according to general procedure 2, using PhCl, (S)-Indanyl-BOX, chromone (53.6 mg, 0.20 mmol) and phenyl acetylene (29 μL, 0.26 mmol). 7ag was isolated as a yellow oil (50.2 mg, 0.136 mmol, 68% yield). Rf=0.42 (4:1, Hexanes:EtOAc), [α]22D=+40.3 (c=0.9, CHCl3), 1H NMR (500 MHz, CDCl3) δ 7.80 (d, J=8.1 Hz, 1H), 7.39-7.31 (m, 3H), 7.31-7.25 (m, 2H), 7.13 (d, J=1.4 Hz, 1H), 7.05 (dd, J=8.1, 1.5 Hz, 1H), 3.89 (s, 3H), 3.36 (d, J=16.7 Hz, 1H), 3.25 (d, J=16.7 Hz, 1H), 1.47 (tt, J=8.3, 5.0 Hz, 1H), 0.95-0.89 (m, 2H), 0.86-0.80 (m, 2H). 13C NMR (126 MHz, CDCl3) δ 188.26, 167.31, 158.47, 132.59, 132.29, 129.62, 128.44, 126.71, 125.96, 121.33, 120.87, 119.78, 99.05, 88.29, 83.10, 75.26, 54.08, 46.07, 9.12, 0.50 (1 sp carbon signal overlapped). IR (neat, ATR) ν: 3076, 2921, 2199, 1745, 1653, 1477, 1241, 751, 665. Chiral HPLC: 99.3:0.7 e.r., 99% ee, Chiralcel AD-H column (5% iPrOH/Hexanes, 1 mL/min, 254 nm); tR (minor)=10.7 min, tR (major)=16.6 min. HRMS (ESI+) m/z calculated for C24H18O4 [M+H]+ 371.1283, found 371.1278.

Example 31: Synthesis of methyl (R)-4-oxo-2-(phenylethynyl)-7-vinylchromane-2-carboxylate (Compound 7ah)

Prepared according to general procedure 2, using PhCl, (S)-Indanyl-BOX, chromone (46 mg, 0.20 mmol) and phenyl acetylene (29 μL, 0.26 mmol). 7ah was isolated as a pink oil (42.0 mg, 0.126 mmol, 63% yield). Rf=0.44 (4:1, Hexanes:EtOAc), [α]22D=+45.0 (c=1.0, CHCl3), 1H NMR (500 MHz, CDCl3) δ 7.87 (d, J=8.1 Hz, 1H), 7.40-7.36 (m, 2H), 7.36-7.32 (m, 1H), 7.31-7.25 (m, 2H), 7.18 (d, J=1.6 Hz, 1H), 7.14 (dd, J=8.1, 1.7 Hz, 1H), 6.70 (dd, J=17.6, 10.9 Hz, 1H), 5.89 (dd, J=17.5, 0.6 Hz, 1H), 5.44 (dd, J=10.9, 0.6 Hz, 1H), 3.90 (s, 3H), 3.37 (d, J=16.6 Hz, 1H), 3.27 (d, J=16.6 Hz, 1H). 13C NMR (126 MHz, CDCl3) δ 188.39, 167.43, 159.03, 145.90, 135.80, 132.31, 129.63, 128.44, 127.22, 120.91, 120.77, 120.10, 118.16, 115.95, 88.21, 83.20, 77.13, 54.11, 46.04. IR (neat, ATR) ν: 3032, 2911, 2153, 1755, 1652, 1412, 1246, 767, 611 Chiral HPLC: 99.6:0.4 e.r., 99% ee, Chiralcel AD-H column (5% iPrOH/Hexanes, 1 mL/min, 254 nm); tR (minor)=12.7 min, tR (major)=14.3 min. HRMS (ESI+) m/z calculated for C21H16O4 [M+H]+ 333.1127, found 333.1121.

Example 32: Synthesis of methyl (R)-7-allyl-4-oxo-2-(phenylethynyl)chromane-2-carboxylate (Compound 7ae)

Prepared according to general procedure 2, using PhCl, (S)-Indanyl-BOX, chromone (48.8 mg, 0.20 mmol) and phenyl acetylene (29 μL, 0.26 mmol). 7ae was isolated as a yellow oil (23.0 mg, 0.066 mmol, 33% yield). Rf=0.46 (4:1, Hexanes:EtOAc), [α]22D=+20.6 (c=1.0, CHCl3), 1H NMR (500 MHz, CDCl3-d) δ 7.83 (d, J=8.0 Hz, 1H), 7.41-7.36 (m, 2H), 7.36-7.31 (m, 1H), 7.31-7.24 (m, 2H), 7.00 (dd, J=1.5, 0.6 Hz, 1H), 6.93 (dd, J=8.1, 1.5 Hz, 1H), 5.93 (ddt, J=16.6, 10.5, 6.8 Hz, 1H), 5.14 (tt, J=1.7, 0.7 Hz, 1H), 5.13-5.09 (m, 1H), 3.89 (s, 3H), 3.41 (d, J=6.7 Hz, 2H), 3.36 (d, J=16.6 Hz, 1H), 3.26 (d, J=16.6 Hz, 1H). 13C NMR (126 MHz, CDCl3) δ 188.56, 167.48, 158.93, 150.22, 135.65, 132.31, 129.59, 128.43, 126.99, 123.37, 120.96, 119.11, 118.30, 117.36, 88.08, 83.29, 77.09, 54.07, 46.01, 40.45. IR (neat, ATR) ν: 3030, 2965, 2112, 1754, 1616, 1476, 1217, 787, 612. Chiral HPLC: 98.5:1.5 e.r., 97% ee, Chiralcel AD-H column (5% iPrOH/Hexanes, 1 mL/min, 254 nm); tR (minor)=10.5 min, tR (major)=11.7 min. HRMS (ESI+) m/z calculated for C22H18O4 [M+H]+: 347.1283, found: 347.1278.

Example 33: Synthesis of methyl (R)-5-(cyclopropylethynyl)-4-oxo-2-(phenylethynyl)chromane-2-carboxylate (Compound 7aj)

Prepared according to general procedure 2, using PhCl, (S)-Indanyl-BOX, chromone (53.6 mg, 0.20 mmol) and phenyl acetylene (29 μL, 0.26 mmol). 7aj was isolated as a yellow oil (23.2 mg, 0.062 mmol, 31% yield). Rf=0.39 (4:1, Hexanes:EtOAc), [α]22D=73.1 (c=1.0, CHCl3), 1H NMR (500 MHz, CDCl3) δ 7.41-7.36 (m, 2H), 7.36-7.32 (m, 1H), 7.31-7.24 (m, 3H), 7.14 (dd, J=7.6, 1.1 Hz, 1H), 7.05 (dd, J=8.3, 1.1 Hz, 1H), 3.89 (s, 3H), 3.36 (d, J=16.3 Hz, 1H), 3.26 (d, J=16.4 Hz, 1H), 1.60-1.49 (m, 1H), 0.99-0.88 (m, 4H). 13C NMR (126 MHz, CDCl3) δ 187.22, 167.36, 159.14, 134.83, 132.31, 129.58, 129.10, 128.41, 124.11, 121.12, 120.92, 117.78, 100.51, 88.20, 83.11, 76.66, 75.32, 54.07, 46.54, 9.30, 9.27, 1.01. IR (neat, ATR) ν: 3035, 2921, 2143, 1753, 1635 1468, 1212, 765, 623. Chiral HPLC: 99.0:1.0 e.r., 98% ee, Chiralcel AD-H column (5% iPrOH/Hexanes, 1 mL/min, 254 nm); tR (minor)=12.5 min, tR (major)=16.1 min. HRMS (ESI+) m/z calculated for C24H18O4 [M+H]+: 371.1283, found: 371.1285.

Example 34: Synthesis of methyl (R)-6-(cyclopropylethynyl)-4-oxo-2-(phenylethynyl)chromane-2-carboxylate (Compound 7ai)

Prepared according to general procedure 2, using PhCl, (S)-Indanyl-BOX, chromone (53.6 mg, 0.20 mmol) and phenyl acetylene (29 μL, 0.26 mmol). 7ai was isolated as a yellow solid (29.6 mg, 0.080 mmol, 40% yield). Rf=0.43 (4:1, Hexanes:EtOAc), [α]22D=+63.8 (c=0.6, CHCl3), 1H NMR (500 MHz, CDCl3) δ 7.92 (d, J=2.2 Hz, 1H), 7.52 (dd, J=8.6, 2.2 Hz, 1H), 7.40-7.31 (m, 3H), 7.31-7.23 (m, 2H), 7.07 (d, J=8.6 Hz, 1H), 3.89 (s, 3H), 3.36 (d, J=16.7 Hz, 1H), 3.26 (d, J=16.7 Hz, 1H), 1.42 (tt, J=8.3, 5.0 Hz, 1H), 0.90-0.83 (m, 2H), 0.81-0.74 (m, 2H). 13C NMR (126 MHz, CDCl3) δ 188.20, 167.21, 157.82, 139.40, 132.30, 130.10, 129.69, 128.46, 120.77, 120.68, 118.80, 118.78, 93.85, 88.46, 82.92, 77.24, 74.23, 54.12, 46.08, 8.76, 0.21. IR (neat, ATR) ν: 3082, 2901, 2124, 1765, 1610, 1457, 1245, 714, 612. Chiral S45 HPLC: 90.7:9.3 e.r., 81% ee, Chiralcel AD-H column (5% iPrOH/Hexanes, 1 mL/min, 254 nm); tR (minor)=10.5 min, tR (major)=14.5 min. HRMS (ESI+) m/z calculated for C24H18O4 [M+H]+: 371.1283, found: 371.1285.

Example 35: Synthesis of methyl (R)-7-methyl-4-oxo-2-(phenylethynyl)chromane-2-carboxylate (Compound 7z)

Prepared according to general procedure 2, using PhCl, (S)-Indanyl-BOX, chromone (43.6 mg, 0.20 mmol) and phenyl acetylene (29 μL, 0.26 mmol). 7z was isolated as a yellow oil (26.8 mg, 0.084 mmol, 42% yield). Rf=0.39 (4:1, Hexanes:EtOAc), [α]22D=19.4 (c=0.6, CHCl3), 1H NMR (500 MHz, CDCl3) δ 7.79 (d, J=8.0 Hz, 1H), 7.41-7.36 (m, 2H), 7.36-7.31 (m, 1H), 7.31-7.25 (m, 2H), 6.97 (s, 1H), 6.90 (ddd, J=8.0, 1.5, 0.7 Hz, 1H), 3.89 (s, 3H), 3.36 (d, J=16.7 Hz, 1H), 3.25 (d, J=16.6 Hz, 1H), 2.38 (s, 3H). 13C NMR (126 MHz, CDCl3) δ 188.54, 167.53, S46 158.85, 148.34, 132.30, 129.57, 128.42, 126.81, 124.02, 120.99, 118.69, 118.64, 88.00, 83.36, 77.08, 54.05, 46.02, 22.17. IR (neat, ATR) ν: 3065, 2921, 2254, 1733, 1686, 1495, 1245, 761, 683. Chiral HPLC: 90.8:9.2 e.r., 82% ee, Chiralcel AD-H column (5% iPrOH/Hexanes, 1 mL/min, 254 nm); tR (minor)=12.5 min, tR (major)=14.4 min. HRMS (ESI+) m/z calculated for C20H16O4 [M+H]+: 321.1127, found: 321.1121.

Example 36: Synthesis of methyl (R)-7-bromo-4-oxo-2-(phenylethynyl)chromane-2-carboxylate (Compound 7aa)

Prepared according to general procedure 2, using PhCl, (S)-Indanyl-BOX, chromone (57.1 mg, 0.20 mmol) and phenyl acetylene (29 μL, 0.26 mmol). 7aa was isolated as a yellow oil (46.1 mg, 59% yield). Rf=0.45 (3:1, Hexanes:EtOAc), [α]22D=+26.3 (c=0.5, CHCl3), 1H NMR (500 MHz, CDCl3) δ 8.02 (d, J=8.5 Hz, 1H), 7.66 (d, J=8.2 Hz 1H), 7.61 (dd, 1H), 7.39-7.27 (m, 5H), 3.90 (s, 3H), 3.40-3.24 (m, 2H). 13C NMR (126 MHz, CDCl3) δ 188.04, 167.03, 158.97, 132.32, 131.08, 129.78, 128.49, 128.13, 126.38, 121.94, 119.79, 88.65, 82.69, 54.20, 45.98 IR (neat, ATR) ν: 3020, 2921, 2232, 1743, 1691, 1455, 1269, 1215, 739, 635. Chiral HPLC: 92.3:7.6 e.r., 85% ee, Chiralcel OD-H column (1% iPrOH/Hexanes, 1 mL/min, 254 nm); tR (minor)=19.2 min, S47 tR (major)=16.6 min. HRMS (ESI+) m/z calculated for C19H13BrO4 [M+H]+: 385.0075, found: 385.0070.

Example 37: Synthesis of methyl (R)-8-bromo-4-oxo-2-(phenylethynyl)chromane-2-carboxylate (Compound 7ab)

Prepared according to general procedure 2, using PhCl, (S)-Indanyl-BOX, chromone (57.1 mg, 0.20 mmol) and phenyl acetylene (29 μL, 0.26 mmol). 7ab was isolated as a yellow oil (56.3 mg, 73% yield). Rf=0.34 (1:1, Hexanes: EtOAc), [α]22D=+20.1 (c=0.5, CHCl3), 1H NMR (500 MHz, CDCl3) δ 7.87 (ddd J=8.0 Hz, J=6.4, J=1.0 1H), 7.79 (ddd J=7.5, J=5.0, J=0.7 1H), 7.41-7.27 (m, 5H), 7.0-7.27 (t, 1H), 3.44-3.28 (m, 2H). 13C NMR (126 MHz, CDCl3) δ 188.59, 188.30, 167.29, 159.23, 155.81, 140.21, 132.63, 132.59, 128.75, 126.64, 123.59, S48 122.44, 120.97, 112.68, 89.06, 88.91, 82.95, 54.49, 46.22. IR (neat, ATR) ν: 3019, 2954, 2212, 1743, 1676, 1451, 1277, 1263, 751, 630. Chiral HPLC: 97.2:2.8 e.r., 95% ee, Chiralcel OD-H column (1% iPrOH/Hexanes, 1 mL/min, 254 nm); tR (minor)=19.39 min, tR (major)=16.73 min. HRMS (ESI+) m/z calculated for C19H13BrO4 [M+H]+: 385.0075, found: 385.0070.

Example 38: Synthesis of methyl (R)-4-oxo-2-(phenylethynyl)-7-(trifluoromethyl)chromane-2-carboxylate (Compound 7ad)

Prepared according to general procedure 2, using PhCl, (S)-Indanyl-BOX, chromone (54.4 mg, 0.20 mmol) and phenyl acetylene (29 µL, 0.26 mmol). 7ad was isolated as a yellow oil (74.8 mg, 73% yield). Rf=0.30 (6:2, Hexanes: EtOAc), [α]22D=+78.1 (c=1.0, CHCl3), 1H NMR (500 MHz, CDCl3) δ 7.91 (d, J=7.8, 1H), 7.39 (bs, 1H), 7.28-7.21 (m, 4H), 7.0-7.14 (m, 2H), 3.32 S49-3.19 (m, 2H). 13C NMR (126 MHz, CDCl3) δ 188.04, 166.85, 158.56, 137.83, 132.32, 129.85, 128.51, 127.90, 124.22, 122.97, 120.58, 119.21, 116.40, 88.94, 54.25, 46.07. IR (neat, ATR) ν: 3070, 2926, 2235, 1745, 1691, 1202, 1111, 865, 730, 659. Chiral HPLC: 97.3:2.7 e.r., 95% ee, Chiralcel AD-H column (1% iPrOH/Hexanes, 1 mL/min, 254 nm); tR (minor)=7.99 min, tR (major)=6.95 min. HRMS (ESI+) m/z calculated for C20H13F3O4 [M+H]+: 375.0844, found: 375.0856.

Example 39: Synthesis of methyl (R)-7-fluoro-4-oxo-2-(phenylethynyl)chromane-2-carboxylate (Compound 7ac)

Prepared according to general procedure 2, using PhCl, (S)-Indanyl-BOX, chromone (44.8 mg, 0.20 mmol) and phenyl acetylene (29 µL, 0.26 mmol). 7ac was isolated as a yellow oil (45.1 mg, 70% yield). Rf=0.37 (4:1, Hexanes: EtOAc), [α]22D=+59.8 (c=0.6, CHCl3), 1H NMR (500 MHz, CDCl3) δ 7.87 (d, J=8.0 Hz 1H), 7.78 (d, J=7.8 1H), 7.41-7.27 (m, 5H), 6.98 (t, 1H), 3.90 (s, 3H), 3.44-3.28 (m, 2H). 13C NMR (126 MHz, CDCl3) δ 188.88, 167.44, 154.87, 153.19, S50 132.17, 129.47, 128.31, 125.40, 120.82, 120.74, 119.85, 107.42, 87.90, 83.22, 55.89, 53.92, 45.88. IR (neat, ATR) ν: 3047, 2926, 2231, 1751, 1689, 1459, 1271, 1222, 810, 652. Chiral HPLC: 95.5:4.5 e.r., 91% ee, Chiralcel OD-H column (1% iPrOH/Hexanes, 1 mL/min, 254 nm); tR (minor)=24.8 min, tR (major)=27.31 min. HRMS (ESI+) m/z calculated for C19H13FO4 [M+H]+: 325.0876, found: 325.0871.

Example 40: Synthesis of methyl (R)-5-methoxy-4-oxo-2-(phenylethynyl)chromane-2-carboxylate (Compound 7x)

Prepared according to general procedure 2, using PhCl, (S)-Indanyl-BOX, chromone (47.2 mg, 0.20 mmol) and phenyl acetylene (29 µL, 0.26 mmol). 7x was isolated as a clear oil (43.4 mg, 64% S51 yield). Rf=0.45 (3:2, Hexanes: EtOAc), [α]22D=+86.6 (c=0.6, CHCl3), 1H NMR (500 MHz, CDCl3) δ 7.45-7.42 (t, 1H), 7.40-7.27 (m, 5H) 6.76 (d, J=7.8 1H), 6.59 (d, J=6.6 1H), 3.91 (s, 3H), 3.88 (s, 3H), 3.36-3.22 (m, 2H). 13C NMR (126 MHz, CDCl3) δ 188.30, 167.28, 159.22, 132.58, 131.84, 130.03, 128.74, 128.38, 126.63, 122.19, 120.96, 120.05, 88.70, 82.94, 54.45, 46.23. IR (neat, ATR) ν: 3022, 2945, 2233, 1752, 1675, 1490, 1255, 1216, 1095, 721, 633. Chiral HPLC: 98.1:1.9 e.r., 96% ee, Chiralcel AD-H column (5% iPrOH/Hexanes, 1 mL/min, 254 nm); tR (minor)=23.6 min, tR (major)=33.2 min. HRMS (ESI+) m/z calculated for C20H16O5 [M+H]+: 337.1076, found: 337.1071.

Example 41: Synthesis of methyl (R)-7-methoxy-4-oxo-2-(phenylethynyl)chromane-2-carboxylate (Compound 7y)

Prepared according to general procedure 2, using PhCl, (S)-Indanyl-BOX, chromone (47.2 mg, 0.20 mmol) and phenyl acetylene (29 µL, 0.26 mmol). 7y was isolated as a clear oil (48.4 mg, 75% yield). Rf=0.45 (3:2, Hexanes: EtOAc), [α]22D=+86.6 (c=0.6, CHCl3), 1H NMR (500 MHz, CDCl3) δ 7.86 (d, 1H), 7.43-7.27 (m, 5H), 7.27-7.26 (t, 1H), 6.67 (d, J=7.0 Hz, 1H), 6.65 (dd, J=8.5, 1.0 Hz, 1H), 3.91 (s, 3H), 3.87 (s, 3H), 3.38-3.26 (m, 2H). 13C NMR (126 MHz, CDCl3) δ 188.30, 167.28, 159.22, 132.58, 131.84, 130.03, 128.74, 128.38, 126.63, 122.19, 120.96, 120.05, 88.70, 82.94, 54.45, 46.23. IR (neat, ATR) ν: 3022, 2945, 2233, 1752, 1675, 1490, 1255, 1216, 1095, 721, 633. Chiral HPLC: 99.6:0.3. e.r., 99% ee, Chiralcel OD-H column (5% iPrOH/Hexanes, 1 mL/min, 254 nm); tR (minor) =24.4 min, tR (major)=34.3 min. HRMS (ESI+) m/z calculated for C20H16O5 [M+H]+: 337.1076, found: 337.1071.

Example 42: Synthesis of methyl (S)-4-oxo-2-phenethylchromane-2-carboxylate (Compound 17)

Procedure in Guan, Y., et al., *Chem. Eur. J.* 2020, 26, 1742-1747 was followed. A solution of (R)-7a (287.5 mg, 0.94 mmol) dissolved in methanol (10 mL) was bubbled with N2 for 15 minutes. 10% Pd/C (77 mg, 20-30 wt %) was then added. N2 bubbling was continued for another 15 minutes before switching to H2 and then bubbling for another 15 minutes. The reaction vessel was then closed and watched for signs of H2 absorption. If rapid H2 absorption was not observed more catalyst was added (50 mg increments) and the atmosphere was again purged with H2 by bubbling for an additional 15 minutes. Once H2 absorption was observed the reaction was allowed to proceed for 5 h. The reaction was deemed complete, by NMR, once a mixture of chromanone and chroman was observed with no trace of alkenes. The reaction mixture was then filtered through a celite pad, and the pad was washed with EtOAc (3×20 mL). The solvent was removed to yield the crude product. The crude material was purified by column chromatography on SiO2 (eluent=4:1 Hexanes:EtOAc) to afford chromanone 17 as a yellow oil (190 mg, 0.613 mmol, 65% yield). Rf=0.42 (4:1, Hexanes:EtOAc), [α]23D=(c=−12.9, CHCl3), 1H NMR (500 MHz, CDCl3) δ 7.85 (dd, J=7.8, 1.7 Hz, 1H), 7.53 (ddd, J=8.4, 7.2, 1.8 Hz, 1H), 7.29 (tt, J=6.7, 0.8 Hz, 2H), 7.24-7.17 (m, 3H), 7.12 (dd, J=8.4, 1.0 Hz, 1H), 7.04 (ddd, J=8.0, 7.2, 1.1 Hz, 1H), 3.65 S57 (s, 3H), 3.19 (d, J=16.7 Hz, 1H), 2.97 (d, J=16.7 Hz, 1H), 2.90 (ddd, J=13.7, 10.3, 6.5 Hz, 1H), 2.70 (ddd, J=13.8, 10.5, 6.4 Hz, 1H), 2.34 (ddd, J=11.0, 6.1, 4.0 Hz, 2H). 13C NMR (126 MHz, CDCl3) δ 190.04, 171.60, 160.28, 140.49, 136.67, 128.70, 128.52, 126.93, 126.45, 122.01, 120.66, 118.33, 83.89, 53.06, 44.56, 39.71, 29.72. IR (neat, ATR) ν: 2893, 2251, 1735, 1699, 1607, 1411, 1299, 1259, 665. Chiral HPLC: 94.8:5.2 e.r., 90% ee, Chiralcel AD-H column (4% iPrOH/Hexanes, 1 mL/min, 254 nm); tR (minor)=12.3 min, tR (major)=13.3 min. HRMS (ESI+) m/z calculated for C19H18O4 [M+H]+ 311.1283, found 311.1278.

Example 43: Synthesis of methyl (S)-5-oxo-2-phenethyl-2,3,4,5-tetrahydrobenzo[f][1,4]oxazepine-2-carboxylate (Compound 18)

Followed a procedure from Trost, B. M. et al., *J. Am. Chem. Soc.* 2019, 141, 1489-1493. To a flame dried vial was added compound 17 (15.5 mg, 0.050 mmol), NaN3 (6.5 mg, 0.10 mmol) and toluene (0.5 mL). The mixture was cooled to 0° C. and S58 concentrated H2SO4 (24 µL, 0.45 mmol) was added dropwise. The solution was warmed up to room temperature and stirred vigorously at room temperature for 18 h. The reaction was quenched with water (0.5 mL) and 1M NaOH (1 mL), then extracted with EtOAc (3×10 mL). The combined organic phase was washed with brine (1×10 mL), then dried over Na2SO4. The solvent was removed under vacuum to yield crude methyl (S)-5-oxo-2-phenethyl- 2,3,4,5-tetrahydrobenzo[f][1,4]oxazepine-2-carboxylate. The crude product was purified by column chromatography on SiO2 (eluent EtOAc) to yield pure compound 18 as a colorless oil (13.0 mg, 0.040 mmol, 80% yield). Rf=0.62 (EtOAc), [α]23D=−63.1 (c=1.0, CHCl3), 1H NMR (500 MHz, CDCl3) δ 7.77 (dd, J=7.7, 1.8 Hz, 1H), 7.49 (ddd, J=8.0, 7.4, 1.8 Hz, 1H), 7.33-7.28 (m, 2H), 7.27-7.18 (m, 5H), 6.22 (t, J=6.1 Hz, 1H), 3.78 (s, 3H), 3.66 (dd, J=15.4, 6.1 Hz, 1H), 3.37 (dd, J=15.4, 6.2 Hz, 1H), 3.00 (ddd, J=13.8, 11.2, 4.9 Hz, 1H), 2.64 (ddd, J=13.9, 11.2, 5.9 Hz, 1H), 2.30 (ddd, J=13.8, 11.2, 4.9 Hz, 1H), 2.18 (ddd, J=13.8, 11.3, 5.9 Hz, 1H). 13C NMR (126 MHz, CDCl3) δ 171.65, 171.00, 153.40, 140.75, 133.40, 130.55, 128.68, 128.55, 127.24, 126.41, 124.87, 123.71, 90.36, 52.84, 46.51, 37.50, 29.95. IR (neat, ATR) ν: 2912, 2213, 1745, 1651, 1645, 1412, 1241, 1257, 1223, 1135, 1121, 741, 667. Chiral HPLC: 95.0:5.0 e.r., 90% ee, Chiralcel OD-H column (10% iPrOH/Hexanes, 1 mL/min, 254 nm); tR (minor)=19.4 min, tR (major)=26.6 min. HRMS (ESI+) m/z calculated for C19H19NO4 [M+H]+ 326.1392, found 326.1387.

Example 44: Synthesis of methyl (S)-2-phenethylchromane-2-carboxylate (Compound 19)

The procedure from Guan Y. et al., was followed. A solution of (R)-7a (25.5.5 mg, 0.083 mmol) dissolved in methanol (5 mL) was bubbled with N2 for 15 minutes. 10% Pd/C (10 mg, 20-30 wt %) was then added. N2 bubbling was continued for another 15 minutes before switching to H2 and then bubbling for another 15 minutes. The reaction vessel was then closed and watched for signs of H2 absorption. If rapid H2 absorption was not observed more catalyst was added (50 mg increments) and the atmosphere was again purged with H2 by bubbling for an additional 15 minutes. Once H2 absorption was observed the reaction was allowed to proceed for 10 h. The reaction was deemed complete, by NMR, once a mixture of chromanone and chroman was observed with no trace of alkenes. The reaction mixture was then filtered through a celite pad, and the pad was washed with EtOAc (3×20 mL). The solvent was removed to yield the crude product as a mixture of chromanone and chroman (9:1). The crude material was purified by column chromatography on SiO2 (eluent=4:1 Hexanes:EtOAc) to afford chromane (19) as a colorless oil (19.8 mg, 0.067 mmol, 81% yield). Rf=0.61 (4:1, Hexanes:EtOAc), [α]23D=−16.7 (c=1.0, CHCl3), 1H NMR (500 MHz, CDCl3) δ 7.31-7.27 (m, 2H), 7.23-7.17 (m, 3H), 7.16-7.11 (m, 1H), 7.04-6.99 (m, 1H), 6.97 (dd, J=8.2, 1.2 Hz, 1H), 6.86 (td, J=7.4, 1.2 Hz, 1H), 3.69 (s, 3H), 2.96 (ddd, J=13.7, 11.9, 5.0 Hz, 1H), 2.79-2.58 (m, 3H), 2.39 (ddd, J=13.5, 5.5, 3.6 Hz, 1H), 2.30 (ddd, J=13.9, 12.0, 5.1 Hz, 1H), 2.16 (ddd, J=13.8, 12.0, 5.0 Hz, 1H), 1.99 (ddd, J=13.5, 11.2, 6.2 Hz, 1H). 13C NMR (126 MHz, CDCl3) δ 173.56, 153.79, 141.52, 129.41, 128.58, 128.56, 127.72, 126.14, 120.99, 120.68, 117.03, 80.77, 52.58, 40.51, 29.86, 29.47, 22.63. IR (neat, ATR) ν: 2841, 2114, 1731, 1651, 1654, 1241, 1225, 611. Chiral HPLC: 94.8:5.2 e.r., 90% ee, Chiralcel AD-H column (3% iPrOH/Hexanes, 1 mL/min, 254 nm); tR (minor)=5.2 min, tR (major)=5.8 min. HRMS (ESI+) m/z calculated for C19H18O4 [M+H]+ 297.1491, found 297.1496.

Example 45: Synthesis of (S)-(2-phenethylchroman-2-yl)methyl 4-methylbenzenesulfonate (Compound 20)

To a flame dried vial was added methyl (S)-2-phenethylchromane-2-carboxylate (32.0 mg, 0.108 mmol), and dry THF (1 mL). The mixture was cooled to 0° C. and LAH (10 mg, 0.26 mmol) was added. The reaction was then warmed up to room temperature and stirred vigorously at room temperature overnight. The reaction was quenched with 1N HCl (0.5 mL), then extracted with EtOAc (3×10 mL). The combined organic phase was washed with brine (1×10 mL), then dried over Na2SO4. The solvent was removed under vacuum to yield the corresponding alcohol. To the vial containing purified alcohol (25.7 mg, 0.096 mmol) was added DMAP (1 mg, 0.008 mmol) and dry DCM (1 mL). Et3N (28 μL, 0.20 mmol) was added and the reaction vessel was cooled S61 to 0° C. and TsCl (21 mg, 0.11 mmol) was added. The reaction was then stirred at room temperature and monitored by TLC. Upon completion the reaction then extracted with EtOAc (3×10 mL). The combined organic phase was washed with brine (1×10 mL), then dried over Na2SO4. The solvent was removed under vacuum to yield crude (S)-(2-phenethylchroman-2-yl)methyl 4-methylbenzenesulfonate. The crude product was purified by column chromatography on SiO2 (eluent EtOAc) to yield pure 20 as a colorless oil (35.0 mg, 0.083 mmol, 77% yield over 2 steps). Rf=0.53 (EtOAc), [α]23D=−35.0 (c=1.0, CHCl3), 1H NMR (500 MHz, CDCl3) δ 7.79 (d, J=8.4 Hz, 2H), 7.37-7.29 (m, 2H), 7.29-7.21 (m, 2H), 7.21-7.14 (m, 1H), 7.14-7.04 (m, 3H), 7.01 (dd, J=7.6, 1.6 Hz, 1H), 6.83 (td, J=7.4, 1.2 Hz, 1H), 6.72 (dd, J=8.2, 1.3 Hz, 1H), 4.07 (d, J=9.8 Hz, 1H), 4.01 (d, J=9.9 Hz, 1H), 2.77-2.63 (m, 3H), 2.58 (td, J=13.4, 12.8, 5.6 Hz, 1H), 2.44 (s, 3H), 2.05-1.85 (m, 4H). 13C NMR (126 MHz, CDCl3) δ 153.01, 145.18, 141.68, 132.70, 130.08, 129.61, 128.56, 128.45, 128.16, 127.65, 126.09, 120.89, 120.60, 117.31, 75.90, 70.69, 37.29, 29.12, 26.59, 21.80, 21.27. IR (neat, ATR) ν: 2789, 2122, 1611, 1383, 1315, 1231, 655. Chiral HPLC: 95.0:5.0 e.r., 90% ee, Chiralcel AD-H column (5% iPrOH/Hexanes, 1 mL/min, 254 nm); tR (minor)=9.8 min, tR (major)=12.1 min. HRMS (ESI+) m/z calculated for C25H26O4S [M+H]+ 423.1630, found 423.1631.

Example 46: Synthesis of methyl 5-ethynylfuran-2-carboxylate

To a flame dried vial was added methyl 5-bromofuran-2-carboxylate (10.25 g, 50 mmol), Pd(PPh3)2Cl2 (702 mg, 1 mmol), CuI (190 mg, 1 mmol), dry THF (25 mL), and Et3N (25 mL). The mixture was stirred and degassed with nitrogen. TMS acetylene (8.30 mL, 60 mmol) was added under a nitrogen atmosphere. The reaction was stirred at 80° C. for 24 h. The reaction was then cooled to room temperature and filtered through a pad of celite to be then concentrated. The crude product was purified by column chromatography on SiO2 (eluent 1:4 DCM:Hexanes) to yield pure methyl 5-((trimethylsilyl)ethynyl)furan-2-carboxylate 3a as an off-white solid (10.5 g, 95% yield). Rf=0.43. 1H NMR (500 MHz, CDCl3-d) δ 7.13 (d, J=3.6 Hz, 1H), 6.63 (d, J=3.6 Hz, 1H), 3.90 (s, 3H), 0.25 (s, 9H). 13C NMR (126 MHz, CDCl3) δ 158.52, 144.39, 140.24, 118.73, 116.98, 102.31, 93.16, 52.25, −0.36. To a flame dried vial was then added CsF (1.14 g, 7.5 mmol), methyl 5-((trimethylsilyl)ethynyl)furan-2-carboxylate (1.11 g, 5 mmol), and MeOH (10 mL). The reaction was then stirred at room temperature for 24 hours. The reaction was quenched with water (10 mL), then extracted with EtOAc (3×10 mL). The combined organic phase was washed with brine (1×10 mL), then dried over Na2SO4. The solvent was removed under vacuum to yield crude methyl 5-ethynylfuran-2-carboxylate. The crude product was purified by column chromatography on SiO2 (eluent 1:2 DCM:Hexanes) to yield pure 4a as a white solid (715 mg, 95% yield). Rf=0.49. 1H NMR (500 MHz, CDCl3) δ 7.14 (d, J=3.6 Hz, 1H), 6.70 (d, J=3.5 Hz, 1H), 3.91 (s, 3H), 3.44 (s, 1H). 13C NMR (126 MHz, CDCl3) δ 158.42, 144.83, 139.34, 118.54, 117.59, 83.70, 73.04, 52.29. HRMS (ESI+) m/z calculated for C8H6O3 [M+H]+ 150.0395, found 150.0390.

Example 47: Synthesis of Methyl chromone-2-carboxylate (Compound 5a) by General Method A To a flame dried round bottom flask was added chromone-2-carboxylic acid (1.9 g, 10 mmol), thionyl chloride (9 mL, 123 mmol), and dry DMF (39 μL, 0.5 mmol). The reaction mixture was stirred at room temperature for 24 hours. Upon completion, the reaction mixture is homogenous. The reaction mixture is then concentrated under vacuum to obtain crude chromone-2-acid chloride which was carried to the next step without purification. To the flask containing the crude acid chloride was added DCM (50 mL). The solution was cooled to 0° C. then pyridine (0.85 mL, 10.5 mL) was added dropwise. Methanol (0.43 mL, 10.5 mmol) was then added dropwise and the reaction mixture was stirred at room temperature overnight. The reaction was quenched with water (20 mL), then extracted with DCM (3×20 mL). The combined organic phase was washed with brine (1×10 mL), then dried over Na2SO4. The solvent was removed under vacuum to yield crude methyl chromone-2-carboxylate. The crude was purified by column chromatography on SiO2 (eluent 1:5 EtOAc:Hexanes) to yield pure 5a as a white solid (1.55 g, 76% yield). Rf=0.25 (4:1, Hexanes:EtOAc), 1H NMR (500 MHz, CDCl3) δ 8.25-8.16 (m, 1H), 7.79-7.71 (m, 1H), 7.64-7.58 (m, 1H), 7.49-7.42 (m, 1H), 7.12 (s, 1H), 4.02 (s, 3H). 13C NMR (126 MHz, CDCl3) δ 178.43, 161.17, 156.08, 152.08, 134.89, 126.06, 125.90, 124.57, 118.88, 115.06, 53.67.

Example 48: Synthesis of Ethyl chromone-2-carboxylate (Compound 5ab)

Prepared according to the general method A using ethanol (0.61 mL, 10.5 mmol). Purified by column chromatography on SiO2 (eluent 1:6, EtOAc:Hexanes) to yield pure 5ab as a white solid (1.74 g, 80% yield). Rf=0.31 (4:1, Hexanes: EtOAc), 1H NMR (500 MHz, CDCl3) δ 8.25-8.17 (m, 1H), 7.79-7.71 (m, 1H), 7.65-7.59 (m, 1H), 7.50-7.41 (m, 1H), 7.12 (s, 1H), 4.47 (d, J=7.1 Hz, 2H), 1.44 (t, J=7.1 Hz, 3H). 13C NMR (126 MHz, CDCl3) δ 178.57, 160.69, 156.14, 152.37, 134.85, 126.03, 125.89, 124.58, 118.93, 114.92, 63.15, 14.23.

Example 49: Synthesis of Iso-propyl chromone-2-carboxylate (Compound 5ac)

Prepared according to the general method A using isopropanol (0.8 mL, 10.4 mmol). Purified by column chromatography on SiO2 (eluent 1:6, EtOAc:Hexanes) to yield pure 5ac as a white solid (1.45 g, 63% yield). Rf=0.40 (4:1, Hexanes:EtOAc), 1H NMR (500 MHz, CDCl3) δ 8.24-8.16 (m, 1H), 7.78-7.70 (m, 1H), 7.65-7.60 (m, 1H), 7.49-7.42 (m, 1H), 7.11 (s, 1H), 5.30 (hept, J=6.3 Hz, 1H), 1.41 (d, J=6.3 Hz, 7H). 13C NMR (126 MHz, CDCl3) δ 178.68, 160.18, 156.16, 152.67, 134.81, 125.98, 125.86, 124.57, 118.96, 114.78, 71.38, 21.84.

Example 50: Synthesis of Tert-butyl chromone-2-carboxylate (Compound 5ad)

Prepared according to the general method A using tert-butanol (1.0 mL, 10.5 mmol). Purified by column chromatography on SiO2 (eluent 1:8, EtOAc:Hexanes) to yield pure 5ad as a white solid (2.02 g, 82% yield). Rf=0.42 (4:1, Hexanes:EtOAc), 1H NMR (500 MHz, CDCl3) δ 7.77-7.70 (m, 1H), 7.63-7.58 (m, 1H), 7.48-7.41 (m, 1H), 7.05 (s, 1H), 1.62 (s, 9H). 13C NMR (126 MHz, CDCl3) δ 178.92, 159.52, 156.17, 153.23, 134.75, 125.91, 125.83, 124.51, 118.95, 114.46, 84.75, 28.07. HRMS (ESI+) m/z calculated for C14H15O4 [M+H]+ 247.0965, found 247.0965.

Example 51: Synthesis of benzyl 4-oxo-4H-chromene-2-carboxylate (Compound 5ae)

Prepared according to the general method A using benzyl alcohol (1.0 mL, 10.5 mmol). Purified by column chromatography on SiO2, (eluent 4:1, Hexanes:EtOAc) to yield pure 5ae as a white solid (2.02 g, 82% yield). Rf=0.32. 1H NMR (500 MHz, CDCl3) δ 8.19 (ddd, J=8.0, 1.7, 0.5 Hz, 1H), 7.74 (ddd, J=8.7, 7.1, 1.7 Hz, 1H), 7.61 (dd, J=8.5, 1.0 Hz, 1H), 7.49-7.37 (m, 6H), 7.15 (s, 1H), 5.43 (s, 2H). 13C NMR (126 MHz, CDCl3) δ 178.50, 160.57, 156.13, 152.14, 134.89, 134.57, 129.06, 128.94, 128.74, 126.08, 125.90, 124.59, 118.95, 115.21, 68.62. HRMS (ESI+) m/z calculated for C17H12O4 [M+H]+ 281.0814, found 281.0808.

Example 52: Synthesis of 2,2,2-trichloroethyl 4-oxo-4H-chromene-2-carboxylate (Compound 5af)

Prepared according to the general method A using trichloroethanol (0.96 mL, 10 mmol). Purified by column chromatography on SiO2, (eluent 4:1, Hexanes:EtOAc) to yield pure 5af as a white solid (1.52 g, 47% yield). Rf=0.34. 1H NMR (500 MHz, CDCl3) δ 8.22 (ddd, J=8.0, 1.7, 0.5 Hz, 1H), 7.77 (ddd, J=8.7, 7.1, 1.7 Hz, 1H), 7.64 (ddd, J=8.5, 1.1, 0.5 Hz, 1H), 7.48 (ddd, J=8.1, 7.1, 1.1 Hz, 1H), 7.25 (s, 1H), 5.02 (s, 2H). 13C NMR (126 MHz, CDCl3) δ 178.25, 159.23, 156.15, 150.82, 135.13, 126.31, 125.98, 124.64, 118.97, 116.10, 94.05, 75.32. HRMS (ESI+) m/z calculated for C12H7C13O4 [M+H]+ 320.0931, found 320.0943.

Example 53: Synthesis of isobutyl 4-oxo-4H-chromene-2-carboxylate (Compound 5g)

Prepared according to the general method A using isobutanol (1.4 mL, 15 mmol). Purified by column chromatography on SiO2, (eluent 8:1, Hexanes:EtOAc) to yield pure 5g as a white solid (1.75 g, 71% yield). Rf=0.44. 1H NMR (500 MHz, CDCl3) δ 8.22 (ddd, J=8.0, 1.7, 0.5 Hz, 1H), 7.77 (ddd, J=8.7, 7.1, 1.7 Hz, 1H), 7.64 (ddd, J=8.5, 1.1, 0.5 Hz, 1H), 7.48 (ddd, J=8.1, 7.1, 1.1 Hz, 1H), 7.25 (s, 1H), 5.02 (s, 2H). 13C NMR (126 MHz, CDCl3) δ 178.25, 159.23, 156.15, 150.82, 135.13, 126.31, 125.98, 124.64, 118.97, 116.10, 94.05, 75.32. HRMS (ESI+) m/z calculated for C14H14O4 [M+H]+ 247.0970, found 247.0965.

Example 54: Synthesis of methyl 7-(cyclopropylethynyl)-4-oxo-4H-chromene-2-carboxylate (Compound 5aj) by General Method B To a flame dried vial was added methyl 4-oxo-7-(((trifluoromethyl)sulfonyl)oxy)-4H-chromene-2-carboxylate (282 mg, 0.80 mmol), Pd(PPh3)4 (46 mg, 0.04 mmol), CuI (15 mg, 0.08 mmol), PPh3 (21 mg, 0.08 mmol), dry THF (8 mL), and Et3N (8 mL). The mixture was stirred and degassed with nitrogen. Ethynylcyclopropane (0.20 mL, 24 mmol) was added under a nitrogen atmosphere. The reaction was stirred at 80° C. for 20 h. The reaction was then cooled to room temperature and filtered through a pad of celite to be then concentrated. The crude product was purified by column chromatography on $SiO_2$ (eluent 1:5 EtOAc: Hexanes) to yield pure 5aj as a beige solid (142 mg, 66% yield). Rf=0.50. 1H NMR (500 MHz, $CDCl_3$) δ 8.07 (dd, J=8.2, 0.5 Hz, 1H), 7.62-7.51 (m, 1H), 7.39 (dd, J=8.3, 1.4 Hz, 1H), 7.08 (s, 1H), 4.00 (s, 3H), 1.50 (tt, J=8.3, 5.1 Hz, 1H), 0.98-0.92 (m, 2H), 0.89-0.84 (m, 2H). 13C NMR (126 MHz, $CDCl_3$) δ 177.90, 161.08, 155.85, 152.11, 131.20, 129.26, 125.65, 123.35, 121.35, 115.24, 99.44, 74.64, 53.66, 9.15, 0.47. HRMS (ESI+) m/z calculated for $C_{16}H_{12}O_4$ [M+H]+ 269.0814, found 269.0808.

Example 55: Synthesis of methyl 6-(cyclopropylethynyl)-4-oxo-4H-chromene-2-carboxylate (Compound 5al)

Prepared according to the general method B. Purified by column chromatography on $SiO_2$, (eluent 2:1, Hexanes: EtOAc) to yield pure 5al as a beige solid (140 mg, 65% yield). Rf=0.56. 1H NMR (500 MHz, $CDCl_3$-d) δ 8.17 (d, J=2.1 Hz, 1H), 7.69 (dd, J=8.7, 2.1 Hz, 1H), 7.50 (dd, J=8.7, 0.5 Hz, 1H), 7.08 (s, 1H), 4.01 (s, 3H), 1.46 (tt, J=8.2, 5.1 Hz, 1H), 0.94-0.87 (m, 2H), 0.87-0.80 (m, 2H). 13C NMR (126 MHz, $CDCl_3$) δ 177.72, 161.06, 154.98, 152.02, 137.72, 128.82, 124.39, 122.51, 118.94, 115.04, 95.75, 74.16, 53.70, 8.89, 0.28. HRMS (ESI+) m/z calculated for $C_{16}H_{12}O_4$ [M+H]+ 269.0814, found 269.0808.

Example 56: Synthesis of methyl 5-(cyclopropylethynyl)-4-oxo-4H-chromene-2-carboxylate (Compound 5ak) by general method C Prepared according to the general method C. Purified by column chromatography on $SiO_2$, (eluent 5:1, Hexanes: EtOAc) to yield pure 5ak as a beige solid (142 mg, 66% yield). Rf=0.45. 1H NMR (500 MHz, $CDCl_3$) δ 7.56 (dd, J=8.7, 7.3 Hz, 1H), 7.48-7.38 (m, 2H), 7.01 (s, 1H), 4.00 (s, 3H), 1.58 (tt, J=8.0, 5.2 Hz, 1H), 1.03-0.90 (m, 4H). 13C NMR (126 MHz, $CDCl_3$) δ 177.63, 161.10, 156.77, 150.84, 133.39, 131.97, 124.74, 123.57, 117.77, 115.93, 101.52, 74.79, 53.61, 9.31, 1.08. HRMS (ESI+) m/z calculated for $C_{16}H_{12}O_4$ [M+H]+ 269.0814, found 269.0808.

Example 57: Synthesis of methyl 4-oxo-7-phenyl-4H-chromene-2-carboxylate (Compound 5am) by General Method D To a flame dried Schlenk flask was added methyl 7-bromo-4-oxo-4H-chromene-2-carboxylate (566 mg, 2.0 mmol), phenylboronic acid (488 mg, 4 mmol), $Pd(PPh_3)_4$ (231 mg, 0.20 mmol), $K_3PO_4$ (1.27 g, 6.0 mmol), and dry toluene (20 mL). The mixture was stirred and degassed with nitrogen. The reaction was stirred at 100° C. for 20 h. The reaction was then cooled to room temperature. The reaction was quenched with water (20 mL), then extracted with EtOAc (3×20 mL). The combined organic phase was washed with brine (1×10 mL), then dried over $Na_2SO_4$. The solvent was removed under vacuum to yield crude methyl 4-oxo-7-phenyl-4H-chromene-2-carboxylate. The crude product was purified by column chromatography on $SiO_2$ (eluent 1:1:4 EtOAc:DCM:Hexanes) to yield pure 5am as a white solid (390 mg, 70% yield). Rf=0.47. 1H S68 NMR (500 MHz, $CDCl_3$) δ 8.25 (dd, J=8.3, 0.5 Hz, 1H), 7.83 (dd, J=1.7, 0.5 Hz, 1H), 7.74-7.63 (m, 3H), 7.51 (tt, J=6.7, 0.9 Hz, 2H), 7.48-7.42 (m, 1H), 7.14 (s, 1H), 4.03 (s, 3H). 13C NMR (126 MHz, $CDCl_3$) δ 178.20, 161.20, 156.47, 152.17, 148.06, 138.83, 129.31, 129.10, 127.52, 126.36, 125.17, 123.28, 116.72, 115.29, 53.69. HRMS (ESI+) m/z calculated for $C_{17}H_{12}O_4$ [M+H]+ 281.0814, found 281.0808.

Example 58: Synthesis of methyl 7-allyl-4-oxo-4H-chromene-2-carboxylate (Compound 5an) by General Method E To a flame dried Schlenk flask was added methyl 7-bromo-4-oxo-4H-chromene-2-carboxylate (566 mg, 2.0 mmol), $Pd(PPh_3)_4$ (116 mg, 0.1 mmol), allyltributylstannane (0.68 mL, 2.2 mmol) and benzene (20 mL). The mixture was stirred and degassed with nitrogen. The reaction was stirred at 95° C. for 18 h. The reaction was then cooled to room temperature and filtered through a pad of celite to be then concentrated. The reaction then extracted with EtOAc (3×20 mL). The combined organic phase was washed with brine (1×10 mL), then dried over $Na_2SO_4$. The solvent was removed under vacuum to yield crude methyl 7-allyl-4-oxo-4H-chromene-2-carboxylate. The crude product was purified by column chromatography on $SiO_2$ (eluent 1:4 EtOAc:Hexanes) to yield pure 5an as a white solid (370 mg, 76% yield). Rf=0.32. 1H NMR (500 MHz, $CDCl_3$-d) δ 8.12 (d, J=8.2 Hz, 1H), 7.44 (dd, J=1.5, 0.7 Hz, 1H), 7.31-7.27 (m, 1H), 7.09 (s, 1H), 5.97 (ddt, J=16.9, 10.1, 6.7 Hz, 1H), 5.21-5.12 (m, 2H), 4.01 (s, 3H), 3.53 (dt, J=6.8, 0.6 Hz, 2H). 13C NMR (126 MHz, $CDCl_3$) δ 178.29, 161.24, 156.32, 151.95, 148.50, 135.43, 127.01, 125.87, 122.86, 118.24, 117.75, 115.14, 53.64, 40.27. HRMS (ESI+) m/z calculated for $C_{14}H_{12}O_4$ [M+H]+ 245.0814, found 245.0814.

Example 59: Synthesis of methyl 4-oxo-7-vinyl-4H-chromene-2-carboxylate (Compound 5ao)

Prepared according to the general method E using tributyl (vinyl)stannane. Purified by column chromatography on $SiO_2$, (eluent 4:1, Hexanes:EtOAc) to yield pure 5ao as a white solid (145 mg, 64% yield). Rf=0.29. 1H NMR (500 MHz, $CDCl_3$) δ 8.14 (d, J=8.3 Hz, 1H), 7.59 (d, J=1.5 Hz, 1H), 7.50 (dd, J=8.4, 1.6 Hz, 1H), 7.10 (s, 1H), 6.85-6.74 (m, 1H), 5.97 (d, J=17.5 Hz, 1H), 5.52 (d, J=10.9 Hz, 1H), 4.02 (s, 3H). 13C NMR (126 MHz, $CDCl_3$) δ 178.06, 161.17, 156.46, 152.10, 144.40, 135.28, 126.09, 123.96, 118.75, 116.10, 115.25, 53.67 (1 sp2 carbon signal overlapped). HRMS (ESI+) m/z calculated for $C_{13}H_{10}O_4$ [M+H]+ 231.0657, found 231.0655.

Example 60: General Procedure for the Chromenone Synthesis (General Procedure F)

A solution of the 2'-hydroxy-6'-methoxyacetophenone (1 mmol) and the diester (1.1 mmol, 1.1 equiv.) in dry THF (5 mL) under nitrogen atmosphere was cooled to 0° C. Into this mixture was added NaH (60% in oil, 3.5 equiv.). The temperature was allowed to rise to room temperature and stirred overnight. The crude mixture was quenched with MeOH (2.5 mL) and acidified (pH 0-1) with concentrated HCl. The resultant heterogeneous mixture was stirred at room temperature an additional 24 h. MeOH was removed by rotary evaporation and the residue was diluted with EtOAc. The two layers were separated and the aqueous layer was washed with EtOAc (25 mL×3). The combined organic solution was dried using anhydrous $Na_2SO_4$, filtered, and concentrated under reduced pressure to give the crude product. The crude material was then purified on silica gel.

Example 61: General Procedure for Aryl Stannanes Syntheses (General Procedure G)

To a 20 mL reaction vial was added the aryl halide (0.1 mmol), (nBuSn)2 (2.0 equiv.), Pddba2 (0.1 equiv.), PtBu3HBF4 (0.2 equiv.), LiCl (5.0 equiv.), and dry dioxane (1 mL).

Nitrogen gas was then bubbled through the resulting mixture and the reaction was allowed to stirred at 50° C. for 4 h. The crude mixture was then filtered through celite and rinsed with EtOAc. The crude material was then concentrated under reduced pressure and purified by silica flash chromatography. Products were obtained as oils.

Example 62: General Procedure for Stille Coupling (General Procedure H)

To a 20 mL reaction vial was added the aryl tin monomer (0.1 mmol) and a magnetic stir bar. The vial was then placed under nitrogen atmosphere using a glovebox and CuCl (5.0 equiv.) and CuCl2 (1.0 equiv.) was added. The vial was sealed followed by addition of dry DMA (1 mL) and N2 was bubbled through. The reaction was allowed to stir at room temperature overnight. The mixture was quenched with NH4Cl (20 mL) and extracted with EtOAc (5×20 mL). The combined organic solution was dried using anhydrous Na2SO4, filtered, and concentrated under reduced pressure to give the crude product.

Example 63: BBr3-Mediated Demethylations (General Procedure I)

A solution of the methoxy dimer (0.02 mmol) in dry DCM (1.0 mL) under nitrogen atmosphere was cooled to −78° C. The BBr3 solution (1 M in heptane, 0.40 mmol, 20 equiv.) was slowly syringed into the reaction flask. The temperature was stirred at −78° C. for 2 h. The crude mixture is quenched with sat. aq. NH4Cl (4 mL) and diluted with DCM (5 mL). The two layers were separated, and the aq. layer was washed with DCM (10 mL×3). The combined organic solution was dried using anhydrous Na2SO4, filtered, and concentrated under reduced pressure to give the crude product. The crude material was then purified on silica gel.

Example 64: General Procedure for the PIFA Iodination (General Procedure J)

A solution of the chromenone/xanthone (1.0 mmol) in dry DCM at room temperature was treated with PIFA (1.2 equiv.) and 12 (0.6 equiv.). The mixture was then stirred under nitrogen at room temperature for 24 h. The solution was then quenched using saturated aqueous sodium bisulfite (10 mL) and extracted using DCM (25 mL×3). The combined organic solution was dried using anhydrous Na2SO4, filtered, and concentrated under reduced pressure to give the crude product. The crude material was then purified on silica gel.

Example 65: General Procedure for Suzuki Coupling (General Procedure K)

A flame-dried round-bottomed flask containing magnetic stir bar was charged with the degassed DCM/H2O solvent [4:1 (v/v)]. The flask was then charged with the aryl halide (0.1 mmol), Pd(OAc)2 (0.01 mmol, 10 mmol-%), S-Phos (0.06 mmol, 0.6 equiv.), B2Pin2 (0.06 mmol, 0.6 equiv.), K3PO4 (0.3 mmol, 3 equiv.). The mixture is heated under reflux (70° C.) for 18 hours and cooled to room temperature. The solids are then filtered off. The filtrate was diluted with DCM and water. The layers were separated and the aqueous layer was washed with DCM (20 mL×3). The combined organic solution was dried using anhydrous Na2SO4, filtered, and concentrated under reduced pressure to give the crude product. The crude material was then purified on silica gel.

Example 66: General Procedure for the Syntheses of Chiral Compounds (General Procedure L)

Into a round-bottomed flask containing 1-(2-hydroxy-6-methoxyphenyl)butane-1,3-dione (2 mmol) in anhydrous DCM (25 mL) was added anhydrous Et3N (0.45 mL, 6 mmol). The mixture was then cooled to 0° C. and the appropriate acid halide (2.5 mmol) was added. The mixture was then warmed to room temperature and stirred overnight. The mixture was then quenched with water (25 mL) and the two layers were separated. The aqueous layer was extracted with DCM (2×25 mL) and the combined organic solution was dried using anhydrous Na2SO4, filtered, and concentrated under reduced pressure to give the crude product as a dark brown oil. The crude product was then taken up with 25 mL of anhydrous DCM. Into this mixture was added anhydrous Et3N (0.45 mL, 6 mmol). The mixture was then stirred at room temperature for 36 h for complete reaction. The mixture was quenched with water and two layers were separated. The aqueous layer was extracted with DCM (2×25 mL) and the combined organic solution was dried using anhydrous Na2SO4, filtered, and concentrated under reduced pressure to give the crude product as a dark black oil. The crude product was then purified on silica gel.

Example 67: Synthesis of 2-Acetyl-3-hydroxy 4-Methylbenzenesulfonate

To a flame-dried round-bottomed flask was added dihydroxyacetophenone (15 g, 98.6 mmol) and dry DCM (500 mL). The solution was put under N2 cooled to 0° C. in an ice bath followed by the addition of N,Ndiisopropylethylamine (20.6 mL, 1.2 equiv.) and portion-wise addition of 4-toluenesulfonyl chloride (20.7 g, 1.1 equiv.). The reaction was brought to room temperature and left to stir for three days. The reaction was washed with deionized water (2×100 mL), $NaHCO_3$ (1×100 mL), and brine (1×100 mL). The combined organic solution was dried using anhydrous Na2SO4, filtered, and concentrated under reduced pressure to give the crude product. The crude material was then purified by flash chromatography (20% EtOAc/hexanes). Product obtained as white solid (62%). Rf=0.47 (EtOAc/hex, 1:4); M.p. 74-75° C.; 1H NMR (500 MHz, CDCl3) δ=12.44 (s, 1H), 7.73 (d, J=8.4 Hz, 2H), 7.35 (d, J=7.9 Hz, 2H), 7.29 (d, J=8.3 Hz, 2H), 6.89 (dd, J=8.5, 1.1 Hz, 1H), 6.46 (dd, J=8.1, 1.1 Hz, 1H), 2.69 (s, 3H), 2.47 (s, 3H). 13C NMR (126 MHz, CDCl3) δ=204.11, 163.76, 149.91, 146.52, 135.20, 132.45, 130.39, 128.89, 117.80, 115.63, 113.27, 32.90, 22.11; vmax=2925, 1635, 1493, 1371, 1189, 821, 769 cm-1; HRMS (ESI): calcd. for C15H15O5S [M+H+]: 307.0635, found 307.0633.

Example 68: Synthesis of 2-Acetyl-3-hydroxy-4-iodophenyl-methylbenzenesulfonate (Compound 30)

To a flame-dried round-bottomed flask was added 2-acetyl-3-hydroxy 4-methylbenzenesulfonate (17.8 g, 58.1 mmol) and dry DCM (550 mL). The solution was put under N2 cooled to 0° C. in an ice bath followed by the addition of trifluoroacetic acid (53 mL) and portion-wise addition of N-iodosuccinimide (14.3 g, 1.1 equiv.). The reaction was brought to room temperature and reacted for four days. The crude mixture was quenched with sodium sulfite (100 mL) and washed with $NaHCO_3$ (1×100 mL) and brine (1×100 mL). The combined organic solution was dried using anhydrous Na2SO4, filtered, and concentrated under reduced pressure to give the crude product. The crude material was then purified by flash chromatography (80% DCM/hexanes). Product obtained as yellow solid (86%). Rf=0.49 (EtOAc/hex, 1:4); M.p. 118-120° C.; 1H NMR (500 MHz, CDCl3) δ=13.39 (s, 1H), 7.79 (d, J=8.6 Hz, 1H), 7.73 (d, J=8.4 Hz, 2H), 7.37 (d, J=7.9 Hz, 2H), 6.30 (d, J=8.6 Hz, 1H), 2.71 (s, 3H), 2.48 (s, 3H). 13C NMR (126 MHz, CDCl3) δ=203.91, 162.22, 150.28, 146.82, 144.31, 132.16, 130.53, 128.93, 115.65, 115.02, 85.07, 32.66, 22.16; IR (neat): ṽmax=1627, 1410, 1356, 1170, 1090, 810, 754 cm-1; HRMS (ESI): calcd. for C15H14IO5S [M+H+]: 432.9601, found 432.9604.

Example 69: Synthesis of 1-(6-Hydroxy-3-iodo-2-methoxy)-acetophenone (Compound 31)

To a solution of 2-acetyl-3-hydroxy-4-iodophenyl-methylbenzenesulfonate (17.5 g, 40.5 mmol) in acetone (250 mL) was added K2CO3 (11.2 g, 2 equiv.). The reaction was stirred at room temperature for 30 min before the dropwise-addition of MeI (5.0 mL, 2 equiv.) and was then brought to reflux for 24 h. The crude mixture was brought to room temperature and filtered followed by extraction with DCM (2×100 mL) and concentrated under reduced pressure. The crude product was used immediately in the next step. To a round-bottomed flask was added 2-acetyl-4-iodophenyl-3-methoxy-methylbenzenesulfonate (18 g), 20% NaOH (67 mL), and tBuOH (112 mL). The mixture was brought to reflux for 24 h. The reaction was then brought to room temperature and neutralized with 2 N HCl (70 mL). The crude mixture was extracted with DCM (2×100 mL) and washed with deionized water (1×100 mL) and brine (1×100 mL). The combined organic layers were dried using anhydrous Na2SO4, filtered, and concentrated under reduced pressure to give the crude product. The crude material was then purified by flash chromatography (60% DCM/hexanes). Product obtained as yellow solid (80%). Rf=0.56 (EtOAc/hex, 1:9); M.p. 54-55° C.; 1H NMR (500 MHz, CDCl3) δ=12.58 (s, 1H), 7.79 (d, J=8.9 Hz, 1H), 6.61 (d, J=8.9 Hz, 1H), 3.84 (s, 3H), 2.76 (s, 3H). 13C NMR (126 MHz, CDCl3) δ=204.95, 164.37, 161.64, 145.60, 117.21, 116.56, 78.89, 62.78, 31.89; IR (neat): ṽmax=2940, 1621, 1447, 1323, 1210, 829 cm-1 HRMS (ESI): calcd. for C9H10IO3 [M+H+]: 292.9669, found 292.9668.

Example 70: Synthesis of Methyl 4-(6-Iodo-5-methoxy-4-oxo-4H-chromen-2-yl)butanoate (Compound 32a)

Prepared from common starting material 1-(6-hydroxy-3-iodo-2-methoxy)-acetophenone and the corresponding diester as outlined in Procedure F. Product obtained as an off-white solid (62%). Rf=0.24 (EtOAc/hex, 1:2); M.p. 87-89° C.; 1H NMR (500 MHz, CDCl3) δ=7.98 (d, J=8.9 Hz, 1H), 7.01 (d, J=8.9 Hz, 1H), 6.12 (s, 1H), 3.91 (s, 3H), 3.69 (s, 3H), 2.67-2.60 (t, J=7.2 Hz, 2H), 2.43 (t, J=7.2 Hz, 2H), 2.06 (p, J=7.3 Hz, 2H). 13C NMR (126 MHz, CDCl3) δ=176.42, 173.34, 166.87, 159.09, 158.63, 142.65, 119.31, 116.23, 111.72, 88.83, 62.27, 52.06, 33.23, 33.13, 22.08; IR (neat): ṽmax=1734, 1639, 1403, 1335, 1138, 1035, 844, 744 cm-1; HRMS (ESI): calcd. For C15H16IO5 [M+H+]: 403.0037, found 403.0027.

Example 71: Methyl 3-(6-Iodo-5-methoxy-4-oxo-4H-chromen-2-yl)propanoate (Compound 32b)

Prepared from common starting material 1-(6-hydroxy-3-iodo-2-methoxy)-acetophenone and the corresponding diester as outlined in Procedure F. Product obtained as a yellow solid (30%). Rf=0.25 (EtOAc/hex, 1:2); M.p. 103-104° C.; 1H NMR (500 MHz, CDCl3) δ=7.98 (d, J=8.9 Hz, 1H), 7.00 (d, J=8.9 Hz, 1H), 3.91 (s, 3H), 3.72 (s, 3H), 2.92 (t, J=7.5 Hz, 2H), 2.74 (t, J=7.4 Hz, 2H). 13C NMR (126 MHz, CDCl3) δ=176.35, 172.21, 165.88, 159.14, 158.56, 142.73, 119.32, 116.16, 111.57, 88.93, 62.29, 52.40, 30.92, 29.18; IR (neat): ṽmax=1731, 1649, 1411, 1352, 1168, 1048, 845, 793 cm-1; HRMS (ESI): calcd. for C14H14IO5 [M+H+]: 388.9880, found 388.9874.

Example 72: Synthesis of Methyl 2-(6-Iodo-5-methoxy-4-oxo-4H-chromen-2-yl)-2-methylpropanoate (Compound 32c)

Prepared from common starting material 1-(6-hydroxy-3-iodo-2-methoxy)-acetophenone and the corresponding diester as outlined in Procedure F. Product obtained as an off-white solid (50%). Rf=0.43 (EtOAc/hex, 1:2); M.p. 114-115° C.; 1H NMR (500 MHz, CDCl3) δ=7.99 (d, J=8.9 Hz, 1H), 7.01 (d, J=8.9 Hz, 1H), 6.27 (s, 1H), 3.92 (s, 3H), 3.72 (s, 3H), 1.58 (s, 6H). 13C NMR (126 MHz, CDCl3) δ=176.73, 173.83, 168.57, 159.08, 158.48, 142.90, 119.16, 116.24, 110.00, 88.90, 62.29, 53.20, 47.69, 23.82; IR (neat): ṽmax=1729, 1649, 1461, 1346, 1149, 1035, 827 cm-1; HRMS (ESI): calcd. for C15H16IO5 [M+H+]: 403.0037, found 403.0027.

Example 73: Synthesis of Methyl 6-Iodo-5-methoxy-4-oxo-4H-chromene-2-carboxylate (Compound 32d)

Prepared from common starting material 1-(6-hydroxy-3-iodo-2-methoxy)-acetophenone and the corresponding diester as outlined in Procedure F. Product obtained as a white solid (86%). Rf=0.27 (EtOAc/hex, 1:4); M.p. 153-155° C.; 1H NMR (500 MHz, CDCl3) δ=8.07 (d, J=9.0 Hz, 1H), 7.19 (d, J=8.9 Hz, 1H), 7.04 (s, 1H), 4.00 (s, 3H), 3.92 (s, 3H). 13C NMR (126 MHz, CDCl3) δ=176.45, 161.04, 159.17, 158.00, 150.87, 143.91, 120.11, 116.88, 116.46, 89.87, 62.37, 53.90; IR (neat): ṽmax=1731, 1639, 1409, 1368, 1258, 1125, 1041, 840, 770 cm-1; HRMS (ESI): calcd. for C12H10IO5 [M+H+]: 360.9567, found 360.9551.

Example 74: Synthesis of 6-Iodo-5-Methoxy-2-(tetrahydrofuran-2-yl)-4H-chromen-4-one (Compound 32e)

Prepared from common starting material 1-(6-hydroxy-3-iodo-2-methoxy)-acetophenone and the corresponding diester as outlined in Procedure F. Product obtained as yellow solid (74%). Rf=0.36 (EtOAc/Hex, 2:3); M.p. 94-95° C.; 1H NMR (500 MHz CDCl3) δ=7.98 (d, J=8.9 Hz, 1H), 7.02 (d, J=8.9 Hz, 1H), 6.36 (d, J=0.9 Hz, 1H), 4.80-4.73 (m, 1H), 4.10-4.04 (m, 1H), 3.99-3.93 (m, 1H), 3.91 (s, 3H), 2.42-2.29 (m, 1H), 2.14-2.05 (m, 1H), 2.05-1.97 (m, 2H); 13C NMR (126 MHz, [D]Chloroform) 6=176.37, 167.73, 159.02, 158.30, 142.54, 119.47, 116.09, 109.17, 88.73, 76.59, 69.57, 62.12, 31.12, 25.54; IR (neat): ν~max=2930, 1657, 1431, 1329, 1044, 856, 787 cm-1; HRMS (ESI): calcd. for C14H13IO4 [M+H+]: 372.9859, found 372.9915.

Example 75: Synthesis of Methyl 4-[5-Methoxy-4-oxo-6-(tributylstannyl)-4H-chromen-2-yl]butanoate (Compound 34a)

Prepared from corresponding aryl halide as outlined in Procedure G. Product obtained as a colorless oil (96%). Rf=0.22 (EtOAc/hex, 1:4); 1H NMR (500 MHz, CDCl3) δ=7.59 (d, J=8.2 Hz, 1H), 7.17 (d, J=8.1 Hz, 1H), 6.10 (s, 1H), 3.85 (s, 3H), 3.69 (s, 3H), 2.63 (t, J=7.5 Hz, 2H), 2.43 (t, J=7.3 Hz, 2H), 2.10-2.03 (m, 2H), 1.57-1.47 (m, 6H), 1.38-1.27 (m, 6H), 1.14-1.07 (m, 6H), 0.88 (t, J=7.3 Hz, 9H). 13C NMR (126 MHz, CDCl3) δ=177.82, 173.47, 166.34, 164.32, 159.55, 141.38, 132.13, 117.26, 114.25, 112.00, 63.06, 52.05, 33.27, 33.22, 29.44, 27.71, 22.21, 14.02, 10.50; HRMS (ESI): calcd. for C27H43O5Sn [M+H+]: 567.2127, found 567.2125.

Example 76: Synthesis of Methyl 3-[5-Methoxy-4-oxo-6-(tributylstannyl)-4H-chromen-2-yl]propanoate (Compound 34b)

Prepared from corresponding aryl halide as outlined in Procedure G. Product obtained as a colorless oil (95%). Rf=0.22 (EtOAc/hex, 1:4); 1H NMR (500 MHz, CDCl3) δ=7.59 (d, J=8.2 Hz, 1H), 7.16 (d, J=8.2 Hz, 1H), 6.12 (s, 1H), 3.84 (s, 3H), 3.72 (s, 3H), 2.92 (t, J=7.5 Hz, 2H), 2.75 (t, J=7.4 Hz, 2H), 1.57-1.47 (m, 6H), 1.38-1.27 (m, 6H), 1.14-1.06 (m, 6H), 0.88 (t, J=7.3 Hz, 9H). 13C NMR (126 MHz, CDCl3) δ=177.74, 172.39, 165.33, 164.33, 159.47, 141.45, 132.25, 117.25, 114.17, 111.79, 63.06, 52.37, 31.08, 29.44, 29.23, 27.70, 14.02, 10.50; HRMS (ESI): calcd. for C26H41O5Sn [M+H+]: 553.1970, found 553.1970.

Example 77: Synthesis of Methyl 2-[5-Methoxy-4-oxo-6-(tributylstannyl)-4H-chromen-2-yl]-2-methylpropanoate (Compound 34c)

Prepared from corresponding aryl halide as outlined in Procedure G. Product obtained as a colorless oil (95%). Rf=0.47 (EtOAc/hex, 1:4); 1H NMR (500 MHz, CDCl3) δ=7.59 (d, J=8.2 Hz, 1H), 7.17 (d, J=8.2 Hz, 1H), 6.26 (s, 1H), 3.86 (s, 3H), 3.72 (s, 3H), 1.58 (s, 6H), 1.54-1.48 (m, 7H), 1.37-1.29 (m, 6H), 1.14-1.07 (m, 6H), 0.88 (t, J=7.3 Hz, 9H). 13C NMR (126 MHz, CDCl3) δ=178.09, 174.13, 168.09, 164.28, 159.39, 141.63, 132.25, 117.12, 114.26, 110.17, 63.05, 53.15, 47.66, 29.44, 27.71, 23.90, 14.02, 10.50; HRMS (ESI): calcd. for C27H43O5Sn [M+H+]: 567.2127, found 567.2125.

Example 78: Synthesis of Methyl 5-Methoxy-4-oxo-6-(tributylstannyl)-4H-chromene-2-carboxylate (Compound 34d)

Prepared from corresponding aryl halide as outlined in Procedure G. Product obtained as a yellow oil (99%). Rf=0.56 (EtOAc/hex, 1:4); 1H NMR (500 MHz, CDCl3) δ=7.68 (d, J=8.2 Hz, 1H), 7.35 (d, J=8.2 Hz, 1H), 7.03 (s, 1H), 4.00 (s, 3H), 3.85 (s, 3H), 1.58-1.47 (m, 6H), 1.37-1.29 (m, 6H), 1.15-1.08 (m, 6H), 0.88 (t, J=7.3 Hz, 9H). 13C NMR (126 MHz, CDCl3) δ=177.80, 164.29, 161.43, 158.91, 150.54, 142.66, 133.49, 118.09, 116.82, 114.87, 63.14, 53.77, 29.42, 27.69, 14.01, 10.56; IR (neat): ν~max=2924, 1745, 1656, 1404, 1359, 1253, 1108, 1045, 873, 774 cm-1; HRMS (ESI): calcd. For C24H37O5Sn [M+H+]: 525.1657, found 525.1656.

Example 79: Synthesis of 5-Methoxy-2-(tetrahydrofuran-2-yl)-6-(tributylstannyl)-4Hchromen-4-one (Compound 34e)

Prepared from corresponding aryl halide as outlined in Procedure G. Product obtained as yellow oil (87%). Rf=0.67 (EtOAc/Hex, 2:3); 1H NMR (500 MHz, [D]Chloroform) δ=7.58 (d, J=8.1 Hz, 1H), 7.17 (d, J=8.2, 1.4 Hz, 1H), 6.33 (s, 1H), 4.77 (dd, J=8.0, 5.1 Hz, 1H), 4.10-3.91 (m, 2H), 3.84 (s, 3H), 2.39-2.06 (m, 2H), 2.03-1.98 (m, 2H), 1.54-1.49 (m, 5H), 1.37-1.28 (m, 7H), 1.13-1.07 (m, 5H), 0.90-0.85 (m, 9H); 13C NMR (126 MHz, [D]Chloroform) δ=178.00, 167.44, 164.45, 159.43, 141.49, 132.26, 114.34, 109.64, 76.96, 69.76, 63.11, 31.35, 29.57, 29.49, 29.41, 27.75, 25.77, 10.55; IR (neat): ν~max=2923, 1656, 1402, 1321, 1050, 862 cm-1; HRMS (ESI): calcd. for C26H40O4Sn[M+H+]: 537.1949, found 537.2004.

Example 80: Synthesis of Dimethyl 4,4'-(5,5'-Dimethoxy-4,4'-dioxo-4H,4'H-[6,6'-bichromene]-2,2'-diyl)dibutyrate (Compound 35a)

Prepared from corresponding aryl stannane as outlined in the Procedure H. Product obtained as a white solid (28%). Rf=0.59 (EtOAc/hex, 2:1); M.p. 57-58° C.; 1H NMR (500 MHz, CDCl3) δ=7.61 (d, J=9.0 Hz, 1H), 7.16 (d, J=9.0 Hz, 1H), 6.10 (s, 1H), 3.96 (s, 3H), 3.69 (s, 3H), 2.64 (t, J=7.6 Hz, 2H), 2.43 (t, J=7.3 Hz, 2H), 2.06 (p, J=7.3 Hz, 2H). 13C NMR (126 MHz, CDCl3) δ=176.87, 173.36, 166.94, 156.82, 155.45, 134.28, 125.30, 119.81, 115.02, 111.74, 62.20, 52.08, 33.24, 33.15, 22.12; IR (neat): ν~max=1741, 1642, 1408, 1341, 1296, 1143, 1041, 882, 751 cm-1; calcd. for [M+H+]: 560.1839.

Example 81: Synthesis of Dimethyl 3,3'-(5,5'-Dimethoxy-4,4'-dioxo-4H,4'H-[6,6'-bichromene]-2,2'-diyl)dipropionate (Compound 35b)

Prepared from corresponding aryl stannane as outlined in the Procedure H. Product obtained as a white solid (26%). Rf=0.33 (EtOAc/hex, 1:1); M.p. 112-113° C.; 1H NMR (500 MHz, CDCl3) δ=7.61 (d, J=9.0 Hz, 1H), 7.15 (d, J=9.0 Hz, 1H), 6.11 (s, 1H), 3.96 (s, 3H), 3.72 (s, 3H), 2.93 (t, J=7.3 Hz, 2H), 2.74 (t, J=7.3 Hz, 2H). 13C NMR (126 MHz, CDCl3) δ=176.77, 172.21, 165.93, 156.73, 155.46, 134.33, 125.38, 119.80, 114.95, 111.56, 62.19, 52.40, 30.93, 29.16; IR (neat): ν~max=1736, 1647, 1409, 1367, 1295, 1176, 1056, 830, 790 cm-1; calcd. for [M+H+]: 523.1526.

Example 82: Synthesis of Dimethyl 2,2'-(5,5'-Dimethoxy-4,4'-dioxo-4H,4'H-[6,6'-bichromene]-2,2'-diyl)bis(2-methylpropanoate) (Compound 35c)

Prepared from corresponding aryl stannane as outlined in the Procedure H Product obtained as a white solid (24%). Rf=0.50 (EtOAc/hex, 1:2); M.p. 109-110° C.; 1H NMR (500 MHz, CDCl3) δ=7.62 (d, J=9.0 Hz, 1H), 7.16 (d, J=9.0 Hz, 1H), 6.25 (s, 1H), 3.97 (s, 3H), 3.72 (s, 3H), 1.58 (s, 6H). 13C NMR (126 MHz, CDCl3) δ=177.15, 173.86, 168.63, 156.65, 155.40, 134.51, 125.40, 119.66, 115.03, 110.00, 62.20, 53.20, 47.68, 23.84; IR (neat): ν~max=1733, 1651, 1407, 1350, 1255, 1152, 1045, 822 cm-1; calcd. for [M+H+]: 551.1839.

Example 83: Synthesis of Dimethyl 5,5'-Dimethoxy-4,4'-dioxo-4H,4'H-[6,6'-bichromene]-2,2'-dicarboxylate (Compound 35d)

Prepared from corresponding aryl stannane as outlined in the Procedure H. Product obtained as a white solid (35%). Rf=0.21 (EtOAc/hex, 1:4); M.p. 151-153° C.; 1H NMR (500 MHz, CDCl3) δ=7.71 (d, J=9.1 Hz, 1H), 7.35 (d, J=9.1 Hz, 1H), 7.02 (s, 1H), 4.00 (s, 3H), 3.97 (s, 3H). 13C NMR (126 MHz, CDCl3) δ=176.93, 161.06, 156.19, 155.47, 150.94, 135.53, 126.25, 120.65, 116.37, 115.76, 62.28, 53.90; IR (neat): ν̃max=1744, 1651, 1455, 1314, 1257, 1121, 1044, 832, 776 cm-1; calcd. for [M+H+]: 467.0900.

Example 84: Synthesis of 5-Methoxychromone-2-tetrahydrofuran Dimer (Compound 35e)

Prepared from corresponding aryl stannane as outlined in the Procedure H. Product obtained as white solid (16%). Rf=0.33 (EtOAc/Hex, 2:3); M.p. 72-73° C.; 1H NMR (500 MHz CDCl3) δ=7.61 (d, J=9.0, 1.4 Hz, 1H), 7.16 (d, J=9.0, 1.0 Hz, 1H), 6.33 (s, 1H), 4.87-4.64 (m, 1H), 4.12-4.01 (m, 1H), 4.01-3.88 (m, 4H), 2.40-2.04 (m, 2H), 2.04-1.97 (m, 2H); 13C NMR (126 MHz, [D]Chloroform) 6=176.79, 167.81, 156.46, 155.32, 134.13, 125.18, 119.93, 114.86, 109.13, 76.57, 69.55, 62.01, 31.11, 25.53; IR (neat): ν̃max=1655, 1405, 1337, 1231, 1105, 1055, 855 cm-1; HRMS (ESI): calcd. for C28H26O8[M+H+]: 491.1628.

Example 85: Synthesis of Dimethyl 4,4'-(5,5'-Dihydroxy-4,4'-dioxo-4H,4'H-[6,6'-bichromene]-2,2'-diyl)dibutyrate (Compound 27a)

Prepared from the corresponding methoxy dimer as described in the Procedure I. Product obtained as an off-white solid (88%). Rf=0.42 (EtOAc/hex, 1:2); M.p. 63-64° C.; 1H NMR (500 MHz, CDCl3) δ=13.17 (s, 1H), 7.58 (d, J=9.0 Hz, 1H), 6.87 (d, J=9.0 Hz, 1H), 6.16 (s, 1H), 3.69 (s, 2H), 2.70 (t, J=7.6 Hz, 2H), 2.44 (t, J=7.2 Hz, 2H), 2.08 (p, J=7.3 Hz, 2H). 13C NMR (126 MHz, CDCl3) δ=183.31, 173.24, 170.74, 156.41, 155.40, 135.60, 115.61, 111.44, 109.04, 107.90, 77.61, 77.36, 77.11, 52.14, 33.83, 33.10, 22.22; IR (neat): ν̃max=1737, 1650, 1410, 1307, 1231, 1168, 1033, 963, 844 cm-1; calcd. for [M+H+]: 523.1526.

Example 86: Synthesis of Dimethyl 3,3'-(5,5'-Dihydroxy-4,4'-dioxo-4H,4'H-[6,6'-bichromene]-2,2'-diyl)dipropionate (Compound 27b)

Prepared from the corresponding methoxy dimer as described in the Procedure I. Product obtained as an off-white solid (89%). Rf=0.35 (EtOAc/hex, 1:2); M.p. 102-103° 1H NMR (500 MHz, CDCl3) δ=13.12 (s, 1H), 7.58 (d, J=9.3 Hz, 1H), 6.86 (d, J=9.0 Hz, 1H), 6.18 (s, 1H), 3.73 (s, 3H), 2.99 (t, J=7.4 Hz, 2H), 2.77 (t, J=7.4 Hz, 2H). 13C NMR (126 MHz, CDCl3) δ=183.27, 172.03, 169.62, 156.43, 155.33, 135.66, 115.73, 111.46, 109.02, 107.85, 52.50, 30.90, 29.75; IR (neat): ν̃max=1740, 1647, 1447, 1381, 1272, 1194, 1036, 970, 854 cm-1; calcd. for [M+H+]: 495.1213.

Example 87: Synthesis of Dimethyl 2,2'-(5,5'-Dihydroxy-4,4'-dioxo-4H,4'H-[6,6'-bichromene]-2,2'-diyl)bis(2-methylpropanoate) (Compound 27c)

Prepared from the corresponding methoxy dimer as described in the Procedure I. Product obtained as an off-white solid (91%). Rf=0.40 (EtOAc/hex, 1:4); M.p. 129-131° C.; 1H NMR (500 MHz, CDCl3) δ=13.04 (s, 1H), 7.60 (d, J=9.0 Hz, 1H), 6.87 (d, J=9.0 Hz, 1H), 6.31 (s, 1H), 3.73 (s, 3H), 1.60 (s, 6H). 13C NMR (126 MHz, CDCl3) δ=183.62, 173.49, 172.14, 156.33, 155.24, 135.85, 115.73, 111.40, 107.96, 107.44, 53.35, 48.23, 23.95; IR (neat): ν̃max=1743, 1656, 1443, 1387, 1256, 1153, 1091, 953, 852 cm-1; calcd. for [M+H+]: 523.1526.

Example 88: Synthesis of Dimethyl 5,5'-Dihydroxy-4,4'-dioxo-4H,4'H-[6,6'-bichromene]-2,2'-dicarboxylate (Compound 27d)

Prepared from the corresponding methoxy dimer as described in the Procedure I. Product obtained as an off-white solid (94%). Rf=0.34 (EtOAc/hex, 1:4); M.p. 149-151° C.; 1H NMR (500 MHz, CDCl3) δ=12.73 (s, 1H), 7.69 (d, J=9.0 Hz, 1H), 7.09 (s, 1H), 7.06 (d, J=9.0 Hz, 1H), 4.03 (s, 3H). 13C NMR (126 MHz, CDCl3) δ=183.59, 160.42, 156.29, 154.75, 153.46, 136.99, 116.65, 113.85, 112.58, 108.76, 54.16; IR (neat): ν̃max=1742, 1647, 1438, 1327, 1240, 1125, 1039, 974, 808 cm-1; calcd. for [M+H+]: 439.0587.

Example 89: Synthesis of 5-Hydroxychromone-2-tetrahydrofuran Dimer (Compound 27e)

Prepared from the corresponding methoxy dimer as described in the Procedure I. Product obtained as a yellow solid (22%). 1H NMR (500 MHz, CDCl3) δ=13.18 (s, 1H), 7.57 (d, J=8.9 Hz, 1H), 6.86 (d, J=9.0 Hz, 1H), 6.41 (s, 1H), 4.92-4.65 (m, 1H), 4.12-4.01 (m, 1H), 4.01-3.94 (m, 1H), 2.45-2.05 (m, 2H), 2.05-1.98 (m, 2H); 13C NMR (126 MHz, CDCl3) δ=183.08, 171.58, 156.05, 154.76, 135.19, 115.23, 111.28, 107.45, 106.09, 76.49, 69.43, 31.17, 25.27; HRMS (ESI): calcd. for C26H22O8[M+H+]: 463.1315.

Example 90: Synthesis of Methyl 4-(5-Methoxy-4-oxo-4H-chromen-2-yl)butanoate (Compound 37a)

Prepared from 2'-hydroxy-6'-methoxyacetophenone and corresponding diester, as described in the general procedure K. Ethyl ester was cleanly converted into the methyl ester under the reaction conditions. The pure product was obtained as a yellow solid (60%). Rf=0.32 (EtOAc); m.p. 76-78° C.; 1H NMR (500 MHz, CDCl3): δ=7.45 (t, J=8.8 Hz, 1H), 6.91 (d, J=9.4 Hz, 1H), 6.71 (d, J=8.3 Hz, 1H), 6.01 (s, 1H), 3.90 (s, 3H), 3.61 (s, 3H), 2.54 (t, J=7.6 Hz, 2H), 2.36 (t, J=7.3 Hz, 2H), 1.99 ppm (q, J=7.4 Hz, 2H); 13C NMR (125 MHz, CDCl3): δ=178.47, 173.49, 166.13, 160.10, 158.87, 133.86, 114.69, 112.04, 110.32, 106.62, 56.80, 52.06, 33.22, 22.13 ppm; IR (neat): ν̃max=1721, 1645, 1600, 1473, 1442, 1429, 1336, 1176, 856, 768 cm-1; HRMS (ESI): calcd. for C15H17O5 [M+H+]: 277.1071, found 277.1063.

Example 91: Synthesis of Methyl 3-(5-Methoxy-4-oxo-4H-chromen-2-yl)propanoate (Compound 37b)

Prepared from 2'-hydroxy-6'-methoxyacetophenone and corresponding diester, as described in the general procedure K. Ethyl ester was cleanly converted into the methyl ester under the reaction conditions. The pure product was obtained as a yellow solid (47%). Rf=0.36 (EtOAc); m.p. 87-89° C.; 1H NMR (500 MHz, CDCl3): δ=7.44 (t, J=10 Hz, 1H), 6.89 (d, J=5 Hz, 1H), 6.72 (d, J=5 Hz, 1H), 6.00 (s, 1H), 3.89 (s, 3H), 3.64 (s, 3H), 2.83 (t, J=8.3 Hz, 2H), 2.66 ppm (t, J=8.4 Hz, 2H); 13C NMR (125 MHz, CDCl3): δ=178.05, 172.16, 164.93, 159.86, 158.55, 133.74, 114.47, 111.60, 110.03, 106.53, 56.60, 52.12, 30.83, 28.92 ppm; IR (neat): ν~max=1721, 1634, 1581, 1470, 1420, 1342, 1076, 855, 706 cm-1; HRMS (ESI): calcd. For C14H15O5 [M+H+]: 263.0914, found 263.0908.

Example 92: Synthesis of Methyl 2,2-Dimethyl-2-(5-methoxy-4-oxo-4H-chromen-2-yl)ethanoate (Compound 37c)

Prepared from 2'-hydroxy-6'-methoxyacetophenone and corresponding diester, as described in the general procedure K. The pure product was obtained as a yellow solid (40%). Rf=0.68 (EtOAc); m.p. 125-127° C.; 1H NMR (500 MHz, CDCl3): δ=7.51 (t, J=8.4 Hz, 1H), 6.96 (d, J=8.6 Hz, 1H), 6.78 (d, J=8.6 Hz, 1H), 6.22 (s, 1H), 3.96 (s, 3H), 3.69 (s, 3H), 1.55 ppm (s, 6H); 13C NMR (125 MHz, CDCl3): δ=178.58, 174.09, 160.03, 158.68, 134.04, 114.53, 110.26, 110.23, 106.66, 56.81, 53.08, 47.55, 23.83 ppm; IR (neat): ν~max=1716, 1632, 1523, 1445, 1100, 965, 926, 827 cm-1; HRMS (ESI): calcd. For C15H17O5 [M+H+]: 277.1071, found 277.1076.

Example 93: Synthesis of Methyl (5-Methoxy-4-oxo-4H-chromen-2-yl)carboxylate (Compound 37d)

Prepared from 2'-hydroxy-6'-methoxyacetophenone and corresponding diester, as described in the general procedure K. The pure product was obtained as a yellow solid (60%). Rf=0.21 (EtOAc/hex, 1:1); m.p. 125-127° C.; 1H NMR (500 MHz, CDCl3): δ=7.65 (t, J=8.4 Hz, 1H), 7.19 (d, J=8.5 Hz, 1H), 7.05 (s, 1H), 6.88 (d, J=8.2 Hz, 1H), 4.02 ppm (s, 6H); 13C NMR (125 MHz, CDCl3): δ=178.41, 161.38, 160.16, 158.33, 150.48, 135.19, 116.93, 115.56, 110.89, 107.26, 56.85, 53.78 ppm; IR (neat): ν~max=1746, 1611, 1630, 1522, 1470, 1422, 1275, 1103, 815 cm-1; HRMS (ESI): calcd. for C12H11O5 [M+H+]: 235.0528, found 235.0593.

Example 94: Synthesis of 5-Methoxy-2-(tetrahydrofuran-2-yl)-4H-chromen-4-one (Compound 37e)

Prepared from 2'-hydroxy-6'-methoxyacetophenone and corresponding furan ester, as described in the general procedure K. The pure product was obtained as an yellow waxy solid (54%). Rf=0.4 (EtOAc); m.p. 56-59° C.; 1H NMR (500 MHz, CDCl3): δ=7.52 (t, J=8.6 Hz, 1H), 7.45 (d, J=8.8 Hz, 1H), 6.99 (d, J=8.2 Hz, 1H), 6.30 (s, 1H), 4.74 (m, 1H), 4.11 (m, 1H), 3.96 (s, 3H), 2.35 (m, 1H), 2.10 (m, 1H), 2.00 (m, 2H) ppm; 13C NMR (125 MHz, CDCl3): δ=177.02, 162.19, 160.61, 156.51, 143.15, 115.88, 114.11, 110.13, 108.89, 73.60, 69.85, 56.97, 31.20, 25.95 ppm; IR (neat): ν~max=1720, 1544, 1480, 1422, 821, 747, 721 cm-1; HRMS (ESI): calcd. for C14H15O4 [M+H+]: 247.0965, found 247.0971.

Example 95: Synthesis of Methyl 4-(8-Iodo-5-methoxy-4-oxo-4H-chromen-2-yl)butanoate (Compound 38a)

Prepared from corresponding 2'-substituted chromenone as described in the general procedure J. The pure product was obtained as a brown solid (62%). Rf=0.30 (EtOAc); m.p. 89-91° C.; 1H NMR (500 MHz, CDCl3): δ=7.90 (d, J=8.8 Hz, 1H), 6.60 (d, J=8.6 Hz, 1H), 6.09 (s, 1H), 3.92 (s, 3H), 3.66 (s, 3H), 2.66 (t, J=7.45 Hz, 2H), 2.45 (d, J=7.2 Hz, 2H), 2.15-2.05 ppm (m, 2H); 13C NMR (125 MHz, CDCl3): δ=203.87, 177.81, 173.22, 166.27, 160.50, 156.80, 143.00, 112.07, 108.78, 73.61, 56.89, 51.98, 41.15, 33.14, 32.98, 21.99 ppm; IR (neat): ν~max=1741, 1640, 1620, 1470, 1430, 1421, 1218, 1076, 820, 760 cm-1; HRMS (ESI): calcd. for C15H16IO5 [M+H+]: 403.0037, found 403.0018.

Example 96: Synthesis of Methyl 4-(8-Iodo-5-methoxy-4-oxo-4H-chromen-2-yl)propanoate (Compound 38b)

Prepared from corresponding 2'-substituted chromenone as described in the general procedure J. The pure product was obtained as a brown solid (68%). Rf=0.34 (EtOAc); m.p. 98-100° C.; 1H NMR (500 MHz, CDCl3): δ=7.93 (d, J=8.8 Hz, 1H), 6.64 (d, J=8.9 Hz, 1H), 6.15 (s, 1H), 3.96 (s, 3H), 3.72 (s, 3H), 2.98 (t, J=7.6 Hz, 2H), 2.84 ppm (t, J=7.05 Hz, 2H); 13C NMR (125 MHz, CDCl3): δ=177.89, 172.35, 165.27, 160.64, 156.82, 143.14, 115.63, 112.09, 108.92, 73.65, 57.0, 52.42, 30.92, 29.07 ppm; IR (neat): ν~max=1733, 1645, 1584, 1472, 1428, 1255, 1064, 846, 823 cm-1; HRMS (ESI): calcd. for C14H14IO5 [M+H+]: 388.9880, found 388.9870.

Example 97: Synthesis of Methyl 2,2-Dimethyl-2-(8-iodo-5-methoxy-4-oxo-4H-chromen-2-yl)ethanoate (Compound 38c)

Prepared from corresponding 2'-substituted chromenone as described in the general procedure J. The pure product was obtained as a off-white solid (58%). Rf=0.34 (EtOAc); m.p. 134-136° C.; 1H NMR (500 MHz, CDCl3): δ=7.94 (d, J=5 Hz, 1H), 6.64 (d, J=10 Hz, 1H), 6.25 (s, 1H), 3.96 (s, 3H), 3.74 (s, 3H), 1.61 ppm (s, 6H); 13C NMR (125 MHz, CDCl3): δ=178.22, 173.89, 168.47, 160.55, 156.72, 143.24, 110.29, 108.89, 73.67, 57.03, 53.27, 47.84, 24.067, 20.39 ppm; IR (neat): ν~max=1732, 1612, 1555, 1560, 1226, 1107, 975, 920, 828 cm-1; HRMS (ESI): calcd. for C15H16IO5 [M+H+]: 403.0037, found 403.0028.

Example 98: Synthesis of Methyl (8-Iodo-5-methoxy-4-oxo-4H-chromen-2-yl)carboxylate (Compound 38d)

Prepared from corresponding 2'-substituted chromenone as described in the general procedure J. The pure product was obtained as an off-white solid (76%). Rf=0.57 (EtOAc); m.p. 122-125° C.; 1H NMR (500 MHz, CDCl3): δ=8.04 (d, J=8.8 Hz, 1H), 7.04 (s, 1H), 6.69 (d, J=8.8 Hz, 1H), 4.01, (s, 3H), 3.99 ppm (s, 3H); 13C NMR (125 MHz, CDCl3): δ=177.89, 160.97, 160.63, 156.63, 150.75, 144.41, 116.92, 116.49, 109.40, 73.75, 57.05, 53.89 ppm; IR (neat): ν~max=1723, 1655, 1634, 1586, 1475, 1422, 1388, 1275, 1113, 815 cm-1; HRMS (ESI): calcd. for C12H10IO5 [M+H+]: 360.9567, found 360.9565.

Example 99: Synthesis of 8-Iodo-5-methoxy-2-(tetrahydrofuran-2-yl)-4H-chromen-4-one (Compound 38e)

Prepared from corresponding 2'-substituted chromenone as described in the general procedure J. The pure product was obtained as a yellow solid (70%). Rf=0.42 (EtOAc); m.p. 155-158° C.; 1H NMR (500 MHz, CDCl3): δ=7.94 (d, J=8.8 Hz, 1H), 6.64 (d, J=8.2 Hz, 1H), 6.34 (s, 1H), 4.83 (m, 1H), 4.11 (m, 1H), 3.98 (m, 1H), 3.95 (s, 3H), 2.37 (m, 1H), 2.20 (m, 1H), 2.10 (m, 1H), 2.01 ppm (m, 1H); 13C NMR (125 MHz, CDCl3): δ=178.02, 167.19, 160.65, 156.80, 143.15, 115.88, 110.13, 108.89, 76.90, 73.60, 69.85, 56.97, 31.20, 25.95 ppm; IR (neat): ν˜max=1648, 1512, 1455, 1225, 825, 790, 785 cm-1; HRMS (ESI): calcd. for C14H14IO4 [M+H+]: 372.9931, found 372.9924.

Example 100: Synthesis of Dimethyl 3,3'-(5,5'-Dimethoxy-4,4'-dioxo-4H,4'H-[8,8'-bichromene]-2,2'-diyl)dibutanoate (Compound 39a)

Prepared from the corresponding aryl iodide under Suzuki coupling conditions as described in the general procedure K. The pure product was obtained as a brown waxy solid (55%). Rf=0.24 (EtOAc/MeOH, 9:1); m.p. 62-68° C.; 1H NMR (500 MHz, CDCl3): δ=7.52 (d, J=10 Hz, 1H), 6.90 (d, J=10 Hz, 1H), 6.09 (s, 1H), 4.04 (s, 3H), 3.62 (s, 3H), 2.39 (t, J=8.8 Hz, 2H), 2.22 (d, J=8.6 Hz, 2H), 1.75 ppm (m, J=8.9 Hz, 2H); 13C NMR (125 MHz, CDCl3): δ=178.42, 173.14, 165.88, 160.03, 155.98, 135.55, 118.41, 114.62, 112.00, 106.46, 56.87, 52.02, 33.04, 32.94, 21.75 ppm; IR (neat): ν˜max=1731, 1647, 1593, 1436, 1262, 1168, 1096, 1072, 847, 817 cm-1; HRMS (ESI): calcd. for C30H31O10 [M+H+]: 551.1912, found 551.1907.

Example 101: Synthesis of Dimethyl 3,3'-(5,5'-Dimethoxy-4,4'-dioxo-4H,4'H-[8,8'-bichromene]-2,2'-diyl)dipropanoate (Compound 39b)

Prepared from the corresponding aryl iodide under Suzuki coupling conditions as described in the general procedure K. The pure product was obtained as a yellow waxy oil (60%). Rf=0.32 (EtOAc/MeOH, 9:1); 1H NMR (500 MHz, CDCl3): δ=7.50 (d, J=8.6 Hz, 1H), 6.89 (d, J=8.5 Hz, 1H), 6.09 (s, 1H), 4.03 (s, 3H), 3.60 (s, 3H), 2.68 (t, J=8.4 Hz, 2H), 2.41 ppm (t, J=8.8 Hz, 2H); 13C NMR (125 MHz, CDCl3): δ=178.25, 171.26, 164.82, 160.00, 155.82, 135.57, 118.27, 114.45, 111.80, 106.52, 56.88, 52.26, 30.33, 28.74 ppm; IR (neat): ν˜max=1734, 1644, 1610, 1593, 1578, 1492, 1389, 1198, 1098, 1076, 981, 859 cm-1; HRMS (ESI): calcd. for C28H27O10 [M+H+]: 523.1599, found 523.1592.

Example 102: Synthesis of Dimethyl 2,2'-(5,5'-Dimethoxy-4,4'-dioxo-4H,4'H-[8,8'-bichromene]-2,2'-diyl)bis(2-methylpropanoate) (Compound 39c)

Prepared from the corresponding aryl iodide under Suzuki coupling conditions as described in the general procedure K. The pure product was obtained as a colorless waxy oil (24%). Rf=0.30 (EtOAc/MeOH, 9.5:0.5); 1H NMR (500 MHz, CDCl3): δ=7.49 (d, J=8.5 Hz, 1H), 6.89 (d, J=8.5 Hz, 1H), 6.21 (s, 1H), 3.03 (s, 3H), 3.48 (s, 3H), 1.29 ppm (s, 6H); 13C NMR (125 MHz, CDCl3): δ=178.54, 173.47, 167.78, 159.95, 155.87, 135.56, 118.02, 110.44, 106.23, 56.91, 52.89, 47.61, 23.75, 19.99 ppm; IR (neat): ν˜max=1728, 1614, 1625, 1578, 1450, 1198, 1098, 1076, 928, 859 cm-1; HRMS (ESI): calcd. for C30H31O10 [M+H+]: 551.1912, found 551.1896.

Example 103: Synthesis of Dimethyl 5,5'-Dimethoxy-4,4'-dioxo-4H,4'H-[8,8'-bichromene]-2,2'-dicarboxylate (Compound 39d)

Prepared from the corresponding aryl iodide under Suzuki coupling conditions as described in the general procedure K. The pure product was obtained as a yellow oil (35%). Rf=0.24 (EtOAc/MeOH, 9.5:0.5); 1H NMR (500 MHz, CDCl3): δ=7.67 (d, J=8.5 Hz, 1H), 7.02 (s, 1H), 6.96 (d, J=8.6 Hz, 1H), 4.05, (s, 3H), 3.72 ppm (s, 3H); 13C NMR (125 MHz, CDCl3): δ=179.25, 160.12, 159.63, 157.63, 150.14, 144.41, 121.45, 117.92, 116.49, 110.40, 56.05, 53.80 ppm; IR (neat): ν˜max=1728, 1652, 1596, 1582, 1248, 1130, 1074, 1057, 815, 786 cm-1; HRMS (ESI): calcd. for C24H19O10 [M+H+]: 467.0973, found 467.0981.

Example 104: Synthesis of 5,5'-Dimethoxy-2,2'-bis(tetrahydrofuran-2-yl)-4H,4'H-[8,8'-bichromene]-4,4'-dione (Compound 39e)

Prepared from the corresponding aryl iodide under Suzuki coupling conditions as described in the general procedure K. The pure product was obtained as a waxy yellow oil (55%). Rf=0.16 (EtOAc/MeOH, 9.5:0.5); 1H NMR (500 MHz, CDCl3): δ=7.53 (d, J=10 Hz, 1H), 6.91 (d, J=10 Hz, 1H), 6.29 (s, 1H), 4.44 (m, 1H), 4.04 (s, 3H), 3.73 (m, 1H), 3.63 (m, 1H), 2.00 (m, 1H), 1.74-1.62 ppm (m, 3H); 13C NMR (125 MHz, CDCl3): δ=178.57, 166.89, 160.10, 155.99, 135.33, 118.77, 110.15, 106.49, 69.79, 69.72, 56.94, 30.90, 25.92 ppm; IR (neat): ν˜max=1655, 1601, 1512, 1411, 1220, 821, 785 cm-1; HRMS (ESI): calcd. for C28H27O8 [M+H+]: 491.1700, found 491.1690.

Example 105: Synthesis of Dimethyl 3,3'-(5,5'-Dihydroxy-4,4'-dioxo-4H,4'H-[8,8'-bichromene]-2,2'-diyl)dibutanoate (Compound 28a)

Prepared from the corresponding methoxy dimer as described in the general procedure I. However, the reaction was run for 6 hours at 0° C. The pure product was obtained as a yellow oil (60%). Rf=0.21 (EtOAc); 1H NMR (500 MHz, CDCl3): δ=12.11 (s, 1H), 7.55 (d, J=8.6 Hz, 1H), 6.92 (d, J=8.8 Hz, 1H), 6.11 (s, 1H), 3.61 (s, 3H), 2.38 (t, J=8.8 Hz, 2H), 2.22 (d, J=8.6 Hz, 2H), 1.75 ppm (m, J=8.9 Hz, 2H); 13C NMR (125 MHz, CDCl3): δ=177.42, 174.13, 166.88, 162.03, 156.98, 132.55, 119.41, 111.62, 112.00, 106.46, 52.02, 33.04, 32.94, 21.75 ppm; IR (neat): ν˜max=3418, 1723, 1548, 1478, 1466, 826, 723, 703 cm-1; HRMS (ESI): calcd. For C28H27O10 [M+H+]: 523.1599, found 523.1567.

Example 106: Synthesis of Dimethyl 3,3'-(5,5'-Dihydroxy-4,4'-dioxo-4H,4'H-[8,8'-bichromene]-2,2'-diyl)dipropanoate (Compound 28b)

Prepared from the corresponding methoxy dimer as described in the general procedure I. However, the reaction was run for 6 h at 0° C. The pure product was obtained as a waxy yellow oil (82%). Rf=0.21 (EtOAc); 1H NMR (500 MHz, CDCl3): δ=12.72 (s, 1H), 7.50 (d, J=5 Hz, 1H), 6.89 (d, J=5 Hz, 1H), 6.18 (s, 1H), 3.63 (s, 3H), 2.83 (t, J=8.6 Hz, 2H), 2.52 ppm (t, J=8.9 Hz, 2H); 13C NMR (125 MHz, CDCl3): δ=183.89, 171.88, 168.95, 161.23, 153.98, 137.55, 114.90, 111.78, 110.94, 109.11, 52.42, 30.38, 29.44 ppm; IR (neat): ν˜max=3220, 1730, 1649, 1612, 1579, 1415, 1238, 1169, 968, 783, 630 cm-1; HRMS (ESI): calcd. for C26H23O10 [M+H+]: 495.1286, found 495.1273.

Example 107: Synthesis of Dimethyl 2,2'-(5,5'-Dihydroxy-4,4'-dioxo-4H,4'H-[8,8'-bichromene]-2,2'-diyl)bis(2-methylpropanoate) (Compound 28c)

Prepared from the corresponding methoxy dimer as described in the general procedure I. However, the reaction was run for 6 h at 0° C. The pure product was obtained as a waxy yellow solid (46%). Rf=0.10 (EtOAc/MeOH, 9.9:

0.01); 1H NMR (500 MHz, CDCl3): δ=12.61 (s, 1H), 7.50 (d, J=8.5 Hz, 1H), 6.87 (d, J=8.5 Hz, 1H), 6.28 (s, 1H), 3.57 (s, 3H), 1.40 ppm (s, 6H); 13C NMR (125 MHz, CDCl3): δ=184.12, 173.22, 171.65, 160.99, 153.86, 137.67, 114.47, 111.43, 110.81, 107.70, 53.13, 48.29, 23.98 ppm; IR (neat): ν˜max=3318, 1734, 1646, 1620, 1578, 1411, 1055, 1013, 915, 828 cm-1; HRMS (ESI): calcd. for C28H27O10 [M+H+]: 523.1599, found 523.1622.

Example 108: Synthesis of Dimethyl 5,5'-Dihydroxy-4,4'-dioxo-4H,4'H-[8,8'-bichromene]-2,2'-dicarboxylate (Compound 28d)

Prepared from the corresponding methoxy dimer as described in the general procedure I. However, the reaction was run for 6 h at 0° C. The pure product was obtained as a yellow oil (47%). Rf=0.16 (EtOAc); 1H NMR (500 MHz, CDCl3): δ=7.68 (d, J=8.5 Hz, 1H), 7.05 (s, 1H), 6.92 (d, J=8.6 Hz, 1H), 3.78 ppm (s, 3H); 13C NMR (125 MHz, CDCl3): δ=178.25, 161.12, 160.43, 156.61, 151.14, 142.41, 120.45, 118.92, 116.50, 111.40, 50.80 ppm; IR (neat): ν˜max=2946, 1755, 1610, 1556, 1520, 1100, 1086, 1047, 811, 768 cm-1; HRMS (ESI): calcd. for C22H15O10 [M+H+]: 439.0660, found 439.071.

Example 109: Synthesis of 5,5'-Dihydroxy-2,2'-bis (tetrahydrofuran-2-yl)-4H,4'H-[8,8'-bichromene]-4,4'-dione (Compound 28e)

Prepared from the corresponding methoxy dimer as described in the general procedure I. However, the reaction was run for 6 h at 0° C. The pure product was obtained as a yellow solid (82%). Rf=0.37 (EtOAc/MeOH, 9.5:0.5); m.p. 172-175° C.; 1H NMR (500 MHz, CDCl3): δ=12.56 (s, 1H), 7.55 (d, J=8.6 Hz, 1H), 6.91 (d, J=8.5 Hz, 1H), 6.40 (s, 1H), 4.37 (m, 1H), 3.32 (m, 1), 1.74-1.62 ppm (m, 4H); 13C NMR (125 MHz, CDCl3): δ=184.11, 161.13, 153.61, 137.44, 111.97, 41.14, 33.54, 33.47, 33.36, 33.29, 29.94, 28.25 ppm; IR (neat): ν˜max=3475, 1649, 1591, 1471, 1410, 1240, 820, 800 cm-1; HRMS (ESI): calcd. for C26H23O8 [M+H+]: 463.1387, found 463.1375.

Example 110: Synthesis of 3-Acetyl-5-methoxy-2-methyl-4H-1-benzopyran-4-one (Compound 40)

Into a round-bottomed flask containing 1-(2-hydroxy-6-methoxyphenyl) butane-1,3-dione (2 g, 9.6 mmol) in acetic anhydride (15 mL) was added NaOAc (0.85 g, 10 mmol). The insoluble mixture was heated at reflux for 24 h. The solution was cooled to room temperature and diluted with water (25 mL) and stirred at room temperature for 15 min. The mixture was then extracted with DCM (3×50 mL) and the combined organic solution was dried using anhydrous Na2SO4, filtered, and concentrated under reduced pressure to give the crude product as a yellow flaky solid. The crude product was then purified on silica column to give the desired product as a flaky white solid (1.73 g, 78%). Rf=0.16 (EtOAc/hex, 1:1); m.p. 144-146° C.; 1H NMR (500 MHz, CDCl3): δ=7.55 (t, J=8 Hz, 1H), 6.98 (d, J=5 Hz, 1H), 6.82 (d, J=5 Hz, 1H), 3.98 (s, 3H), 2.60 (s, 3H), 2.43 ppm (s, 3H); 13C NMR (125 MHz, CDCl3): δ=201.33, 176.30, 166.50, 160.30, 157.73, 134.48, 125.40, 114.51, 110.09, 107.14, 32.52, 33.03, 19.56 ppm; IR (neat): ν˜max=1734, 1624, 1532, 1410, 1400, 1021, 1015, 840, 786 cm-1; HRMS (ESI): calcd. for C13H13O4 [M+H+]: 233.0808, found 233.0798.

Example 111: Synthesis of 3-Acetyl-8-iodo-5-methoxy-2-methyl-4H-1-benzopyran-4-one (Compound 41)

Prepared from corresponding 2', 3'-substituted chromenone as described in the general procedure J. The pure product was obtained as a pale white solid (67%). Rf=0.31 (EtOAc); m.p. 189-191° C.; 1H NMR (500 MHz, CDCl3): δ=7.97 (d, J=8.8 Hz, 1H), 6.67 (d, J=8.9 Hz, 1H), 3.99 (s, 3H), 2.60 (s, 3H), 2.52 ppm (s, 3H); 13C NMR (125 MHz, CDCl3): δ=200.70, 175.94, 166.79, 160.79, 156.07, 143.69, 125.34, 115.51, 109.31, 73.28, 57.02, 32.43, 19.48 ppm; IR (neat): ν˜max=1762, 1684, 1552, 1430, 1384, 1228, 1022, 1005, 845, 722 cm-1; HRMS (ESI): calcd. for C13H12IO4 [M+H+]: 358.9775, found 358.9770.

Example 112: Synthesis of 3,3'-Diacetyl-5,5'-dimethoxy-2,2'-dimethyl-4H,4'H-[8,8'-bichromene]-4,4'-dione (Compound 42)

The corresponding aryl iodide was homodimerized by subjecting it to Suzuki coupling as described in general procedure G. The pure product was obtained as a white solid (59%). Rf=0.50 (EtOAc/hex, 9:1); m.p. 176-178° C.; 1H NMR (500 MHz, CDCl3): δ=7.55 (d, J=10 Hz, 1H), 6.94 (d, J=10 Hz, 1H), 4.06 (s, 3H), 2.61 (s, 3H), 2.22 ppm (s, 3H); 13C NMR (125 MHz, CDCl3): δ=200.83, 176.30, 166.22, 160.34, 154.80, 136.24, 125.31, 117.72, 114.61, 107.07, 56.95, 32.53, 30.04, 19.45 ppm; IR (neat): ν˜max=1732, 1642, 1582, 1444, 1400, 1122, 1075, 914, 755 cm-1; HRMS (ESI): calcd. for C26H23O8 [M+H+]: 463.1387, found 463.1371.

Example 113: Synthesis of 3-Acetyl-5-hydroxy-2-methyl-4H-1-benzopyran-4-one Dimer (Compound 43)

Prepared from the corresponding methoxy dimer as described in the general procedure I. However, the reagents were mixed at 0° C. and the reaction was run overnight at room temperature. The pure product was obtained as a yellow solid (62%). Rf=0.17 (EtOAc); m.p. 124-126° C.; 1H NMR (500 MHz, CDCl3): δ=12.67 (s, 1H) 7.54 (d, J=5 Hz, 1H), 6.94 (d, J=5 Hz, 1H), 2.64 (s, 3H), 2.36 ppm (s, 3H); 13C NMR (125 MHz, CDCl3): δ=199.37, 182.08, 170.58, 161.83, 153.08, 138.36, 114.78, 112.84, 110.99, 32.95, 30.31, 20.60 ppm; IR (neat): ν˜max=3288, 1686, 1646, 1588, 1478, 1416, 1400, 1132, 1065, 814, 781 cm-1; HRMS (ESI): calcd. for C24H19O8 [M+H+]: 435.1074, found 435.1068.

Example 113: Synthesis of 1-(2-Hydroxy-6-methoxyphenyl)butane-1,3-dione (Compound 44)

A solution of the 2'-hydroxy-6'-methoxyacetophenone (10 g, 60 mmol) and the EtOAc (5.2 g, 10.1 mmol) in dry THF (200 mL) under nitrogen atmosphere was cooled to 0° C. Into this mixture was added NaH (60% in oil, 8.4 g, 3.5 equiv.) in 5 portions. The temperature was allowed to rise to room temperature and stirred overnight. The crude mixture was quenched with 0.1 N HCl and the pH was adjusted to pH 1. Most of the THF was then removed by rotary evaporation and the resulting mixture was diluted with EtOAc (150 mL). The two layers were separated and the aq. layer was washed with EtOAc (3×150 mL). The combined organic solution was dried using anhydrous Na2SO4, filtered, and concentrated under reduced pressure to give the crude product. The crude product was then dried thoroughly in vacuo to remove all EtOAc. The resulting residue was then triturated with hexanes to obtain the corresponding 1-(2-hydroxy-6-methoxyphenyl)butane-1,3-dione (11.2 g, 90%). This product was not purified any further.

Example 114: Synthesis of 3-Acetyl-5-methoxy-2-(methylacetyl)-4H-1-benzopyran-4-one (Compound 46a)

This compound was prepared as described in the general procedure G. 1-(2-hydroxy-6-methoxyphenyl)butane-1,3-dione was treated with commercially available acetoxyacetyl chloride. The crude product was purified on silica column to give the desired compound (72%) as a brown solid. Rf=0.17 (EtOAc/hex, 1:1); m.p. 122-125° C.; 1H NMR (500 MHz, CDCl3): δ=7.58 (t, J=8.4 Hz, 1H), 7.00 (d, J=9.3 Hz, 1H), 6.84 (d, J=8.4 Hz, 1H), 5.20 (s, 3H), 3.99 (s, 3H), 2.52 (s, 3H), 2.17 ppm (s, 3H); 13C NMR (125 MHz, CDCl3): δ=159.80, 176.49, 171.15, 170.36, 160.32, 157.56, 134.89, 122.37, 114.21, 110.14, 107.51, 70.67, 56.87, 20.88, 20.16 ppm; IR (neat): ν̃max=1736, 1697, 1609, 1474, 1442, 1429, 1411, 1221, 1059, 937, 809, 791 cm-1; HRMS (ESI): calcd. for C15H15O6 [M+H+]: 291.0863, found 291.0860.

Example 115: Synthesis of (S)-1-(3-Acetyl-5-methoxy-4-oxo-4H-chromen-2-yl)ethyl Acetate (Compound 46b)

This compound is prepared as described in the general procedure G. 1-(2-hydroxy-6-methoxyphenyl)butane-1,3-dione was treated with (S)-2-acetoxylactyl chloride. The crude product was purified on silica column to give the desired compound (81%) as a brown solid. Rf=0.16 (EtOAc/hex, 1:1); m.p. 75-78° C.; [α]20=0.59 (c=1.0 CHCl3); 1H NMR (500 MHz, CDCl3): δ=7.56 (t, J=8.4 Hz, 1H), 7.00 (d, J=9.2 Hz, 1H), 6.83 (d, J=8.3 Hz, 1H), 5.73 (q, J=6.8, 1H), 3.99 (s, 3H), 2.45 (s, 3H), 2.07 (s, 3H), 1.59 ppm (d, J=6.9, 3H); 13C NMR (125 MHz, CDCl3): δ=200.67, 176.07, 170.92, 169.04, 160.35, 157.70, 134.65, 123.39, 114.31, 110.11, 107.33, 75.87, 56.89, 21.05, 19.88, 16.73 ppm; IR (neat): ν̃max=1739, 1686, 1650, 1610, 1475, 1390, 1234, 1033, 819 cm-1; HRMS (ESI): calcd. for C16H17O6 [M+H+]: 305.1020, found 305.1016.

Example 116: Synthesis of (S)-1-(3-Acetyl-5-methoxy-4-oxo-4H-chromen-2-yl)-2-methylpropyl Acetate (Compound 46c)

This compound is prepared as described in the general procedure G. 1-(2-hydroxy-6-methoxyphenyl)butane-1,3-dione was treated with (S)-2-(acetyloxy)-3-methyl-butanoyl chloride. The crude product was purified on silica column to give the desired compound (66%) as a waxy brown solid. Rf=0.21 (EtOAc/hex, 1:1); m.p. 47-49° C.; [α]20=−44 (c=1.0 CHCl3); 1H NMR (500 MHz, CDCl3): δ=7.59 (t, J=8.4 Hz, 1H), 7.00 (d, J=9.3 Hz, 1H), 6.86 (d, J=8.4 Hz, 1H), 6.01 (d, J=3.2 Hz), 4.01 (s, 3H), 2.51 (s, 3H), 2.17 (s, 3H), 1.11 (d, J=6.9 Hz, 3H), 0.94 ppm (d, J=6.9 Hz, 3H); 13C NMR (125 MHz, CDCl3): δ=198.49, 175.55, 170.78, 169.05, 160.32, 157.47, 134.51, 123.09, 114.32, 109.90, 107.32, 83.29, 56.82, 29.21, 20.90, 20.33, 19.99, 16.82 ppm; IR (neat): ν̃max=1739, 1650, 1686, 1650, 1610, 1476, 1370, 1234, 1073, 1033, 799, 771, 752 cm-1; HRMS (ESI): calcd. for C18H21O6 [M+H+]: 333.1333, found 333.1320.

Example 117: Synthesis of 3-Acetyl-5-methoxy-2-(methylacetyl)-4H-1-benzopyran-4-one (Compound 47a)

Prepared from the corresponding starting material as described in the general procedure J. The pure product was obtained as a yellow solid (62%). Rf=0.27 (EtOAc); m.p. 182-184° C.; 1H NMR (500 MHz, CDCl3): δ=7.99 (d, J=8.8 Hz, 1H), 6.69 (d, J=8.9 Hz, 1H), 5.17 (s, 2H), 3.99 (s, 3H), 2.56 (s, 3H), 2.17 ppm (s, 3H); 13C NMR (125 MHz, CDCl3): δ=195.40, 176.11, 170.48, 160.76, 156.00, 144.06, 122.38, 115.22, 109.63, 73.25, 70.51, 57.07, 20.86, 20.05 ppm; IR (neat): ν̃max=1701, 1655, 1600, 1422, 1410, 1410, 1244, 927, 800, 742 cm-1; HRMS (ESI): calcd. for C15H14IO6 [M+H+]: 416.9830, found 418.9819.

Example 118: Synthesis of (S)-1-(3-Acetyl-8-iodo-5-methoxy-4-oxo-4H-chromen-2-yl)ethyl Acetate (Compound 47b)

Prepared from the corresponding starting material as described in the general procedure J. The pure product was obtained as a yellow solid (54%). Rf=0.24 (EtOAc); m.p. 147-150° C.; [α]20=−48 (c=1.0, CHCl3); 1H NMR (500 MHz, CDCl3): δ=7.99 (d, J=8.8 Hz, 1H), 6.67 (d, J=8.9 Hz, 1H), 5.69 (q, J=6.90 Hz, 1H), 3.98 (s, 3H), 2.52 (s, 3H), 2.07 (s, 3H), 1.57 ppm (d, J=7.0 Hz 3H); 13C NMR (125 MHz, CDCl3): δ=195.40, 176.11, 170.48, 160.76, 156.00, 144.06, 122.38, 115.22, 109.63, 73.25, 70.51, 57.07, 20.86, 20.05 ppm; IR (neat): ν̃max=1721, 1698, 1635, 1569, 1392, 1365, 1275, 1076, 817, 609 cm-1; HRMS (ESI): calcd. for C16H16IO6 [M+H+]: 430.9986, found 430.9974.

Example 119: Synthesis of (S)-1-(3-Acetyl-8-iodo-5-methoxy-4-oxo-4H-chromen-2-yl)-2-methylpropyl Acetate (Compound 47c)

Prepared from the corresponding starting material as described in the general procedure J. The pure product was obtained as a yellow solid (51%). Rf=0.18 (EtOAc); m.p. 132-134° C.; [α]20=−52 (c=1.0, CHCl3); 1H NMR (500 Hz, CDCl3): δ=7.97 (d, J=8.8 Hz, 1H), 6.67 (d, J=8.9 Hz, 1H), 5.93 (d, J=3.2 Hz), 3.97 (s, 3H), 2.55 (s, 3H), 2.48-2.42 (m, 1H), 2.14 (s, 3H), 1.07 (d, J=6.7 Hz, 3H), 0.90 ppm (d, J=6.9 Hz, 3H); 13C NMR (125 MHz, CDCl3): δ=198.11, 175.26, 170.87, 169.21, 160.85, 155.92, 143.80, 123.18, 115.37, 109.56, 83.26, 73.09, 57.09, 29.31, 20.97, 20.39, 19.94, 16.90 ppm; IR (neat): ν̃max=1730, 1662, 1631, 1610, 1410, 1224, 1010, 762, 765, 722 cm-1; HRMS (ESI): calcd. for C18H20IO6 [M+H+]: 459.0299, found 459.0286.

Example 120: Synthesis of (3,3'-Diacetyl-5-methoxy-4,4'-dioxo-4H,4'H-[8,8'-bichromene]-2,2'-diyl)bis(methylene) Diacetate (Compound 48a)

Prepared from the corresponding aryl iodide as described in the general procedure K. The pure product was obtained as a white solid (48%). Rf=0.56 (EtOAc/MeOH, 9:1); m.p. 190-192° C.; 1H NMR (500 MHz, CDCl3): δ=7.58 (d, J=8.8 Hz, 1H), 6.96 (d, J=8.7 Hz, 1H), 5.20 (s, 2H), 4.07 (s, 3H), 2.32 (s, 3H), 2.16 ppm (s, 3H); 13C NMR (125 MHz, CDCl3): δ=195.45, 176.45, 171.14, 169.98, 160.40, 154.64, 136.68, 122.38, 117.50, 114.35, 107.45, 70.61, 57.02, 20.85, 20.05 ppm; IR (neat): ν̃max=1721, 1621, 1551, 1420, 1403, 1021, 920, 852, 767 cm-1; HRMS (ESI): calcd. for C30H27O12 [M+H+]: 579.1487, found 579.1472.

Example 121: Synthesis of (1S,1'S)-(3,3'-Diacetyl-5-methoxy-4,4'-dioxo-4H,4'H-[8,8'-bichromene]-2,2'-diyl)bis(ethane-1,1-diyl) Diacetate (Compound 48b)

Prepared from the corresponding aryl iodide as described in the general procedure K. The pure product was obtained as a white brown solid (52%). Rf=0.60 (EtOAc/MeOH, 9:1); m.p. 153-155° C.; [α]20=−71 (c=1.0, CHCl3); 1H NMR (500 MHz, CDCl3): δ=7.57 (d, J=8.6 Hz, 1H), 6.95 (d, J=8.6 Hz, 1H), 5.71 (q, J=5.30 Hz, 1H), 4.06 (s, 3H), 2.23 (s, 3H), 2.06 (s, 3H), 1.59 ppm (d, J=6.8 Hz 3H); 13C NMR (125 MHz, CDCl3): δ=200.37, 176.11, 170.95, 168.66, 160.40, 154.75, 136.36, 123.48, 117.70, 114.40, 107.28, 75.74, 57.02, 21.01, 19.67, 16.69 ppm; IR (neat): ν̃max=1718, 1643, 1622, 1607, 1551, 1418, 1078, 903, 760, 745 cm-1; HRMS (ESI): calcd. for C32H31O12 [M+H+]: 607.1810, found 607.1804.

Example 122: Synthesis of (1S,1'S)-(3,3'-Diacetyl-5-methoxy-4,4'-dioxo-4H,4'H-[8,8'-bichromene]-2,2'-diyl)bis(2-methylpropane-1,1-diyl) Diacetate (Compound 48c)

Prepared from the corresponding aryl iodide as described in the general procedure K. The pure product was obtained as a waxy brown solid (40%). Rf=0.35 (EtOAc/MeOH, 9.5:0.5); m.p. 86-88° C.; [α]20=−26 (c=1.0, CHCl3); 1H NMR (500 MHz, CDCl3): δ=7.56 (d, J=8.6 Hz, 1H), 6.94 (d, J=8.7 Hz, 1H), 5.95 (d, J=3.3 Hz), 4.05 (s, 3H), 2.47 (m, 1H), 2.25 (s, 3H), 2.13 (s, 3H), 1.08 (d, J=6.9 Hz, 3H), 0.89 ppm (d, J=6.9 Hz, 3H); 13C NMR (125 MHz, CDCl3): δ=198.19, 175.62, 170.87, 168.634, 160.42, 154.57, 136.29, 123.23, 117.53, 107.34, 83.21, 57.01, 29.28, 25.19, 20.94, 19.83, 16.84 ppm; IR (neat): ν̃max=1744, 1632, 1611, 1607, 1455, 1483, 1070, 754, 761, 741 cm-1; HRMS (ESI): calcd. for C36H39O12 [M+H+]: 663.2436, found 663.2430.

Example 123: Cell Culture

Jurkat and L5178Y cells were cultured in RPMI 1640 (ATCC), HL60 cells were cultured in Iscove's Modified Dulbecco's Medium (IMDM, ATCC), KB and MCF7 cells were cultured in Eagles Minimum Essential Medium (EMEM, ATCC), and SKOV3 cells in McCoy's 5a Medium (ATCC) supplemented with 10% Heat Inactivated Fetal Bovine Serum (FBS), and Penicillin and Streptomycin (P/S) at 37° C. in a 5% CO2 incubator.

Example 124: Cytotoxicity Assays

Proliferating cells were seeded at approximately 20×103 cells per 50 μL per well into 96 well plates using a MultiFlo FX multi-mode dispenser (BioTek). On reaching ≈40% cell density, the cells were then incubated with varying concentrations (195 nM to 200 μM final) of test samples using a Biomek FXP Automated Workstation (Beckman Coulter). 48 hours post drug incubation, cell viability was determined using Promega's CellTiter-Glo Luminescent Cell Viability Assay according to the manufacturer's protocol on a plate reader (EnVision from PerkinElmer) in Luminescence mode. In each experiment, each unique condition (i.e., different sample type and concentration) was tested in triplicate. The percentage of test sample induced toxicity was calculated with respect to DMSO treated cells and graphed to give dose response curves. IC50 values for each treatment were calculated using Graph-Pad Prism 8.0 Software.

Example 125: Reagents

Anhydrous toluene, dichloromethane, diethyl ether and THF were dried using a pure process technologies solvent system. Anhydrous DCE, chlorobenzene, m-xylene, and o-xylene were used as received. Chromone was used as received. Substituted chromones were used as received or prepared according to literature. CuI was used as received and stored in a desiccator under ambient lab conditions. TBSOTf was vacuum distilled and stored under dry nitrogen. DIPEA was used as received. Alkynes were used as received. All other reagents were used directly as received from the manufacturer unless otherwise noted. Preparative silica gel chromatography was performed using SiliaFlash F60 silica gel (40-63 μm). Analytical thin layer chromatography was performed using Analtech 250 μm silica gel HLF plates and visualized under UV 254 nm or 365 nm. All 1H NMR spectra were acquired using a Bruker BioSpin 500 MHz Avance III Digital NMR spectrometer and calibrated using the solvent signal (CDCl3 7.26 ppm). J Coupling constants are reported in Hz. Multiplicities are reported as follows: s, singlet; d, doublet; t, triplet; q, quartet; p, pentet; hept, heptet; m, multiplet; b, broad; dd, doublet of doublets; ddd, doublet of doublet of doublets; td, triplet of doublets; ddt, doublet of doublet of triplets; dtd, doublet of triplet of doublets. All 13C NMR spectra were acquired using a Bruker BioSpin 126 MHz Avance III Digital NMR spectrometer and calibrated using the solvent signal (CDCl3 77.16 ppm). Infrared spectra were acquired using a Bruker Vertex 70 with an ATR accessory. High resolution mass spectra were acquired using an Agilent 6520 Q-TOF mass spectrometer. Chiral HPLC analysis was performed using an Agilent 1260 equip with a diode array detector using Chiralcel OD-H or AD-H columns. Optical Rotations were acquired on a JASCO P-2000 Digital Polarimeter with a sodium lamp (λ=589 nm).

Example 126: General Procedure for Enantioselective Alkynylation with Cu-BOX Catalyst Procedure I (Pre-Generation of Siloxybenzopyrylium)

To an 8 mL screw top vail was added chromone (17.5 mg, 0.12 mmol, 1.2 eq) and o-xylene (0.8 mL). TBSOTf (30 μL, 0.13 mmol, 1.3 eq) was then added and the mixture was stirred for 1 h at 80° C. to generate siloxybenzopyrylium. To a separate 8 mL vial was added CuI (1.9 mg, 0.01 mmol, 10 mol %), (S)-Bn-Box (4.4 mg, 0.012 mmol, 12 mol %) and o-xylene (0.2 mL). The atmosphere in the flask was purged with dry N2. This flask was then cooled to −78° C. on a dry ice and acetone bath, then iPr2NEt (26 μL, 0.15 mmol, 1.5 eq), phenyl acetylene (11 μL, 0.1 mmol, 1.0 eq) and the pre-generated solution of siloxybenzopyrylium were added. The reaction mixture was transferred to the lab freezer at −28° C. and was allowed to react for 48 h. The reaction was quenched by the addition of 6N HCl (1 mL) and stirred for 2 hours. The reaction mixture was extracted with EtOAc (3×2 mL), washed with saturated $NaHCO_3$ solution, dried over anhydrous NaSO4, and the solvent removed under vacuum to obtain the crude product. The crude product was purified by column chromatography on silica gel with Hexane:EtOAc (9:1) to afford an off white solid (72% yield, 97% ee).

Example 127: General Procedure II (In-Situ Generation of Siloxybenzopyrylium)

To an 8 mL screw top vial was added chromone (29.2 mg, 0.2 mmol, 1.0 eq), CuI (3.8 mg, 0.02 mmol, 10 mol %), (S)-Bn-BOX (8.8 mg, 0.024 mmol, 12 mol %), o-xylene (2 mL), i-Pr2NEt (52.3 μL, 0.3 mmol, 1.5 eq), and phenyl acetylene (28.6 μL, 0.26 mmol, 1.3 eq) in that order at room temperature. This mixture was allowed to stir for 30 minutes. The vial was purged with dry N2 and then cooled to −78° C. TBSOTf (60 μL, 0.26 mmol, 1.3 eq) was added at −78° C., then the reaction was transferred to the lab freezer at −28° C. and allowed to react for 48 h. The reaction S3 was quenched by the addition of 6N HCl (2 mL) and stirred for 2 hours. The reaction mixture was extracted with EtOAc (3×2 mL), washed with saturated $NaHCO_3$ solution, dried over anhydrous NaSO4, and the solvent removed under vacuum to obtain the crude product. The crude product was purified by column chromatography on silica gel with Hexane:EtOAc (9:1) to afford an off white solid (48.8 mg, 98% yield, 97% ee).

Example 128: Synthesis of (R)-(−)-2-(phenylethynyl)chroman-4-one (Compound 50a)

Prepared according to general procedure II, using chromone 5a (29.2 mg, 0.20 mmol) and phenyl acetylene (28.6 μl, 0.26 mmol). 50a was isolated as an off white solid (48.8 mg, 0.197 mmol, 98% yield). Rf=0.60 (8:2, Hexanes: EtOAc), [α]22D=−113.3 (c=0.7, CHCl3), lit. [4] for R isomer [α]22D=−99.84 (c=1.0, CHCl3), 1H NMR (500 MHz, CDCl3) δ 7.93 (dd, J=8.2, 1.8 Hz, 1H), 7.52 (ddd, J=8.3, 7.2, 1.8 Hz, 1H), 7.45-7.40 (m, 2H), 7.37-7.28 (m, 3H), 7.10-7.04 (m, 2H), 5.50 (dd, J=7.7, 5.2 Hz, 1H), 3.14-3.02 (m, 2H). 13C NMR (126 MHz, CDCl3) δ 190.58, 160.32, 136.37, 132.13, 129.24, 128.46, 127.12, 122.14, 121.63, 121.24, 118.40, 87.54, 84.65, 68.20, 43.62. IR (neat, ATR) ν: 3035, 2921, 2232, 1693, 1609, 1472, 1342, 1218, 753, 689. Chiral HPLC: 98.6:1.4 e.r., 97% ee, Chiralcel OD-H column (5% iPrOH/Hexanes, 1 mL/min, 254 nm); tR (minor)=9.6 min, tR (major)=12.0 min. HRMS (ESI+) m/z calculated for C17H13O2 [M+H]+ 249.0910, found 249.0904.

Example 129: Synthesis of (R)-2-((4-methoxyphenyl)ethynyl)chroman-4-one (Compound 50b)

Prepared according to general procedure II, using chromone 5a (29.2 mg, 0.20 mmol) and 4-ethynylanisole (33.7 μl, 0.26 mmol). Purified by Column Chromatography on SiO2 (eluent 4:1, Hexanes:EtOAc with 5% Et3N). 50b was isolated as a yellow solid (34.8 mg, 0.126 mmol, 63% yield). Rf=0.39 (8:2, Hexanes:EtOAc), [α]23D=−111.2 (c=0.9, CHCl3), 1H NMR (500 MHz, CDCl3) δ 7.92 (dd, J=8.1, 1.8 Hz, 1H), 7.51 (ddd, J=8.3, 7.3, 1.8 Hz, 1H), 7.40-7.34 (m, 2H), 7.09-7.03 (m, 2H), 6.86-6.79 (m, 2H), 5.49 (dd, J=7.4, 5.7 Hz, 1H), 3.81 (s, 3H), 3.11-3.03 (m, 2H). 13C NMR (126 MHz, CDCl3) δ 190.74, 160.41, 160.37, 136.33, 133.71, 127.11, 122.07, 121.26, 118.42, 114.11, 113.66, 87.66, 83.40, 68.36, 55.44, 43.76. IR (neat, ATR) ν: 2928, 2229, 1689, 1603, 1509, 1462, 1250, 1036, 766. Chiral HPLC: 98.0:2.0 e.r., 96% ee, Chiralcel AD-H column (5% iPrOH/Hexanes, 1 mL/min, 254 nm); tR (minor)=13.9 min, tR (major)=12.9 min. HRMS (ESI+) m/z calculated for C18H15O3 [M+H]+ 279.1016, found 279.1010.

Example 130: Synthesis of (R)-2-((4-(trifluoromethyl)phenyl)ethynyl)chroman-4-one (Compound 50c)

Prepared according to general procedure II, using chromone 5a (29.2 mg, 0.20 mmol) and 1-ethynyl-4-(trifluoromethyl) benzene (42.4 μl, 0.26 mmol). 50c was isolated as a white solid (53.7 mg, 0.17 mmol, 85% yield). Rf=0.52 (8:2, Hexanes:EtOAc), [α]23D=−96.6 (c=1.0, CHCl3), 1H NMR (500 MHz, CDCl3) δ 7.93 (dd, J=7.8, 1.7 Hz, 1H), 7.60-7.50 (m, 5H), 7.12-7.04 (m, 2H), 5.52 (dd, J=8.2, 4.7 Hz, 1H), 3.15-3.02 (m, 2H). 13C NMR (126 MHz, CDCl3) δ 190.21, 160.14, 136.48, 132.38, 130.99 (q, J=32.5 Hz), 127.16, 125.43 (q, J=3.8 Hz), 123.86 (q, J=270 Hz), 122.31, 121.21, 118.37, 87.01, 86.00, 67.98, 43.38. IR (neat, ATR) ν: 3056, 2917, 2241, 1686, 1612, 1463, 1326, 1303, 1103, 833, 759. Chiral HPLC: 98.6:1.4 e.r., 97% ee, Chiralcel OD-H column (5% iPrOH/Hexanes, 1 mL/min, 254 nm); tR (minor)=8.3 min, tR (major)=9.4 min. HRMS (ESI+) m/z calculated for C18H12F3O2 [M+H]+ 317.0784, found 317.0776.

Example 131: Synthesis of (R)-2-(p-tolylethynyl) chroman-4-one (Compound 50d)

Prepared according to general procedure II, using chromone 5a (29.2 mg, 0.20 mmol) and 4-ethynyltoluene (33.0 μl, 0.26 mmol). 50d was isolated as a white solid (43.6 mg, 0.166 mmol, 83% yield). Rf=0.58 (8:2, Hexanes:EtOAc), [α]23D=−119.7 (c=1.0, CHCl3), 1H NMR (500 MHz, CDCl3) δ 7.92 (dd, J=8.1, 1.8 Hz, 1H), 7.51 (ddd, J=8.3, 7.2, 1.8 Hz, 1H), 7.32 (d, J=8.2 Hz, 2H), 7.11 (d, J=7.8 Hz, 2H), 7.09-7.03 (m, 2H), 5.49 (dd, J=7.4, 5.7 Hz, 1H), 3.10-3.04 (m, 2H), 2.34 (s, 3H). 13C NMR (126 MHz, CDCl3) δ 190.69, 160.39, 139.51, 136.36, 132.05, 129.23, 127.12, 122.10, 121.25, 118.55, 118.42, 87.78, 84.01, 68.31, 43.72, 21.68. IR (neat, ATR) ν: 3031, 2914, 2233, 1685, 1464, 1307, 1218, 764. Chiral HPLC: 98.1:1.9 e.r., 96% ee, Chiralcel OD-H column (5% iPrOH/Hexanes, 1 mL/min, 254 nm); tR (minor)=9.0 min, tR (major)=10.3 min. HRMS (ESI+) m/z calculated for C18H15O2 [M+H]+ 263.1067, found 263.1061.

Example 132: Synthesis (R)-2-((4-chlorophenyl) ethynyl)chroman-4-one (Compound 50e)

Prepared according to general procedure II, using chromone 5a (29.2 mg, 0.2 mmol) and 4-chlorophenylacetylene (35.5 mg, 0.26 mmol). 50e was isolated a white solid (48.5 mg, 0.172 mmol, 86% yield). Rf=0.53 (8:2, Hexanes: EtOAc), [α]23D=−110.4 (c=0.9, CHCl3), 1H NMR (500 MHz, CDCl3) δ 7.93 (dd, J=7.9, 1.7 Hz, 1H), 7.52 (ddd, J=8.3, 7.2, 1.8 Hz, 1H), 7.38-7.32 (m, 2H), 7.31-7.27 (m, 2H), 7.11-7.03 (m, 2H), 5.50 (dd, J=8.1, 4.8 Hz, 1H), 3.12-3.02 (m, 2H). 13C NMR (126 MHz, CDCl3) δ 190.40, 160.22, 136.43, 135.42, 133.36, 128.86, 127.14, 122.22, 121.22, 120.09, 118.38, 86.39, 85.62, 68.10, 43.50. IR (neat, ATR) ν: 3036, 2924, 2231, 1687, 1607, 1466, 1305, 1220, 765. Chiral HPLC: 98.5:1.5 e.r., 97% ee, Chiralcel OD-H column (5% iPrOH/Hexanes, 1 mL/min, 254 nm); tR (minor)=12.0 min, tR (major)=13.1 min. HRMS (ESI+) m/z calculated for C17H12ClO2 [M+H]+ 283.0520, found 283.0515.

Example 133: Synthesis of (R)-2-(m-tolylethynyl) chroman-4-one (Compound 50f)

Prepared according to general procedure II, using chromone 5a (29.2 mg, 0.20 mmol) and m-Tolylacetylene (33.6 μl, 0.26 mmol). 50f was isolated as an off white crystalline solid (43.2 mg, 0.164 mmol, 82% yield). Rf=0.57 (8:2, Hexanes:EtOAc), [α]23D=−119.7 (c=1.0, CHCl3) 1H NMR (500 MHz, CDCl3) δ 7.93 (dd, J=8.4, 1.8 Hz, 1H), 7.55-7.48 (m, 1H), 7.28-7.12 (m, 3H), 7.11-7.03 (m, 2H), 5.50 (dd, J=7.8, 5.2 Hz, 1H), 3.12-3.01 (m, 2H), 2.31 (s, 3H). 13C NMR (126 MHz, CDCl3) δ 190.63, 160.34, 138.21, 136.36, 132.68, 130.13, 129.19, 128.36, 127.11, 122.11, 121.42, 121.24, 118.41, 87.74, 84.28, 68.23, 43.67, 21.30. IR (neat, ATR) ν: 3039, 2921, 2235, 1693, 1608, 1461, 1297, 1220, 762, 690. Chiral HPLC: 98.5:1.5 e.r., 97% ee, Chiralcel OD-H column (5% iPrOH/Hexanes, 1 mL/min, 254 nm); tR (minor)=8.8 min, tR (major)=11.0 min. HRMS (ESI+) m/z calculated for C18H15O2 [M+H]+ 263.1067, found 263.1061.

Example 134: Synthesis of (R)-2-(o-tolylethynyl)chroman-4-one (Compound 50g)

Prepared according to general procedure II, using chromone 5a (29.2 mg, 0.20 mmol) and 2-ethynyltoluene (32.8 μl, 0.26 mmol). 50g was isolated as an off white solid (35.2 mg, 0.134 mmol, 67% yield). Rf=0.57 (8:2, Hexanes:EtOAc), [α]23D=−139.2 (c=1.0, CHCl3), 1H NMR (500 MHz, CDCl3) δ 7.93 (dd, J=8.3, 1.7 Hz, 1H), 7.55-7.48 (m, 1H), 7.37 (dd, J=7.6, 1.4 Hz, 1H), 7.22 (td, J=7.5, 1.5 Hz, 1H), 7.16 (ddt, J=7.6, 1.4, 0.7 Hz, 1H), 7.13-7.09 (m, 1H), 7.09-7.04 (m, 2H), 5.56 (dd, J=7.5, 4.4 Hz, 1H), 3.14 (dd, J=16.8, 4.5 Hz, 1H), 3.05 (dd, J=16.8, 7.5 Hz, 1H), 2.27 (s, 3H). 13C NMR (126 MHz, CDCl3) δ 190.60, 160.18, 140.89, 136.32, 132.29, 129.62, 129.22, 127.05, 125.67, 122.11, 121.45, 121.41, 118.49, 88.63, 86.47, 68.31, 43.81, 20.57. IR (neat, ATR) ν: 3062, 2921, 2227, 1683, 1611, 1462, 1363, 1304, 1219, 1116, 880, 752. Chiral HPLC: 91.1:8.9 e.r., 82% ee, Chiralcel OD-H column (5% iPrOH/Hexanes, 1 mL/min, 254 nm); tR (minor)=8.3 min, tR (major)=10.9 min. HRMS (ESI+) m/z calculated for C18H15O2 [M+H]+ 263.1067, found 263.1060.

Example 135: Synthesis of (R)-2-((trimethylsilyl)ethynyl)chroman-4-one (Compound 50h)

Prepared according to general procedure II, using (S)-tBu-BOX (51d), chromone 5a (29.2 mg, 0.20 mmol) and trimethylsilylacetylene (36.0 μl, 0.26 mmol). 50 h was isolated as a white solid (42.2 mg, 0.172 mmol, 86% yield). Rf=0.65 (8:2, Hexanes:EtOAc), [α]23D=−99.1 (c=1.0, CHCl3), 1H NMR (500 MHz, CDCl3) δ 7.89 (dd, J=7.8, 1.7 Hz, 1H), 7.50 (ddd, J=8.3, 7.2, 1.8 Hz, 1H), 7.09-7.01 (m, 2H), 5.23 (dd, J=8.0, 5.8 Hz, 1H), 3.00-2.95 (m, 2H), 0.17 (s, 9H). 13C NMR (126 MHz, CDCl3) δ 190.54, 160.35, 136.29, 127.05, 122.09, 121.15, 118.36, 100.59, 93.33, 68.05, 43.59, −0.24. IR (neat, ATR) ν: 2962, 2903, 2187, 1684, 1602, 1366, 1219, 1119, 838, 779, 760. Chiral HPLC: 97.6:2.4 e.r., 95% ee, Chiralcel AD-H column (0.5% iPrOH/Hexanes, 0.8 mL/min, 254 nm); tR (minor)=8.3 min, tR (major)=7.9 min. HRMS (ESI+) m/z calculated for C14H17O2Si [M+H]+ 245.0992, found 245.0987.*note racemic trace was run with 1.0 mL/min*

Example 136: Synthesis of (R)-2-(3-(benzyloxy)prop-1-yn-1-yl)chroman-4-one (Compound 50i)

Prepared according to general procedure II, using (S)-Ph-Bn-BOX (51k), chromone 1a (29.2 mg, 0.20 mmol) and benzyl propargyl ether (37.6 μl, 0.26 mmol). Purified by Column Chromatography on SiO2 (eluent 4:1, Hexanes:EtOAc). 50i was isolated as a colorless oil (49.8 mg, 0.17 mmol, 85% yield). The major enantiomer was the same if (S)-Bn-BOX (51a) was used. Rf=0.35 (8:2, Hexanes:EtOAc), [α]22D=−77.0 (c=1.0, CHCl3), 1H NMR (500 MHz, CDCl3) δ 7.89 (dd, J=7.8, 1.8 Hz, 1H), 7.49 (ddd, J=8.7, 7.2, 1.8 Hz, 1H), 7.35-7.20 (m, 5H), 7.08-6.97 (m, 2H), 5.33 (ddt, J=8.0, 4.5, 1.7 Hz, 1H), 4.48 (s, 2H), 4.15 (d, J=1.7 Hz, 2H), 3.08-2.86 (m, 2H). 13C NMR (126 MHz, CDCl3) δ 190.30, 160.07, 137.16, 136.37, 128.57, 128.27, 128.09, 127.07, 122.17, 121.25, 118.39, 83.80, 82.42, 71.75, 67.63, 57.14, 43.41. IR (neat, ATR) ν: 3032, 2925, 2856, 1692, 1606, 1461, 1298, 1067, 764, 747, 698. Chiral HPLC: 92.3:7.7 e.r., 85% ee, Chiralcel OD-H column (10% iPrOH/Hexanes, 1 mL/min, 254 nm); tR (minor)=10.0 min, tR (major)=9.4 min. HRMS (ESI+) m/z calculated for C19H17O3 [M+H]+ 293.1172, found 293.1166.

Example 137: Synthesis of (S)-2-(4-(benzyloxy)but-1-yn-1-yl)chroman-4-one (Compound 50j)

Prepared according to general procedure II, using (S)-(2-nap)-BnBOX (511), chromone 1a (29.2 mg, 0.20 mmol) and benzyl but-3-ynyl ether (42.7 μl, 0.26 mmol). Purified by Column Chromatography on SiO2 (eluent 4:1, Hexanes:EtOAc). 50j was isolated as a colorless oil (59.0 mg, 0.192 mmol, 96% yield). The major enantiomer was opposite if (S)-Bn-BOX (51a) was used. Rf=0.59 (8:2, Hexanes:EtOAc), [α]23D=+61.9 (c=1.2, CHCl3), 1H NMR (500 MHz, CDCl3) δ 7.89 (dd, J=7.9, 1.8 Hz, 1H), 7.49 (ddd, J=8.7, 7.2, 1.8 Hz, 1H), 7.39-7.26 (m, 5H), 7.08-6.96 (m, 2H), 5.26 (ddt, J=8.6, 4.7, 2.0 Hz, 1H), 4.52 (s, 2H), 3.56 (t, J=6.9 Hz, 2H), 3.04-2.84 (m, 2H), 2.53 (td, J=6.9, 2.0 Hz, 2H). 13C NMR (126 MHz, CDCl3) δ 190.75, 160.31, 138.08, 136.26, 128.55, 127.85, 127.80, 127.03, 121.97, 121.18, 118.33, 85.60, 77.16, 73.13, 68.01, 67.93, 43.76, 20.33. 13C NMR (126 MHz, DMSOd6) δ 190.22, 159.55, 138.22, 136.23, 128.20, 127.43, 127.39, 126.13, 121.67, 120.75, 118.08, 85.39, 77.48, 71.70, 67.42, 67.19, 42.95, 19.34. IR (neat, ATR) ν: 3063, 2863, 2244, 1691, 1607, 1461, 1299, 1112, 765, 738, 698. Chiral HPLC: 92.7:7.3 e.r., 85% ee, Chiralcel OD-H column (10% iPrOH/Hexanes, 1 mL/min, 254 nm); tR (minor)=13.7 min, tR (major)=12.2 min. HRMS (ESI+) m/z calculated for $C_{20}H_{19}O_3$[M+H]+ 307.1329, found 307.1323.

Example 138: Synthesis of (R)-2-(cyclopropylethynyl)chroman-4-one (Compound 50k)

Prepared according to general procedure II, using chromone 5a (29.2 mg, 0.20 mmol) and cyclopropylacetylene (22.0 μl, 0.26 mmol). 50k was isolated as a colorless oil (18.9 mg, 0.089 mmol, 45% yield). Rf=0.59 (8:2, Hexanes:EtOAc), [α]23D=−104.7 (c=0.7, CHCl3), 1H NMR (500 MHz, CDCl3) δ 7.89 (dd, J=7.9, 1.7 Hz, 1H), 7.49 (ddd, J=8.4, 7.2, 1.8 Hz, 1H), 7.08-6.99 (m, 2H), 5.21 (ddd, J=8.3, 5.0, 1.8 Hz, 1H), 2.95-2.89 (m, 2H), 1.30-1.21 (m, 1H), 0.83-0.75 (m, 2H), 0.73-0.66 (m, 2H). 13C NMR (126 MHz, CDCl3) δ 190.95, 160.39, 136.24, 127.01, 121.92, 121.16, 118.35, 92.07, 71.25, 68.12, 43.94, 8.60, −0.48. IR (neat, ATR) ν: 3081, 3013, 2239, 1689, 1607, 1461, 1298, 1223, 1116, 909, 762. Chiral HPLC: 91.1:8.9 e.r., 82% ee, Chiralcel OD-H column (5% iPrOH/Hexanes, 1 mL/min, 254 nm); tR (minor)=7.0 min, tR (major)=8.4 min. HRMS (ESI+) m/z calculated for C14H13O2 [M+H]+ 213.0910, found 213.0905.

Example 139: Synthesis of (R)-2-(cyclohex-1-en-1-ylethynyl)chroman-4-one (Compound 50l)

Prepared according to general procedure II, using chromone 5a (29.2 mg, 0.20 mmol) and (1-cyclohexenyl) acetylene (31 μl, 0.26 mmol). Purified by Column Chromatography on SiO2 (eluent 19:1, Hexanes:EtOAc). 50l was isolated as a colorless oil (25.4 mg, 0.1 mmol, 50% yield). Rf=0.70 (8:2, Hexanes:EtOAc), [α]23D=−126.8 (c=1.0, CHCl3), 1H NMR (500 MHz, CDCl3) δ 7.90 (dd, J=7.8, 1.5 Hz, 1H), 7.49 (ddd, J=8.4, 7.2, 1.8 Hz, 1H), 7.16-6.94 (m, 2H), 6.15 (p, J=2.0 Hz, 1H), 5.37 (dd, J=8.0, 5.2 Hz, 1H), 3.04-2.91 (m, 2H), 2.17-1.93 (m, 4H), 1.66-1.52 (m, 4H). 13C NMR (126 MHz, CDCl3) δ 190.82, 160.42, 137.32, 136.24, 127.04, 121.95, 121.20, 119.55, 118.38, 89.48, 81.99, 68.31, 43.83, 28.92, 25.76, 22.23, 21.44. IR (neat, ATR) ν: 2929, 2859, 2220, 1693, 1608, 1462. Chiral HPLC: 85.5:14.5 e.r., 71% ee, Chiralcel OD-H column (1% iPrOH/Hexanes, 1 mL/min, 254 nm); tR (minor)=8.9 min, tR (major)=9.5 min. HRMS (ESI+) m/z calculated for C17H16O2 [M+H]+ 253.1223, found 253.1224.

Example 140: Synthesis of (R)-2-(phenylethynyl)-6-(trifluoromethyl)chroman-4-one (Compound 50m)

Prepared according to general procedure II using chromone 5m (42.8 mg, 0.20 mmol) and phenyl acetylene (28.6 μl, 0.26 mmol). 50m was isolated as a white crystalline solid (57.2 mg, 0.181 mmol, 90% yield). Rf=0.65 (8:2, Hexanes:EtOAc), [α]22D=−117.4 (c=1.0, CHCl3), 1H NMR (500 MHz, CDCl3) δ 8.22 (d, J=2.4 Hz, 1H), 7.74 (dd, J=8.7, 2.4 Hz, 1H), 7.44-7.38 (m, 2H), 7.38-7.28 (m, 3H), 7.17 (d, J=8.7 Hz, 1H), 5.59 (dd, J=7.7, 4.5 Hz, 1H), 3.20-3.04 (m, 2H). 13C NMR (126 MHz, CDCl3) δ 189.24, 162.15, 132.67 (q, J=3.3 Hz), 132.15, 129.47, 128.52, 124.96 (q, J=4.0 Hz), 124.69 (q, J=33.6 Hz), 123.82 (q, J=271.7 Hz), 121.28, 120.90, 119.42, 88.23, 83.79, 68.56, 43.26. IR (neat, ATR) ν: 3072, 2926, 2235, 1686, 1630, 1111, 861, 725. Chiral HPLC: 97.3:2.7 e.r., 95% ee, Chiralcel OD-H column (5% iPrOH/Hexanes, 1 mL/min, 254 nm); tR (minor)=9.1 min, tR (major)=13.0 min. HRMS (ESI+) m/z calculated for C18H12F3O2 [M+H]+ 317.0784, found 317.0773.

Example 141: Synthesis of (R)-6-methyl-2-(phenylethynyl)chroman-4-one (Compound 50n)

Prepared according to general procedure II, using chromone 5n (32.0 mg, 0.20 mmol) and phenyl acetylene (28.6 μl, 0.26 mmol). 50n was isolated as an off white solid (47.0 mg, 0.175 mmol, 90% yield). Rf=0.60 (8:2, Hexanes:EtOAc), [α]23D=−124.9 (c=0.9, CHCl3), 1H NMR (500 MHz, CDCl3) δ 7.71 (dd, J=2.2, 1.0 Hz, 1H), 7.46-7.40 (m, 2H), 7.37-7.26 (m, 5H), 6.96 (d, J=8.4 Hz, 1H), 5.47 (dd, J=7.5, 5.5 Hz, 1H), 3.10-3.02 (m, 2H), 2.32 (s, 3H). 13C NMR (126 MHz, CDCl3) δ 190.84, 158.40, 137.43, 132.13, 131.64, 129.20, 128.45, 126.72, 121.69, 120.84, 118.17, 87.38, 84.82, 68.15, 43.66, 20.59. IR (neat, ATR) ν: 3066, 2922, 2234, 1686, 1485, 1287, 1218, 760, 695. Chiral HPLC: 98.5:1.5 e.r., 97% ee, Chiralcel OD-H column (5% iPrOH/Hexanes, 1 mL/min, 254 nm); tR (minor)=8.5 min, tR (major)=10.8 min. HRMS (ESI+) m/z calculated for C18H15O2 [M+H]+ 263.1067, found 263.1059.

Example 142: Synthesis of (R)-6-fluoro-2-(phenylethynyl)chroman-4-one (Compound 50o)

Prepared according to general procedure II, using chromone 5o (32.8 mg, 0.20 mmol) and phenyl acetylene (29 μl, 0.26 mmol). 50o was isolated as an off white solid (51.0 mg, 0.192 mmol, 96% yield). Rf=0.65 (8:2, Hexanes:EtOAc), [α]23D=−126.8 (c=1.0, CHCl3), 1H NMR (500 MHz, CDCl3) δ 7.57 (dd, J=8.2, 3.2 Hz, 1H), 7.44-7.39 (m, 2H), 7.37-7.27 (m, 3H), 7.23 (ddd, J=9.1, 7.7, 3.2 Hz, 1H), 7.05 (dd, J=9.0, 4.2 Hz, 1H), 5.49 (dd, J=8.1, 4.6 Hz, 1H), 3.23-2.90 (m, 2H). 13C NMR (126 MHz, CDCl3) δ 189.80 (d, J=1.9 Hz), 158.66, 156.73, 156.44 (d, J=2.0 Hz), 132.12, 129.33, 128.49, 123.83 (d, J=24.5 Hz), 121.75 (d, J=6.5 Hz), 121.48, 120.14 (d, J=7.3 Hz), 112.18 (d, J=23.5 Hz), 87.76, 84.34, 68.36, 43.35. IR (neat, ATR) ν: 3040, 2925, 2234, 1688, 1479, 1271, 829, 687. Chiral HPLC: 98.7:1.3 e.r., 97% ee, Chiralcel OD-H column (5% iPrOH/Hexanes, 1 mL/min, 254 nm); tR (minor)=9.5 min, tR (major)=13.3 min. HRMS (ESI+) m/z calculated for C17H12FO2 [M+H]+ 267.0816, found 267.0809.

Example 143: Synthesis of (R)-6-chloro-2-(phenylethynyl)chroman-4-one (Compound 50p)

Prepared according to general procedure II, using chromone 5p (36.1 mg, 0.20 mmol) and phenyl acetylene (29 μl, 0.26 mmol). 50p was isolated as a white solid (38.8 mg, 0.138 mmol, 69% yield). Rf=0.65 (8:2, Hexanes:EtOAc), [α]22D=−138.6 (c=1.0, CHCl3), 1H NMR (500 MHz, CDCl3) δ 7.88 (d, J=2.6 Hz, 1H), 7.45 (dd, J=8.8, 2.7 Hz, 1H), 7.43-7.38 (m, 2H), 7.38-7.27 (m, 3H), 7.02 (d, J=8.8 Hz, 1H), 5.51 (dd, J=7.9, 4.6 Hz, 1H), 3.17-2.98 (m, 2H). 13C NMR (126 MHz, CDCl3) δ 189.43, 158.66, 136.19, 132.15, 129.38, 128.51, 127.75, 126.49, 122.05, 121.43, 120.18, 87.93, 84.17, 68.38, 43.32. IR (neat, ATR) ν: 2923, 2232, 1697, 1270, 1213, 756. Chiral HPLC: 97.1:2.9 e.r., 94% ee, Chiralcel OD-H column (5% iPrOH/Hexanes, 1 mL/min, 254 nm); tR (minor)=9.5 min, tR (major)=13.5 min. HRMS (ESI+) m/z calculated for C17H11ClO2 [M+H]+ 283.0520, found 283.0521.

Example 144: Synthesis of (R)-6-bromo-2-(phenylethynyl)chroman-4-one (Compound 50q)

Prepared according to general procedure II, using chromone 5q (45.0 mg, 0.20 mmol) and phenyl acetylene (29 μl, 0.26 mmol). 50q was isolated as a white solid (46.3 mg, 0.142 mmol, 71% yield). Rf=0.65 (8:2, Hexanes:EtOAc), [α]23D=−126.2 (c=0.9, CHCl3), 1H NMR (500 MHz, CDCl3) δ 8.03 (d, J=2.5 Hz, 1H), 7.59 (dd, J=8.8, 2.5 Hz, 1H), 7.44-7.38 (m, 2H), 7.38-7.26 (m, 3H), 6.97 (d, J=8.8 Hz, 1H), 5.51 (dd, J=7.9, 4.6 Hz, 1H), 3.16-2.98 (m, 2H). 13C NMR (126 MHz, CDCl3) δ 189.30, 159.12, 138.99, 132.15, 129.60, 129.39, 128.51, 122.51, 121.42, 120.53, 114.91, 87.96, 84.14, 68.35, 43.27. IR (neat, ATR) ν: 2922, 2232, 1691, 1269, 1214, 755. Chiral HPLC: 98.0:2.0 e.r., 96% ee, Chiralcel OD-H column (5% iPrOH/Hexanes, 1 mL/min, 254 nm); tR (minor)=9.8 min, tR (major)=14.0 min. HRMS (ESI+) m/z calculated for C17H11BrO2 [M+H]+ 327.0015, found 327.0017.

Example 145: Synthesis of (R)-7-methoxy-2-(phenylethynyl)chroman-4-one (Compound 50r)

Prepared according to general procedure II, using chromone 5r (35.3 mg, 0.20 mmol) and phenyl acetylene (28.6 μl, 0.26 mmol). Purified by Column Chromatography on SiO2 (eluent 4:1, Hexanes:EtOAc). 50r was isolated as an amber oil (38.0 mg, 0.136 mmol, 68% yield). Rf=0.40 (8:2, Hexanes:EtOAc), [α]23D=+27.8 (c=0.9, CHCl3), 1H NMR (500 MHz, CDCl3) δ 7.86 (d, J=8.8 Hz, 1H), 7.47-

7.40 (m, 2H), 7.38-7.28 (m, 3H), 6.62 (dd, J=8.8, 2.4 Hz, 1H), 6.51 (d, J=2.4 Hz, 1H), 5.48 (t, J=6.6 Hz, 1H), 3.84 (s, 3H), 3.04-2.99 (m, 2H) 13C NMR (126 MHz, CDCl3) δ 189.19, 166.31, 162.33, 132.13, 129.21, 128.87, 128.46, 121.66, 115.09, 110.60, 101.36, 87.40, 84.74, 68.53, 55.81, 43.25. IR (neat, ATR) ν: 3058, 2972, 2234, 1671, 1613, 1572, 1260, 1202, 1159, 759, 688. Chiral HPLC: 98.9:1.1 e.r., 98% ee, Chiralcel OD-H column (5% iPrOH/Hexanes, 1 mL/min, 254 nm); tR (minor)=17.2 min, tR (major)=19.9 min. HRMS (ESI+) m/z calculated for C18H15O3 [M+H]+ 279.1016, found 279.1008.

Example 146: Synthesis of (R)-7-methyl-2-(phenylethynyl)chroman-4-one (Compound 50s)

Prepared according to general procedure II, using chromone 5s (32.0 mg, 0.20 mmol) and phenyl acetylene (28.6 μl, 0.26 mmol). 50s was isolated as an off white crystalline solid (12.0 mg, 0.046 mmol, 23% yield). Rf=0.60 (8:2, Hexanes:EtOAc), [α]22D=−44.2 (c=0.7, CHCl3), 1H NMR (500 MHz, CDCl3) δ 7.81 (d, J=7.9 Hz, 1H), 7.45-7.40 (m, 2H), 7.38-7.27 (m, 3H), 6.92-6.84 (m, 2H), 5.47 (dd, J=7.7, 5.2 Hz, 1H), 3.08-3.01 (m, 2H), 2.37 (s, 3H). 13C NMR (126 MHz, CDCl3) δ 190.30, 160.36, 147.99, 132.14, 129.19, 128.45, 127.00, 123.49, 121.70, 119.00, 118.39, 87.36, 84.83, 68.18, 43.54, 22.13. IR (neat, ATR) ν: 2922, 2862, 2232, 1677, 1618, 1152, 1128, 813, 758, 689. Chiral HPLC: 98.3:1.7 e.r., 97% ee, Chiralcel OD-H column (5% iPrOH/Hexanes, 1 mL/min, 254 nm); tR (minor)=11.0 min, tR (major)=12.1 min. HRMS (ESI+) m/z calculated for C18H15O2 [M+H]+ 263.1067, found 263.1030.

Example 147: Synthesis of (R)-8-phenyl-2-(phenylethynyl)chroman-4-one (Compound 50t)

Prepared according to general procedure II, using chromone 5t (44.4 mg, 0.20 mmol) and phenyl acetylene (28.6 μl, 0.26 mmol). 50t was isolated as an off white crystalline solid (60.0 mg, 0.186 mmol, 93% yield). Rf=0.55 (8:2, Hexanes:EtOAc), [α]23D=+116.8 (c=1.1, CHCl3), 1H NMR (500 MHz, CDCl3) δ 7.97 (dd, J=7.8, 1.8 Hz, 1H), 7.61-7.55 (m, 3H), 7.50-7.43 (m, 2H), 7.42-7.35 (m, 3H), 7.36-7.25 (m, 3H), 7.18-7.10 (m, 1H), 5.56 (dd, J=6.5, 4.7 Hz, 1H), 3.22-2.99 (m, 2H). 13C NMR (126 MHz, CDCl3) δ 190.73, 156.91, 137.29, 136.84, 132.10, 131.91, 129.59, 129.15, 128.43, 128.37, 127.71, 126.48, 122.01, 121.99, 121.70, 87.36, 84.87, 68.11, 43.42. IR (neat, ATR) ν: 3060, 2923, 2234, 1692, 1213, 758, 691. Chiral HPLC: 92.0:8.0 e.r., 84% ee, Chiralcel OD-H column (5% iPrOH/Hexanes, 1 mL/min, 254 nm); tR (minor)=9.7 min, tR (major)=16.8 min. HRMS (ESI+) m/z calculated for C23H17O2 [M+H]+ 325.1223, found 325.1216.

Example 148: Synthesis of (R)-5-methoxy-2-(phenylethynyl)chroman-4-one (Compound 50u)

Prepared according to general procedure II, using chromone 5u (35.2 mg, 0.20 mmol) and phenyl acetylene (28.6 μl, 0.26 mmol). Purified by Column Chromatography on SiO2 (eluent 4:1, Hexanes:EtOAc). 50u was isolated as an off white solid (42.0 mg, 0.151 mmol, 75% yield). Rf=0.15 (8:2, Hexanes:EtOAc), [α]22D=−197.8 (c=0.9, CHCl3), 1H NMR (500 MHz, CDCl3) δ 7.45-7.37 (m, 3H), 7.36-7.27 (m, 3H), 6.61 (ddd, J=49.7, 8.4, 1.0 Hz, 2H), 5.43 (dd, J=7.6, 5.6 Hz, 1H), 3.92 (s, 3H), 3.08-2.97 (m, 2H). 13C NMR (126 MHz, CDCl3) δ 189.18, 161.93, 160.83, 136.23, 132.12, 129.15, 128.42, 121.70, 111.62, 110.45, 104.68, 87.42, 84.63, 67.77, 56.37, 44.80. IR (neat, ATR) ν: 2921, 2223, 1676, 1490, 1251, 1098, 1084, 1076, 758. Chiral HPLC: 96.5:3.5 e.r., 93% ee, Chiralcel OD-H column (20% iPrOH/Hexanes, 1 mL/min, 254 nm); tR (minor)=9.7 min, tR (major)=11.4 min. HRMS (ESI+) m/z calculated for C18H15O3 [M+H]+ 279.1016, found 279.1009.

Example 149: Synthesis of (2R,3R)-2-(phenylethynyl)-3-(p-tolyl)chroman-4-one (Compound 50v)

Prepared according to general procedure II, using 3-(p-tolyl)chromone (5v) (47.3 mg, 0.20 mmol) and phenyl acetylene (29 μl, 0.26 mmol). Purified by Column Chromatography on SiO2 (eluent 19:1, Hexanes:EtOAc). 50v was isolated as an off white solid (36.5 mg, 0.108 mmol, 54% yield) as a 2:1 mixture of diastereomers. Rf=0.70 (8:2, Hexanes:EtOAc), [α]23D=−126.8 (c=1.0, CHCl3), 1H NMR (500 MHz, CDCl3) δ 8.055-7.931 (m, 1H), 7.613-7.491 (m, 1H), 7.345-7.262 (m, 6H), 7.257-7.194 (m, 1H), 7.193-7.143 (m, 2H), 7.135-7.043 (m, 2H), 5.630 (d, J=4.4 Hz, 1H), *5.614 (d, J=7.3 Hz, 1H), 4.220 (d, J=4.4 Hz, 1H), *4.102 (d, J=7.3 Hz, 1H), 2.343 (s, 3H), *2.335 (s, 3H). 13C NMR (126 MHz, CDCl3) δ*191.35, 191.12, 159.90, *159.76, 137.93, *137.84, *136.39, 136.28, 132.02, 131.94, 130.19, 129.92, 129.68, 129.35, 129.14, *129.09, 128.78, 128.39, *128.37, *127.74, 127.70, 122.29, 121.72, 121.42, 121.06, 118.43, *118.40, 89.10, *88.13, *84.79, 83.57, 72.86, *57.67, 56.59, 21.30, *21.27 (3 aromatic signals overlap and 2-position signal overlaps).*minor diastereomer. IR (neat, ATR) ν: 3019, 2232, 1691, 1606, 1461, 752. Chiral HPLC: 81.6:18.4 e.r., 63% ee (major diastereomer); 81.1:18.9 e.r., 62% ee (minor diastereomer), Chiralcel ODH column (5% iPrOH/Hexanes, 1 mL/min, 254 nm); tR (minor)=7.9 min, tR (major)=9.5 min (major diastereomer); tR (minor)=15.7 min, tR (major)=8.8 min (minor diastereomer). HRMS (ESI+) m/z calculated for C24H19O2 [M+H]+ 339.1380, found 339.1379.

Example 150: Synthesis of (R)-2-(3,3-dimethylbut-1-yn-1-yl)chroman-4-one (Compound 50x)

Prepared according to general procedure II, using (S)-tBu-BOX (51d), chromone 5a (29.2 mg, 0.20 mmol) and tertbutylacetylene (32 μl, 0.26 mmol). Purified by Column Chromatography on SiO2 (eluent 19:1, Hexanes:EtOAc). 50× was isolated as a colorless oil (22.7 mg, 0.10 mmol, 50% yield). Rf=0.70 (4:1, Hexanes:EtOAc), [α]23D=−95.6 (c=0.8, CHCl3), 1H NMR (500 MHz, CDCl3) δ 7.95-7.83 (m, 1H), 7.55-7.41 (m, 1H), 7.08-6.97 (m, 2H), 5.22 (dd, J=8.0, 5.4 Hz, 1H), 3.02-2.85 (m, 2H), 1.19 (s, 9H). 13C NMR (126 MHz, CDCl3) δ 191.04, 160.48, 136.14, 126.96, 121.87, 121.25, 118.38, 97.07, 74.73, 68.12, 44.17, 30.76, 27.54. IR (neat, ATR) ν: 2970, 2244, 1694, 1462, 1302, 762. Chiral HPLC: 98.1:1.9 e.r., 96% ee, Chiralcel OD-H column (2% iPrOH/Hexanes, 1 mL/min, 254 nm); tR (minor)=5.3 min, tR (major)=5.7 min. HRMS (ESI+) m/z calculated for C15H17O2 [M+H]+ 229.1223, found 229.1218.

Example 151: Synthesis of (R)-2-(cyclohexylethynyl)chroman-4-one (Compound 50y)

Prepared according to general procedure II, using (S)-tBu-BOX (51d), chromone 5a (29.2 mg, 0.20 mmol) and cyclohexylacetylene (34 μl, 0.26 mmol). 50y was isolated as a colorless oil (29.8 mg, 0.118 mmol, 59% yield). Rf=0.65 (4:1, Hexanes:EtOAc), [α]23D=−91.6 (c=1.3, CHCl3), 1H NMR (500 MHz, CDCl3) δ 7.94-7.84 (m, 1H), 7.54-7.44 (m, 1H), 7.08-6.99 (m, 2H), 5.26 (ddd, J=8.4, 4.4, 1.9 Hz, 1H), 3.04-2.86 (m, 2H), 2.45-2.35 (m, 1H), 1.79-1.68 (m, 2H), 1.66-1.57 (m, 2H), 1.51-1.35 (m, 3H), 1.32-1.20 (m, 3H). 13C NMR (126 MHz, CDCl3) δ 191.00, 160.38, 136.16, 126.95, 121.86, 121.30, 118.38, 92.93, 76.21, 68.14, 44.14, 32.28, 28.96, 25.86, 24.68. IR (neat, ATR) ν: 2927, 2853, 2227, 1685, 1461, 1295, 772. Chiral HPLC: 91.8:8.2 e.r., 84% ee, Chiralcel OD-H column (2% iPrOH/Hexanes, 1 mL/min, 254 nm); tR (minor)=6.6 min, tR (major)=7.3 min. HRMS (ESI+) m/z calculated for C17H19O2 [M+H]+ 255.1380, found 255.1374.

Example 152: Synthesis of methyl 4-oxo-2-(phenylethynyl)chromane-2-carboxylate (Compound 50aa)

Prepared according to general procedure II, using PhCl, (S)-tBu-BOX (51d), chromone 5aa (40.8 mg, 0.20 mmol) and phenyl acetylene (29 μl, 0.26 mmol). 50aa was isolated as a colorless oil (53.3 mg, 0.174 mmol, 87% yield). Rf=0.43 (8:2, Hexanes:EtOAc), [α]23D=+90.7 (c=0.9, CHCl3), 1H NMR (500 MHz, CDCl3) δ 7.91 (ddd, J=7.8, 1.7, 0.5 Hz, 1H), 7.55 (ddd, J=8.4, 7.2, 1.8 Hz, 1H), 7.40-7.26 (m, 5H), 7.19-7.06 (m, 2H), 3.90 (s, 3H), 3.43-3.24 (m, 2H). 13C NMR (126 MHz, CDCl3) δ 188.88, 167.41, 158.79, 136.64, 132.28, 129.62, 128.44, 126.93, 122.70, 120.90, 118.67, 88.20, 83.18, 77.10, 54.09, 46.12 (1 aromatic signal overlapped). IR (neat, ATR) ν: 3066, 2955, 2234, 1751, 1695, 1607, 1460, 1299, 1259, 1221, 1116, 756, 645. Chiral HPLC: 83.3:16.7 e.r., 67% ee, Chiralcel OD-H column (5% iPrOH/Hexanes, 1 mL/min, 254 nm); tR (minor)=11.3 min, tR (major)=9.6 min. HRMS (ESI+) m/z calculated for C19H15O4 [M+H]+ 307.0965, found 307.0958.

Example 153: Synthesis of ethyl 4-oxo-2-(phenylethynyl)chromane-2-carboxylate (Compound 50ab)

Prepared according to general procedure II, using PhCl, (S)-tBu-BOX (51d), chromone 5ab (43.6 mg, 0.20 mmol) and phenyl acetylene (29 μl, 0.26 mmol). 50ab was isolated as a yellow oil (58.4 mg, 0.182 mmol, 91% yield). Rf=0.45 (4:1, Hexanes:EtOAc), [α]22D=+75.1 (c=1.1, CHCl3), 1H NMR (500 MHz, CDCl3) δ 7.91 (dd, J=7.8, 1.7 Hz, 1H), 7.55 (ddd, J=8.4, 7.2, 1.8 Hz, 1H), 7.40-7.27 (m, 5H), 7.17 (dd, J=8.4, 1.1 Hz, 1H), 7.09 (ddd, J=8.0, 7.2, 1.1 Hz, 1H), 4.34 (qd, J=7.1, 1.2 Hz, 2H), 3.44-3.25 (m, 2H), 1.30 (t, J=7.1 Hz, 3H). 13C NMR (126 MHz, CDCl3) δ 189.02, 166.93, 158.95, 136.60, 132.28, 129.58, 128.45, 126.91, 122.65, 121.01, 120.95, 118.72, 88.07, 83.34, 63.33, 46.11, 14.09 (tertiary carbon signal overlapped). IR (neat, ATR) ν: 2984, 2233, 1745, 1696. Chiral HPLC: 82.4:17.6 e.r., 65% ee, Chiralcel OD-H column (2% iPrOH/Hexanes, 1 mL/min, 254 nm); tR (minor)=13.4 min, tR (major)=11.3 min. HRMS (ESI+) m/z calculated for C20H17O4 [M+H]+ 321.1121, found 321.1122.

Example 154: Synthesis of isopropyl 4-oxo-2-(phenylethynyl)chromane-2-carboxylate (Compound 50ac)

Prepared according to general procedure II, using PhCl, (S)-tBu-BOX (51d), chromone 5ac (46.4 mg, 0.20 mmol) and phenyl acetylene (29 μl, 0.26 mmol). 50ac was isolated as a yellow oil (58.5 mg, 0.176 mmol, 88% yield). Rf=0.54 (4:1, Hexanes:EtOAc), [α]22D=+48.4 (c=1.1, CHCl3), 1H NMR (500 MHz, CDCl3) δ 7.96-7.85 (m, 1H), 7.61-7.49 (m, 1H), 7.43-7.26 (m, 5H), 7.20-7.14 (m, 1H), 7.12-7.06 (m, 1H), 5.13 (hept, J=6.3 Hz, 1H), 3.45-3.23 (m, 2H), 1.30 (d, J=6.3 Hz, 3H), 1.23 (d, J=6.3 Hz, 3H). 13C NMR (126 MHz, CDCl3) δ 189.11, 166.48, 159.10, 136.56, 132.25, 129.55, 128.45, 126.89, 122.60, 121.10, 120.98, 118.74, 87.94, 83.44, 77.25, 71.34, 46.08, 21.60, 21.50. IR (neat, ATR) ν: 2983, 2237, 1738, 1696, 1607, 1461. Chiral HPLC: 77.2:22.8 e.r., 54% ee, Chiralcel AD-H column (5% iPrOH/Hexanes, 1 mL/min, 254 nm); tR (minor)=9.4 min, tR (major)=7.4 min. HRMS (ESI+) m/z calculated for C21H19O4 [M+H]+ 335.1278, found 335.1280.

Example 155: Synthesis of tert-butyl 4-oxo-2-(phenylethynyl)chromane-2-carboxylate (Compound 50ad)

Prepared according to general procedure II, using PhCl, (S)-tBu-BOX (51d), chromone 5ad (49.2 mg, 0.20 mmol) and phenyl acetylene (29 μl, 0.26 mmol). 50ad was isolated as a yellow oil (10.5 mg, 0.03 mmol, 15% yield). Rf=0.58 (4:1, Hexanes:EtOAc), [α]22D=+41.3 (c=0.5, CHCl3), 1H NMR (500 MHz, CDCl3) δ 7.95-7.85 (m, 1H), 7.58-7.49 (m, 1H), 7.43-7.27 (m, 5H), 7.19-7.13 (m, 1H), 7.12-7.05 (m, 1H), 3.45-3.14 (m, 2H), 1.46 (s, 9H). 13C NMR (126 MHz, CDCl3) δ 189.35, 165.86, 159.28, 136.53, 132.24, 129.48, 128.45, 126.84, 122.49, 121.24, 121.01, 118.71, 87.64, 84.48, 83.77, 77.56, 46.20, 27.82. IR (neat, ATR) ν: 2980, 2236, 1736, 1697, 1608, 1491. Chiral HPLC: 80.1:19.9 e.r., 60% ee, Chiralcel AD-H column (5% iPrOH/Hexanes, 1 mL/min, 254 nm); tR (minor)=9.8 min, tR (major)=6.3 min. HRMS (ESI+) m/z calculated for C22H21O4 [M+H]+ 349.1434, found 249.1436.

Example 156: Synthesis of (S)-2-phenethylchromane (Compound 56)

To a 2 dram vial was added 50a (48.9 mg, 0.2 mmol, 97% ee) and EtOAc (2 mL). The solution was bubbled with dry N2 for 10 minutes. After which, 10% Pd/C catalyst (10 mg, 20 wt %) was added. The reaction mixture was again bubbled with nitrogen for 10 minutes. The gas was switched to H2 and bubbling continued for 10 minutes then the vial was then closed to the atmosphere. Rapid adsorption of H2 can be observed, typically within 30 minutes. After stirring overnight or the reaction was deemed complete by NMR spectroscopy (note: it was necessary to add additional catalyst if the reaction is stalled), the reaction mixture was filtered through celite and the celite pad was washed with EtOAc (3×2 mL). The solvent was removed, under vacuum, to afford the crude (S)-2-phenylethylchromane as a colorless oil (38 mg, 0.16 mmol, 80% yield). Rf=0.7 (9:1, Hexanes: EtOAc), [α]23D=−127.7 (c=0.6, CHCl3), lit. [6] for (S) enantiomer [α]23D=−116.3 (c=1.0, CHCl3), lit. [4] for (S) enantiomer [α]23D=−103.2.3 (c=1.0, CHCl3), lit. [7] for (R) enantiomer [α]24D=+43.1 (c=0.8, CHCl3), 1H NMR (500 MHz, CDCl3) δ 7.33-7.27 (m, 2H), 7.27-7.23 (m, 2H), 7.23-7.17 (m, 1H), 7.13-7.08 (m, 1H), 7.07-7.02 (m, 1H), 6.88-6.81 (m, 2H), 4.04-3.94 (m, 1H), 2.97-2.71 (m, 4H), 2.13-2.06 (m, 1H), 2.03-1.96 (m, 1H), 1.96-1.87 (m, 1H), 1.83-1.74 (m, 1H). 13C NMR (126 MHz, CDCl3) δ 155.13, 142.06, 129.66, 128.69, 128.53, 127.30, 125.97, 122.20, 120.13, 116.92, 74.91, 37.22, 31.68, 27.65, 24.88. IR (neat, ATR) ν: 3025, 2926, 2850, 1582, 1487, 1456, 1231, 750, 698. Chiral HPLC: 98.1:1.9 e.r., 96% ee, Chiralcel AD-H column (0.5% iPrOH/Hexanes, 0.8 mL/min, 254 nm); tR (minor)=12.1 min, tR (major)=13.6 min.

Example 157: Synthesis of (S)-Findersiachromanone (Compound 53)

To a 2 dram vial was added (R)-50a (48.9 mg, 0.2 mmol, 97% ee) and EtOAc (2 mL). The solution was bubbled with dry N2 for 10 minutes. After which, 5% Pd/CaCO3+Pb catalyst (10 mg, 20 wt %) was added. The reaction mixture was again bubbled with nitrogen for 10 minutes. The gas was switched to H2 and bubbling continued for 10 minutes then the vial was then closed to the atmosphere. Rapid adsorption of H2 can be observed, typically within 30 minutes. After stirring overnight or the reaction was deemed complete by NMR spectroscopy (note: it was necessary to add additional catalyst if the reaction is stalled), the reaction mixture was filtered through celite and the celite pad was washed with EtOAc (3×2 mL). The solvent was removed under vacuum to afford the crude (S)-Findersiachromanone as a colorless oil (42 mg, 0.168 mmol, 84% yield). Rf=0.45 (9:1, Hexanes:EtOAc), [α]23D=−72.4 (c=1.0, CHCl3), lit. [6] for (S) enantiomer [α]23D=−52.5 (c=1.0, CH3OH), lit. [8] for (R) enantiomer [α]20D=+63 (c=0.62, EtOH), 1H NMR (500 MHz, CDCl3) δ 7.88 (dd, J=8.1, 1.8 Hz, 1H), 7.49 (ddd, J=8.4, 7.2, 1.8 Hz, 1H), 7.33-7.27 (m, 2H), 7.25-7.18 (m, 3H), 7.05-6.98 (m, 2H), 4.44 (ddt, J=11.3, 8.4, 4.3 Hz, 1H), 2.99-2.79 (m, 2H), 2.79-2.63 (m, 2H), 2.31-2.17 (m, 1H), 2.04-1.95 (m, 1H). 13C NMR (126 MHz, CDCl3) δ 192.43, 161.66, 141.05, 136.13, 128.69, 128.60, 127.13, 126.30, 121.42, 121.22, 118.05, 76.94, 43.15, 36.66, 31.26. IR (neat, ATR) ν: 3027, 2926, 2864, 1689, 1605, 1463, 1305, 1226, 1119, 762, 699. Chiral HPLC: 98.3:1.7 e.r., 97% ee, Chiralcel OD-H column (10% iPrOH/Hexanes, 1.0 mL/min, 254 nm); tR (minor)=14.8 min, tR (major) =26.6 min.

Example 158: Synthesis of (R,Z)-2-styrylchroman-4-one (Compound 52)

To a 2 dram vial was added 50a (24.9 mg, 0.1 mmol, 97% ee) and EtOAc (1 mL). The solution was bubbled with dry N2 for 10 minutes. After which, 5% Pd/CaCO3+Pb catalyst (5 mg, 20 wt %) and 3,6-dithia-1,8-octandiol (0.25 mg, 5 wt % of catalyst) were added. The reaction mixture was again bubbled with nitrogen for 10 minutes. The gas was switched to H2 and bubbling continued for 10 minutes then the vial was then closed to the atmosphere. Rapid adsorption of H2 can be observed, typically within 30 minutes. After stirring overnight or the reaction was deemed complete by NMR spectroscopy (note: it was necessary to add additional catalyst if the reaction is stalled), the reaction mixture was filtered through celite and the celite pad was washed with EtOAc (3×2 mL). The crude product S40 was purified by passing through a silica gel plug with DCM. The solvent was removed, under vacuum, to afford the pure (R,Z)-2-styrylchroman-4-one (Compound 52) as a slightly yellow oil (24 mg, 0.096 mmol, 96% yield). Rf=0.45 (9:1, Hexanes:EtOAc), [α]23D=−121.0 (c=1.0, CHCl3), 1H NMR (500 MHz, CDCl3) δ 7.90 (dd, J=8.0, 1.7 Hz, 1H), 7.49 (ddd, J=8.4, 7.2, 1.8 Hz, 1H), 7.38-7.31 (m, 2H), 7.31-7.27 (m, 3H), 7.07-6.99 (m, 2H), 6.81 (d, J=11.5 Hz, 1H), 5.93 (dd, J=11.5, 9.0 Hz, 1H), 5.42-5.32 (m, 1H), 2.99-2.74 (m, 2H). 13C NMR (126 MHz, CDCl3) δ 191.77, 161.44, 136.26, 135.81, 134.73, 128.76, 128.70, 128.31, 128.09, 127.11, 121.61, 121.15, 118.23, 74.35, 43.33. IR (neat, ATR) ν: 3024, 1688, 1605, 1461, 1302, 1221, 762, 701. Chiral HPLC: 98.0:2.0 e.r., 96% ee, Chiralcel OD-H column (5% iPrOH/Hexanes, 1.0 mL/min, 254 nm); tR (minor)=7.5 min, tR (major)=6.2 min.

Example 159: Synthesis of (R)-5-methoxy-2-((trimethylsilyl)ethynyl)chroman-4-one (Compound 50w)

Prepared according to general procedure II, using (S)-tBu-BOX (51d), chromone 5u (352 mg, 2.0 mmol) and trimethylsilylacetylene (360 μl, 2.6 mmol). Purified by Column Chromatography on SiO2 (eluent 4:1, Hexanes:EtOAc). 50w was isolated as an off white solid (422 mg, 1.54 mmol, 77% yield). Rf=0.25 (8:2, Hexanes:EtOAc), [α]23D=−147.3 (c=0.6, CHCl3), 1H NMR (500 MHz, CDCl3) δ 7.39 (t, J=8.4 Hz, 1H), 6.64 (dd, J=8.3, 1.0 Hz, 1H), 6.55 (dd, J=8.4, 1.0 Hz, 1H), 5.16 (dd, J=9.5, 4.7 Hz, 1H), 3.91 (s, 3H), 3.02-2.82 (m, 2H), 0.17 (s, 9H). 13C NMR (126 MHz, CDCl3) δ 189.12, 162.02, 160.80, 136.15, 111.56, 110.43, 104.66, 100.60, 93.11, 67.63, 56.35, 44.78, −0.24. IR (neat, ATR) ν: 2971, 1683, 1470, 1261, 1095, 843. Chiral HPLC: 96:4 e.r., 92% ee, Chiralcel OD-H column (10% iPrOH/Hexanes, 1 mL/min, 254 nm); tR (minor)=6.1 min, tR (major)=7.0 min. HRMS (ESI+) m/z calculated for C15H19O3Si [M+H]+ 275.1098, found 275.1093.

Example 160: Synthesis of ethyl 4-((R)-5-methoxy-4-oxochroman-2-yl)buta-2,3-dienoate (Compound 50w-2)

To a solution of chromanone 50w (384 mg, 1.4 mmol) dissolved in MeOH (12 mL), was added CsF (319 mg, 2.1 mmol, 1.5 eq). The reaction mixture was stirred at room temperature overnight. After the reaction was deemed complete by TLC, it was quenched with water and the solvent volume was reduced by half under vacuum. The resulting solution was extracted with DCM (3×10 mL), then the combined organic phase was washed with brine (1×10 mL), dried over Na2SO4, and the solvent was removed under vacuum to yield the crude terminal alkyne, which was used directly in the next step without purification. Note: terminal alkyne is not stable on silica gel. To the crude terminal alkyne dissolved in MeCN (40 mL), was added CuI (267 mg, 1.4 mmol, 1 eq based on full conversion from previous step) and ethyl diazoacetate (200 μL, 1.66 mmol, 1.19 eq). The reaction mixture was stirred at room temperature for 24 h. The solvent was removed under vacuum to yield the crude product. The crude product was purified by column chromatography on SiO2 (eluent=4:1 Hexanes:EtOAc) to afford allene 50w-2 as an yellow oil (0.255 g, 0.884 mmol, 63% yield). Rf=0.25 (3:2, Hexanes:EtOAc), 1H NMR (500 MHz, CDCl3) δ 7.38 (td, J=8.3, 1.0 Hz, 1H), 6.60 (dt, J=8.4, 1.0 Hz, 1H), 6.54 (dt, J=8.4, 1.3 Hz, 1H), 5.94-5.87 (m, 1H), 5.84-5.78 (m, 1H), 5.20-5.09 (m, 1H), 4.23-4.14 (m, 2H), 3.91 (s, 3H), 2.91-2.78 (m, 2H), 1.27 (td, J=7.1, 2.7 Hz, 3H).

Example 161: Synthesis of ethyl (S)-4-(5-methoxy-4-oxochroman-2-yl)butanoate (Compound 54)

A solution of allene (R)-50w-2 (255 mg, 0.88 mmol) dissolved in EtOAc (10 mL) was bubbled with N2 for 15 minutes. 10% Pd/C (50 mg, 20-30 wt %) was then added. N2 bubbling was continued for another 15 minutes before switching to H2 and then bubbling for another 15 minutes. The reaction vessel was then closed and watched for signs of H2 absorption. If rapid H2 absorption was not observed more catalyst was added (50 mg increments) and the atmosphere was again purged with H2 by bubbling for an additional 15 minutes. Once H2 absorption was observed the reaction was allowed to proceed for 10 h. The reaction was deemed complete, by NMR, once a mixture of chromanone S43 and chroman was observed with no trace of alkenes. The reaction mixture was then filtered through a celite pad, and the pad was washed with EtOAc (3×20 mL). The solvent was removed to yield the crude product as a mixture of chromanone and chroman (9:1). The crude material was purified by column chromatography on SiO2 (eluent=4:1 to 3:2 Hexanes:EtOAc) to afford chromanone (S)-54 as a colorless oil (165 mg, 0.56 mmol, 60% yield, 40% yield over 3 steps) Rf=0.25 (3:2, Hexanes:EtOAc), [α]23D=−61.7 (c=0.9, CHCl3), 1H NMR (500 MHz, CDCl3) δ 7.33 (t, J=8.3 Hz, 1H), 6.54 (dd, J=8.3, 1.0 Hz, 1H), 6.48 (dd, J=8.3, 1.0 Hz, 1H), 4.43-4.34 (m, 1H), 4.12 (q, J=7.2 Hz, 2H), 3.88 (s, 3H), 2.72-2.56 (m, 2H), 2.36 (t, J=7.1 Hz, 2H), 1.94-1.66 (m, 3H), 1.24 (t, J=7.1 Hz, 3H). 13C NMR (126 MHz, CDCl3) δ 191.07, 173.24, 163.19, 160.76, 135.90, 111.48, 110.12, 103.83, 76.95, 60.46, 56.24, 44.43, 34.13, 33.94, 20.56, 14.33. IR (neat, ATR) ν: 2938, 1729, 1683, 1600, 1575, 1472, 1279, 1081, 793. Chiral HPLC: 95:5 e.r., 90% ee, Chiralcel OD-H column (20% iPrOH/Hexanes, 1 mL/min, 254 nm); tR (minor)=10.0 min, tR (major)=12.5 min. HRMS (ESI+) m/z calculated for C16H21O5 [M+H]+ 293.1384, found 293.1377.

Example 162: Synthesis of (S)-1-hydroxy-8-methoxy-2,3,4,4a-tetrahydro-9H-xanthen-9-one (Compound 55)

1.0 M TiCl4 (0.97 mL, 0.97 mmol, 2.6 eq) was mixed with Ti(OiPr)4 (98 μL, 0.32 mmol, 0.87 eq) and stirred for 30 minutes to generate TiCl3OiPr solution. Et3N (146 μL, 1.0 mmol, 2.8 eq) was added to a solution of chromone (S)-54 (109 mg, 0.37 mmol, 90% ee) dissolved in DCM at 0° C. The TiCl3OiPr solution was then added dropwise via a syringe at 0° C. After the reaction was deemed complete by TLC, or 1 h, the reaction was quenched with sat. NH4Cl (3 mL) and diluted water (3 mL). the mixture was extracted with EtOAc (3×10 mL), washed with Brine (1×10 mL), then the solvent was removed to yield the crude product. The crude material was purified by column chromatography on SiO2 (eluent=9:1 to 8:2 Hexanes:EtOAc) to afford tetrahydroxanthone (S)-55 as a yellow crystalline solid (44 mg, 0.18 mmol, 48% yield, 37% ee). (S)-55 was crystallized by slow evaporation of a solution of hexanes:DCM (9:1) to yield and orange crystalline solid (15 mg, 16% yield, racemic) which was removed by filtration. A yellow crystalline solid (23 mg, 25% yield, 66% ee) was obtained by removing the solvent from the mother liquor under vacuum. Rf=0.55 (3:2, Hexanes:EtOAc, λ=365 nm), [α]22D=−80.5 (c=1.2, CHCl3), 1H NMR (500 MHz, CDCl3) δ 15.57 (s, 1H), 7.33 (t, J=8.3 Hz, 1H), 6.54 (d, J=8.4 Hz, 2H), 4.96-4.84 (m, 1H), 3.93 (s, 3H), 2.53-2.42 (m, 1H), 2.40-2.33 (m, 1H), 2.33-2.26 (m, 1H), 2.01-1.91 (m, 1H), 1.90-1.79 (m, 1H), 1.73-1.63 (m, 1H). 13C NMR (126 MHz, CDCl3) δ 183.10, 181.44, 162.31, 160.83, 135.49, 111.62, 110.13, 105.82, 104.81, 74.45, 56.34, 30.54, 28.83, 18.48. IR (neat, ATR) ν: 2941, 1595, 1470, 1122, 1102, 1084. Chiral HPLC: 68.6:31.4 e.r., 37% ee (before crystallization). 83.6:16.4 e.r., 66% ee (mother liquor). Chiralcel OD-H column (20% iPrOH/Hexanes, 1 mL/min, λ=330 nm); tR (minor)=8.7 min, tR (major)=7.7 min. HRMS (ESI+) m/z calculated for C14H15O4 [M+H]+ 247.0965, found 247.0960.

Example 163: General method III and synthesis of Methyl chromone-2-carboxylate (Compound 5aa)

To a flame dried round bottom flask was added chromone-2-carboxylic acid (1.9 g, 10 mmol), thionyl chloride (9 mL, 123 mmol), and dry DMF (39 μL, 0.5 mmol). The reaction mixture was stirred at room temperature for 24 hours. Upon completion, the reaction mixture is homogenous. The reaction mixture is then concentrated under vacuum to obtain crude chromone-2-acid chloride which was carried to the next step without purification. To the flask containing the crude acid chloride was added DCM (50 mL). The solution was cooled to 0° C. then pyridine (0.85 mL, 10.5 mL) was added dropwise. Methanol (0.43 mL, 10.5 mmol) was then added dropwise and the reaction mixture was stirred at room temperature overnight. The reaction was quenched with water (20 mL), then extracted with DCM (3×20 mL). The combined organic phase was washed with brine (1×10 mL), then dried over Na2SO4. The solvent was removed under vacuum to yield crude methyl chromone-2-carboxylate. The crude was purified by column chromatography on SiO2 (eluent 1:5 EtoAc:Hexanes) to yield pure 5aa as a white solid (1.55 g, 76% yield). Rf=0.25 (4:1, Hexanes:EtOAc), 1H NMR (500 MHz, CDCl3) δ 8.25-8.16 (m, 1H), 7.79-7.71 (m, 1H), 7.64-7.58 (m, 1H), 7.49-7.42 (m, 1H), 7.12 (s, 1H), 4.02 (s, 3H). 13C NMR (126 MHz, CDCl3) δ 178.43, 161.17, 156.08, 152.08, 134.89, 126.06, 125.90, 124.57, 118.88, 115.06, 53.67.

Example 164: Synthesis of Ethyl chromone-2-carboxylate (Compound 5ab)

Prepared according to the general method III using ethanol (0.61 mL, 10.5 mmol). Purified by column chromatography on SiO2 (eluent 1:6, EtOAc:Hexanes) to yield pure 5ab as a white solid (1.74 g, 80% yield). Rf=0.31 (4:1, Hexanes:EtOAc), 1H NMR (500 MHz, CDCl3) δ 8.25-8.17 (m, 1H), 7.79-7.71 (m, 1H), 7.65-7.59 (m, 1H), 7.50-7.41 (m, 1H), 7.12 (s, 1H), 4.47 (d, J=7.1 Hz, 2H), 1.44 (t, J=7.1 Hz, 3H). 13C NMR (126 MHz, CDCl3) δ 178.57, 160.69, 156.14, 152.37, 134.85, 126.03, 125.89, 124.58, 118.93, 114.92, 63.15, 14.23.

Example 165: Synthesis of Iso-propyl chromone-2-carboxylate (Compound 5ac)

Prepared according to the general method III using iso-propanol (0.8 mL, 10.4 mmol). Purified by column chromatography on SiO2 (eluent 1:6, EtOAc:Hexanes) to yield pure 5ac as a white solid (1.45 g, 63% yield). Rf=0.40 (4:1, Hexanes:EtOAc), 1H NMR (500 MHz, CDCl3) δ 8.24-8.16 (m, 1H), 7.78 S47-7.70 (m, 1H), 7.65-7.60 (m, 1H), 7.49-7.42 (m, 1H), 7.11 (s, 1H), 5.30 (hept, J=6.3 Hz, 1H), 1.41 (d, J=6.3 Hz, 7H). 13C NMR (126 MHz, CDCl3) δ 178.68, 160.18, 156.16, 152.67, 134.81, 125.98, 125.86, 124.57, 118.96, 114.78, 71.38, 21.84.

Example 166: Synthesis of Tert-butyl chromone-2-carboxylate (5ad)

Prepared according to the general method III using tert-butanol (1.0 mL, 10.5 mmol). Purified by column chromatography on SiO2 (eluent 1:8, EtOAc:Hexanes) to yield pure 5ad as a white solid (2.02 g, 82% yield). Rf=0.42 (4:1, Hexanes:EtOAc), 1H NMR (500 MHz, CDCl3) δ 7.77-7.70 (m, 1H), 7.63-7.58 (m, 1H), 7.48-7.41 (m, 1H), 7.05 (s, 1H), 1.62 (s, 9H). 13C NMR (126 MHz, CDCl3) δ 178.92, 159.52, 156.17, 153.23, 134.75, 125.91, 125.83, 124.51, 118.95, 114.46, 84.75, 28.07. HRMS (ESI+) m/z calculated for C14H15O4 [M+H]+ 247.0965, found 247.0965.

Example 167: General Method M and synthesis of (S,S)-2,2'-Isopropylidenebis [4-phenyl-2-oxazoline] (5ib)

To a flask containing fused ZnCl2 (1.4 g, 10.6 mmol, 3 eq.) under nitrogen was added dimethylmalononitrile (0.5 g, 5.3 mmol, 1.0 eq.), (S)-phenyl glycinol (1.45 g, 10.6 mmol, 3 eq.), and chlorobenzene (25 mL, 0.25 M malononitrile). The reaction mixture was refluxed for 24 h. After cooling to room temperature, the reaction mixture was quenched with H2O (3 mL) and ethylenediamine (6 mL) and stirred for 1 h. Additional water (approx. 15 mL) was added to ensure all the solids were dissolved, then the mixture was extracted with DCM (3×15 mL). The combined organic phase was then washed with brine and dried over anhydrous Na2SO4. The solvent was removed under vacuum to yield the crude product. The crude product was purified by column chromatography on SiO2 (eluent=1:3, Hexanes:EtoAc) to afford 1.57 g (89% yield) of a viscous oil. Rf=0.70 (3:1, EtOAc: Hexanes), [α]23D=−163.0, (c=1.1, CHCl3), 1H NMR (500 MHz, CDCl3) δ 7.37-7.29 (m, 4H), 7.32-7.23 (m, 6H), 5.24 (dd, J=10.1, 7.6 Hz, 2H), 4.68 (dd, J=10.1, 8.3 Hz, 2H), 4.17 (dd, J=8.4, 7.6 Hz, 2H), 1.69 (s, 6H).

Example 168: Synthesis of (S,S)-2,2'-Isopropylidenebis [4-benzyl-2-oxazoline] (Compound 51a)

Prepared according to Method M, using dimethylmalononitrile (0.75 g, 7.97 mmol, 1.0 eq), (S)-2-amino-3-phenyl-1-propanol (3.61 g, 23.9 mmol, 3.0 eq), ZnCl2 (3.26 g, 23.9 mmol, 3.0 eq), and chlorobenzene (32 ml). The crude product was purified by column chromatography on SiO2 (eluent=1:6, Hexanes:EtoAc with 1% Et3N) to afford 2.2 g (75% yield) of an off-white crystalline solid. Rf=0.60 (6:1, EtOAc:Hexanes), [α]23D=−43.0 (c=1.3, CHCl3), 1H NMR (500 MHz, CDCl3) δ 7.32-7.25 (m, 4H), 7.27-7.16 (m, 6H), 4.45-4.36 (m, 2H), 4.17 (dd, J=9.3, 8.5 Hz, 2H), 4.01 (dd, J=8.5, 6.8 Hz, 2H), 3.10 (dd, J=13.7, 4.7 Hz, 2H), 2.66 (dd, J=13.8, 8.6 Hz, 2H), 1.46 (s, 6H).

Example 169: General method N, step 1 synthesis of N,N'-bis((S)-1-hydroxy-3-methylbutan-2-yl)-2,2-dimethylmalonamide To a flame dried flask were added (S)-valinol (1.32 mL, 11.84 mmol, 2.0 eq), triethylamine (2.75 mL, 20.65 mmol, 3.5 eq), and DCM (10 mL). The reaction mixture was cooled to 0° C. then dimethylmalonyldichloride (0.8 mL, 5.92 mmol, 1.0 eq) was added dropwise. The reaction mixture was warmed to room temperature and stirred overnight. The slurry was filtered and then the product was crystallized from DCM with Hexanes to afford a white crystalline solid (0.62 g, 35% yield). 1H NMR (500 MHz, CDCl3) δ 6.46 (d, J=8.9 Hz, 2H), 3.82-3.69 (m, 4H), 3.50 (dd, J=11.4, 7.1 Hz, 2H), 3.38 (s, 2H), 1.86-1.74 (m, 2H), 1.47 (s, 6H), 0.93 (d, J=6.8 Hz, 6H), 0.90 (d, J=6.8 Hz, 6H).

Example 170: General method N, step 2 synthesis of (S,S)-2,2'-Isopropylidenebis [4-isopropyl-2-oxazoline] (Compound 51c)

To a flame dried flask were added N,N'-bis((S)-1-hydroxy-3-methylbutan-2-yl)-2,2-dimethylmalonamide, (0.5 g, 1.65 mmol, 1.0 eq), triethylamine (1.1 mL, 8.25 mmol, 5.0 eq), and DCM (20 mL). The reaction mixture was cooled to 0° C. then MsCl (0.32 mL, 4.13 mmol, 2.5 eq) was added dropwise. The reaction was warmed to room temperature and stirred overnight. The solution was then quenched with 30 mL of saturated NH4Cl solution. The aqueous phase was extracted with DCM (3×20 mL). The combined organic phase was dried over Na2SO4 and the solvent was removed under vacuum to yield the bis-mesylate as a yellow oil. To the flask containing the crude bis-mesylate product was added 0.5M NaOH in MeOH/H2O (1:1) and refluxed for 3 h. The solution was cooled to room temperature, then the about half the solvent was removed under vacuum. The solution was then extracted with DCM (3×20 mL), then the combined organic phase was dried over Na2SO4. The solvent was removed to yield the crude product as a yellow oil. The product was purified by column chromatography on SiO2 (eluent=3:1 EtOAc:Hexanes with 1% triethylamine) to afford the product as a clear colorless liquid (0.264 g, 60% yield). Rf=0.35 (3:1, EtOAc:Hexanes), [α]23D=−108.2 (c=1.1, CHCl3), 1H S50 NMR (500 MHz, CDCl3) δ 4.22-4.17 (m, 2H), 4.02-3.92 (m, 4H), 1.86-1.74 (m, 2H), 1.51 (s, 6H), 0.91 (d, J=6.8 Hz, 6H), 0.85 (d, J=6.8 Hz, 6H).

Example 171: General Method 0, step 1 synthesis of bis((3aS,8aR)-3a,8a-dihydro-8Hindeno[1,2-d] oxazol-2-yl)methane To a flame dried flask was transferred Diethyl malonimidate dihydrochloride (5.0 g, 21.6 mmol, 1.0 eq) in the glove box. The flask was transferred out of the glove box and then DCM (250 mL) and (1S,2R)-1-aminoindanol (8.1 g, 54.1 mmol, 2.5 eq) were added. The flask was then purged with nitrogen and stirred at 40° C. for 24 hours. The reaction was quenched with water (50 mL) and then extracted with DCM (3×50 mL). The combined organic phase was dried over Na2SO4 and the solvent was removed under vacuum. The crude product was purified by washing with 1:1, EtOH:H2O to afford a white solid (2.36 g, 33% yield). [α]23D=−409.4 (c=0.6, CHCl3), 1H NMR (500 MHz, CDCl3) δ 7.50-7.42 (m, 2H), 7.30-7.21 (m, 6H), 5.56 (dd, J=7.9, 0.9 Hz, 2H), 5.34 (ddd, J=7.9, 7.0, 1.8 Hz, 2H), 3.39 (ddt, J=17.9, 7.0, 0.9 Hz, 2H), 3.26 (t, J=0.9 Hz, 2H), 3.16 (ddt, J=18.0, 1.7, 0.8 Hz, 2H).

Example 172: General method 0, step 2 synthesis of (3aS,3a'S,8aR,8a'R)-2,2'-(propane-2,2-diyl)bis(3a, 8a-dihydro-8H-indeno[1,2-d]oxazole), (51e)

To a flame dried flask, purged with dry nitrogen, was added THF (20 mL), TMEDA (0.45 mL, 3.02 mmol, 2.0 eq), HN(iPr)2 (0.43 mL, 3.02 mmol, 2.0 eq), and nBuLi (1.35 mL of 2.23 M solution, 3.02 mmol, 2.0 eq) at −20° C. to generate LDA. This solution was stirred at −20° C. for 1 h. A solution of bis((3aS,8aR)-3a,8a-dihydro-8H-indeno[1,2-d]oxazol-2-yl)methane (0.5 g, 1.51 mmol, 1.0 eq) dissolved in THF (20 mL) was added at −20° C. and the reaction was stirred at that temperature for 1 h. MeI (0.38 mL, 6.04 mmol, 4.0 eq) was then added dropwise at −20° C. After this addition the reaction was warmed to room temperature overnight. The reaction was quenched with concentrated NH4Cl solution (20 mL) and then S51 extracted with EtOAc (3×20 mL). The combined organic phase was washed with brine, dried over Na2SO4, and the solvent was removed under vacuum. The crude product was purified by column chromatography on SiO2 (eluent=4:1 EtOAc:Hexanes) to afford the product as an off white solid (0.32 g, 60% yield).

[α]23D=−406.5 (c=0.6, CHCl3), 1H NMR (500 MHz, CDCl3) δ 7.53-7.45 (m, 2H), 7.30-7.20 (m, 6H), 5.52 (dd, J=7.9, 0.8 Hz, 2H), 5.25 (ddd, J=7.9, 7.1, 1.9 Hz, 2H), 3.30 (ddt, J=17.8, 7.0, 0.9 Hz, 2H), 2.99-2.91 (m, 2H), 1.42 (s, 6H).

Example 173: Synthesis of bis((4R,5S)-4,5-diphenyl-4,5-dihydrooxazol-2-yl)methane Prepared according to general Method 0, Step 1, using Diethyl malonimidate dihydrochloride (3.0 g, 12.9 mmol, 1.0 eq), (1S,2R)-2-amino-1,2-diphenylethan-1-ol (5.54 g, 25.96 mmol, 2.0 eq), and DCM (60 mL). Purified by recrystallization from EtOAc to afford the product as white needles (3.01 g, 51% yield). [α]23D=+158.9 (c=0.7, CHCl3), 1H NMR (500 MHz, CDCl3) δ 7.09-6.92 (m, 20H), 5.99 (d, J=10.3 Hz, 2H), 5.65 (dt, J=10.3, 1.3 Hz, 2H), 3.90 (t, J=1.3 Hz, 2H).

Example 174: Synthesis of (4R,4'R,5S,5'S)-2,2'-(propane-2,2-diyl)bis(4,5-diphenyl-4,5-dihydrooxazole) (Compound 51f)

Prepared according to general Method 0, Step 2 using bis((4R,5S)-4,5-diphenyl-4,5-dihydrooxazol-2-yl)methane (0.5 g, 1.09 mmol, 1.0 eq), MeI (0.2 mL, 3.27 mmol, 3.0 eq), nBuLi (1.43 mL of 2.29 M solution, 3.27 mmol, 3.0 eq), HN(iPr)2 (0.46 mL, 3.27 mmol, 3.0 eq), TMEDA (0.49 mL, 3.27 mmol, 3.0 eq), and THF (16 mL). The crude product was purified by column chromatography on SiO2 (eluent=3:2 Hexanes:EtOAc with 1% triethylamine) to afford the pure product as a white solid (0.38 g, 72% yield). [α]23D=+340.1 (c=0.6, CHCl3), 1H NMR (500 MHz, CDCl3) δ 7.06-6.94 (m, 20H), 5.97 (d, J=10.2 Hz, 2H), 5.60 (d, J=10.1 Hz, 2H), 1.92 (s, 6H).

Example 175: Synthesis of bis((S)-4-phenyl-4,5-dihydrooxazol-2-yl)methane (Compound 51ka)

Prepared according to General Method 0, step 1: using diethyl malonimidate dihydrochloride (2.0 g, 8.62 mmol, 1.0 eq), (S)-phenyl glycinol (2.37 g, 17.3 mmol, 2.0 eq), and DCM (25 mL). Purified by column chromatography on SiO2 (eluent=3:2 Hexanes:EtOAc with 0.5% Et3N) to afford 51ka as a viscous oil (1.01 g, 38% yield). 1H NMR (500 MHz, CDCl3) δ 7.37-7.26 (m, 10H), 5.34-5.18 (m, 2H), 4.70 (dd, J=10.2, 8.4 Hz, 2H), 4.19 (dd, J=8.4, 8.0 Hz, 2H), 3.58 (t, J=1.2 Hz, 2H).

Example 176: General Method P and synthesis of (4S,4'S)-2,2'-(1,3-diphenylpropane-2,2-diyl)bis(4-phenyl-4,5-dihydrooxazole) (Compound 51k)

Compound 51ka (0.25 g, 0.82 mmol, 1.0 eq) and THF (16 mL) were added to a flame dried round bottom flask and purged with dry N2. NaH (60% dispersion in mineral oil, 0.23 g, 5.7 mmol, 7.0 eq) was added slowly at room temperature. Evolution of hydrogen gas was observed. After stirring for 1 h at room temperature, Benzyl bromide (0.29 mL, 2.45 mmol, 3.0 eq) was added dropwise at room temperature and then allowed to react overnight. The reaction was quenched by the addition of water, extracted with EtOAc (3×5 ml), dried over anhydrous NaSO4, then the solvent was removed to afford the crude product. The crude product was purified by column chromatography on SiO2 (eluent=8:2, Hexanes:EtOAc with 0.5% Et3N) to afford 51k as a foamy white solid (0.346 g, 87% yield). 1H NMR (500

MHz, CDCl3) δ 7.41-7.33 (m, 4H), 7.33-7.22 (m, 12H), 7.06-6.96 (m, 4H), 5.18 (dd, J=10.3, 8.8 Hz, 2H), 4.63 (dd, J=10.3, 8.3 Hz, 3H), 4.03 (t, J=8.6 Hz, 2H), 3.60-3.39 (m, 4H).

Example 177: Synthesis of bis((S)-4-(naphthalen-2-yl)-4,5-dihydrooxazol-2-yl)methane (51lb)

Prepared according to General Method 0, step 1: using diethyl malonimidate dihydrochloride (0.148 g, 0.64 mmol, 1.0 eq), (S)-2-amino-2-(naphthalen-2-yl)ethan-1-ol, 511a (0.241 g, 1.28 mmol, 2.0 eq), and DCM (10 mL). Purified by column chromatography on SiO2 (eluent=8:2 Hexanes:EtOAc with 0.5% Et3N) to afford 51lb as a viscous oil (0.196 g, 75% yield). 1H NMR (500 MHz, CDCl3) δ 7.89-7.76 (m, 6H), 7.75-7.66 (m, 2H), 7.52-7.34 (m, 6H), 5.46 (ddt, J=9.0, 7.9, 1.3 Hz, 2H), 4.79 (dd, J=10.2, 8.5 Hz, 2H), 4.29 (dd, J=8.5, 7.8 Hz, 2H), 3.67 (t, J=1.2 Hz, 2H).

Example 178: Synthesis of (4S,4'S)-2,2'-(1,3-diphenylpropane-2,2-diyl)bis(4-(naphthalen-2-yl)-4,5-dihydrooxazole) (Compound 511)

Prepared according to General Method P: using 51lb (0.196 g, 0.48 mmol, 1.0 eq), NaH (60% dispersion in mineral oil, 0.134 g, 3.36 mmol, 7.0 eq), Benzyl bromide (0.174 mL, 1.45 mmol, 3.0 eq), and THF (10 mL). Purified by column chromatography on SiO2 (eluent=8:2, Hexanes: EtOAc with 0.5% Et3N) to afford compound 511 as a foamy white solid (0.24 g, 85% yield). [α]22D=−169.2 (c=0.5, CHCl3), lit. [28] [α]20D=−182 (c=0.1, CHCl3) 1H NMR (500 MHz, CDCl3) δ 7.86-7.67 (m, 6H), 7.58-7.51 (m, 2H), 7.49-7.27 (m, 14H), 7.14-7.06 (m, 2H), 5.39 (dd, J=10.2, 8.8 Hz, 2H), 4.73 (dd, J=10.3, 8.4 Hz, 2H), 4.13 (t, J=8.6 Hz, 2H), 3.70-3.45 (m, 4H).

REFERENCES (1) (a) Rönsberg, D.; Debbab, A.; Mándi, A.; Vasylyeva, V.; Böhler, P.; Stork, B.; Engelke, L.; Hamacher, A.; Sawadogo, R.; Diederich, M.; Wray, V.; Lin, W.; Kassack, M. U.; Janiak, C.; Scheu, S.; Wesselborg, S.; Kurtán, T.; Aly, A. H.; Proksch, P. Pro-Apoptotic and Immunostimulatory Tetrahydroxanthone Dimers from the Endophytic Fungus Phomopsis longicolla. J. Org. Chem. 2013, 78, 12409-12425. (b) Bohler, P.; Stuhldreier, F.; Anand, R.; Kondadi, A. K.; Schlütermann, D.; Berleth, N.; Deitersen, J.; Wallot-Hieke, N.; Wu, W.; Frank, M.; Niemann, H.; Wesbuer, E.; Barbian, A.; Luyten, T.; Parys, J.; Weidtkamp-Peters, S.; Borchardt, A.; Reichert, A. S.; Peña-Blanco, A.; García-Sáez, A.; Itskanov, S.; van der Bliek, A.; Proksch, P.; Wesselborg, S.; Stork, B. The Mycotoxin Phomoxanthone A Disturbs the Form and Function of the Inner Mitochondrial Membrane. Cell Death Dis. 2018, 9, 286-303. (c) Wang, C.; Engelke, L.; Bickel, D.; Hamacher, A.; Frank, M.; Proksch, P.; Gohlke, H.; Kassack, M. U. The Tetrahydroxanthone-dimer Phomoxanthone A is a Strong Inducer of Apoptosis in Cisplatin-resistant Solid Cancer Cells. Bioorg. Med. Chem. 2019, 27, 115044-115056. (d) Yang, R.; Dong, Q.; Xu, H.; Gao, X.; Zhao, Z.; Qin, J.; Chen, C.; Luo, D. Identification of Phomoxanthone A and B as Protein Tyrosine Phosphate Inhibitors. ACS Omega 2020, 5, 25927-25935.
(2) Isaka, M.; Jaturapat, A.; Rukseree, K.; Danwisetkanjana, K.; Tanticharoen, M.; Thebtaranonth, Y. Phomoxanthones A and B, Novel Xanthone Dimers from the Endophytic FungusPhomopsisSpecies. J. Nat. Prod. 2001, 64, 1015-1018.

(3) For a review, see: Nibbs, A. E.; Scheidt, K. A. AsymmetricMethods for the Synthesis of Flavanones, Chromanones, and Azaflavanones. Eur. J. Org. Chem. 2012, 2012, 449-462 for select examples of enantioselective 2-alkylchromanone synthesis, see: (a) Rao, A. R.; Gaitonde, A. S.; Prakash, K. R. C.; Rao, S. P. ConciseSynthesis of Chiral 2-Methyl Chromanon-4-ones: Stereoselective Build-up of the Chromanol Moiety of Anti-HIV Agent Calanolide. Tetrahedron Lett. 1994, 35, 6347-6350. (b) Kawasaki, M.; Kakuda, H.; Goto, M.; Kawabata, S.; Kometani, T. Asymmetric Synthesis of 2-Substituted Chroman-4-ones using Lipase-Catalyzed Kinetic Resolutions. Tetrahedron: Asymmetry 2003, 14, 1529-1534. (c) Biddle, M. M.; Lin, M.; Scheidt, K. A. Catalytic Enantioselective Synthesis of Flavanones and Chromanones. J. Am. Chem. Soc. 2007, 129, 3830-3831. (d) Boekl, H.; Mackert, R.; Muramann, C.; Schweickert, N.; U.S. 66/646,136B1, 2013. (e) Termath, A. O.; Sebode, H.; Schlundt, W.; Stemmler, R. T.; Netscher, T.; Bonrath, W.; Schmalz, H.-G. Total Synthesis of (R,R,R)-α-Tocopherol through Asymmetric Cu-Catalyzed 1,4-Addition. Chem.□Eur J. 2014, 20, 12051-12055. (f) Brown, M. K.; Degrado, S. J.; Hoveyda, A. H. Highly Enantioselective Cu-Catalyzed Conjugate Additions of Dialkylzinc Reagents to Unsaturated Furanones and Pyranones: Preparation of Air-Stable and Catalytically Active Cu-Peptide Complexes. Angew. Chem., Int. Ed. 2005, 44, 5306-5310. (g) Vila, C.; Hornillos, V.; Fananis-Mastral, M.; Feringa, B. L. Catalytic Asymmetric Conjugate Addition of Grignard Reagents to Chromones. Chem. Commun. 2013, 49, 5933-5935. (h) Trost, B. M.; Gnanamani, E.; Kalnmals, C. A.; Hung, C.-I. J.; Tracy, J. S. Direct and Enantio- and Diastereoselective Vinylogous Addition of Butenolides to Chromones Catalyzed by Zn-ProPhenol. J. Am. Chem. Soc. 2019, 141, 1489-1493.

(4) For a recent review on the importance of chiral tertiary ethers and their limited synthetic accessibility, see: Liu, Y.-L.; Lin, X.-T. Recent Advances in Catalytic Asymmetric Synthesis of Tertiary Alcohols via Nucleophilic Addition to Ketones. Adv. Synth. Catal. 2019, 361, 876-918 For select reports demonstrating the importance of constructing tertiary ether stereocenters from chromanones, see: (a) Baek, D.; Ryu, H.; Ryu, J. Y.; Lee, J.; Stoltz, B. M.; Hong, S. Catalytic Enantioselective Synthesis of Tetrasubstituted Chromanones via Palladium Catalyzed Asymmetric Conjugate Arylation using Chiral Pyridine-Dihydroisoquinoline Ligands. Chem. Sci. 2020, 11, 4602-4607. (b) Gerten, A. L.; Stanley, L. M. Palladium-Catalyzed Conjugate Additional of Arylboronic Acids to 2-Substituted Chromones in Aqueous Media. Tetrahedron Lett. 2016, 57, 5460-5463.

(5) For recent reviews on dimeric chromanones and tetrahydroxanthones, see: (a) Wezeman, T.; Bräse, S.; Masters, K.-S. Xanthone Dimers: A Compound Family which is both Common and Privileged. Nat. Prod. Rep. 2015, 32, 6-28. (b) For isolation and biological activities of gontyolides, see: Masters, K.-S.; Bräse, S. Xanthones from Fungi, Lichens, and Bacteria: The Natural Products and their Synthesis. Chem. Rev. 2012, 112, 3717-3776. (c) For isolation and biological activities of the blennolides, see: Kikuchi, H.; Isobe, M.; Sekiya, M.; Abe, Y.; Hoshikawa, T.; Ueda, K.; Kurata, S.; Katou, Y.; Oshima, Y. Structures of the Dimeric and Monomeric Chromanones, Gonytolides A-C, Isolated from the Fungus *Gonytrichum* sp. And Their Promoting Activities of the Innate Immune Responses. Org. Lett. 2011, 13, 4624-4627. (d) For isolation and biological data on the dicerandrols, see: Zhang, W.; Krohn, K.; Zia-Ullah; Flörke, U.; Pescitelli, G.; Di Bari, L.; Antus, S.; Kurtian, T.; Rheinheimer, J.; Draeger, S.; Schulz, B. New Mono- and Dimeric Members of the Secalonic Acid Family: Blennolides A-G Isolated from the Fungus *Blennoria* sp. Chem.□Eur J. 2008, 14, 4913-4923. (e) For isolation and biological data on the versixanthones, see: Wagenaar, M. M.; Clardy, J. Dicerandrols, New Antibiotic and Cytotoxic Dimers Produced by the Fungus Phomposis longicolla Isolated from an Endagered Mint. J. Nat. Prod. 2001, 64, 1006-1009. (f) For isolation and biological data on the rugulotrosins, see: Wu, G.; Yu, G.; Kurtán, T.; Mándi, A.; Peng, J.; Mo, X.; Liu, M.; Li, H.; Sun, X.; Li, J.; Zhu, T.; Gu, Q.; Li, D. Versixanthones A-F, Cytotoxic Xanthone-Chromanone Dimers from the Marine-Derived Fungus Aspergillus versicolor HDN1009. J. Nat. Prod. 2015, 78, 2691-2698. (g) Stewart, M.; Capon, R. J.; White, J. M.; Lacey, E.; Tennant, S.; Gill, J. H.; Shaddock, M. P. Rugulotrosins A and B:Two New Antibacterial Metabolites from an Australian Isolate of a *Penicillium* sp. J. Nat. Prod. 2004, 67, 728-730.

(6) (a) Qin, T.; Skraba-Joiner, S. L.; Khalil, Z. G.; Johnson, R. P.; Capon, R. J.; Porco, J. A. Atropselective Synthesis of (−) and (+) Rugulotrosin A Utilizing Point-to-Axial Chirality Transfer. Nat. Chem. 2015, 7, 234-240. (b) Chen, J.; Li, Y.; Xiao, Z.; He, H.; Gao, S. Asymmetric Synthesis of Rugulotrosin A. Org. Lett. 2020, 22, 1485-1489.

(7) Ganapathy, D.; Reiner, J. R.; Valdomir, G.; Senthilkumar, S.; Tietze, L. F. Enantioselective Total Synthesis and Structure Confirmation of the Natural Dimeric Tetrahydroxanthenone Diceradrol C. Chem.□Eur J. 2017, 23, 2299-2302.

(8) (a) Qin, T.; Iwata, T.; Ransom, T. T.; Beutler, J. A.; Porco, J. A. Syntheses of Dimeric Tetrahydroxanthones with Varied Linkages: Investigations of "Shapeshifting" Properties. J. Am. Chem. Soc. 2015, 137, 15225-15233. (b) Qin, T.; Porco, J. A. Total Syntheses of Secalonic Acids A and D. Angew. Chem., Int. Ed. 2014, 53, 3107-3110. (c) Qin, T.; Johnson, R. P.; Porco, J. A. Vinylogous Addition of Siloxyfurans to Benzopyryliums: A Concise Approach to the Tetrahydroxanthone Natural Products. J. Am. Chem. Soc. 2011, 133, 1714-1717.

(9) Tietze, L. F.; Ma, L.; Reiner, J. R.; Jackenkroll, S.; Heidemann, S. Enantioselective Total Synthesis of (−)-Blennolide A. Chem.□Eur J. 2013, 19, 8610-8614.

(10) Guan, Y.; Attard, J. W.; Mattson, A. E. Copper Bis (oxazoline)-Catalyzed Enantioselective Alkynylation of Benzopyrylium Ions. Chem.□Eur J. 2020, 26, 1742-1747.

(11) DeRatt, L. G.; Pappoppula, M.; Aponick, A. A Facile Enantioselective Alkynylation of Chromones. Angew. Chem., Int. Ed. 2019, 58, 8416-8420.

(12) For a review on bis(oxazoline) ligands in asymmetric catalysis, see: Desimoni, G.; Faita, G.; Jørgensen, K. A. C2-Symmetric Chiral Bis(Oxazoline) Ligands in Asymmetric Catalysis. Chem. Rev. 2006, 106, 3561-3651.

(14) For related reactions that support this hypothesized pathway, see: (a) Srinivas, H. D.; Maity, P.; Yap, G. P. A.; Watson, M. P. Enantioselective Copper-Catalyzed Alkynylation of Benzopyranyl Oxocarbenium Ions. J. Org. Chem. 2015, 80, 4003-4016. (b) Zhong, K.; Shan, C.; Zhu, L.; Liu, S.; Zhang, T.; Liu, F.; Shen, B.; Lan, Y.; Bai, R. Theroetical Study of the Addition of Cu-Carbenes to Acetylenes to Form Chiral Allenes. J. Am. Chem. Soc. 2019, 141, 5772-5780.

(15) For select work on the generation and reactions of benzopyrylium triflates, see: (a) Iwasaki, H.; Kume, T.; Yamamoto, Y.; Akiba, K.-y. Reaction of 4-t-Butyldimethylsiloxy-1-benzopyrylium Salt with Enol Silyl Ethers and Active Methylenes. Tetrahedron Lett. 1987, 28, 6355-6358. (b) Stubbing, L. A.; Li, F. F.; Furkert, D. P.; Caprio, V. E.; Brimble, M. A. Access to 2-Alkyl Chromanones via Conjugate Addition Approach. Tetrahedron 2012, 68, 6948-6956. (c) Liu, J.; Li, Z.; Tong, P.; Xie, Z.; Zhang, Y.; Li, Y. TMSI-Promoted Vinylogous Michael Addition of Siloxyfuran to 2-Substituted Chromones: A General Approach for the Total Synthesis of Chromanone Lactone Natural Products. J. Org. Chem. 2015, 80, 1632-1643.

(17) For citations on the level of theory, see: (a) Becke, A. D. Density-Functional Thermochemistry. III. The Role of Exact Exchange. J. Chem. Phys. 1993, 98, 5648-5652. (b) Stephens, P. J.; Devlin, F. J.; Chabalowski, C. F.; Frisch, M. J. Ab Initio Calculation of Vibrational Absorption and Circular Dichroism Spectra Using Density Functional Force Fields. J. Phys. Chem. 1994, 98, 11623-11627. (c) Kim, K.; Jordan, K. D. Comparison of Density Functional and MP2 Calculations on the Water Monomer and Dimer. J. Phys. Chem. 1994, 98, 10089-10094. (d) Nicklass, A.; Dolg, M.; Stoll, H.; Preuss, H.; Nicklass, A.; Dolg, M.; Stoll, H.; Preuss, H. Ab Initio Energy-Adjusted Pseudopotentials for the Noble Gases Ne through Xe: Calculation of Atomic Dipole and Quadrupole Polarizabilities. J. Chem. Phys. 1995, 102, 8942-8952. (e) Hariharan, P. C.; Pople, J. A. The Influence of Polarization Functions on Molecular Orbital Hydrogenation Energies. Theor. Chim. Acta 1973, 28, 213-222. (f) Ditchfield, R.; Hehre, W. J.; Pople, J. A. Self-Consistent Molecular-Orbital Methods. IX. An Extended Gaussian-Type Basis for Molecular-Orbital Studies of Organic Molecules. J. Chem. Phys. 1971, 54, 724-728. (g) Gordon, M. S. The Isomers of Silacyclopropane. Chem. Phys. Lett. 1980, 76, 163-168. (h) Hariharan, P. C.; Pople, J. A. Accuracy of AHn Equilibrium Geometries by Single Determinant Molecular Orbital Theory. Mol. Phys. 1974, 27, 209-214. (i) Hehre, W. J.; Ditchfield, R.; Pople, J. A. Self-Consistent Molecular Orbital Methods. XII. Further Extensions of Gaussian-Type Basis Sets for Use in Molecular Orbital Studies of Organic Molecules. J. Chem. Phys. 1972, 56, 2257-2261.

(18) Contreras-Garcia, J.; Johnson, E. R.; Keinan, S.; Chaudret, R.; Piquemal, J.-P.; Beratan, D. N.; Yang, W. NCI-PLOT: A Program for Plotting Noncovlaent Interaction Reagions. J. Chem. Theory Comput. 2011, 7, 625-632.

(19) Schneebeli, S. T.; Hall, M. L.; Breslow, R.; Friesner, R. Quantitative DFT Modeling of the Enantiomeric Excess for Dioxirane-Catalyze Epoxidations. J. Am. Chem. Soc. 2009, 131, 3965-3973.

(20) Sigman, M. S.; Miller, J. J. Examination of the Role of Taft-Type Steric Parameters in Asymmetric Catalysis. J. Org. Chem. 2009, 74, 7633-7643.

What is claimed is:

1. A composition having the general formula:

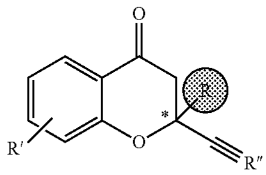

wherein R is the ester having the formula $CO_2R_1$, and $R_1$ is selected from benzyl, trichloroethyl, and trichloromethyl;

R' is selected from: a hydrogen, a benzyl, a trifluoromethyl, and a cyclopropyl;

R" is selected from an alkyl, a vinyl, an aryl, a heteroaryl, and a phenyl acetylene; and the R, R' and R" selected based on an affinity for biomolecular targets of Phomoxanthone A.

2. The composition according to claim 1, wherein R" is selected from naphthalene and furan.

* * * * *